US012644135B2

(12) United States Patent
Smith et al.

(10) Patent No.: US 12,644,135 B2
(45) Date of Patent: Jun. 2, 2026

(54) POLYPEPTIDE LINKERS FOR USE IN ENGINEERED MEGANUCLEASES

(71) Applicant: Precision BioSciences, Inc., Durham, NC (US)

(72) Inventors: James Jefferson Smith, Morrisville, NC (US); Hui Li, Apex, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

(21) Appl. No.: 19/273,982

(22) Filed: Jul. 18, 2025

(65) Prior Publication Data

US 2025/0382641 A1       Dec. 18, 2025

Related U.S. Application Data

(63) Continuation of application No. PCT/US2024/055190, filed on Nov. 8, 2024.

(60) Provisional application No. 63/696,582, filed on Sep. 19, 2024, provisional application No. 63/597,244, filed on Nov. 8, 2023.

(51) Int. Cl.
| | |
|---|---|
| *C12N 15/11* | (2006.01) |
| *C12N 9/22* | (2006.01) |
| *C12N 15/10* | (2006.01) |
| *C12N 15/90* | (2006.01) |

(52) U.S. Cl.
CPC .............. *C12N 15/90* (2013.01); *C12N 9/22* (2013.01); *C12N 15/1082* (2013.01); *C12N 15/11* (2013.01); *C12N 2310/20* (2017.05)

(58) Field of Classification Search
CPC ...... C12N 15/90; C12N 9/22; C12N 15/1082; C12N 15/11; C12N 2310/20
See application file for complete search history.

(56) References Cited

U.S. PATENT DOCUMENTS

2014/0223606 A1     8/2014   Bermudez et al.

FOREIGN PATENT DOCUMENTS

| | | | | |
|---|---|---|---|---|
| AU | 2015 201 270 A1 | 4/2015 | | |
| CA | 2 729 124 A1 | 8/2009 | | |
| EP | 3 098 309 A1 | 11/2016 | | |
| EP | 3098309 B1 * | 4/2019 | .............. | A61P 43/00 |
| WO | WO 2011/141820 A1 | 11/2011 | | |
| WO | WO 2012/138901 A1 | 10/2012 | | |

OTHER PUBLICATIONS

Grizot, S., et al., "Efficient targeting of a SCID gene by an engineered single-chain homing endonuclease," *Nucleic Acids Research*, 2009, vol. 37(16), pp. 5405-5419.
Li, H., et al., "Generation of single-chain LAGLIDADG homing endonucleases from nature homodimeric precursor proteins," *Nucleic Acids Research*, 2009, vol. 37(5), pp. 1650-1662.
Muñoz, I. et al., "Molecular basis of engineered meganuclease targeting of the endogenous human RAG1 locus," *Nucleic Acids Research*, 2011, vol. 39(2), pp. 729-743.

* cited by examiner

Primary Examiner — Celine X Qian
Assistant Examiner — Tiffany Nicole Grooms
(74) Attorney, Agent, or Firm — Womble Bond Dickinson (US) LLP

(57) ABSTRACT

The present disclosure encompasses engineered meganucleases that comprise two subunits connected by a polypeptide linker that is smaller than polypeptide linkers used in the art. The engineered meganucleases can exhibit at least one improved characteristic, such as increased efficiency of binding and/or cleavage, when compared to meganucleases comprising longer polypeptide linkers. The present disclosure also encompasses methods of using engineered nucleases to make genetically-modified cells and the use of such cells in a pharmaceutical composition and in methods for treating diseases.

13 Claims, 25 Drawing Sheets

Specification includes a Sequence Listing.

Linker1923     SLPGIQLNKESNNHASTQRPSRNVNHFPYSG     31 (SEQ ID NO: 4)
Linker1766     SLPGIGVQVHRNNHASTQRPSRNVNHFPYKG     31 (SEQ ID NO: 5)
Linker1771     SLPGVRLHCPLNNHASTQRPSRNVNHFPQG-     30 (SEQ ID NO: 6)
Linker1808     SLPGIRLSQGANNHASTQRPSRNVNHFPLG-     30 (SEQ ID NO: 7)
Linker1814     SLPGARPGGVSNNHASTQRPSRNVNHFPYSG     31 (SEQ ID NO: 8)
               **                 *********************

FIG. 1A

Linker1923     SLPGIQLNK----ESNNHAS-TQRPSRNVNHFPYSG--------     31 (SEQ ID NO: 4)
Linker1766     SLPGIGVQV----HRNNHAS-TQRPSRNVNHFPYKG--------     31 (SEQ ID NO: 5)
Linker1771     SLPGVRLHC----PLNNHAS-TQRPSRNVNHFPQG---------     30 (SEQ ID NO: 6)
Linker1808     SLPGIRLSQ----GANNHAS-TQRPSRNVNHFPLG---------     30 (SEQ ID NO: 7)
Linker1814     SLPGARPGG----VSNNHAS-TQRPSRNVNHFPYSG--------     31 (SEQ ID NO: 8)
Linker1        SLPGSVGGLSPSQASSAASSASSSPGSGISEALRAGAGSGTG     42 (SEQ ID NO: 27)
               ****                  *              *

FIG. 1B

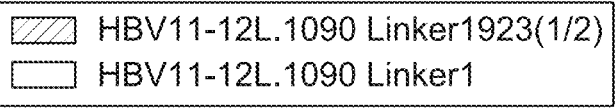
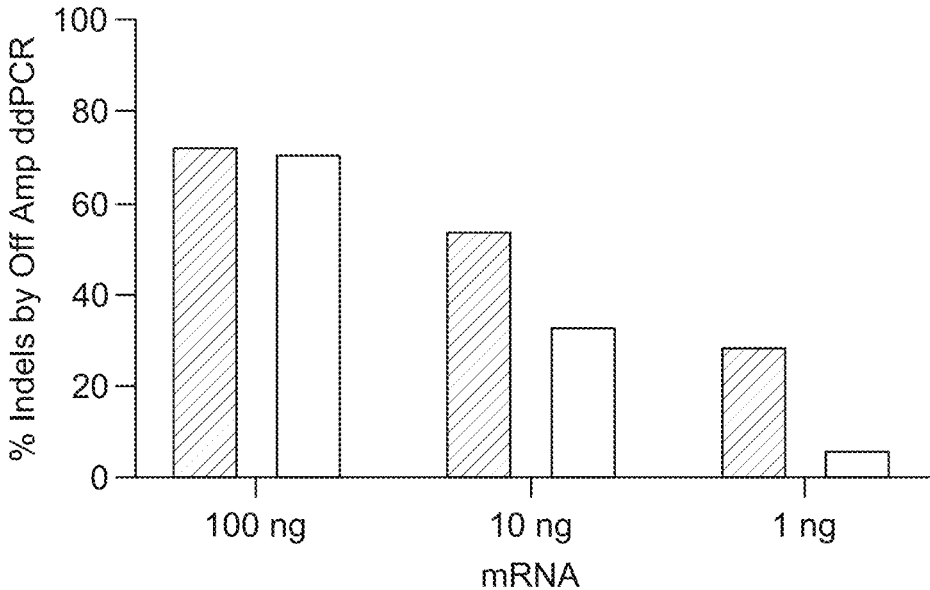
FIG. 17A
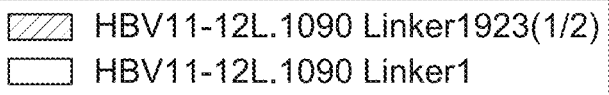
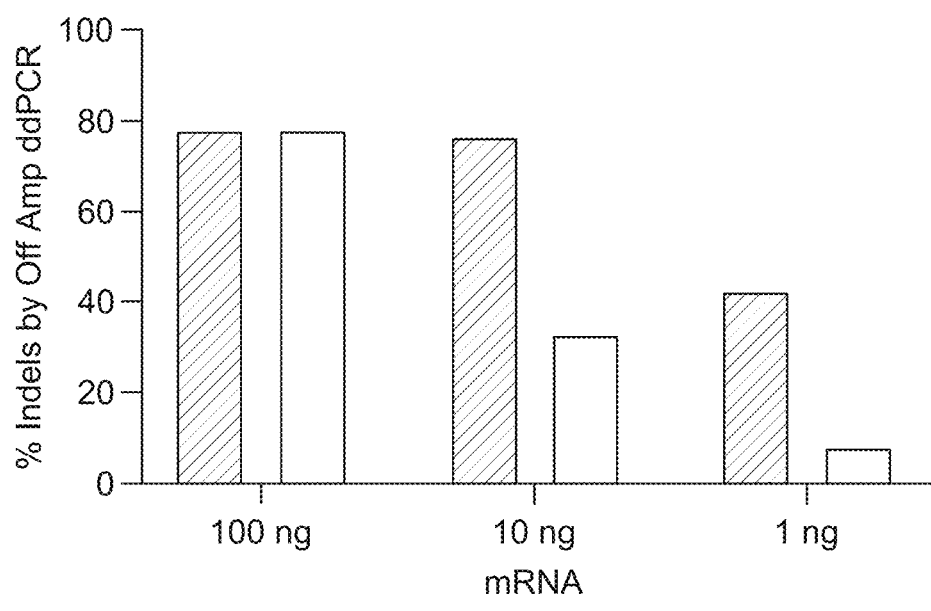
FIG. 17B

HBV 11-12L.1090 Indels by ddPCR, Day 2 & Day 6

POLYPEPTIDE LINKERS FOR USE IN ENGINEERED MEGANUCLEASES

CROSS-REFERENCE TO RELATED APPLICATIONS

This application is a continuation of International Application No. PCT/US2024/055190, filed Nov. 8, 2024, which claims priority to U.S. Provisional Application Nos. 63/597,244, filed Nov. 8, 2023, and 63/696,582, filed Sep. 19, 2024, each of which is incorporated by reference herein in its entirety.

FIELD OF THE INVENTION

The disclosure relates to the field of protein engineering, molecular biology, recombinant nucleic acid technology, and gene editing. In particular, the disclosure relates to novel polypeptide linkers and their use in generating engineered meganucleases. The disclosure further relates to the use of such engineered meganucleases in methods for generating genetically-modified cells, particularly for the treatment of a disease in a subject.

REFERENCE TO A SEQUENCE LISTING SUBMITTED ELECTRONICALLY AS AN XML FILE

The instant application contains a Sequence Listing which has been submitted in XML format via USPTO Patent Center and is hereby incorporated by reference in its entirety. Said XML copy, created on Sep. 9, 2024, is named "P89339_2040US.P2.xml", and is 165,177 KB in size.

BACKGROUND OF THE INVENTION

Genetic modification of genomic DNA can be performed using site-specific, rare-cutting endonucleases that are engineered to recognize DNA sequences in the locus of interest. Homing endonucleases are a group of naturally-occurring nucleases that recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), Q. Rev. Biophys. 38:49-95). Homing endonucleases are commonly grouped into four families: the LAGLIDADG (SEQ ID NO: 2) family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif (see Chevalier et al. (2001), Nucleic Acids Res. 29 (18): 3757-3774). The LAGLIDADG homing endonucleases with a single copy of the LAGLIDADG motif form homodimers, whereas members with two copies of the LAGLIDADG motif are found as monomers.

I-CreI (SEQ ID NO: 1) is a member of the LAGLIDADG family of homing endonucleases that recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004), J.

Mol. Biol. 342:31-41: Chames et al. (2005), Nucleic Acids Res. 33: e178: Seligman et al. (2002), Nucleic Acids Res. 30:3870-9, Arnould et al. (2006), J. Mol. Biol. 355:443-58). A method of rationally-designing mono-LAGLIDADG homing endonucleases has been described that is capable of comprehensively redesigning I-CreI and other homing endonucleases to target widely-divergent DNA sites, including sites in mammalian, yeast, plant, bacterial, and viral genomes (WO 2007/047859). As first described in WO 2009/059195, I-CreI and its engineered derivatives are normally dimeric but can be fused into a single polypeptide using a short peptide linker that joins the C-terminus of a first subunit to the N-terminus of a second subunit (Li et al. (2009), Nucleic Acids Res. 37:1650-62; Grizot et al. (2009), Nucleic Acids Res. 37:5405-19). Thus, a functional "single-chain" meganuclease can be expressed from a single transcript.

In the present disclosure, Applicants have improved upon peptide linker sequences taught in the prior art that are used to join the two meganuclease subunits to create a "single-chain" meganuclease. Through extensive experimentation, Applicants have generated novel peptide linkers which are shorter in length than those taught in the prior art. The shorter length allows for greater ease in packaging polynucleotides encoding the engineered meganucleases for delivery to host cells and in some cases, results in enhanced nuclease activity in comparison to those engineered meganucleases comprising the longer prior art peptide linker sequences.

SUMMARY OF THE INVENTION

In one aspect, the disclosure provides an engineered meganuclease comprising, from 5' to 3', a first subunit, a polypeptide linker, and a second subunit, wherein the first subunit and the second subunit are connected by the polypeptide linker, wherein the engineered meganuclease is capable of binding to a recognition sequence in a double-stranded DNA (dsDNA), and wherein the polypeptide linker comprises an amino acid sequence of: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$-$X_{21}$-$X_{22}$-$X_{23}$-$X_{24}$-$X_{25}$-$X_{26}$-$X_{27}$-$X_{28}$-$X_{29}$-$X_{30}$ (SEQ ID NO: 3).

In some embodiments, the polypeptide linker comprises, from 5' to 3', a first turn, a first coil, a second coil, and a second turn.

In some embodiments, the first turn comprises between 3-6 amino acids. In some embodiments, the first turn comprises 4 amino acids. In some embodiments, the first turn comprises residues $X_1$-$X_4$. In some embodiments, $X_1$ comprises S. In some embodiments, $X_2$ comprises L. In some embodiments, $X_3$ comprises P. In some embodiments, $X_4$ comprises G. In some embodiments, residues $X_1$-$X_4$ of the first turn comprises an SLPG motif (SEQ ID NO: 9). In some embodiments, the first turn comprises an amino acid sequence having at least 75% sequence identity to SEQ ID NO: 9. In some embodiments, the first turn comprises an amino acid sequence of SEQ ID NO: 9 or an amino acid sequence that differs from SEQ ID NO: 9 by 1 amino acid residue. In some embodiments, the first turn comprises an amino acid sequence of SEQ ID NO: 9. In some embodiments, the first coil comprises between 11-15 amino acids. In some embodiments, the first coil comprises 13 amino acids. In some embodiments, the first coil comprises residues $X_5$-$X_{17}$. In some embodiments, $X_5$ comprises a nonpolar amino acid. In some embodiments, $X_5$ comprises I, V, or A. In some embodiments, $X_5$ comprises I. In some embodiments, $X_6$ comprises a polar amino acid. In some embodiments, $X_6$ comprises Q, G, or R. In some embodiments, $X_6$ comprises Q. In some embodiments, $X_7$ comprises a non-polar amino acid. In some embodiments, $X_7$ comprises L, V, or P. In some embodiments, $X_7$ comprises L. In some embodiments, $X_8$ comprises N, Q, H, S, or G. In some embodiments, $X_8$ comprises N. In some embodiments, $X_9$ comprises K, V, C, Q, or G. In some embodiments, $X_9$ comprises K. In some embodiments, $X_{10}$ comprises E, H, P, G, or V. In some embodiments, $X_{10}$ comprises E. In some embodiments, $X_{11}$ comprises S, R, L, or A. In some embodiments, $X_{11}$ comprises S. In some embodiments, $X_{12}$ comprises a polar amino acid. In some embodiments, $X_{12}$ comprises N. In some embodiments, $X_{13}$ comprises N. In some embodiments, $X_{14}$ comprises a polar amino acid. In some embodiments, $X_{14}$ comprises N. In some embodiments, $X_{15}$ comprises a polar amino acid. In some embodiments, $X_{15}$ comprises a small amino acid. In some embodiments, $X_{15}$ comprises A. In some embodiments, $X_{16}$ comprises a polar amino acid. In some embodiments, $X_{16}$ comprises S. In some embodiments, $X_{17}$ comprises a polar amino acid. In some embodiments, $X_{17}$ comprises a small amino acid. In some embodiments, the first coil comprises an amino acid sequence having at least 75% sequence identity to any one of SEQ ID NOs: 10-14. In some embodiments, $X_{17}$ comprises T. In some embodiments, the first coil comprises an amino acid sequence having at least 76%, at least 84%, at least 92%, or more, sequence identity to any one of SEQ ID NOs: 10-14. In some embodiments, the first coil comprises an amino acid sequence of any one of SEQ ID NOS: 10-14 or an amino acid sequence that differs from any one of SEQ ID NOs: 10-14 by 1 amino acid residue, 2 amino acid residues, or 3 amino acid residues. In some embodiments, the first coil comprises an amino acid sequence of any one of SEQ ID NOs: 10-14.

In some embodiments, the second coil comprises between 7-11 amino acids. In some embodiments, the second coil comprises 9 amino acids. In some embodiments, the second coil comprises residues $X_{18}$-$X_{26}$. In some embodiments, $X_{18}$ comprises Q. In some embodiments, X 19 comprises R. In some embodiments, $X_{20}$ comprises P. In some embodiments, residues $X_{18}$-$X_{20}$ of the second coil comprises a QRP motif (SEQ ID NO: 15). In some embodiments, $X_{21}$ comprises S. In some embodiments, $X_{22}$ comprises R. In some embodiments, $X_{23}$ comprises a polar amino acid. In some embodiments, $X_{23}$ comprises N. In some embodiments, $X_{24}$ comprises a non-polar amino acid. In some embodiments, $X_{24}$ comprises V. In some embodiments, $X_{25}$ comprises a polar amino acid. In some embodiments, $X_{25}$ comprises N. In some embodiments, $X_{26}$ comprises a polar amino acid. In some embodiments, $X_{26}$ comprises N. In some embodiments, the second coil comprises an amino acid sequence having at least 75% sequence identity to SEQ ID NO: 16. In some embodiments, the second coil comprises an amino acid sequence having at least 77%, at least 88%, or more, sequence identity to SEQ ID NO: 16. In some embodiments, the second coil comprises an amino acid sequence of SEQ ID NO: 16 or an amino acid sequence that differs from SEQ ID NO: 16 by 1 or 2 amino acid residues. In some embodiments, the second coil comprises an amino acid sequence of SEQ ID NO: 16.

In some embodiments, the second turn comprises between 3-7 amino acids. In some embodiments, the second turn comprises 5 amino acids. In some embodiments, the second turn comprises residues $X_{27}$-$X_{30}$. In some embodiments, $X_{27}$ comprises a non-polar amino acid. In some embodiments, $X_{27}$ comprises F. In some embodiments, $X_{28}$ comprises P. In some embodiments, $X_{29}$ comprises Y, Q, or L. In some embodiments, $X_{29}$ comprises Y. In some embodiments, $X_{30}$ comprises a polar amino acid. In some embodiments, $X_{30}$ comprises a small amino acid. In some embodiments, $X_{30}$ comprises S, K, or G. In some embodiments, $X_{30}$ comprises S. In some embodiments, the second turn further comprises residue $X_{31}$. In some embodiments, $X_{31}$ comprises G. In some embodiments, the second turn comprises an amino acid sequence having at least 80% sequence identity to any one of SEQ ID NOs: 17-21. In some embodiments, the second turn comprises an amino acid sequence of any one of SEQ ID NOs: 17-21 or an amino acid sequence that differs from any one of SEQ ID NOs: 17-21 by 1 amino acid residue. In some embodiments, the second turn comprises an amino acid sequence of any one of SEQ ID NOs: 17-21.

In some embodiments, (a) the first turn comprises an amino acid sequence having at least 75% sequence identity to SEQ ID NO: 9; (b) the first coil comprises an amino acid sequence having at least 76%, at least 84%, at least 92%, or more sequence identity to any one of SEQ ID NOs: 10-14; (c) the second coil comprises an amino acid sequence having at least 77%, at least 88%, or more sequence identity to SEQ ID NO: 16; and (d) the second turn comprises an amino acid sequence having at least 80% sequence identity to any one of SEQ ID NOs: 17-21. In some embodiments, (a) the first turn comprises an amino acid sequence having at least 75% sequence identity to SEQ ID NO: 9; (b) the first coil comprises an amino acid sequence having at least 75% sequence identity to any one of SEQ ID NOs: 10-14; (c) the second coil comprises an amino acid sequence having at least 75% sequence identity to SEQ ID NO: 16; and (d) the second turn comprises an amino acid sequence having at least 80% sequence identity to any one of SEQ ID NOs: 17-21. In some embodiments. (a) the first turn comprises an amino acid sequence of SEQ ID NO: 9) or an amino acid sequence that differs from SEQ ID NO: 9 by 1 amino acid residue; (b) the first coil comprises an amino acid sequence of any one of SEQ ID NOs: 10-14 or an amino acid sequence that differs from any one of SEQ ID NOs: 10-14 by 1 amino acid residue. 2 amino acid residues, or 3 amino acid residues; (c) the second coil comprises an amino acid sequence of SEQ ID NO: 16 or an amino acid sequence that differs from SEQ ID NO: 16 by 1 or 2 amino acid residues; and (d) the second turn comprises an amino acid sequence of any one of SEQ ID NOS: 17-21 or an amino acid sequence that differs from any one of SEQ ID NOs: 17-21 by 1 amino acid residues. In some embodiments. (a) the first turn comprises an amino acid sequence of SEQ ID NO: 9; (b) the first coil comprises an amino acid sequence of any one of SEQ ID NOs: 10-14; (c) the second coil comprises an amino acid sequence of SEQ ID NO: 16; and (d) the second turn comprises an amino acid sequence of any one of SEQ ID NOs: 17-21.

In some embodiments, the polypeptide linker comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to any one of SEQ ID NOs: 4-8. In some embodiments, the polypeptide linker comprises an amino acid sequence of any one of SEQ ID NOs: 4-8 or an amino acid sequence that differs from any one of SEQ ID NOs: 4-8 by 1 amino acid residue. 2 amino acid residues. 3 amino acid residues. 4 amino acid residues. 5 amino acid residues, or 6 amino acid residues. In some embodiments, the polypeptide linker comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to SEQ ID NO: 4. In some embodiments, the polypeptide linker comprises an amino acid sequence of SEQ ID NO: 4 or an amino acid sequence that differs from SEQ ID NO: 4 by 1 amino acid residue, 2 amino acid residues, 3 amino acid residues, 4 amino acid residues, 5 amino acid residues, or 6 amino acid residues. In some embodiments, the polypeptide linker comprises an amino acid sequence of any one of SEQ ID NOs: 4-8. In some embodiments, the polypeptide linker comprises an amino acid sequence of SEQ ID NO: 4.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 6-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 4-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 3-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 1. In some embodiments, the first subunit comprises a residue other than M at a position corresponding to position 1 of SEQ ID NO: 1. In some embodiments, the first subunit comprises an A residue at a position corresponding to position 1 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 1. In some embodiments, the first subunit comprises a Y at a position corresponding to position 37 of SEQ ID NO: 1. In some embodiments, the first subunit comprises an A at a position corresponding to position 96 of SEQ ID NO: 1. In some embodiments, the first subunit comprises an A at a position corresponding to position 99 of SEQ ID NO: 1. In some embodiments, the first subunit comprises a D at a position corresponding to position 100 of SEQ ID NO: 1. In some embodiments, the first subunit comprises an A at a position corresponding to position 99 of SEQ ID NO: 1 and a D at a position corresponding to position 100 of SEQ ID NO: 1. In some embodiments, the first subunit comprises an A at a position corresponding to position 96 of SEQ ID NO: 1, an A at a position corresponding to position 99 of SEQ ID NO: 1, and a D at a position corresponding to position 100 of SEQ ID NO: 1. In some embodiments, the first subunit comprises a Y at a position corresponding to position 37 of SEQ ID NO: 1 and an A at a position corresponding to position 96 of SEQ ID NO: 1. In some embodiments, the first subunit comprises a Y at a position corresponding to position 37 of SEQ ID NO: 1, an A at a position corresponding to position 99 of SEQ ID NO: 1, and a D at a position corresponding to position 100 of SEQ ID NO: 1. In some embodiments, the first subunit comprises a Y at a position corresponding to position 37 of SEQ ID NO: 1, an A at a position corresponding to position 96 of SEQ ID NO: 1, an A at a position corresponding to position 99 of SEQ ID NO: 1, and a D at a position corresponding to position 100 of SEQ ID NO: 1. In some embodiments, the first subunit comprises a specificity-altering amino acid modification at one or more positions corresponding to positions 24, 26, 28, 30, 32, 33, 38, 40, 42, 44, 46, 66, 68, 70, 76, 77, 79, or 139 of SEQ ID NO: 1. In some embodiments, the first subunit comprises a specificity-altering amino acid modification at one or more positions corresponding to positions 71, 72, 73, or 74 of SEQ ID NO: 1. In some embodiments, the first subunit comprises a DNA binding affinity-altering modification at one or more positions corresponding to positions 29, 34, 48, 51, 64, 80, 81, 82, 112, 116, 137, 139, or 143 of SEQ ID NO: 1. In some embodiments, the first subunit comprises a cleavage activity-altering modification at one or more positions corresponding to positions 19, 48, and 50 of SEQ ID NO: 1.

In some embodiments, the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 1. In some embodiments, the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1. In some embodiments, the second subunit comprises an F at a position corresponding to position 53 of SEQ ID NO: 1. In some embodiments, the second subunit comprises a Y at a position corresponding to position 57 of SEQ ID NO: 1. In some embodiments, the second subunit comprises a T at a position corresponding to position 61 of SEQ ID NO: 1. In some embodiments, the second subunit comprises a Y at a position corresponding to position 57 of SEQ ID NO: 1 and a T at a position corresponding to position 61 of SEQ ID NO: 1. In some embodiments, the second subunit comprises an F at a position corresponding to position 53 of SEQ ID NO: 1, a Y at a position corresponding to position 57 of SEQ ID NO: 1, and a T at a position corresponding to position 61 of SEQ ID NO: 1. In some embodiments, the second subunit comprises a specificity-altering amino acid modification at one or more positions corresponding to positions 24, 26, 28, 30, 32, 33, 38, 40, 42, 44, 46, 66, 68, 70, 76, 77, 79, or 139 of SEQ ID NO: 1. In some embodiments, the second subunit comprises a specificity-altering amino acid modification at one or more positions corresponding to positions 71, 72, 73, or 74 of SEQ ID NO: 1. In some embodiments, the second subunit comprises a DNA binding affinity-altering modification at one or more positions corresponding to positions 29, 34, 48, 51, 64, 80, 81, 82, 112, 116, 137, 139, or 143 of SEQ ID NO: 1. In some embodiments, the second subunit comprises a cleavage activity-altering modification at one or more positions corresponding to positions 19, 48, and 50 of SEQ ID NO: 1.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 1, wherein the first subunit comprises an A at a position corresponding to position 96 of SEQ ID NO: 1, an A at a position corresponding to position 99 of SEQ ID NO: 1, and a D at a position corresponding to position 100 of SEQ ID NO: 1, and the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1, wherein the second subunit comprises a Y at a position corresponding to position 57 of SEQ ID NO: 1 and a T at a position corresponding to position 61 of SEQ ID NO: 1. In one embodiment, the polypeptide linker comprises the sequence of SEQ ID NO: 4.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 1, wherein the first subunit comprises an A at a position corresponding to position 96 of SEQ ID NO: 1, an A at a position corresponding to position 99 of SEQ ID NO: 1, and a D at a position corresponding to position 100 of SEQ ID NO: 1, and the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1, wherein the second subunit comprises a Y at a position corresponding to position 57 of SEQ ID NO: 1 and a T at a position corresponding to position 61 of SEQ ID NO: 1. In one embodiment, the polypeptide linker comprises the sequence of SEQ ID NO: 4.

In some embodiments, the N-terminus of the polypeptide linker is covalently bound to the first subunit at a residue corresponding to any one of positions 153-163 of SEQ ID NO: 1. In some embodiments, the N-terminus of the polypeptide linker is covalently bound to the first subunit at a D residue corresponding to position 153 of SEQ ID NO: 1. In some embodiments, the C-terminus of the polypeptide linker is covalently bound to the second subunit at a residue corresponding to any one of positions 1-9 of SEQ ID NO: 1. In some embodiments, the C-terminus of the polypeptide linker is covalently bound to the second subunit at a Y residue corresponding to position 5 of SEQ ID NO: 1.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to any one of SEQ ID NOs: 22-26.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to SEQ ID NO: 22, wherein the polypeptide linker comprises SEQ ID NO: 4, wherein the N-terminus of the polypeptide linker is covalently bound to the first subunit at a D residue at position 153 of SEQ ID NO: 22, and wherein the C-terminus of the polypeptide linker is covalently bound to the second subunit at a Y residue at position 185 of SEQ ID NO: 22.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to SEQ ID NO: 22, wherein the polypeptide linker comprises SEQ ID NO: 4, wherein the N-terminus of the polypeptide linker is covalently bound to the first subunit at a D residue at a position corresponding to position 153 of SEQ ID NO: 22, wherein the C-terminus of the polypeptide linker is covalently bound to the second subunit at a Y residue at a position corresponding to position 185 of SEQ ID NO: 22, wherein the first subunit comprises an A at position 96, an A at position 99, and a D at position 100, and wherein the second subunit comprises a Y at position 237 and a T at position 241, or positions corresponding to the identified positions when aligned for maximum identity across the subunit as described herein.

In some embodiments, the engineered meganuclease comprises a targeting signal. In some embodiments, the targeting signal is attached to the N-terminus of the first subunit. In some embodiments, the targeting signal is attached to the C-terminus of the second subunit. In some embodiments, the targeting signal comprises a nuclear localization sequence (NLS). In some embodiments, the targeting signal comprises a mitochondrial targeting sequence (MTS). In some embodiments, the targeting signal comprises a chloroplast targeting sequence (CTS). In some embodiments, a first targeting signal is attached to the N-terminus of the first subunit and a second targeting signal is attached to the C-terminus of the second subunit. In some embodiments, the first targeting signal and the second targeting signal are not identical. In some embodiments, the first targeting signal and the second targeting signal are an NLS.

In some embodiments, the first targeting signal and the second targeting signal are an MTS.

In some embodiments, the engineered meganuclease comprises (i) an inactivating amino acid in the first subunit that reduces or abolishes cleavage activity: (ii) an inactivating amino acid in the second subunit that reduces or abolishes cleavage activity; or (iii) an inactivating amino acid in the first subunit that reduces or abolishes cleavage activity and an inactivating amino acid in the second subunit that reduces or abolishes cleavage activity. In some embodiments, the inactivating amino acid is an A at a position corresponding to position 20 of SEQ ID NO: 1. In some embodiments, the inactivating amino acid is an E at a position corresponding to position 47 of SEQ ID NO: 1. In some embodiments, the first subunit and the second subunit each comprise an E at a position corresponding to position 47 of SEQ ID NO: 1, wherein the engineered meganuclease does not comprise cleavage activity. In some embodiments, the first subunit, the second subunit, or both of the first subunit and the second subunit, comprises an A at a position corresponding to position 20 of SEQ ID NO: 1, wherein the engineered meganuclease does not comprise cleavage activity. In some embodiments, the first subunit comprises an E at a position corresponding to position 47 of SEQ ID NO: 1 and the second subunit does not comprise the inactivating amino acid, wherein the engineered meganuclease is a nickase that is only capable of cleaving the antisense strand of a dsDNA target site. In some embodiments, the second subunit comprises an E at a position corresponding to position 47 of SEQ ID NO: 1 the first subunit does not comprise the inactivating amino acid, wherein the engineered meganuclease is a nickase that is only capable of cleaving the sense strand of a dsDNA target site.

In another aspect, the disclosure provides an engineered meganuclease described herein for use as a medicament.

In another aspect, the disclosure provides a polynucleotide comprising a nucleic acid sequence encoding an engineered meganuclease described herein.

In some embodiments, the polynucleotide is an mRNA.

In another aspect, the disclosure provides a polynucleotide comprising a nucleic acid sequence encoding an engineered meganuclease described herein for use as a medicament.

In another aspect, the disclosure provides a recombinant DNA construct comprising a polynucleotide described herein (i.e., comprising a nucleic acid sequence encoding an engineered meganuclease described herein).

In some embodiments, the recombinant DNA construct is a plasmid DNA.

In some embodiments, the recombinant DNA construct encodes a recombinant virus comprising the polynucleotide. In some embodiments, the recombinant virus is a recombinant adenovirus, a recombinant lentivirus, a recombinant retrovirus, or a recombinant adeno-associated virus (AAV). In some embodiments, the recombinant virus is a recombinant AAV.

In another aspect, the disclosure provides a recombinant DNA construct comprising a polynucleotide described herein (i.e., comprising a nucleic acid sequence encoding an engineered meganuclease described herein) for use as a medicament.

In another aspect, the disclosure provides a recombinant virus comprising a polynucleotide described herein (i.e., comprising a nucleic acid sequence encoding an engineered meganuclease described herein).

In some embodiments, the recombinant virus is a recombinant adenovirus, a recombinant lentivirus, a recombinant retrovirus, or a recombinant AAV. In some embodiments, the recombinant virus is a recombinant AAV.

In another aspect, the disclosure provides a recombinant virus comprising a polynucleotide described herein (i.e., comprising a nucleic acid sequence encoding an engineered meganuclease described herein) for use as a medicament.

In another aspect, the disclosure provides a lipid nanoparticle composition comprising lipid nanoparticles comprising a polynucleotide described herein (i.e., comprising a nucleic acid sequence encoding an engineered meganuclease described herein). In some embodiments, the polynucleotide is an mRNA.

In another aspect, the disclosure provides a lipid nanoparticle composition comprising lipid nanoparticles comprising an engineered meganuclease described herein.

In another aspect, the disclosure provides a lipid nanoparticle composition described herein for use as a medicament.

In another aspect, the disclosure provides a pharmaceutical composition comprising a pharmaceutically acceptable carrier and an engineered meganuclease described herein.

In another aspect, the disclosure provides a pharmaceutical composition comprising a pharmaceutically acceptable carrier and a polynucleotide described herein (i.e., comprising a nucleic acid sequence encoding an engineered meganuclease described herein).

In another aspect, the disclosure provides a pharmaceutical composition comprising a pharmaceutically acceptable carrier and a recombinant DNA construct described herein (i.e., comprising a polynucleotide comprising a nucleic acid sequence encoding an engineered meganuclease described herein).

In another aspect, the disclosure provides a pharmaceutical composition comprising a pharmaceutically acceptable carrier and a recombinant virus described herein (i.e., comprising a polynucleotide comprising a nucleic acid sequence encoding an engineered meganuclease described herein).

In another aspect, the disclosure provides a pharmaceutical composition comprising a pharmaceutically acceptable carrier and a lipid nanoparticle composition described herein.

In another aspect, the disclosure provides a pharmaceutical composition described herein for use as a medicament.

In another aspect, the disclosure provides a host cell comprising a polynucleotide described herein (i.e., comprising a nucleic acid sequence encoding an engineered meganuclease described herein).

In another aspect, the disclosure provides a method for producing a genetically-modified cell by modifying a target site in a chromosome, the method comprising introducing into a cell; (a) a polynucleotide comprising a nucleic acid sequence encoding an engineered meganuclease described herein, wherein the engineered meganuclease is expressed in the cell; or (b) an engineered meganuclease described herein: wherein the engineered meganuclease binds to a recognition sequence in the target site and produces a cleavage site, and wherein the target site is modified by introduction of an insertion or deletion (indel) at the cleavage site by non-homologous end-joining (NHEJ).

In some embodiments, the target site is a gene of interest, and expression of the gene of interest is disrupted. In some embodiments, the disrupted gene of interest does not encode a full-length and/or functional wild-type polypeptide.

In some embodiments, the cell is a eukaryotic cell. In some embodiments, the eukaryotic cell is a human cell. In some embodiments, the eukaryotic cell is a plant cell.

In some embodiments, the polynucleotide is an mRNA described herein (i.e., comprising a nucleic acid sequence encoding an engineered meganuclease described herein). In some embodiments, the mRNA is comprised by a lipid nanoparticle that is contacted with the cell.

In some embodiments, the polynucleotide is comprised by a recombinant virus and is introduced into the cell by the recombinant virus. In some embodiments, the recombinant virus is a recombinant virus described herein (i.e., comprising a polynucleotide comprising a nucleic acid sequence encoding an engineered meganuclease described herein).

In some embodiments, the method is performed ex vivo.

In some embodiments, the method is performed in vivo.

In some embodiments, the cell is a target cell in a subject, and wherein the polynucleotide or the engineered meganuclease is delivered to the target cell in the subject.

In some embodiments, the method comprises administering a therapeutically-effective amount of the polynucleotide or the engineered meganuclease to the subject, wherein the method is a method of treatment for a disease.

In another aspect, the disclosure provides a method for cleaving a double-stranded DNA (dsDNA) target site in a cell, the method comprising introducing into the cell; (a) a polynucleotide comprising a nucleic acid sequence encoding an engineered meganuclease described herein, wherein the engineered meganuclease is expressed in the cell; or (b) an engineered meganuclease described herein: wherein the engineered meganuclease binds to a recognition sequence in the dsDNA target site and produces a cleavage site.

In some embodiments, the dsDNA target site is comprised by a mitochondrial DNA (mtDNA). In some embodiments, the mtDNA is degraded following production of the cleavage site.

In some embodiments, the dsDNA target site is comprised by an episome. In some embodiments, the episome is a viral episome. In some embodiments, the episome is degraded following production of the cleavage site. In some embodiments, the dsDNA target site is comprised by a gene of interest. In some embodiments, the gene of interest is disrupted by introduction of an indel at the cleavage site by NHEJ. In some embodiments, the disrupted gene of interest does not encode a full-length and/or functional wild-type polypeptide.

In some embodiments, the cell is a eukaryotic cell. In some embodiments, the eukaryotic cell is a human cell. In some embodiments, the eukaryotic cell is a plant cell.

In some embodiments, the polynucleotide is an mRNA described herein (i.e., comprising a nucleic acid sequence encoding an engineered meganuclease described herein). In some embodiments, the mRNA is comprised by a lipid nanoparticle that is contacted with the cell.

In some embodiments, the polynucleotide is comprised by a recombinant virus described herein (i.e., comprising a polynucleotide comprising a nucleic acid sequence encoding an engineered meganuclease described herein) and is introduced into the cell by the recombinant virus. In some embodiments, the recombinant virus is a recombinant virus described herein (i.e., comprising a polynucleotide comprising a nucleic acid sequence encoding an engineered meganuclease described herein).

In some embodiments, the method is performed ex vivo.

In some embodiments, the method is performed in vivo.

In some embodiments, the cell is a target cell in a subject, and wherein the polynucleotide or the engineered meganuclease is delivered to the target cell in the subject.

In some embodiments, the method comprises administering a therapeutically-effective amount of the polynucleotide or the engineered meganuclease to the subject, wherein the method is a method of treatment for a disease.

In another aspect, the disclosure provides a method for binding a dsDNA target site in a cell, the method comprising introducing into the cell; (a) a polynucleotide comprising a nucleic acid sequence encoding an engineered meganuclease described herein, wherein the engineered meganuclease is expressed in the cell; or (b) an engineered meganuclease described herein; wherein the engineered meganuclease binds to a recognition sequence in the dsDNA target site, and wherein the engineered meganuclease comprises (i) an inactivating amino acid in the first subunit that reduces or abolishes cleavage activity; (ii) an inactivating amino acid in the second subunit that reduces or abolishes cleavage activity; or (iii) an inactivating amino acid in the first subunit that reduces or abolishes cleavage activity and an inactivating amino acid in the second subunit that reduces or abolishes cleavage activity.

In some embodiments, the inactivating amino acid is an A at a position corresponding to position 20 of SEQ ID NO: 1. In some embodiments, the inactivating amino acid is an E at a position corresponding to position 47 of SEQ ID NO: 1.

In some embodiments, the first subunit and the second subunit each comprise an E at a position corresponding to position 47 of SEQ ID NO: 1, wherein the engineered meganuclease does not comprise cleavage activity.

In some embodiments, the first subunit, the second subunit, or both of the first subunit and the second subunit, comprises an A at a position corresponding to position 20 of SEQ ID NO: 1, wherein the engineered meganuclease does not comprise cleavage activity.

In some embodiments, the first subunit comprises an E at a position corresponding to position 47 of SEQ ID NO: 1 and the second subunit does not comprise the inactivating amino acid, wherein the engineered meganuclease is a nickase that is only capable of cleaving the antisense strand of a dsDNA target site.

In some embodiments, the second subunit comprises an E at a position corresponding to position 47 of SEQ ID NO: 1 the first subunit does not comprise the inactivating amino acid, wherein the engineered meganuclease is a nickase that is only capable of cleaving the sense strand of a dsDNA target site.

In some embodiments, the dsDNA target site is comprised by a chromosome.

In some embodiments, the dsDNA target site is comprised by mtDNA.

In some embodiments, the dsDNA target site is comprised by an episome. In some embodiments, the episome is a viral episome.

In some embodiments, the cell is a eukaryotic cell. In some embodiments, the eukaryotic cell is a human cell. In some embodiments, the eukaryotic cell is a plant cell.

In some embodiments, the polynucleotide is an mRNA described herein (i.e., comprising a nucleic acid sequence encoding an engineered meganuclease described herein). In some embodiments, the mRNA is comprised by a lipid nanoparticle that is contacted with the cell.

In some embodiments, the polynucleotide is comprised by a recombinant virus and is introduced into the cell by the recombinant virus. In some embodiments, the recombinant virus is a recombinant virus described herein (i.e., comprising a polynucleotide comprising a nucleic acid sequence encoding an engineered meganuclease described herein).

In some embodiments, the method is performed ex vivo.

In some embodiments, the method is performed in vivo.

In some embodiments, the cell is a target cell in a subject, and wherein the polynucleotide or the engineered meganuclease is delivered to the target cell in the subject.

In some embodiments, the method comprises administering a therapeutically-effective amount of the polynucleotide or the engineered meganuclease to the subject, wherein the method is a method of treatment for a disease.

In another aspect, the disclosure provides a method for producing a genetically-modified cell by modifying a target site in a chromosome, the method comprising introducing into a cell; (a) a first polynucleotide comprising a nucleic acid sequence encoding an engineered meganuclease described herein, wherein the engineered meganuclease is expressed in the cell, or an engineered meganuclease described herein; and (b) a second polynucleotide comprising a sequence of interest; wherein the engineered meganuclease binds to a recognition sequence in the target site and produces a cleavage site, and wherein the sequence of interest is inserted into the chromosome at the cleavage site.

In some embodiments, the second polynucleotide further comprises sequences homologous to sequences flanking the cleavage site and the sequence of interest is inserted at the cleavage site by homologous recombination.

In some embodiments, the target site is a gene of interest, and expression of the gene of interest is disrupted. In some embodiments, the disrupted gene of interest does not encode a full-length and/or functional wild-type polypeptide.

In some embodiments, the second polynucleotide comprises an exogenous promoter operably linked to the sequence of interest.

In some embodiments, the sequence of interest is operably linked to an endogenous promoter following insertion at the cleavage site.

In some embodiments, the cell is a eukaryotic cell. In some embodiments, the eukaryotic cell is a human cell. In some embodiments, the eukaryotic cell is a plant cell.

In some embodiments, the first polynucleotide is an mRNA described herein (i.e., comprising a nucleic acid sequence encoding an engineered meganuclease described herein). In some embodiments, the mRNA is comprised by a lipid nanoparticle that is contacted with the cell.

In some embodiments, the first polynucleotide is comprised by a recombinant virus and introduced into the cell by the recombinant virus. In some embodiments, the recombinant virus is a recombinant virus described herein (i.e., comprising a polynucleotide comprising a nucleic acid sequence encoding an engineered meganuclease described herein). In some embodiments, the recombinant virus is a recombinant AAV.

In some embodiments, the second polynucleotide is comprised by a recombinant virus and is introduced into the cell by the recombinant virus. In some embodiments, the recombinant virus is a recombinant AAV.

In some embodiments, the first polynucleotide is an mRNA comprised by a lipid nanoparticle that is contacted with the cell, and the second polynucleotide is comprised by a recombinant virus (e.g., a recombinant AAV) and is introduced into the cell by the recombinant virus.

In some embodiments, the first polynucleotide is comprised by a first recombinant virus (e.g., a recombinant AAV) and is introduced into the cell by the first recombinant virus, and the second polynucleotide is comprised by a second recombinant virus (e.g., a recombinant AAV) and is introduced into the cell by the second recombinant virus.

In some embodiments, the sequence of interest encodes a therapeutic protein or a fragment of a therapeutic protein.

In some embodiments, the method is performed ex vivo.

In some embodiments, the method is performed in vivo.

In some embodiments, the cell is a target cell in a subject, and wherein the polynucleotide or the engineered meganuclease, and the second polynucleotide comprising the sequence of interest, is delivered to the target cell in the subject.

In some embodiments, the method comprises administering a therapeutically-effective amount of the polynucleotide or the engineered meganuclease, and a therapeutically-effective amount of the second polynucleotide comprising the sequence of interest, to the subject, and wherein the method is a method of treatment for a disease.

In another aspect, the disclosure provides a polypeptide comprising any polypeptide linker described herein (i.e., any one of SEQ ID NOs: 4-8, and variants thereof described herein).

In another aspect, the disclosure provides a polynucleotide comprising a nucleic acid sequence encoding any polypeptide linker described herein (i.e., any one of SEQ ID NOs: 4-8, and variants thereof described herein).

BRIEF DESCRIPTION OF THE FIGURES

FIG. 1. Alignment of the polypeptide linkers Linker1923 (SEQ ID NO: 4), Linker1766 (SEQ ID NO: 5), Linker1771 (SEQ ID NO: 6), Linker 1808 (SEQ ID NO: 7), Linker 1814 (SEQ ID NO: 8), and Linker1 (SEQ ID NO: 27). FIG. 1A shows an alignment of the polypeptide linkers Linker1923, Linker1766, Linker1771, Linker1808, and Linker 1814 compared to one another. FIG. 1B shows an alignment of the polypeptide linkers Linker1923, Linker1766, Linker1771, Linker1808, and Linker 1814 compared to Linker1.

FIG. 5. Results from a CHO reporter cell assay of 92 clones from the first library of linkers (i.e., Flinkers) in the HBV 11-12L.520 engineered meganuclease scaffold.

FIG. 6. Results from a CHO reporter cell assay of 92 clones from the second library of linkers (i.e., Wlinkers) in the HBV 11-12L.520 engineered meganuclease scaffold.

FIG. 17A-FIG. 17B. Provides a bar graph that shows indel formation by HBV 11-12L.1090QQ Linker1923(1/2) and HBV 11-12L.1090QQ Linker1 engineered meganucleases in HepG2-sAg cells at 2 days (FIG. 17A) and at 6 days (FIG. 17B).

FIG. 19A, FIG. 19C, and FIG. 19E provide the percentage of indels in HepG2-sAg cells transfected with Ing. 10 ng, or 100 ng of RNA of each of the indicated meganucleases, respectively. FIG. 19B, FIG. 19D, and FIG. 19F provide the percentage HBsAg inhibition in HepG2-sAg Cells transfected with Ing. 10 ng, or 100 ng of RNA of each of the indicated meganucleases, respectively.

BRIEF DESCRIPTION OF THE SEQUENCES

Figure 2:
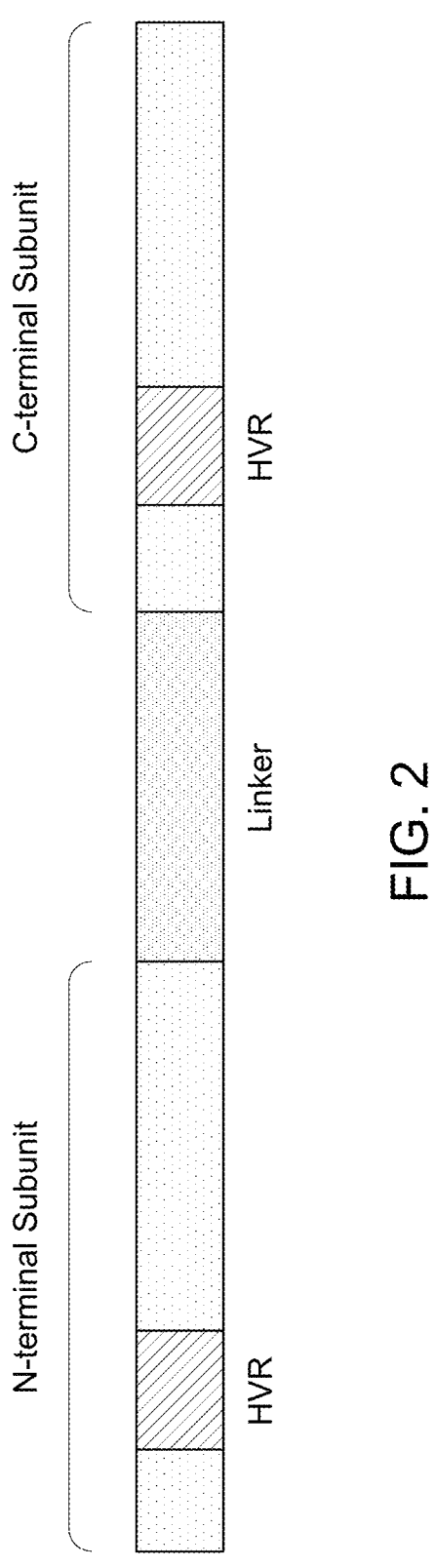
FIG. 2. The engineered meganucleases of the present disclosure comprise two subunits, wherein the first subunit comprising a first hypervariable region (HVR) region binds to a first recognition half-site and the second subunit comprising a second HVR region binds to a second recognition half-site.
Figure 3:
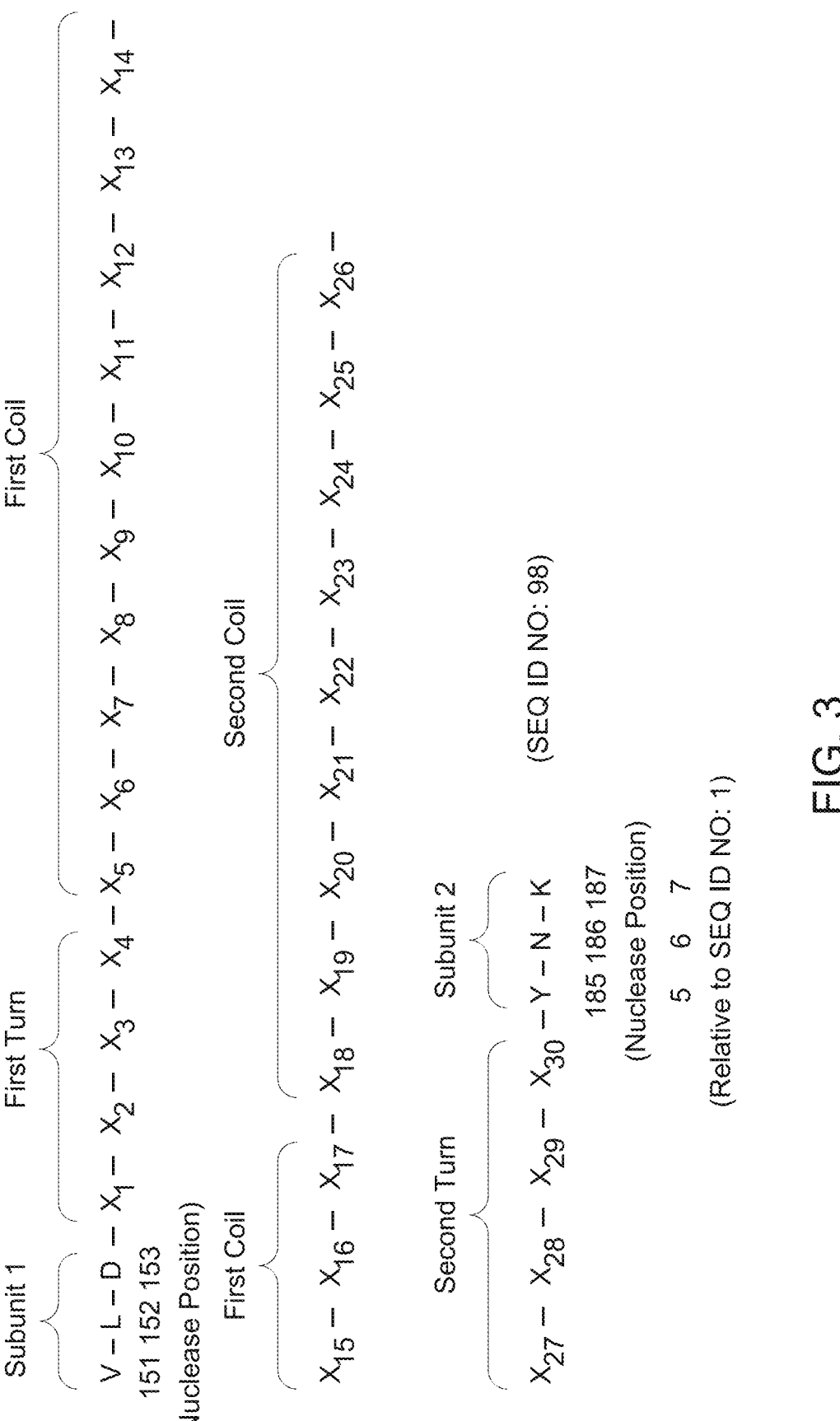
FIG. 3. A depiction of a portion of an engineered meganuclease of the disclosure comprising amino acid residues V, L, and D at positions 151, 152, and 153, respectively, of the first subunit, followed by a linker comprising $X_1$-$X_{30}$, wherein the linker comprises a first turn comprising amino acid residues $X_1$-$X_4$, a first coil comprising amino acid residues $X_5$-$X_{17}$, a second coil comprising amino acid residues $X_{18}$-$X_{26}$, a second turn comprising $X_{27}$-$X_{30}$, and then followed by amino acid residues Y, N, and K of the second subunit at positions 185, 186, and 187 of the nuclease, which correspond to positions 5, 6, and 7 of the wild-type I-CreI meganuclease sequence set forth as SEQ ID NO: 1.
Figure 4:
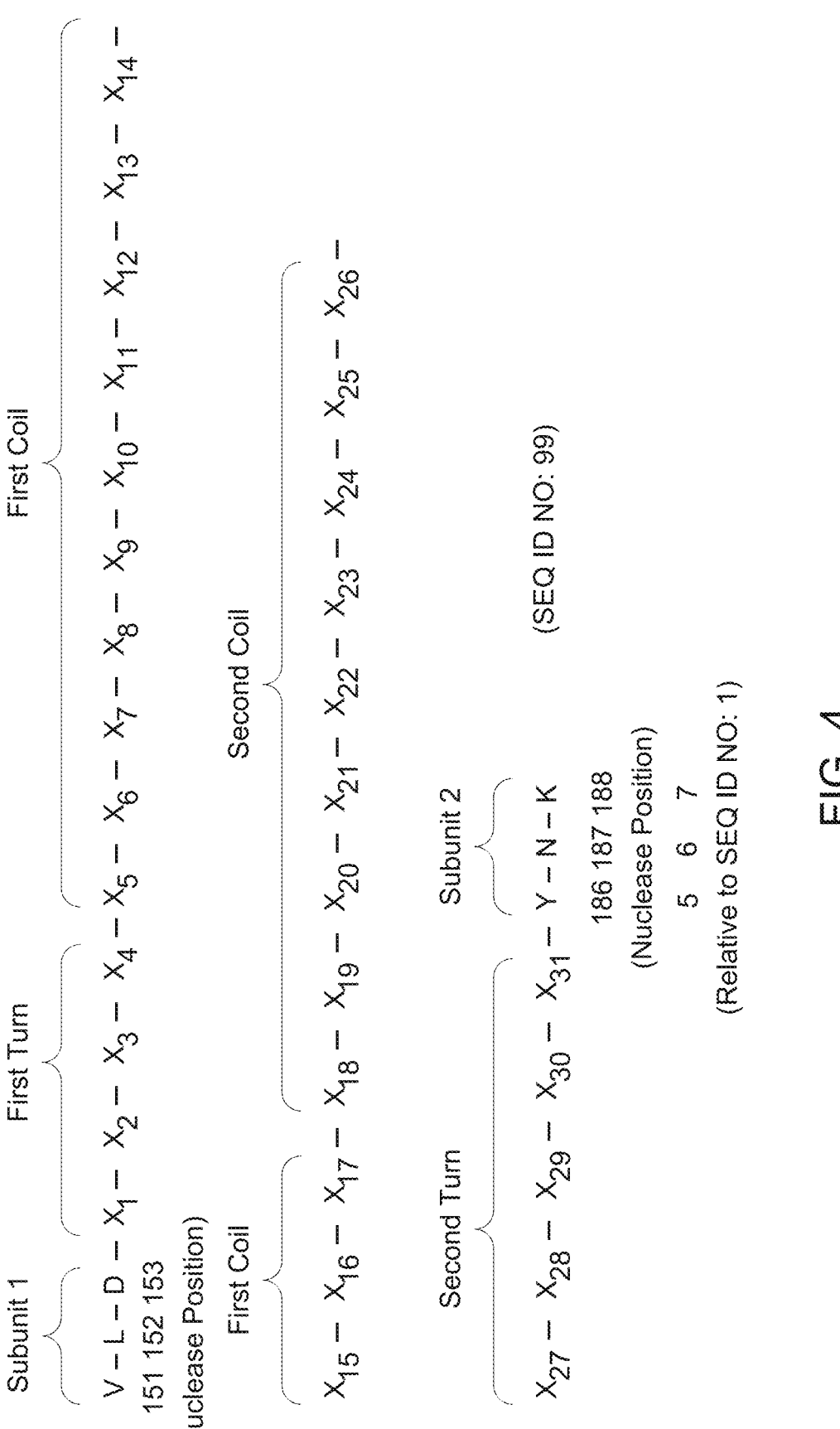
FIG. 4. A depiction of a portion of an engineered meganuclease of the disclosure comprising amino acid residues V, L, and D at positions 151, 152, and 153, respectively, of the first subunit, followed by a linker comprising $X_1$-$X_{31}$, wherein the linker comprises a first turn comprising amino acid residues $X_1$-$X_4$, a first coil comprising amino acid residues $X_5$-$X_{17}$, a second coil comprising amino acid residues $X_{18}$-$X_{26}$, a second turn comprising $X_{27}$-$X_{31}$, and then followed by amino acid residues Y, N, and K of the second subunit at positions 186, 187, and 188 of the nuclease, relative to positions 5, 6, and 7 of the wild-type I-CreI meganuclease set forth as SEQ ID NO: 1.

SEQ ID NO: 1 sets forth the amino acid sequence of the wild-type I-CreI meganuclease from *Chlamydomonas reinhardtii*.

SEQ ID NO: 2 sets forth the amino acid sequence of the LAGLIDADG motif.

SEQ ID NO: 3 sets forth the generic amino acid sequence of the presently disclosed polypeptide linkers.

SEQ ID NO: 4 sets forth the amino acid sequence of Linker1923.

SEQ ID NO: 5 sets forth the amino acid sequence of Linker1766.

SEQ ID NO: 6 sets forth the amino acid sequence of Linker1771.

SEQ ID NO: 7 sets forth the amino acid sequence of Linker1808.

SEQ ID NO: 8 sets forth the amino acid sequence of Linker1814.

SEQ ID NO: 9 sets forth the amino acid sequence of the first turn of the polypeptide linkers disclosed in SEQ ID NOs: 4-8.

SEQ ID NO: 10 sets forth the amino acid sequence of the first coil of Linker1923.

SEQ ID NO: 11 sets forth the amino acid sequence of the first coil of Linker1766.

SEQ ID NO: 12 sets forth the amino acid sequence of the first coil of Linker1771.

SEQ ID NO: 13 sets forth the amino acid sequence of the first coil of Linker1808.

SEQ ID NO: 14 sets forth the amino acid sequence of the first coil of Linker1814.

SEQ ID NO: 15 sets forth the amino acid sequence of a QRP motif.

SEQ ID NO: 16 sets forth the amino acid sequence of the second coil of the polypeptide linkers disclosed in SEQ ID NOs: 4-8.

SEQ ID NO: 17 sets forth the amino acid sequence of the second turn of Linker1923.

SEQ ID NO: 18 sets forth the amino acid sequence of the second turn of Linker1766.

SEQ ID NO: 19 sets forth the amino acid sequence of the second turn of Linker1771.

SEQ ID NO: 20 sets forth the amino acid sequence of the second turn of Linker1808.

SEQ ID NO: 21 sets forth the amino acid sequence of the second turn of Linker1814.

SEQ ID NO: 22 sets forth the amino acid sequence of a Linker1923 reference meganuclease.

SEQ ID NO: 23 sets forth the amino acid sequence of a Linker1766 reference meganuclease.

SEQ ID NO: 24 sets forth the amino acid sequence of a Linker1771 reference meganuclease.

SEQ ID NO: 25 sets forth the amino acid sequence of a Linker1808 reference meganuclease.

SEQ ID NO: 26 sets forth the amino acid sequence of a Linker1814 reference meganuclease.

SEQ ID NO: 27 sets forth the amino acid sequence of Linker1.

SEQ ID NO: 28 sets forth the amino acid sequence of the Flinker parental sequence.

SEQ ID NO: 29 sets forth the amino acid sequence of a Flinker library sequence.

SEQ ID NO: 30 sets forth the amino acid sequence of the Wlinker parental sequence.

SEQ ID NO: 31 sets forth the amino acid sequence of a Wlinker library sequence.

SEQ ID NO: 32 sets forth the amino acid sequence of a Flinker sequence.

SEQ ID NO: 33 sets forth the amino acid sequence of a Flinker library sequence.

SEQ ID NO: 34 sets forth the amino acid sequence of a Flinker sequence.

SEQ ID NO: 35 sets forth the amino acid sequence of a Flinker library sequence.

SEQ ID NO: 36 sets forth the amino acid sequence of a Flinker sequence.

SEQ ID NO: 37 sets forth the amino acid sequence of a Flinker library sequence.

SEQ ID NO: 38 sets forth the amino acid sequence of a Wlinker sequence.

SEQ ID NO: 39 sets forth the amino acid sequence of a Wlinker library sequence.

SEQ ID NO: 40 sets forth the amino acid sequence of a Wlinker sequence.

SEQ ID NO: 41 sets forth the amino acid sequence of a Wlinker library sequence.

SEQ ID NO: 42 sets forth the amino acid sequence of a Flinker library 2.1 sequence.

SEQ ID NO: 43 sets forth the amino acid sequence of a Flinker library 2.1 sequence.

SEQ ID NO: 44 sets forth the amino acid sequence of a Flinker library 2.1 sequence.

SEQ ID NO: 45 sets forth the amino acid sequence of a Flinker library 2.1 sequence.

SEQ ID NO: 46 sets forth the amino acid sequence of a Flinker library 2.1 sequence.

SEQ ID NO: 47 sets forth the amino acid sequence of a Flinker library 2.1 sequence.

SEQ ID NO: 48 sets forth the amino acid sequence of a Flinker library 2.1 sequence.

SEQ ID NO: 49 sets forth the amino acid sequence of a Flinker library 2.1 sequence.

SEQ ID NO: 50 sets forth the amino acid sequence of a Flinker library 2.1 sequence.

SEQ ID NO: 51 sets forth the amino acid sequence of a Wlinker library 2.1 sequence.

SEQ ID NO: 52 sets forth the amino acid sequence of a Wlinker library 2.1 sequence.

SEQ ID NO: 53 sets forth the amino acid sequence of a Wlinker library 2.1 sequence.

SEQ ID NO: 54 sets forth the amino acid sequence of a Flinker C-terminal sequence.

SEQ ID NO: 55 sets forth the amino acid sequence of a Flinker library 2.2 sequence.

SEQ ID NO: 56 sets forth the amino acid sequence of a Flinker library 2.2 sequence.

SEQ ID NO: 57 sets forth the amino acid sequence of a Flinker library 2.2 sequence.

SEQ ID NO: 58 sets forth the amino acid sequence of a Wlinker C-terminal sequence.

SEQ ID NO: 59 sets forth the amino acid sequence of a Wlinker library 2.2 sequence.

SEQ ID NO: 60 sets forth the amino acid sequence of a Wlinker library 2.2 sequence.

SEQ ID NO: 61 sets forth the amino acid sequence of a Wlinker library 2.2 sequence.

SEQ ID NO: 62 sets forth the amino acid sequence of a Wlinker library 2.2 sequence.

SEQ ID NO: 63 sets forth the amino acid sequence of a Wlinker library 2.2 sequence.

SEQ ID NO: 64 sets forth the amino acid sequence of a Wlinker library 2.2 sequence.

SEQ ID NO: 65 sets forth the amino acid sequence of a Wlinker library 2.2 sequence.

SEQ ID NO: 66 sets forth the amino acid sequence of a Wlinker library 2.2 sequence.

SEQ ID NO: 67 sets forth the amino acid sequence of a Wlinker library 2.2 sequence.

SEQ ID NO: 68 sets forth the amino acid sequence of Linker1779.

SEQ ID NO: 69 sets forth the amino acid sequence of Linker1825.

SEQ ID NO: 70 sets forth the amino acid sequence of Linker1976.

SEQ ID NO: 71 sets forth the amino acid sequence of Linker1993.

SEQ ID NO: 72 sets forth the amino acid sequence of Linker2006.

SEQ ID NO: 73 sets forth the amino acid sequence of Linker2048.

SEQ ID NO: 74 sets forth the amino acid sequence of Linker2056.

SEQ ID NO: 75 sets forth the amino acid sequence of Linker2078.

SEQ ID NO: 76 sets forth the amino acid sequence of Linker2094.

SEQ ID NO: 77 sets forth the amino acid sequence of Linker2118.

SEQ ID NO: 78 sets forth the nucleic acid sequence of the HAO 25-26 recognition sequence.

SEQ ID NO: 79 sets forth the amino acid sequence of the HAO 25-26L.908 engineered meganuclease.

SEQ ID NO: 80 sets forth the amino acid sequence of the HAO 25-26L.908 engineered meganuclease with Linker1814 and no subunit modifications.

SEQ ID NO: 81 sets forth the amino acid sequence of the HAO 25-26L.908 engineered meganuclease with Linker1814 and subunit modifications (H37Y, K96A, Q99A, K100D/W53F, K57Y, E61T).

SEQ ID NO: 82 sets forth the amino acid sequence of the HAO 25-26L.908 engineered meganuclease with Linker1766 and no subunit modifications.

SEQ ID NO: 83 sets forth the amino acid sequence of the HAO 25-26L.908 engineered meganuclease with Linker1766 and subunit modifications (H37Y, K96A, Q99A, K100D/W53F, K57Y, E6IT).

SEQ ID NO: 84 sets forth the amino acid sequence of the HAO 25-26L.908 engineered meganuclease with Linker1771 and no subunit modifications.

SEQ ID NO: 85 sets forth the amino acid sequence of the HAO 25-26L.908 engineered meganuclease with Linker1771 and subunit modifications (H37Y, K96A, Q99A, K100D/W53F, K57Y, E61T).

SEQ ID NO: 86 sets forth the amino acid sequence of the HAO 25-26L.908 engineered meganuclease with Linker1808 and no subunit modifications.

SEQ ID NO: 87 sets forth the amino acid sequence of the HAO 25-26L.908 engineered meganuclease with Linker1808 and subunit modifications (H37Y, K96A, Q99A, K100D/W53F, K57Y, E61T).

SEQ ID NO: 88 sets forth the amino acid sequence of the HAO 25-26L.908 engineered meganuclease with Linker1923 and no subunit modifications.

SEQ ID NO: 89 sets forth the amino acid sequence of the HAO 25-26L.908 engineered meganuclease with Linker1923 and subunit modifications (H37Y, K96A, Q99A, K100D/W53F, K57Y, E61T).

SEQ ID NO: 90 sets forth the amino acid sequence of the HAO 25-26L.1434 engineered meganuclease.

SEQ ID NO: 91 sets forth the amino acid sequence of the HBV 27-28L.385 engineered meganuclease.

SEQ ID NO: 92 sets forth the nucleic acid sequence of the HBV 27-28 recognition sequence.

SEQ ID NO: 93 sets forth the amino acid sequence of the HAO 25-26L.1434 engineered meganuclease with Linker1923 and Group 1 (K96A/K57Y, E61T) and Group 2 (Q99A, K100D/none) ("1/2") subunit modifications.

SEQ ID NO: 94 sets forth the amino acid sequence of the HBV 27-28L.385 engineered meganuclease with Linker1923 and Group 1 (K96A/K57Y, E61T) and Group 2 (Q99A, K100D/none) ("1/2") subunit modifications.

SEQ ID NO: 95 sets forth the amino acid sequence of the SV40 nuclear localization signal.

SEQ ID NO: 96 sets forth the amino acid sequence of the HBV 11-12L.520 engineered meganuclease.

SEQ ID NO: 97 sets forth the nucleic acid sequence of the HBV 11-12 recognition sequence.

SEQ ID NO: 98 sets forth the amino acid sequence of a portion of a meganuclease comprising VLD from the C-terminus of the first subunit, a $X_1$-$X_{30}$ linker, and YNK from the N-terminus of the second subunit.

SEQ ID NO: 99 sets forth the amino acid sequence of a portion of a meganuclease comprising VLD from the C-terminus of the first subunit, a $X_1$-$X_{31}$ linker, and YNK from the N-terminus of the second subunit.

SEQ ID NO: 100 sets forth the amino acid sequence of the HBV 11-12L.1090QQ Linker1923(1/2) meganuclease comprising Linker1923 and Group 1 (K96A/K57Y, E61T) and Group 2 (Q99A, K100D/none) subunit modifications.

SEQ ID NO: 101 sets forth the amino acid sequence of the HBV 11-12L.1090QQ Linker1 meganuclease.

SEQ ID NO: 102 sets forth the nucleic acid sequence of a primer.

SEQ ID NO: 103 sets forth the nucleic acid sequence of a primer.

SEQ ID NO: 104 sets forth the nucleic acid sequence of a primer.

SEQ ID NO: 105 sets forth the nucleic acid sequence of a primer.

SEQ ID NO: 106 sets forth the nucleic acid sequence of a primer.

SEQ ID NO: 107 sets forth the nucleic acid sequence of a primer.

SEQ ID NO: 108 sets forth the amino acid sequence of the HBV 11-12L.1090QE Linker1 meganuclease.

SEQ ID NO: 109 sets forth the amino acid sequence of the HBV 11-12L.1090QE Linker1923(1/2) meganuclease comprising Linker1923 and Group 1 (K96A/K57Y, E61T) and Group 2 (Q99A, K100D/none) subunit modifications.

SEQ ID NO: 110 sets forth the nucleic acid sequence of a primer.

SEQ ID NO: 111 sets forth the nucleic acid sequence of a primer.

SEQ ID NO: 112 sets forth the nucleic acid sequence of a primer.

SEQ ID NO: 113 sets forth the nucleic acid sequence of a primer.

SEQ ID NO: 114 sets forth the nucleic acid sequence of a primer.

SEQ ID NO: 115 sets forth the nucleic acid sequence of a primer.

SEQ ID NO: 116 sets forth the amino acid sequence of an HBV 11-12L.1766 linker sequence.

SEQ ID NO: 117 sets forth the amino acid sequence of an HBV 11-12L.1771 linker sequence.

SEQ ID NO: 118 sets forth the amino acid sequence of an HBV 11-12L.1808 linker sequence.

SEQ ID NO: 119 sets forth the amino acid sequence of an HBV 11-12L.1814 linker sequence.

SEQ ID NO: 120 sets forth the amino acid sequence of an HBV 11-12L.1923 linker sequence.

SEQ ID NO: 121 sets forth the amino acid sequence of an HBV 11-12L.1090 engineered meganuclease comprising Linker1923 and no subunit modifications.

SEQ ID NO: 122 sets forth the amino acid sequence of an HBV 11-12L.1090 engineered meganuclease comprising Linker1923 and Group 1 (K96A/K57Y, E61T) subunit modifications.

SEQ ID NO: 123 sets forth the amino acid sequence of an HBV 11-12L.1090 engineered meganuclease comprising Linker1923 and Group 2 (Q99A, K100D/none) subunit modifications.

SEQ ID NO: 124 sets forth the amino acid sequence of an HBV 11-12L.1090 engineered meganuclease comprising Linker1923 and Group 3 (H37Y/W53F) subunit modifications.

SEQ ID NO: 125 sets forth the amino acid sequence of an HBV 11-12L.1090 engineered meganuclease comprising Linker1923 and Group 1 (K96A/K57Y, E61T) and Group 3 (H37Y/W53F) subunit modifications.

SEQ ID NO: 126 sets forth the amino acid sequence of an HBV 11-12L.1090 engineered meganuclease comprising Linker1923 and Group 2 (Q99A, K100D/none) and Group 3 (H37Y/W53F) subunit modifications.

SEQ ID NO: 127 sets forth the amino acid sequence of an HBV 11-12L.1090 engineered meganuclease comprising Linker1923 and Group 1 (K96A/K57Y, E6IT), Group 2 (Q99A, K100D/none), and Group 3 (H37Y/W53F) subunit modifications.

SEQ ID NO: 128 sets forth the amino acid sequence of an HBV 11-12L.1090 engineered meganuclease comprising Linker1766 and no subunit modifications.

SEQ ID NO: 129 sets forth the amino acid sequence of an HBV 11-12L.1090 engineered meganuclease comprising Linker1766 and Group 1 (K96A/K57Y, E6IT) and Group 2 (Q99A, K100D/none) subunit modifications.

SEQ ID NO: 130 sets forth the amino acid sequence of an HBV 11-12L.1090 engineered meganuclease comprising Linker1766 and Group 1 (K96A/K57Y, E6IT), Group 2 (Q99A, K100D/none), and Group 3 (H37Y/W53F) subunit modifications.

SEQ ID NO: 131 sets forth the amino acid sequence of an HBV 11-12L.1090 engineered meganuclease comprising Linker1771 and no subunit modifications.

SEQ ID NO: 132 sets forth the amino acid sequence of an HBV 11-12L.1090 engineered meganuclease comprising Linker1771 and Group 1 (K96A/K57Y, E6IT) and Group 2 (Q99A, K100D/none) subunit modifications.

SEQ ID NO: 133 sets forth the amino acid sequence of an HBV 11-12L.1090 engineered meganuclease comprising Linker1771 and Group 1 (K96A/K57Y, E61T), Group 2 (Q99A, K100D/none), and Group 3 (H37Y/W53F) subunit modifications.

SEQ ID NO: 134 sets forth the amino acid sequence of an HBV 11-12L.1090 engineered meganuclease comprising Linker1808 and no subunit modifications.

SEQ ID NO: 135 sets forth the amino acid sequence of an HBV 11-12L.1090 engineered meganuclease comprising Linker1808 and Group 1 (K96A/K57Y, E61T) and Group 2 (Q99A, K100D/none) subunit modifications.

SEQ ID NO: 136 sets forth the amino acid sequence of an HBV 11-12L.1090 engineered meganuclease comprising Linker1808 and Group 1 (K96A/K57Y, E61T), Group 2 (Q99A, K100D/none), and Group 3 (H37Y/W53F) subunit modifications.

SEQ ID NO: 137 sets forth the amino acid sequence of an HBV 11-12L.1090 engineered meganuclease comprising Linker1814 and no subunit modifications.

SEQ ID NO: 138 sets forth the amino acid sequence of an HBV 11-12L.1090 engineered meganuclease comprising Linker1814 and Group 1 (K96A/K57Y, E6IT) and Group 2 (Q99A, K100D/none) subunit modifications.

SEQ ID NO: 139 sets forth the amino acid sequence of an HBV 11-12L.1090 engineered meganuclease comprising Linker1814 and Group 1 (K96A/K57Y, E6IT), Group 2 (Q99A, K100D/none), and Group 3 (H37Y/W53F) subunit modifications.

SEQ ID NO: 140 sets forth the amino acid sequence of an F8R 1-2x.9 engineered meganuclease.

SEQ ID NO: 141 sets forth the amino acid sequence of an F8R 1-2x.9 engineered meganuclease comprising Linker1923 and no subunit modifications.

SEQ ID NO: 142 sets forth the amino acid sequence of an F8R 1-2x.9 engineered meganuclease comprising Linker1923 and Group 1 (K96A/K57Y, E61T) subunit modifications.

SEQ ID NO: 143 sets forth the amino acid sequence of an F8R 1-2x.9 engineered meganuclease comprising Linker1923 and Group 2 (Q99A, K100D/none) subunit modifications.

SEQ ID NO: 144 sets forth the amino acid sequence of an F8R 1-2x.9 engineered meganuclease comprising Linker1923 and Group 3 (H37Y/W53F) subunit modifications.

SEQ ID NO: 145 sets forth the amino acid sequence of an F8R 1-2x.9 engineered meganuclease comprising Linker1923 and Group 1 (K96A/K57Y, E61T) and Group 2 (Q99A, K100D/none) subunit modifications.

SEQ ID NO: 146 sets forth the amino acid sequence of an F8R 1-2x.9 engineered meganuclease comprising Linker1923 and Group 1 (K96A/K57Y, E61T) and Group 3 (H37Y/W53F) subunit modifications.

SEQ ID NO: 147 sets forth the amino acid sequence of an F8R 1-2x.9 engineered meganuclease comprising Linker1923 and Group 2 (Q99A, K100D/none) and Group 3 (H37Y/W53F) subunit modifications.

SEQ ID NO: 148 sets forth the amino acid sequence of an F8R 1-2x.9 engineered meganuclease comprising Linker1923 and Group 1 (K96A/K57Y, E61T), Group 2 (Q99A, K100D/none), and Group 3 (H37Y/W53F) subunit modifications.

SEQ ID NO: 149 sets forth the amino acid sequence of an F8R 1-2x.9 engineered meganuclease comprising Linker1766 and no subunit modifications.

SEQ ID NO: 150 sets forth the amino acid sequence of an F8R 1-2x.9 engineered meganuclease comprising Linker1766 and Group 1 (K96A/K57Y, E61T) and Group 2 (Q99A, K100D/none) subunit modifications.

SEQ ID NO: 151 sets forth the amino acid sequence of an F8R 1-2x.9 engineered meganuclease comprising Linker1766 and Group 1 (K96A/K57Y, E6IT), Group 2 (Q99A, K100D/none), and Group 3 (H37Y/W53F) subunit modifications.

SEQ ID NO: 152 sets forth the amino acid sequence of an F8R 1-2x.9 engineered meganuclease comprising Linker1771 and no subunit modifications.

SEQ ID NO: 153 sets forth the amino acid sequence of an F8R 1-2x.9 engineered meganuclease comprising Linker1771 and Group 1 (K96A/K57Y, E61T) and Group 2 (Q99A, K100D/none) subunit modifications.

SEQ ID NO: 154 sets forth the amino acid sequence of an F8R 1-2x.9 engineered meganuclease comprising Linker1771 and Group 1 (K96A/K57Y, E6IT), Group 2 (Q99A, K100D/none), and Group 3 (H37Y/W53F) subunit modifications.

SEQ ID NO: 155 sets forth the amino acid sequence of an F8R 1-2x.9 engineered meganuclease comprising Linker1808 and no subunit modifications.

SEQ ID NO: 156 sets forth the amino acid sequence of an F8R 1-2x.9 engineered meganuclease comprising Linker1808 and Group 1 (K96A/K57Y, E6IT) and Group 2 (Q99A, K100D/none) subunit modifications.

SEQ ID NO: 157 sets forth the amino acid sequence of an F8R 1-2x.9 engineered meganuclease comprising Linker1808 and Group 1 (K96A/K57Y, E61T), Group 2 (Q99A, K100D/none), and Group 3 (H37Y/W53F) subunit modifications.

SEQ ID NO: 158 sets forth the amino acid sequence of an F8R 1-2x.9 engineered meganuclease comprising Linker1814 and no subunit modifications.

SEQ ID NO: 159 sets forth the amino acid sequence of an F8R 1-2x.9 engineered meganuclease comprising Linker1814 and Group 1 (K96A/K57Y, E6IT) and Group 2 (Q99A, K100D/none) subunit modifications.

SEQ ID NO: 160 sets forth the amino acid sequence of an F8R 1-2x.9 engineered meganuclease comprising Linker1814 and Group 1 (K96A/K57Y, E6IT), Group 2 (Q99A, K100D/none), and Group 3 (H37Y/W53F) subunit modifications.

SEQ ID NO: 161 sets forth the amino acid sequence of a RHO2-L3-3 engineered meganuclease.

SEQ ID NO: 162 sets forth the amino acid sequence of a RHO2-L3-3 engineered meganuclease comprising Linker1923 and Group 1 (K96A/K57Y, E61T) and Group 2 (Q99A, K100D/none) subunit modifications.

SEQ ID NO: 163 sets forth the amino acid sequence of a Linker1923 reference meganuclease comprising wild-type I-CreI subunits.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present disclosure can be embodied in different forms and should not be construed as limited to the embodiments set forth herein. Rather, these embodiments are provided so that this disclosure will be thorough and complete, and will fully convey the scope of the disclosure to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant disclosure.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

All publications, patent applications, patents, and other references mentioned herein are incorporated by reference herein in their entirety.

As used herein, "a." "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" are used interchangeably to refer to naturally-occurring or engineered enzymes which cleave a phosphodiester bond within a polynucleotide chain.

As used herein, with respect to double-stranded DNA, the terms "cleave" or "cleavage" refer to the endonuclease-mediated hydrolysis of phosphodiester bonds within the backbone of a recognition sequence within a target sequence that results in a break within the target sequence, referred to herein as a "cleavage site". The break can be a double-stranded break or a single-stranded break (as by a nickase). Depending upon the endonuclease, cleavage can result in double-stranded fragments with blunt ends or fragments with 5' or 3' base overhangs.

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI, and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g. WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in the targeted cells as described herein, such that cells can be transfected and maintained at 37° C. without 30) observing substantial deleterious effects on overall cell viability or significant reductions in meganuclease cleavage activity when measured using the methods described herein.

As used herein, the term "single-chain meganuclease" refers to a polypeptide comprising a pair of nuclease subunits joined by a linker such that the subunits interact functionally like a heterodimer to cleave a double-stranded recognition site. A single-chain meganuclease has the organization: N-terminal subunit-Linker-C-terminal subunit. The two meganuclease subunits will generally be non-identical in amino acid sequence and will recognize non-identical DNA half-sites within a recognition sequence. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, an "inactivating amino acid" in relation to an engineered meganuclease refers to an amino acid substitution that renders the engineered meganuclease partially catalytically inactive (if present in only one subunit) or completely catalytically inactive (if present in both subunits). Non-limiting examples of inactivating amino acids include an A at a position corresponding to position 20 of SEQ ID NO: 1 or an E at a position corresponding to position 47 of SEQ ID NO: 1.

As used herein, a "nickase" refers to a nuclease that is capable of cleaving only a single strand of a double-stranded target site. In some embodiments, the nickase is only capable of cleaving a sense strand of a double-stranded target site. In some embodiments, the nickase is only capable of cleaving an antisense strand of a double-stranded target site. In some embodiments, the first or second subunit of an engineered meganuclease that functions as a nickase comprises an E at position corresponding to position 47 of SEQ ID NO: 1.

As used herein, the term "linker" refers to an exogenous peptide sequence used to join two meganuclease subunits into a single polypeptide. A linker may have a propensity to form a specific three-dimensional structure under physiological conditions, such as turns and/or coils. In some embodiments, the linker is 30 or 31 amino acids in length. In some embodiments, a linker may have at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to any one of SEQ ID NOs: 4-8. In some embodiments, a linker may have an amino acid sequence comprising any one of SEQ ID NOs: 4-8.

As used herein, the term "turn" as it relates to a polypeptide linker refers to a secondary structure component of a polypeptide in which the direction of the polypeptide chain changes direction. The turn can be facilitated by the formation of an inter main chain hydrogen bond between residues. In some embodiments, the change in direction is approximately a 180° change in direction. A non-limiting example of a turn is the beta turn in which the change of direction is executed in the space of four residues. A turn can also be introduced into an amino acid chain, for example, by a proline which back bonds to the main chain can often introduce a direction change in the main chain.

As used herein, the term "coil" as it relates to a polypeptide linker refers to a secondary structure component of a polypeptide in which the polypeptide chain forms a random coil, wherein the amino acid residues are oriented randomly.

As used herein, with respect to a protein, the term "recombinant" or "engineered" means having an altered amino acid sequence as a result of the application of genetic engineering techniques to nucleic acids which encode the protein, and cells or organisms which express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation and other gene transfer technologies: homologous recombination: site-directed mutagenesis; and gene fusion. In accordance with this definition, a protein having an amino acid sequence identical to a naturally-occurring protein, but produced by cloning and expression in a heterologous host, is not considered recombinant.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein with respect to recombinant proteins, the term "modification" means any insertion, deletion, or substitution of an amino acid residue in the recombinant sequence relative to a reference sequence (e.g., a wild-type or a native sequence).

As used herein, the terms "recognition sequence" or "recognition site" refers to a DNA sequence that is bound and cleaved by an endonuclease. In the case of a meganuclease, a recognition sequence comprises a pair of inverted. 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' "overhangs". "Overhangs." or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence.

As used herein, the term "target site" or "target sequence" refers to a region of the chromosomal DNA of a cell comprising a recognition sequence for a nuclease.

As used herein, the term "DNA-binding affinity" or "binding affinity" means the tendency of a meganuclease to non-covalently associate with a reference DNA molecule (e.g., a recognition sequence or an arbitrary sequence). Binding affinity is measured by a dissociation constant. Kd. As used herein, a nuclease has "altered" binding affinity if the Kd of the nuclease for a reference recognition sequence is increased or decreased by a statistically significant percent change, or biologically significant amount (e.g., at least 2×, or 2× to 10×), relative to a reference nuclease. As used herein, the term "efficiency of cleavage" refers to the incidence by which a meganuclease cleaves a recognition sequence in a double-stranded DNA molecule relative to the incidence of all cleavage events by the meganuclease on the DNA molecule. "Efficiency of cleavage" is synonymous with DNA editing efficiency or on-target editing. Efficiency of cleavage and/or indel formation by a meganuclease can be measured using any method known in the art, including T7E assay, digital PCR (DDPCR™), mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) Biotechnology Advances 35 (1): 95-104, which is incorporated by reference in its entirety). In some embodiments, efficiency of cleavage is measured by ddDDPCRIM. In some embodiments, the disclosed meganucleases generate efficiencies of cleavage of at least about 35%, 40%, 50%, 60%, 70%, 80%, 85%, 90%, 95%, 98%, or 99% at the recognition sequence.

An "indel", as used herein, refers to the insertion or deletion of a nucleobase within a nucleic acid, such as DNA. In some embodiments, it is desirable to generate one or more insertions or deletions (i.e., indels) in the nucleic acid, e.g., in a foreign nucleic acid such as viral DNA. Accordingly, as used herein. "efficiency of indel formation" refers to the incidence by which a meganuclease generates one or more indels through cleavage of a recognition sequence relative to the incidence of all cleavage events by the meganuclease on the DNA molecule. In some embodiments, efficiency of indel formation is measured by ddDDPCRIM. In some embodiments, the disclosed meganucleases generate efficiencies of indel formation of at least about 35%, 40%, 50%, 60%, 70%, 80%, 85%, 90%, 95%, 98%, or 99% at the recognition sequence. The disclosed meganucleases may generate efficiencies of cleavage and/or efficiencies of indel formation of at least about 60%, 61%, 62%, 63%, 64%, 65%, 66%, 67%, 68%, 69%, 70%, 71%, 72%, 73%, 74%, 75%, 76%, 77%, 78%, 79%, or 80% at the recognition sequence.

As used herein, the term "specificity" means the ability of a nuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific nuclease is capable of cleaving only one or a very few recognition sequences. Specificity can be determined by any method known in the art including, but not limited to, those described herein.

As used herein, a nuclease has "altered" specificity if it binds to and cleaves a recognition sequence which is not bound to and cleaved by a reference nuclease (e.g., a wild-type) under physiological conditions, or if the rate of cleavage of a recognition sequence is increased or decreased by a biologically significant amount (e.g., at least 2×, or 2×-10×) relative to a reference nuclease.

As used herein, the term "targeting signal" refers to a polypeptide sequence that directs the protein to which it is fused to a specific location within a cell. Non-limiting examples of targeting signals are a nuclear localization signal (NLS), a mitochondrial target sequence (MTS), and a chloroplast targeting sequence (CTS).

As used herein, the term "homologous recombination" or "HR" refers to the natural, cellular process in which a double-stranded DNA-break is repaired using a homologous DNA sequence as the repair template (see, e.g. Cahill et al. (2006), Front. Biosci. 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), Front. Biosci. 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function.

Thus, engineered nucleases can be used to effectively knock-out a gene in a population of cells. As used herein. "disrupting a target sequence" refers to the introduction of a mutation (e.g., frameshift mutation) that interferes with the gene function and prevents expression and/or function of the polypeptide/expression product encoded thereby.

As used herein, a "homology arm" or "sequences homologous to sequences flanking a meganuclease cleavage site" refer to sequences flanking the 5' and 3' ends of a nucleic acid molecule which promote insertion of the nucleic acid molecule into a cleavage site generated by a meganuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome.

As used herein with respect to both amino acid sequences and nucleic acid sequences, the terms "percent identity." "sequence identity." "percentage similarity." "sequence similarity" and the like refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information website and are described in, for example. Altschul et al. (1990). J. Mol. Biol. 215:403-410; Gish and States (1993), Nature Genet. 3:266-272: Madden et al. (1996), Meth. Enzymol. 266:131-141: Altschul et al. (1997), Nucleic Acids Res. 25:33 89-3402); Zhang et al. (2000). J. Comput. Biol. 7(1-2):203-14. As used herein, percent similarity of two amino acid sequences is the score based upon the following parameters for the BLASTp algorithm; word size=3; gap opening penalty=−11; gap extension penalty=−1; and scoring matrix=BLOSUM62. As used herein, percent similarity of two nucleic acid sequences is the score based upon the following parameters for the BLASTn algorithm; word size=11; gap opening penalty=−5; gap extension penalty=−2; match reward=1; and mismatch penalty=−3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program) and aligned for maximum sequence identity across the entire subunit or protein. Thus, the modification of residue "X" to amino acid "A" in the first protein will correspond to the modification of residue "Y" to amino acid "A" in the second protein if residues X and Y correspond to each other in a sequence alignment, and despite the fact that X and Y may be at different positions relative to the N-terminus or the C-terminus.

As used herein with respect to both amino acid sequences and nucleic acid sequences, "differs from" refers to a difference in the number or type of amino acid residues or nucleotides. Accordingly, a first amino acid sequence can differ from a second amino acid sequence by 1 amino acid residue in the following ways; a) the first amino acid sequence is 1 amino acid longer in length than the second amino acid sequence; b) the first amino acid sequence is 1 amino acid shorter in length than the second amino acid sequence; or c) the first amino acid sequence is the same length as the second amino acid sequence, but a single amino acid residue at the same position within the first amino acid sequence and the second amino acid sequence are not identical (i.e., there is a substitution of one amino acid residue for another, which can be a conservative or non-conservative substitution).

As used herein, the term "recognition half-site." "recognition sequence half-site." or simply "half-site" means a nucleic acid sequence in a double-stranded DNA molecule which is recognized by a monomer of a homodimeric or heterodimeric meganuclease, or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region in the first subunit may correspond to positions 24-79 of any one of SEQ ID NOs: 22-26. In some embodiments, the residues of a hypervariable region may correspond to positions 204-259 of any one of SEQ ID NOs: 22, 23, or 26, or positions 203-258 of any one of SEQ ID NOs: 24 or 25. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the disclosure, a hypervariable region may comprise between 1-20 residues that exhibit variability and can be modified to influence base preference and/or DNA-binding affinity. In particular embodiments, a hypervariable region comprises between about 15-20 residues that exhibit variability and can be modified to influence base preference and/or DNA-binding affinity.

The term "lipid nanoparticle" refers to a lipid composition having a typically spherical structure with an average diameter between 10 and 1000 nanometers. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use in the disclosure.

As used herein, "episome" refers to an extrachromosomal piece of DNA, often circular, and which are often foreign in origin. In some embodiments, the episomal DNA is viral in origin and referred to herein as a "viral episome".

The terms "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used, then the choice of vector is dependent upon the method that will be used to transform host cells as is well known to those skilled in the art. Vectors can include, without limitation, plasmid vectors and recombinant AAV vectors, or any other vector known in the art suitable for delivering a gene to a target cell. The skilled artisan is well aware of the genetic elements that must be present on the vector in order to successfully transform, select and propagate host cells comprising any of the isolated nucleotides or nucleic acid sequences of the disclosure. In some embodiments, a "vector" also refers to a viral vector. Viral vectors can include, without limitation, retroviral vectors, lentiviral vectors, adenoviral vectors, and adeno-associated viral vectors (AAV).

As used herein, a "polycistronic" mRNA refers to a single messenger RNA that comprises two or more coding sequences (i.e., cistrons) and encodes more than one protein. A polycistronic mRNA can comprise any element known in the art to allow for the translation of two or more genes from the same mRNA molecule including, but not limited to, an IRES element, a T2A element, a P2A element, an E2A element, and an F2A element.

As used herein, the term "operably linked" is intended to mean a functional linkage between two or more elements. For example, an operable linkage between a nucleic acid sequence encoding a nuclease as described herein and a regulatory sequence (e.g., a promoter) is a functional link that allows for expression of the nucleic acid sequence encoding the nuclease. Operably linked elements may be contiguous or non-contiguous. When used to refer to the joining of two protein coding regions, by operably linked is intended that the coding regions are in the same reading frame.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype.

As used herein, the terms "treatment" or "treating a subject" refers to the administration of a genetically-modified T cell or population of genetically-modified T cells of the disclosure to a subject having a disease. For example, the subject can have a disease such as cancer, and treatment can represent immunotherapy for the treatment of the disease. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some aspects, an engineered meganuclease described herein, a nucleic acid encoding an engineered meganuclease described herein, a genetically-modified cell prepared by the methods described herein, or a population of genetically-modified cells described herein, is administered during treatment in the form of a pharmaceutical composition of the disclosure.

The term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition and responsiveness of the subject to be treated. In specific embodiments, an effective amount reduces at least one symptom of a disease in a subject.

As used herein, the term "therapeutic protein" refers to a protein that when expressed in a therapeutically effective amount can affect beneficial or desirable biological and/or clinical results. The therapeutic protein can be a wild-type protein expressed in a subject that normally has suboptimal levels of the protein.

As used herein, the recitation of a numerical range for a variable is intended to convey that the embodiments of the disclosure may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0) and 2 can take the values 0), 1 or 2 if the variable is inherently discrete, and can take the values 0.0, 0.1, 0.01, 0.001, or any other real values ≥0) and ≤2 if the variable is inherently continuous.

2.1 Principle of the Invention

The present disclosure is based, in part, on the discovery, through extensive rounds of protein engineering and library screens, of novel linker polypeptides useful for linking two engineered monomers derived from I-CreI to generate site-specific engineered meganucleases. The 30-31 amino acid linker polypeptides disclosed herein are shorter in length than linker polypeptides currently in use for generating engineered meganucleases (e.g., the 42 amino acid Linker1 sequence set forth as SEQ ID NO: 27). The smaller size of these novel linkers is advantageous for packaging of the engineered meganuclease, or nucleic acids encoding the engineered meganuclease, into delivery vehicles, such as viral vectors (e.g., adeno-associated viral vectors), which can have limitations on packaging size. Engineered meganucleases comprising the presently disclosed linker polypeptides exhibit equal or greater on-target activity than engineered meganucleases comprising previously employed, longer linkers (e.g., Linker1).

In addition to the discovery of these novel linkers, the present disclosure is also based, in part, on the identification of a number of amino acid modifications that can be introduced into the first and second subunits of engineered meganucleases comprising these novel linkers. Such modifications were identified through extensive experimentation and are designed to work in concert with the novel linker structures.

In some embodiments, engineered meganucleases comprising the presently disclosed shorter linker polypeptides (i.e., having 30-31 amino acids), as well as the accompanying subunit modifications, have improved properties when compared to engineered meganucleases comprising the longer prior art peptide linker sequences, such as the 42-amino acid Linker1 set forth as SEQ ID NO: 27. In some embodiments, the improved activity comprises enhanced (i.e., increased) efficiency of binding and/or cleavage and indel formation at a recognition sequence.

Engineered meganucleases comprising the presently disclosed linker polypeptides, as well as the accompanying subunit modifications, are provided, as well as methods of using these engineered meganucleases for binding and/or cleaving a double-stranded DNA at a target site in a cell.

2.2 Engineered Meganucleases Comprising Novel Polypeptide Linkers

It is known in the art that it is possible to use a site-specific nuclease, such as an engineered meganuclease, to make a DNA break in the genome of a living cell, and that such a DNA break can result in permanent modification of the genome via mutagenic NHEJ repair or via homologous recombination with a transgenic DNA sequence. NHEJ can produce mutagenesis at the cleavage site, resulting in inactivation of the allele. NHEJ-associated mutagenesis may inactivate an allele via generation of early stop codons, frameshift mutations producing aberrant non-functional proteins, or could trigger mechanisms such as nonsense-mediated mRNA decay. The use of nucleases to induce mutagenesis via NHEJ can be used to target a specific mutation or a sequence present in a wild-type allele. Further, the use of nucleases to induce a double-stranded break in a target locus is known to stimulate homologous recombination, particularly of transgenic DNA sequences flanked by sequences that are homologous to the genomic target. In this manner, exogenous polynucleotides can be inserted into a target locus. Such exogenous polynucleotides can encode any sequence or polypeptide of interest.

Site-specific nucleases can also be used to cleave a double-stranded DNA (dsDNA) target site. The target site can be within a chromosome, mitochondrial DNA, or an episome, such as a viral episome. In some embodiments, cleavage of the episome can lead to degradation of the episome.

The dsDNA target site can be comprised by a gene of interest. In some embodiments, the modification of the target site via NHEJ that results in an indel or premature stop codon leads to disruption of the gene of interest such that the disrupted gene of interest does not encode a full-length and/or functional wild-type polypeptide. Alternatively, the gene of interest comprises a mutation associated with a disease or disorder and modification of the target site by the site-specific nuclease results in correction of the mutation, either through NHEJ-associated mutagenesis or homologous recombination with an exogenous polynucleotide comprising the wild-type sequence. Site-specific nucleases can also be modified to exhibit modified catalytic activity, wherein they do not generate a double-stranded break in the dsDNA. In some cases, site-specific nucleases can be modified to be nickases that only generate a single-strand break on the sense or antisense strand of the dsDNA. In other cases, site-specific nucleases can be modified such that they bind a recognition sequence on dsDNA but do not cleave the dsDNA. Such modifications can be useful in site-specific nucleases, such as engineered meganucleases, for various gene editing approaches (e.g., base editing and epigenetic editing).

Engineered meganucleases of the disclosure comprise a first subunit, comprising a first hypervariable (HVR) region, and a second subunit, comprising a second HVR region. Engineered meganucleases of the disclose are designed to target a 22 bp recognition sequence in dsDNA, which comprises a first 9 bp half-site, a 4 bp center sequence, and a second 9 bp half-site. Each of the two meganuclease subunits recognizes and binds to one of the recognition half-sites and the site of DNA cleavage is at the middle of the recognition sequence near the interface of the two subunits, between positions 13 and 14 on the sense and antisense strands. DNA strand breaks generated by the disclosed engineered meganucleases are offset by four base pairs such that DNA cleavage generates a pair of four base pair. 3' single-strand overhangs.

In embodiments where the engineered meganuclease is a single-chain meganuclease, the first and second subunits can be oriented such that the first subunit (i.e., the N-terminal subunit) binds the first half-site of the recognition sequence and the second subunit (i.e., the C-terminal subunit) binds the second half-site of the recognition sequence. In alternative embodiments, the first and second subunits can be oriented such that the first subunit (i.e., the N-terminal subunit) binds the second half-site of the recognition sequence and the second subunit (i.e., the C-terminal subunit) binds the first half-site of the recognition sequence.

The presently disclosed engineered meganucleases comprise polypeptide linkers that are shorter in length than those taught in the prior art (e.g., Linker1 set forth as SEQ ID NO: 27). In some embodiments, the polypeptide linker has less than 42, less than 41, less than 40, less than 39, less than 38, less than 37, less than 36, less than 35, less than 34, less than 33, less than 32, or less than 31 amino acids. In some embodiments, the polypeptide linker comprises between 30 and 35 amino acids. In some embodiments, the polypeptide linker comprises 30 amino acid residues. In some embodiments, the polypeptide linker comprises 31 amino acid residues. In some embodiments, the presently disclosed engineered meganucleases comprise, from 5' to 3', a first subunit, a polypeptide linker, and a second subunit, wherein the polypeptide linker comprises an amino acid sequence of: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$-$X_{21}$-$X_{22}$-$X_{23}$-$X_{24}$-$X_{25}$-$X_{26}$-$X_{27}$-$X_{28}$-$X_{29}$-$X_{30}$, set forth as SEQ ID NO: 3. The polypeptide linkers can comprise at least one turn and/or at least one coil. In some embodiments, the polypeptide linkers of the presently disclosed engineered meganucleases comprise, from 5' to 3', a first turn, a first coil, a second coil, and a second turn.

Exemplary polypeptide linkers are provided in SEQ ID NOs: 4-8 and exemplary reference meganucleases are provided in SEQ ID NOs: 22-26 and are further described below. The reference meganucleases provided in SEQ ID NOs: 22-26 comprise: (i) a first subunit comprising amino acids 1-153 of wild-type I-CreI (SEQ ID NO: 1) with modifications of K96A, Q99A, and K100D; (ii) the polypeptide linkers disclosed in SEQ ID NOs: 4-8; and (iii) a second subunit comprising amino acids 5-163 of wild-type I-CreI (SEQ ID NO: 1) with modifications of K57Y and E6IT (at positions corresponding to positions 57 and 61 of I-CreI). Engineered meganucleases of the disclosure can comprise altered HVR sequences as compared to the wild-type I-CreI meganuclease HVR sequences found in the described reference meganucleases, and can further comprise amino acid modifications outside of the HVR regions, such that the meganucleases of the disclosure are engineered to bind to and/or cleave a recognition sequence of interest. Linker1923 Reference Meganuclease In some embodiments, the first turn of the polypeptide linker of a presently disclosed engineered meganuclease comprises 4 amino acid residues. In some embodiments, the first turn comprises residues corresponding to residues 154-157 of SEQ ID NO: 22. In some embodiments, the first turn comprises a residue corresponding to residue 154 of SEQ ID NO: 22. In some embodiments, the first turn comprises a residue corresponding to residue 155 of SEQ ID NO: 22. In some embodiments, the first turn comprises a residue corresponding to residue 156 of SEQ ID NO: 22. In some embodiments, the first turn comprises a residue corresponding to residue 157 of SEQ ID NO: 22. In some embodiments, the first turn of the polypeptide linker comprises an SLPG motif, set forth as SEQ ID NO: 9. In some embodiments, the first turn comprises an amino acid sequence of SEQ ID NO: 9 or an amino acid sequence that differs from SEQ ID NO: 9 by 1 amino acid residue. In some embodiments, the first turn comprises an amino acid sequence having at least 75% sequence identity to SEQ ID NO: 9. In some embodiments, the first turn comprises an amino acid sequence of SEQ ID NO: 9.

In some embodiments, the first coil of the polypeptide linker of a presently disclosed engineered meganuclease comprises 13 amino acids. In some embodiments, the first coil comprises residues corresponding to residues 158-170 of SEQ ID NO: 22. In some embodiments, the first coil comprises a non-polar amino acid at a residue corresponding to residue 158 of SEQ ID NO: 22. In some embodiments, the first coil comprises I, V, or A at residue 158 of SEQ ID NO: 22. In some embodiments, the first coil comprises I at residue 158 of SEQ ID NO: 22. In some embodiments, the first coil comprises a polar amino acid at a residue corresponding to residue 159 of SEQ ID NO: 22. In some embodiments, the first coil comprises Q. G, or R at a residue corresponding to residue 159 of SEQ ID NO: 22. In some embodiments, the first coil comprises Q at a residue corresponding to residue 159 of SEQ ID NO: 22. In some embodiments, the first coil comprises a non-polar amino acid at a residue corresponding to residue 160 of SEQ ID NO: 22. In some embodiments, the first coil comprises L, V, or P at a residue corresponding to residue 160 of SEQ ID NO: 22. In some embodiments, the first coil comprises L at a residue corresponding to residue 160 of SEQ ID NO: 22. In some embodiments, the first coil comprises N, Q, H, S, or G at a residue corresponding to residue 161 of SEQ ID NO: 22. In some embodiments, the first coil comprises N at a residue corresponding to residue 161 of SEQ ID NO: 22. In some embodiments, the first coil comprises K, V, C, Q, or G at a residue corresponding to residue 162 of SEQ ID NO: 22. In some embodiments, the first coil comprises K at a residue corresponding to residue 162 of SEQ ID NO: 22. In some embodiments, the first coil comprises E, H, P, G, or V at a residue corresponding to residue 163 of SEQ ID NO: 22. In some embodiments, the first coil comprises E at a residue corresponding to residue 163 of SEQ ID NO: 22. In some embodiments, the first coil comprises S, R, L, or A at a residue corresponding to residue 164 of SEQ ID NO: 22. In some embodiments, the first coil comprises S at a residue corresponding to residue 164 of SEQ ID NO: 22. In some embodiments, the first coil comprises a polar amino acid at a residue corresponding to residue 165 of SEQ ID NO: 22. In some embodiments, the first coil comprises N at a residue corresponding to residue 165 of SEQ ID NO: 22. In some embodiments, the first coil comprises N at a residue corresponding to residue 166 of SEQ ID NO: 22. In some embodiments, the first coil comprises a polar amino acid at a residue corresponding to residue 167 of SEQ ID NO: 22. In some embodiments, the first coil comprises N at a residue corresponding to residue 167 of SEQ ID NO: 22. In some embodiments, the first coil comprises a polar amino acid at a residue corresponding to residue 168 of SEQ ID NO: 22.

In some embodiments, the first coil comprises a small amino acid at a residue corresponding to residue 168 of SEQ ID NO: 22. In some embodiments, the first coil comprises A at a residue corresponding to residue 168 of SEQ ID NO: 22. In some embodiments, the first coil comprises a polar amino acid at a residue corresponding to residue 169 of SEQ ID NO: 22. In some embodiments, the first coil comprises S at a residue corresponding to residue 169 of SEQ ID NO: 22. In some embodiments, the first coil comprises a polar amino acid at a residue corresponding to residue 170 of SEQ ID NO: 22. In some embodiments, the first coil comprises a small amino acid at a residue corresponding to residue 170 of SEQ ID NO: 22. In some embodiments, the first coil comprises T at a residue corresponding to residue 170 of SEQ ID NO: 22. In some embodiments, the first coil of the polypeptide linker comprises an amino acid sequence of SEQ ID NO: 10 or an amino acid sequence that differs from SEQ ID NO: 10 by 1, 2, or 3 amino acid residues. In some embodiments, the first coil comprises an amino acid sequence having at least 76%, at least 84%, at least 92%, or more, sequence identity to SEQ ID NO: 10. In some embodiments, the first coil comprises an amino acid sequence of SEQ ID NO: 10.

In some embodiments, the second coil of the polypeptide linker of a presently disclosed engineered meganuclease comprises 9 amino acids. In some embodiments, the second coil comprises residues corresponding to residues 171-179 of SEQ ID NO: 22. In some embodiments, the second coil comprises a Q at a residue corresponding to residue 171 of SEQ ID NO: 22. In some embodiments, the second coil comprises R at a residue corresponding to residue 172 of SEQ ID NO: 22. In some embodiments, the second coil comprises P at a residue corresponding to residue 173 of SEQ ID NO: 22. In some embodiments, the second coil comprises a QRP motif (set forth as SEQ ID NO: 15) at residues corresponding to residues 171-173 of SEQ ID NO: 22. In some embodiments, the second coil comprises S at a residue corresponding to residue 174 of SEQ ID NO: 22. In some embodiments, the second coil comprises R at a residue corresponding to residue 175 of SEQ ID NO: 22. In some embodiments, the second coil comprises a polar amino acid at a residue corresponding to residue 176 of SEQ ID NO: 22. In some embodiments, the second coil comprises N at a residue corresponding to residue 176 of SEQ ID NO: 22. In some embodiments, the second coil comprises a non-polar amino acid at a residue corresponding to residue 177 of SEQ ID NO: 22. In some embodiments, the second coil comprises V at a residue corresponding to residue 177 of SEQ ID NO: 22. In some embodiments, the second coil comprises a polar amino acid at a residue corresponding to residue 178 of SEQ ID NO: 22. In some embodiments, the second coil comprises N at a residue corresponding to residue 178 of SEQ ID NO: 22. In some embodiments, the second coil comprises a polar amino acid at a residue corresponding to residue 179 of SEQ ID NO: 22. In some embodiments, the second coil comprises N at a residue corresponding to residue 179 of SEQ ID NO: 22. In some embodiments, the second coil comprise an amino acid sequence of SEQ ID NO: 16 or an amino acid sequence that differs from SEQ ID NO: 16 by 1 or 2 amino acid residues. In some embodiments, the second coil comprises an amino acid sequence having at least 77%, at least 88%, or more, sequence identity to SEQ ID NO: 16. In some embodiments, the second coil comprises an amino acid sequence of SEQ ID NO: 16.

In some embodiments, the second turn of the polypeptide linker of a presently disclosed engineered meganuclease comprises 5 amino acids. In some embodiments, the second turn comprises residues corresponding to residues 180-184 of SEQ ID NO: 22. In some embodiments, the second turn comprises a non-polar amino acid at a residue corresponding to residue 180 of SEQ ID NO: 22. In some embodiments, the second turn comprises F at a residue corresponding to residue 180 of SEQ ID NO: 22. In some embodiments, the second turn comprises P at a residue corresponding to residue 181 of SEQ ID NO: 22. In some embodiments, the second turn comprises Y. Q, or L at a residue corresponding to residue 182 of SEQ ID NO: 22. In some embodiments, the second turn comprises Y at a residue corresponding to residue 182 of SEQ ID NO: 22. In some embodiments, the second turn comprises a polar amino acid at a residue corresponding to residue 183 of SEQ ID NO: 22. In some embodiments, the second turn comprises a small amino acid at a residue corresponding to residue 183 of SEQ ID NO: 22. In some embodiments, the second turn comprises S. K, or G at a position corresponding to residue 183 of SEQ ID NO: 22. In some embodiments, the second turn comprises S at a position corresponding to residue 183 of SEQ ID NO: 22. In some embodiments, the second turn further comprises residue $X_{31}$ such that the polypeptide linker comprises 31 amino acid residues. In some embodiments, the second turn comprises G at a residue corresponding to residue 184 of SEQ ID NO: 22. In some embodiments, the second turn comprises an amino acid sequence of SEQ ID NO: 17 or an amino acid sequence that differs from SEQ ID NO: 17 by 1 amino acid residues. In some embodiments, the second turn comprises an amino acid sequence having at least 80% sequence identity to SEQ ID NO: 17. In some embodiments, the second turn comprises an amino acid sequence of SEQ ID NO: 17.

In some embodiments, the engineered meganuclease comprises a polypeptide linker comprising a first turn comprising an amino acid sequence of SEQ ID NO: 9 or an amino acid sequence that differs from SEQ ID NO: 9 by 1 amino acid residue, a first coil comprising an amino acid sequence of SEQ ID NO: 10 or an amino acid sequence that differs from SEQ ID NO: 10 by 1-3 amino acid residues, a second coil comprising an amino acid sequence of SEQ ID NO: 16 or an amino acid sequence that differs from SEQ ID NO: 16 by 1 or 2 amino acid residues, and a second turn comprising an amino acid sequence of SEQ ID NO: 17 or an amino acid sequence that differs from SEQ ID NO: 17 by 1 amino acid residue.

In some embodiments, the engineered meganuclease comprises a polypeptide linker comprising a first turn comprising an amino acid sequence of SEQ ID NO: 9, a first coil comprising an amino acid sequence of SEQ ID NO: 10, a second coil comprising an amino acid sequence of SEQ ID NO: 16, and a second turn comprising an amino acid sequence of SEQ ID NO: 17.

In some embodiments, the polypeptide linker comprises an amino acid sequence of SEQ ID NO: 4 or an amino acid sequence that differs from SEQ ID NO: 4 by 1, 2, 3, 4, 5, or 6 amino acid residues.

In some embodiments, the engineered meganuclease comprises a first subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 6-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 4-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 3-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 1. In some embodiments, the first subunit comprises a residue other than M at a position corresponding to position 1 of SEQ ID NO: 1. In some embodiments, the first subunit comprises an A residue at a position corresponding to position 1 of SEQ ID NO: 1. In some embodiments, the engineered meganuclease comprises a first subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 1. In some embodiments, the first subunit comprises a Y at a position corresponding to position 37 of SEQ ID NO: 1. In some embodiments, the first subunit comprises an A at a position corresponding to position 96 of SEQ ID NO: 1. In some embodiments, the first subunit comprises an A at a position corresponding to position 99 of SEQ ID NO: 1. In some embodiments, the first subunit comprises a D at a position corresponding to position 100 of SEQ ID NO: 1. In some embodiments, the first subunit comprises an A at a position corresponding to position 99 of SEQ ID NO: 1 and a D at a position corresponding to position 100 of SEQ ID NO: 1.

In some embodiments, the first subunit comprises an A at a position corresponding to position 96 of SEQ ID NO: 1, an A at a position corresponding to position 99 of SEQ ID NO: 1, and a D at a position corresponding to position 100 of SEQ ID NO: 1. In some embodiments, the first subunit comprises a Y at a position corresponding to position 37 of SEQ ID NO: 1 and an A at a position corresponding to position 96 of SEQ ID NO: 1. In some embodiments, the first subunit comprises a Y at a position corresponding to position 37 of SEQ ID NO: 1, an A at a position corresponding to position 99 of SEQ ID NO: 1, and a D at a position corresponding to position 100 of SEQ ID NO: 1. In some embodiments, the first subunit comprises a Y at a position corresponding to position 37 of SEQ ID NO: 1, an A at a position corresponding to position 96 of SEQ ID NO: 1, an A at a position corresponding to position 99 of SEQ ID NO: 1, and a D at a position corresponding to position 100 of SEQ ID NO: 1. In some embodiments, the first subunit comprises a specificity-altering amino acid modification at one or more positions corresponding to positions 24, 26, 28, 30, 32, 33, 38, 40, 42, 44, 46, 66, 68, 70, 76, 77, 79, or 139 of SEQ ID NO: 1. In some embodiments, the first subunit comprises a specificity-altering amino acid modification at one or more positions corresponding to positions 71, 72, 73, or 74 of SEQ ID NO: 1. In some embodiments, the first subunit comprises a DNA binding affinity-altering modification at one or more positions corresponding to positions 29, 34, 48, 51, 64, 80, 81, 82, 112, 116, 137, 139, or 143 of SEQ ID NO: 1. In some embodiments, the first subunit comprises a cleavage activity-altering modification at one or more positions corresponding to positions 19, 48, and 50 of SEQ ID NO: 1.

In some embodiments, the engineered meganuclease comprises a second subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 1. In some embodiments, the engineered meganuclease comprises a second subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1. In some embodiments, the second subunit comprises a Y at a position corresponding to position 57 of SEQ ID NO: 1. In some embodiments, the second subunit comprises a T at a position corresponding to position 61 of SEQ ID NO: 1. In some embodiments, the second subunit comprises a Y at a position corresponding to position 57 of SEQ ID NO: 1 and a T at a position corresponding to position 61 of SEQ ID NO: 1. In some embodiments, the second subunit comprises an F at a position corresponding to position 53 of SEQ ID NO: 1, a Y at a position corresponding to position 57 of SEQ ID NO: 1, and a T at a position corresponding to position 61 of SEQ ID NO: 1. In some embodiments, the second subunit comprises a specificity-altering amino acid modification at one or more positions corresponding to positions 24, 26, 28, 30, 32, 33, 38, 40, 42, 44, 46, 66, 68, 70, 76, 77, 79, or 139 of SEQ ID NO: 1. In some embodiments, the second subunit comprises a specificity-altering amino acid modification at one or more positions corresponding to positions 71, 72, 73, or 74 of SEQ ID NO: 1. In some embodiments, the second subunit comprises a DNA binding affinity-altering modification at one or more positions corresponding to positions 29, 34, 48, 51, 64, 80, 81, 82, 112, 116, 137, 139, or 143 of SEQ ID NO: 1. In some embodiments, the second subunit comprises a cleavage activity-altering modification at one or more positions corresponding to positions 19, 48, and 50 of SEQ ID NO: 1.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 1, wherein the first subunit comprises an A at a position corresponding to position 96 of SEQ ID NO: 1, an A at a position corresponding to position 99 of SEQ ID NO: 1, and a D at a position corresponding to position 100 of SEQ ID NO: 1, and the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1, wherein the second subunit comprises a Y at a position corresponding to position 57 of SEQ ID NO: 1 and a T at a position corresponding to position 61 of SEQ ID NO: 1.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 1, wherein the first subunit comprises an A at a position corresponding to position 96 of SEQ ID NO: 1, an A at a position corresponding to position 99 of SEQ ID NO: 1, and a D at a position corresponding to position 100 of SEQ ID NO: 1, and the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1, wherein the second subunit comprises a Y at a position corresponding to position 57 of SEQ ID NO: 1 and a T at a position corresponding to position 61 of SEQ ID NO: 1.

In some embodiments, the N-terminus of the polypeptide linker is covalently bound to the first subunit at a residue corresponding to any one of positions 153-163 of SEQ ID NO: 1. In some embodiments, the N-terminus of the polypeptide linker is covalently bound to the first subunit at a D residue corresponding to position 153 of SEQ ID NO: 1. In some embodiments, the C-terminus of the polypeptide linker is covalently bound to the second subunit at a residue corresponding to any one of positions 1-9 of SEQ ID NO: 1. In some embodiments, the C-terminus of the polypeptide linker is covalently bound to the second subunit at a Y residue corresponding to position 5 of SEQ ID NO: 1.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91% at least 92%, at least 93%, at least 94%, at least 95%, at least 96%, at least 97%, at least 98%, at least 99%, or more, sequence identity to SEQ ID NO: 22.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91% at least 92%, at least 93%, at least 94%, at least 95%, at least 96%, at least 97%, at least 98%, at least 99%, or more, sequence identity to a nucleic acid sequence of SEQ ID NO: 22, wherein the polypeptide linker comprises SEQ ID NO: 4. In some of these embodiments, the first subunit of the engineered meganuclease comprises an A at position 96, an A at position 99, and a D at position 100, and the said second subunit comprises a Y at position 237 and a T at position 241, or positions corresponding to the identified positions when aligned for maximum identity across the subunit as described herein.

In some embodiments, the engineered meganuclease comprises a targeting signal, such as a nuclear localization signal (NLS) or a mitochondrial targeting signal (MTS). In some embodiments, the targeting signal is at the N-terminus of the engineered meganuclease. In some embodiments, the targeting signal is at the C-terminus of the engineered meganuclease.

Linker1766 Reference Meganuclease

In some embodiments, the first turn of the polypeptide linker of a presently disclosed engineered meganuclease comprises 4 amino acid residues. In some embodiments, the first turn comprises residues corresponding to residues 154-157 of SEQ ID NO: 23. In some embodiments, the first turn comprises a residue corresponding to residue 154 of SEQ ID NO: 23. In some embodiments, the first turn comprises a residue corresponding to residue 155 of SEQ ID NO: 23. In some embodiments, the first turn comprises a residue corresponding to residue 156 of SEQ ID NO: 23. In some embodiments, the first turn comprises a residue corresponding to residue 157 of SEQ ID NO: 23. In some embodiments, the first turn of the polypeptide linker comprises an SLPG motif, set forth as SEQ ID NO: 9. In some embodiments, the first turn comprises an amino acid sequence of SEQ ID NO: 9 or an amino acid sequence that differs from SEQ ID NO: 9 by 1 amino acid residue. In some embodiments, the first turn comprises an amino acid sequence having at least 75% sequence identity to SEQ ID NO: 9. In some embodiments, the first turn comprises an amino acid sequence of SEQ ID NO: 9.

In some embodiments, the first coil of the polypeptide linker of a presently disclosed engineered meganuclease comprises 13 amino acids. In some embodiments, the first coil comprises residues corresponding to residues 158-170 of SEQ ID NO: 23. In some embodiments, the first coil comprises a non-polar amino acid at a residue corresponding to residue 158 of SEQ ID NO: 23. In some embodiments, the first coil comprises I, V, or A at residue 158 of SEQ ID NO: 23. In some embodiments, the first coil comprises I at residue 158 of SEQ ID NO: 23. In some embodiments, the first coil comprises a polar amino acid at a residue corresponding to residue 159 of SEQ ID NO: 23. In some embodiments, the first coil comprises Q, G, or R at a residue corresponding to residue 159 of SEQ ID NO: 23. In some embodiments, the first coil comprises G at a residue corresponding to residue 159 of SEQ ID NO: 23. In some embodiments, the first coil comprises a non-polar amino acid at a residue corresponding to residue 160 of SEQ ID NO: 23. In some embodiments, the first coil comprises L. V, or P at a residue corresponding to residue 160 of SEQ ID NO: 23. In some embodiments, the first coil comprises V at a residue corresponding to residue 160 of SEQ ID NO: 23. In some embodiments, the first coil comprises N, Q. H. S, or G at a residue corresponding to residue 161 of SEQ ID NO: 23. In some embodiments, the first coil comprises Q at a residue corresponding to residue 161 of SEQ ID NO: 23. In some embodiments, the first coil comprises K, V, C, Q, or G at a residue corresponding to residue 162 of SEQ ID NO: 23. In some embodiments, the first coil comprises V at a residue corresponding to residue 162 of SEQ ID NO: 23. In some embodiments, the first coil comprises E, H, P, G, or V at a residue corresponding to residue 163 of SEQ ID NO: 23. In some embodiments, the first coil comprises H at a residue corresponding to residue 163 of SEQ ID NO: 23. In some embodiments, the first coil comprises S, R, L, or A at a residue corresponding to residue 164 of SEQ ID NO: 23. In some embodiments, the first coil comprises R at a residue corresponding to residue 164 of SEQ ID NO: 23. In some embodiments, the first coil comprises a polar amino acid at a residue corresponding to residue 165 of SEQ ID NO: 23. In some embodiments, the first coil comprises N at a residue corresponding to residue 165 of SEQ ID NO: 23. In some embodiments, the first coil comprises N at a residue corresponding to residue 166 of SEQ ID NO: 23. In some embodiments, the first coil comprises a polar amino acid at a residue corresponding to residue 167 of SEQ ID NO: 23. In some embodiments, the first coil comprises N at a residue corresponding to residue 167 of SEQ ID NO: 23. In some embodiments, the first coil comprises a polar amino acid at a residue corresponding to residue 168 of SEQ ID NO: 23. In some embodiments, the first coil comprises a small amino acid at a residue corresponding to residue 168 of SEQ ID NO: 23. In some embodiments, the first coil comprises A at a residue corresponding to residue 168 of SEQ ID NO: 23. In some embodiments, the first coil comprises a polar amino acid at a residue corresponding to residue 169 of SEQ ID NO: 23. In some embodiments, the first coil comprises S at a residue corresponding to residue 169 of SEQ ID NO: 23. In some embodiments, the first coil comprises a polar amino acid at a residue corresponding to residue 170 of SEQ ID NO: 23. In some embodiments, the first coil comprises a small amino acid at a residue corresponding to residue 170 of SEQ ID NO: 23. In some embodiments, the first coil comprises T at a residue corresponding to residue 170 of SEQ ID NO: 23. In some embodiments, the first coil of the polypeptide linker comprises an amino acid sequence of SEQ ID NO: 11 or an amino acid sequence that differs from SEQ ID NO: 11 by 1, 2, or 3 amino acid residues. In some embodiments, the first coil comprises an amino acid sequence having at least 76%, at least 84%, at least 92%, or more, sequence identity to SEQ ID NO: 11. In some embodiments, the first coil comprises an amino acid sequence of SEQ ID NO: 11.

In some embodiments, the second coil of the polypeptide linker of a presently disclosed engineered meganuclease comprises 9 amino acids. In some embodiments, the second coil comprises residues corresponding to residues 171-179 of SEQ ID NO: 23. In some embodiments, the second coil comprises a Q at a residue corresponding to residue 171 of SEQ ID NO: 23. In some embodiments, the second coil comprises R at a residue corresponding to residue 172 of SEQ ID NO: 23. In some embodiments, the second coil comprises P at a residue corresponding to residue 173 of SEQ ID NO: 23. In some embodiments, the second coil comprises a QRP motif (set forth as SEQ ID NO: 15) at residues corresponding to residues 171-173 of SEQ ID NO: 23. In some embodiments, the second coil comprises S at a residue corresponding to residue 174 of SEQ ID NO: 23. In some embodiments, the second coil comprises R at a residue corresponding to residue 175 of SEQ ID NO: 23. In some embodiments, the second coil comprises a polar amino acid at a residue corresponding to residue 176 of SEQ ID NO: 23. In some embodiments, the second coil comprises N at a residue corresponding to residue 176 of SEQ ID NO: 23. In some embodiments, the second coil comprises a non-polar amino acid at a residue corresponding to residue 177 of SEQ ID NO: 23. In some embodiments, the second coil comprises V at a residue corresponding to residue 177 of SEQ ID NO: 23. In some embodiments, the second coil comprises a polar amino acid at a residue corresponding to residue 178 of SEQ ID NO: 23. In some embodiments, the second coil comprises N at a residue corresponding to residue 178 of SEQ ID NO: 23. In some embodiments, the second coil comprises a polar amino acid at a residue corresponding to residue 179 of SEQ ID NO: 23. In some embodiments, the second coil comprises N at a residue corresponding to residue 179 of SEQ ID NO: 23. In some embodiments, the second coil comprise an amino acid sequence of SEQ ID NO: 16 or an amino acid sequence that differs from SEQ ID NO: 16 by 1 or 2 amino acid residues. In some embodiments, the second coil comprises an amino acid sequence having at least 77%, at least 88%, or more, sequence identity to SEQ ID NO: 16. In some embodiments, the second coil comprises an amino acid sequence of SEQ ID NO: 16.

In some embodiments, the second turn of the polypeptide linker of a presently disclosed engineered meganuclease comprises 5 amino acids. In some embodiments, the second turn comprises residues corresponding to residues 180-184 of SEQ ID NO: 23. In some embodiments, the second turn comprises a non-polar amino acid at a residue corresponding to residue 180 of SEQ ID NO: 23. In some embodiments, the second turn comprises F at a residue corresponding to residue 180 of SEQ ID NO: 23. In some embodiments, the second turn comprises P at a residue corresponding to residue 181 of SEQ ID NO: 23. In some embodiments, the second turn comprises Y, Q, or L at a residue corresponding to residue 182 of SEQ ID NO: 23. In some embodiments, the second turn comprises Y at a residue corresponding to residue 182 of SEQ ID NO: 23. In some embodiments, the second turn comprises a polar amino acid at a residue corresponding to residue 183 of SEQ ID NO: 23. In some embodiments, the second turn comprises a small amino acid at a residue corresponding to residue 183 of SEQ ID NO: 23. In some embodiments, the second turn comprises S, K, or G at a position corresponding to residue 183 of SEQ ID NO: 23. In some embodiments, the second turn comprises K at a position corresponding to residue 183 of SEQ ID NO: 23. In some embodiments, the second turn further comprises residues $X_{31}$ such that the polypeptide linker comprises 31 amino acid residues. In some embodiments, the second turn comprises G at a residue corresponding to residue 184 of SEQ ID NO: 23. In some embodiments, the second turn comprises an amino acid sequence of SEQ ID NO: 18 or an amino acid sequence that differs from SEQ ID NO: 18 by 1 amino acid residue. In some embodiments, the second turn comprises an amino acid sequence having at least 80% sequence identity to SEQ ID NO: 18. In some embodiments, the second turn comprises an amino acid sequence of SEQ ID NO: 18.

In some embodiments, the engineered meganuclease comprises a polypeptide linker comprising a first turn comprising an amino acid sequence of SEQ ID NO: 9 or an amino acid sequence that differs from SEQ ID NO: 9 by 1 amino acid residue, a first coil comprising an amino acid sequence of SEQ ID NO: 11 or an amino acid sequence that differs from SEQ ID NO: 11 by 1-3 amino acid residues, a second coil comprising an amino acid sequence of SEQ ID NO: 16 or an amino acid sequence that differs from SEQ ID NO: 16 by 1 or 2 amino acid residues, and a second turn comprising an amino acid sequence of SEQ ID NO: 18 or an amino acid sequence that differs from SEQ ID NO: 18 by 1 amino acid residue.

In some embodiments, the engineered meganuclease comprises a polypeptide linker comprising a first turn comprising an amino acid sequence of SEQ ID NO: 9, a first coil comprising an amino acid sequence of SEQ ID NO: 11, a second coil comprising an amino acid sequence of SEQ ID NO: 16, and a second turn comprising an amino acid sequence of SEQ ID NO: 18.

In some embodiments, the polypeptide linker comprises an amino acid sequence of SEQ ID NO: 5 or an amino acid sequence that differs from SEQ ID NO: 5 by 1, 2, 3, 4, 5, or 6 amino acid residues.

In some embodiments, the engineered meganuclease comprises a first subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 6-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 4-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 3-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 1. In some embodiments, the first subunit comprises a residue other than M at a position corresponding to position 1 of SEQ ID NO: 1. In some embodiments, the first subunit comprises an A residue at a position corresponding to position 1 of SEQ ID NO: 1. In some embodiments, the engineered meganuclease comprises a first subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 1. In some embodiments, the first subunit comprises a Y at a position corresponding to position 37 of SEQ ID NO: 1. In some embodiments, the first subunit comprises an A at a position corresponding to position 96 of SEQ ID NO: 1. In some embodiments, the first subunit comprises an A at a position corresponding to position 99 of SEQ ID NO: 1. In some embodiments, the first subunit comprises a D at a position corresponding to position 100 of SEQ ID NO: 1. In some embodiments, the first subunit comprises an A at a position corresponding to position 99 of SEQ ID NO: 1 and a D at a position corresponding to position 100 of SEQ ID NO: 1. In some embodiments, the first subunit comprises an A at a position corresponding to position 96 of SEQ ID NO: 1, an A at a position corresponding to position 99 of SEQ ID NO: 1, and a D at a position corresponding to position 100 of SEQ ID NO: 1. In some embodiments, the first subunit comprises a Y at a position corresponding to position 37 of SEQ ID NO: 1 and an A at a position corresponding to position 96 of SEQ ID NO: 1. In some embodiments, the first subunit comprises a Y at a position corresponding to position 37 of SEQ ID NO: 1, an A at a position corresponding to position 99 of SEQ ID NO: 1, and a D at a position corresponding to position 100 of SEQ ID NO: 1. In some embodiments, the first subunit comprises a Y at a position corresponding to position 37 of SEQ ID NO: 1, an A at a position corresponding to position 96 of SEQ ID NO: 1, an A at a position corresponding to position 99 of SEQ ID NO: 1, and a D at a position corresponding to position 100 of SEQ ID NO: 1. In some embodiments, the first subunit comprises a specificity-altering amino acid modification at one or more positions corresponding to positions 24, 26, 28, 30, 32, 33, 38, 40, 42, 44, 46, 66, 68, 70, 76, 77, 79, or 139 of SEQ ID NO: 1. In some embodiments, the first subunit comprises a specificity-altering amino acid modification at one or more positions corresponding to positions 71, 72, 73, or 74 of SEQ ID NO: 1. In some embodiments, the first subunit comprises a DNA binding affinity-altering modification at one or more positions corresponding to positions 29, 34, 48, 51, 64, 80, 81, 82, 112, 116, 137, 139, or 143 of SEQ ID NO: 1. In some embodiments, the first subunit comprises a cleavage activity-altering modification at one or more positions corresponding to positions 19, 48, and 50 of SEQ ID NO: 1.

In some embodiments, the engineered meganuclease comprises a second subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 1. In some embodiments, the engineered meganuclease comprises a second subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1. In some embodiments, the second subunit comprises a F at a position corresponding to position 53 of SEQ ID NO: 1. In some embodiments, the second subunit comprises a Y at a position corresponding to position 57 of SEQ ID NO: 1. In some embodiments, the second subunit comprises a T at a position corresponding to position 61 of SEQ ID NO: 1. In some embodiments, the second subunit comprises a Y at a position corresponding to position 57 of SEQ ID NO: 1 and a T at a position corresponding to position 61 of SEQ ID NO: 1. In some embodiments, the second subunit comprises an F at a position corresponding to position 53 of SEQ ID NO: 1, a Y at a position corresponding to position 57 of SEQ ID NO: 1, and a T at a position corresponding to position 61 of SEQ ID NO: 1. In some embodiments, the second subunit comprises a specificity-altering amino acid modification at one or more positions corresponding to positions 24, 26, 28, 30, 32, 33, 38, 40, 42, 44, 46, 66, 68, 70, 76, 77, 79, or 139 of SEQ ID NO: 1. In some embodiments, the second subunit comprises a specificity-altering amino acid modification at one or more positions corresponding to positions 71, 72, 73, or 74 of SEQ ID NO: 1. In some embodiments, the second subunit comprises a DNA binding affinity-altering modification at one or more positions corresponding to positions 29, 34, 48, 51, 64, 80, 81, 82, 112, 116, 137, 139, or 143 of SEQ ID NO: 1. In some embodiments, the second subunit comprises a cleavage activity-altering modification at one or more positions corresponding to positions 19, 48, and 50 of SEQ ID NO: 1.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 1, wherein the first subunit comprises an A at a position corresponding to position 96 of SEQ ID NO: 1, an A at a position corresponding to position 99 of SEQ ID NO: 1, and a D at a position corresponding to position 100 of SEQ ID NO: 1, and the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1, wherein the second subunit comprises a Y at a position corresponding to position 57 of SEQ ID NO: 1 and a T at a position corresponding to position 61 of SEQ ID NO: 1.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 1, wherein the first subunit comprises an A at a position corresponding to position 96 of SEQ ID NO: 1, an A at a position corresponding to position 99 of SEQ ID NO: 1, and a D at a position corresponding to position 100 of SEQ ID NO: 1, and the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1, wherein the second subunit comprises a Y at a position corresponding to position 57 of SEQ ID NO: 1 and a T at a position corresponding to position 61 of SEQ ID NO: 1.

In some embodiments, the N-terminus of the polypeptide linker is covalently bound to the first subunit at a residue corresponding to any one of positions 153-163 of SEQ ID NO: 1. In some embodiments, the N-terminus of the polypeptide linker is covalently bound to the first subunit at a D residue corresponding to position 153 of SEQ ID NO: 1. In some embodiments, the C-terminus of the polypeptide linker is covalently bound to the second subunit at a residue corresponding to any one of positions 1-9 of SEQ ID NO: 1. In some embodiments, the C-terminus of the polypeptide linker is covalently bound to the second subunit at a Y residue corresponding to position 5 of SEQ ID NO: 1.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91% at least 92%, at least 93%, at least 94%, at least 95%, at least 96%, at least 97%, at least 98%, at least 99%, or more, sequence identity to SEQ ID NO: 23.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91% at least 92%, at least 93%, at least 94%, at least 95%, at least 96%, at least 97%, at least 98%, at least 99%, or more, sequence identity to a nucleic acid sequence of SEQ ID NO: 23, wherein the polypeptide linker comprises SEQ ID NO: 5. In some of these embodiments, the first subunit of the engineered meganuclease comprises an A at position 96, an A at position 99, and a D at position 100, and the said second subunit comprises a Y at position 237 and a T at position 241, or positions corresponding to the identified positions when aligned for maximum identity across the subunit as described herein.

In some embodiments, the engineered meganuclease comprises a targeting signal, such as a nuclear localization signal (NLS) or a mitochondrial targeting signal (MTS). In some embodiments, the targeting signal is at the N-terminus of the engineered meganuclease. In some embodiments, the targeting signal is at the C-terminus of the engineered meganuclease.

Linker1771 Reference Meganuclease

In some embodiments, the first turn of the polypeptide linker of a presently disclosed engineered meganuclease comprises 4 amino acid residues. In some embodiments, the first turn comprises residues corresponding to residues 154-157 of SEQ ID NO: 24. In some embodiments, the first turn comprises a residue corresponding to residue 154 of SEQ ID NO: 24. In some embodiments, the first turn comprises a residue corresponding to residue 155 of SEQ ID NO: 24. In some embodiments, the first turn comprises a residue corresponding to residue 156 of SEQ ID NO: 24. In some embodiments, the first turn comprises a residue corresponding to residue 157 of SEQ ID NO: 24. In some embodiments, the first turn of the polypeptide linker comprises an SLPG motif, set forth as SEQ ID NO: 9. In some embodiments, the first turn comprises an amino acid sequence of SEQ ID NO: 9 or an amino acid sequence that differs from SEQ ID NO: 9 by 1 amino acid residue. In some embodiments, the first turn comprises an amino acid sequence having at least 75% sequence identity to SEQ ID NO: 9. In some embodiments, the first turn comprises an amino acid sequence of SEQ ID NO: 9.

In some embodiments, the first coil of the polypeptide linker of a presently disclosed engineered meganuclease comprises 13 amino acids. In some embodiments, the first coil comprises residues corresponding to residues 158-170 of SEQ ID NO: 24. In some embodiments, the first coil comprises a non-polar amino acid at a residue corresponding to residue 158 of SEQ ID NO: 24. In some embodiments, the first coil comprises I, V, or A at residue 158 of SEQ ID NO: 24. In some embodiments, the first coil comprises V at residue 158 of SEQ ID NO: 24. In some embodiments, the first coil comprises a polar amino acid at a residue corresponding to residue 159 of SEQ ID NO: 24. In some embodiments, the first coil comprises Q. G, or R at a residue corresponding to residue 159 of SEQ ID NO: 24. In some embodiments, the first coil comprises R at a residue corresponding to residue 159 of SEQ ID NO: 24. In some embodiments, the first coil comprises a non-polar amino acid at a residue corresponding to residue 160 of SEQ ID NO: 24. In some embodiments, the first coil comprises L, V, or P at a residue corresponding to residue 160 of SEQ ID NO: 24. In some embodiments, the first coil comprises L at a residue corresponding to residue 160 of SEQ ID NO: 24. In some embodiments, the first coil comprises N, Q, H, S, or G at a residue corresponding to residue 161 of SEQ ID NO: 24. In some embodiments, the first coil comprises H at a residue corresponding to residue 161 of SEQ ID NO: 24. In some embodiments, the first coil comprises K, V, C, Q, or G at a residue corresponding to residue 162 of SEQ ID NO: 24. In some embodiments, the first coil comprises C at a residue corresponding to residue 162 of SEQ ID NO: 24. In some embodiments, the first coil comprises E, H, P, G, or V at a residue corresponding to residue 163 of SEQ ID NO: 24. In some embodiments, the first coil comprises P at a residue corresponding to residue 163 of SEQ ID NO: 24. In some embodiments, the first coil comprises S, R, L, or A at a residue corresponding to residue 164 of SEQ ID NO: 24. In some embodiments, the first coil comprises L at a residue corresponding to residue 164 of SEQ ID NO: 30) 24. In some embodiments, the first coil comprises a polar amino acid at a residue corresponding to residue 165 of SEQ ID NO: 24. In some embodiments, the first coil comprises N at a residue corresponding to residue 165 of SEQ ID NO: 24. In some embodiments, the first coil comprises N at a residue corresponding to residue 166 of SEQ ID NO: 24. In some embodiments, the first coil comprises a polar amino acid at a residue corresponding to residue 167 of SEQ ID NO: 24. In some embodiments, the first coil comprises N at a residue corresponding to residue 167 of SEQ ID NO: 24. In some embodiments, the first coil comprises a polar amino acid at a residue corresponding to residue 168 of SEQ ID NO: 24. In some embodiments, the first coil comprises a small amino acid at a residue corresponding to residue 168 of SEQ ID NO: 24. In some embodiments, the first coil comprises A at a residue corresponding to residue 168 of SEQ ID NO: 24. In some embodiments, the first coil comprises a polar amino acid at a residue corresponding to residue 169 of SEQ ID NO: 24. In some embodiments, the first coil comprises S at a residue corresponding to residue 169 of SEQ ID NO: 24. In some embodiments, the first coil comprises a polar amino acid at a residue corresponding to residue 170 of SEQ ID NO: 24. In some embodiments, the first coil comprises a small amino acid at a residue corresponding to residue 170 of SEQ ID NO: 24. In some embodiments, the first coil comprises T at a residue corresponding to residue 170 of SEQ ID NO: 24. In some embodiments, the first coil of the polypeptide linker comprises an amino acid sequence of SEQ ID NO: 12 or an amino acid sequence that differs from SEQ ID NO: 12 by 1, 2, or 3 amino acid residues. In some embodiments, the first coil comprises an amino acid sequence having at least 76%, at least 84%, at least 92%, or more, sequence identity to SEQ ID NO: 12. In some embodiments, the first coil comprises an amino acid sequence of SEQ ID NO: 12.

In some embodiments, the second coil of the polypeptide linker of a presently disclosed engineered meganuclease comprises 9 amino acids. In some embodiments, the second coil comprises residues corresponding to residues 171-179 of SEQ ID NO: 24. In some embodiments, the second coil comprises a Q at a residue corresponding to residue 171 of SEQ ID NO: 24. In some embodiments, the second coil comprises R at a residue corresponding to residue 172 of SEQ ID NO: 24. In some embodiments, the second coil comprises P at a residue corresponding to residue 173 of SEQ ID NO: 24. In some embodiments, the second coil comprises a QRP motif (set forth as SEQ ID NO: 15) at residues corresponding to residues 171-173 of SEQ ID NO: 24. In some embodiments, the second coil comprises S at a residue corresponding to residue 174 of SEQ ID NO: 24. In some embodiments, the second coil comprises R at a residue corresponding to residue 175 of SEQ ID NO: 24. In some embodiments, the second coil comprises a polar amino acid at a residue corresponding to residue 176 of SEQ ID NO: 24. In some embodiments, the second coil comprises N at a residue corresponding to residue 176 of SEQ ID NO: 24. In some embodiments, the second coil comprises a non-polar amino acid at a residue corresponding to residue 177 of SEQ ID NO: 24. In some embodiments, the second coil comprises V at a residue corresponding to residue 177 of SEQ ID NO: 24. In some embodiments, the second coil comprises a polar amino acid at a residue corresponding to residue 178 of SEQ ID NO: 24. In some embodiments, the second coil comprises N at a residue corresponding to residue 178 of SEQ ID NO: 24. In some embodiments, the second coil comprises a polar amino acid at a residue corresponding to residue 179 of SEQ ID NO: 24. In some embodiments, the second coil comprises N at a residue corresponding to residue 179 of SEQ ID NO: 24. In some embodiments, the second coil comprise an amino acid sequence of SEQ ID NO: 16 or an amino acid sequence that differs from SEQ ID NO: 16 by 1 or 2 amino acid residues. In some embodiments, the second coil comprises an amino acid sequence having at least 77%, at least 88%, or more, sequence identity to SEQ ID NO: 16. In some embodiments, the second coil comprises an amino acid sequence of SEQ ID NO: 16.

In some embodiments, the second turn of the polypeptide linker of a presently disclosed engineered meganuclease comprises 4 amino acids. In some embodiments, the second turn comprises residues corresponding to residues 180-183 of SEQ ID NO: 24. In some embodiments, the second turn comprises a non-polar amino acid at a residue corresponding to residue 180 of SEQ ID NO: 24. In some embodiments, the second turn comprises F at a residue corresponding to residue 180 of SEQ ID NO: 24. In some embodiments, the second turn comprises P at a residue corresponding to residue 181 of SEQ ID NO: 24. In some embodiments, the second turn comprises Y. Q, or L at a residue corresponding to residue 182 of SEQ ID NO: 24. In some embodiments, the second turn comprises Q at a residue corresponding to residue 182 of SEQ ID NO: 24. In some embodiments, the second turn comprises a polar amino acid at a residue corresponding to residue 183 of SEQ ID NO: 24. In some embodiments, the second turn comprises a small amino acid at a residue corresponding to residue 183 of SEQ ID NO: 24. In some embodiments, the second turn comprises S. K, or G at a position corresponding to residue 183 of SEQ ID NO: 24. In some embodiments, the second turn comprises G at a position corresponding to residue 183 of SEQ ID NO: 24. In some embodiments, the second turn comprises an amino acid sequence of SEQ ID NO: 19 or an amino acid sequence that differs from SEQ ID NO: 19 by 1 amino acid residue. In some embodiments, the second turn comprises an amino acid sequence having at least 80% sequence identity to SEQ ID NO: 19. In some embodiments, the second turn comprises an amino acid sequence of SEQ ID NO: 19.

In some embodiments, the engineered meganuclease comprises a polypeptide linker comprising a first turn comprising an amino acid sequence of SEQ ID NO: 9 or an amino acid sequence that differs from SEQ ID NO: 9 by 1 amino acid residue, a first coil comprising an amino acid sequence of SEQ ID NO: 12 or an amino acid sequence that differs from SEQ ID NO: 12 by 1-3 amino acid residues, a second coil comprising an amino acid sequence of SEQ ID NO: 16 or an amino acid sequence that differs from SEQ ID NO: 16 by 1 or 2 amino acid residues, and a second turn comprising an amino acid sequence of SEQ ID NO: 19 or an amino acid sequence that differs from SEQ ID NO: 19 by 1 amino acid residue.

In some embodiments, the engineered meganuclease comprises a polypeptide linker comprising a first turn comprising an amino acid sequence of SEQ ID NO: 9, a first coil comprising an amino acid sequence of SEQ ID NO: 12, a second coil comprising an amino acid sequence of SEQ ID NO: 16, and a second turn comprising an amino acid sequence of SEQ ID NO: 19.

In some embodiments, the polypeptide linker comprises an amino acid sequence of SEQ ID NO: 6 or an amino acid sequence that differs from SEQ ID NO: 6 by 1, 2, 3, 4, 5, or 6 amino acid residues.

In some embodiments, the engineered meganuclease comprises a first subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 6-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 4-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 3-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 1. In some embodiments, the first subunit comprises a residue other than M at a position corresponding to position 1 of SEQ ID NO: 1. In some embodiments, the first subunit comprises an A residue at a position corresponding to position 1 of SEQ ID NO: 1. In some embodiments, the engineered meganuclease comprises a first subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 1. In some embodiments, the first subunit comprises a Y at a position corresponding to position 37 of SEQ ID NO: 1. In some embodiments, the first subunit comprises an A at a position corresponding to position 96 of SEQ ID NO: 1. In some embodiments, the first subunit comprises an A at a position corresponding to position 99 of SEQ ID NO: 1. In some embodiments, the first subunit comprises a D at a position corresponding to position 100 of SEQ ID NO: 1. In some embodiments, the first subunit comprises an A at a position corresponding to position 99 of SEQ ID NO: 1 and a D at a position corresponding to position 100 of SEQ ID NO: 1. In some embodiments, the first subunit comprises an A at a position corresponding to position 96 of SEQ ID NO: 1, an A at a position corresponding to position 99 of SEQ ID NO: 1, and a D at a position corresponding to position 100 of SEQ ID NO: 1. In some embodiments, the first subunit comprises a Y at a position corresponding to position 37 of SEQ ID NO: 1 and an A at a position corresponding to position 96 of SEQ ID NO: 1. In some embodiments, the first subunit comprises a Y at a position corresponding to position 37 of SEQ ID NO: 1, an A at a position corresponding to position 99 of SEQ ID NO: 1, and a D at a position corresponding to position 100 of SEQ ID NO: 1. In some embodiments, the first subunit comprises a Y at a position corresponding to position 37 of SEQ ID NO: 1, an A at a position corresponding to position 96 of SEQ ID NO: 1, an A at a position corresponding to position 99 of SEQ ID NO: 1, and a D at a position corresponding to position 100 of SEQ ID NO: 1. In some embodiments, the first subunit comprises a specificity-altering amino acid modification at one or more positions corresponding to positions 24, 26, 28, 30, 32, 33, 38, 40, 42, 44, 46, 66, 68, 70, 76, 77, 79, or 139 of SEQ ID NO: 1. In some embodiments, the first subunit comprises a specificity-altering amino acid modification at one or more positions corresponding to positions 71, 72, 73, or 74 of SEQ ID NO: 1. In some embodiments, the first subunit comprises a DNA binding affinity-altering modification at one or more positions corresponding to positions 29, 34, 48, 51, 64, 80, 81, 82, 112, 116, 137, 139, or 143 of SEQ ID NO: 1. In some embodiments, the first subunit comprises a cleavage activity-altering modification at one or more positions corresponding to positions 19, 48, and 50 of SEQ ID NO: 1.

In some embodiments, the engineered meganuclease comprises a second subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 1. In some embodiments, the engineered meganuclease comprises a second subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1. In some embodiments, the second subunit comprises a F at a position corresponding to position 53 of SEQ ID NO: 1. In some embodiments, the second subunit comprises a Y at a position corresponding to position 57 of SEQ ID NO: 1. In some embodiments, the second subunit comprises a T at a position corresponding to position 61 of SEQ ID NO: 1. In some embodiments, the second subunit comprises a Y at a position corresponding to position 57 of SEQ ID NO: 1 and a T at a position corresponding to position 61 of SEQ ID NO: 1. In some embodiments, the second subunit comprises an F at a position corresponding to position 53 of SEQ ID NO: 1, a Y at a position corresponding to position 57 of SEQ ID NO: 1, and a T at a position corresponding to position 61 of SEQ ID NO: 1. In some embodiments, the second subunit comprises a specificity-altering amino acid modification at one or more positions corresponding to positions 24, 26, 28, 30, 32, 33, 38, 40, 42, 44, 46, 66, 68, 70, 76, 77, 79, or 139 of SEQ ID NO: 1. In some embodiments, the second subunit comprises a specificity-altering amino acid modification at one or more positions corresponding to positions 71, 72, 73, or 74 of SEQ ID NO: 1. In some embodiments, the second subunit comprises a DNA binding affinity-altering modification at one or more positions corresponding to positions 29, 34, 48, 51, 64, 80, 81, 82, 112, 116, 137, 139, or 143 of SEQ ID NO: 1. In some embodiments, the second subunit comprises a cleavage activity-altering modification at one or more positions corresponding to positions 19, 48, and 50 of SEQ ID NO: 1.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 1, wherein the first subunit comprises an A at a position corresponding to position 96 of SEQ ID NO: 1, an A at a position corresponding to position 99 of SEQ ID NO: 1, and a D at a position corresponding to position 100 of SEQ ID NO: 1, and the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1, wherein the second subunit comprises a Y at a position corresponding to position 57 of SEQ ID NO: 1 and a T at a position corresponding to position 61 of SEQ ID NO: 1.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 1, wherein the first subunit comprises an A at a position corresponding to position 96 of SEQ ID NO: 1, an A at a position corresponding to position 99 of SEQ ID NO: 1, and a D at a position corresponding to position 100 of SEQ ID NO: 1, and the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1, wherein the second subunit comprises a Y at a position corresponding to position 57 of SEQ ID NO: 1 and a T at a position corresponding to position 61 of SEQ ID NO: 1.

In some embodiments, the N-terminus of the polypeptide linker is covalently bound to the first subunit at a residue corresponding to any one of positions 153-163 of SEQ ID NO: 1. In some embodiments, the N-terminus of the polypeptide linker is covalently bound to the first subunit at a D residue corresponding to position 153 of SEQ ID NO: 1. In some embodiments, the C-terminus of the polypeptide linker is covalently bound to the second subunit at a residue corresponding to any one of positions 1-9 of SEQ ID NO: 1. In some embodiments, the C-terminus of the polypeptide linker is covalently bound to the second subunit at a Y residue corresponding to position 5 of SEQ ID NO: 1.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91% at least 92%, at least 93%, at least 94%, at least 95%, at least 96%, at least 97%, at least 98%, at least 99%, or more, sequence identity to SEQ ID NO: 24.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91% at least 92%, at least 93%, at least 94%, at least 95%, at least 96%, at least 97%, at least 98%, at least 99%, or more, sequence identity to a nucleic acid sequence of SEQ ID NO: 24, wherein the polypeptide linker comprises SEQ ID NO: 6. In some of these embodiments, the first subunit of the engineered meganuclease comprises an A at position 96, an A at position 99, and a D at position 100, and the said second subunit comprises a Y at position 236 and a T at position 240, or positions corresponding to the identified positions when aligned for maximum identity across the subunit as described herein.

In some embodiments, the engineered meganuclease comprises a targeting signal, such as a nuclear localization signal (NLS) or a mitochondrial targeting signal (MTS). In some embodiments, the targeting signal is at the N-terminus of the engineered meganuclease. In some embodiments, the targeting signal is at the C-terminus of the engineered meganuclease.

Linker1808 Reference Meganuclease

In some embodiments, the first turn of the polypeptide linker of a presently disclosed engineered meganuclease comprises 4 amino acid residues. In some embodiments, the first turn comprises residues corresponding to residues 154-157 of SEQ ID NO: 25. In some embodiments, the first turn comprises a residue corresponding to residue 154 of SEQ ID NO: 25. In some embodiments, the first turn comprises a residue corresponding to residue 155 of SEQ ID NO: 25. In some embodiments, the first turn comprises a residue corresponding to residue 156 of SEQ ID NO: 25. In some embodiments, the first turn comprises a residue corresponding to residue 157 of SEQ ID NO: 25. In some embodiments, the first turn of the polypeptide linker comprises an SLPG motif, set forth as SEQ ID NO: 9. In some embodiments, the first turn comprises an amino acid sequence of SEQ ID NO: 9 or an amino acid sequence that differs from SEQ ID NO: 9 by 1 amino acid residue. In some embodiments, the first turn comprises an amino acid sequence having at least 75% sequence identity to SEQ ID NO: 9. In some embodiments, the first turn comprises an amino acid sequence of SEQ ID NO: 9.

In some embodiments, the first coil of the polypeptide linker of a presently disclosed engineered meganuclease comprises 13 amino acids. In some embodiments, the first coil comprises residues corresponding to residues 158-170 of SEQ ID NO: 25. In some embodiments, the first coil comprises a non-polar amino acid at a residue corresponding to residue 158 of SEQ ID NO: 25. In some embodiments, the first coil comprises I, V, or A at residue 158 of SEQ ID NO: 25. In some embodiments, the first coil comprises I at residue 158 of SEQ ID NO: 25. In some embodiments, the first coil comprises a polar amino acid at a residue corresponding to residue 159 of SEQ ID NO: 25. In some embodiments, the first coil comprises Q. G, or R at a residue corresponding to residue 159 of SEQ ID NO: 25. In some embodiments, the first coil comprises R at a residue corresponding to residue 159 of SEQ ID NO: 25. In some embodiments, the first coil comprises a non-polar amino acid at a residue corresponding to residue 160 of SEQ ID NO: 25. In some embodiments, the first coil comprises L, V, or P at a residue corresponding to residue 160 of SEQ ID NO: 25. In some embodiments, the first coil comprises L at a residue corresponding to residue 160 of SEQ ID NO: 25. In some embodiments, the first coil comprises N, Q, H, S, or G at a residue corresponding to residue 161 of SEQ ID NO: 25. In some embodiments, the first coil comprises S at a residue corresponding to residue 161 of SEQ ID NO: 25. In some embodiments, the first coil comprises K, V, C, Q, or G at a residue corresponding to residue 162 of SEQ ID NO: 25. In some embodiments, the first coil comprises Q at a residue corresponding to residue 162 of SEQ ID NO: 25. In some embodiments, the first coil comprises E, H, P, G, or V at a residue corresponding to residue 163 of SEQ ID NO: 25. In some embodiments, the first coil comprises G at a residue corresponding to residue 163 of SEQ ID NO: 25. In some embodiments, the first coil comprises S, R, L, or A at a residue corresponding to residue 164 of SEQ ID NO: 25. In some embodiments, the first coil comprises A at a residue corresponding to residue 164 of SEQ ID NO: 25. In some embodiments, the first coil comprises a polar amino acid at a residue corresponding to residue 165 of SEQ ID NO: 25. In some embodiments, the first coil comprises N at a residue corresponding to residue 165 of SEQ ID NO: 25. In some embodiments, the first coil comprises N at a residue corresponding to residue 166 of SEQ ID NO: 25. In some embodiments, the first coil comprises a polar amino acid at a residue corresponding to residue 167 of SEQ ID NO: 25. In some embodiments, the first coil comprises N at a residue corresponding to residue 167 of SEQ ID NO: 25. In some embodiments, the first coil comprises a polar amino acid at a residue corresponding to residue 168 of SEQ ID NO: 25. In some embodiments, the first coil comprises a small amino acid at a residue corresponding to residue 168 of SEQ ID NO: 25. In some embodiments, the first coil comprises A at a residue corresponding to residue 168 of SEQ ID NO: 25. In some embodiments, the first coil comprises a polar amino acid at a residue corresponding to residue 169 of SEQ ID NO: 25. In some embodiments, the first coil comprises S at a residue corresponding to residue 169 of SEQ ID NO: 25. In some embodiments, the first coil comprises a polar amino acid at a residue corresponding to residue 170 of SEQ ID NO: 25. In some embodiments, the first coil comprises a small amino acid at a residue corresponding to residue 170 of SEQ ID NO: 25. In some embodiments, the first coil comprises T at a residue corresponding to residue 170 of SEQ ID NO: 25. In some embodiments, the first coil of the polypeptide linker comprises an amino acid sequence of SEQ ID NO: 13 or an amino acid sequence that differs from SEQ ID NO: 13 by 1, 2, or 3 amino acid residues. In some embodiments, the first coil comprises an amino acid sequence having at least 76%, at least 84%, at least 92%, or more, sequence identity to SEQ ID NO: 13. In some embodiments, the first coil comprises an amino acid sequence of SEQ ID NO: 13.

In some embodiments, the second coil of the polypeptide linker of a presently disclosed engineered meganuclease comprises 9) amino acids. In some embodiments, the second coil comprises residues corresponding to residues 171-179 of SEQ ID NO: 25. In some embodiments, the second coil comprises a Q at a residue corresponding to residue 171 of SEQ ID NO: 25. In some embodiments, the second coil comprises R at a residue corresponding to residue 172 of SEQ ID NO: 25. In some embodiments, the second coil comprises P at a residue corresponding to residue 173 of SEQ ID NO: 25. In some embodiments, the second coil comprises a QRP motif (set forth as SEQ ID NO: 15) at residues corresponding to residues 171-173 of SEQ ID NO: 25. In some embodiments, the second coil comprises S at a residue corresponding to residue 174 of SEQ ID NO: 25. In some embodiments, the second coil comprises R at a residue corresponding to residue 175 of SEQ ID NO: 25. In some embodiments, the second coil comprises a polar amino acid at a residue corresponding to residue 176 of SEQ ID NO: 25. In some embodiments, the second coil comprises N at a residue corresponding to residue 176 of SEQ ID NO: 25. In some embodiments, the second coil comprises a non-polar amino acid at a residue corresponding to residue 177 of SEQ ID NO: 25. In some embodiments, the second coil comprises V at a residue corresponding to residue 177 of SEQ ID NO: 25. In some embodiments, the second coil comprises a polar amino acid at a residue corresponding to residue 178 of SEQ ID NO: 25. In some embodiments, the second coil comprises N at a residue corresponding to residue 178 of SEQ ID NO: 25. In some embodiments, the second coil comprises a polar amino acid at a residue corresponding to residue 179 of SEQ ID NO: 25. In some embodiments, the second coil comprises N at a residue corresponding to residue 179 of SEQ ID NO: 25. In some embodiments, the second coil comprise an amino acid sequence of SEQ ID NO: 16 or an amino acid sequence that differs from SEQ ID NO: 16 by 1 or 2 amino acid residues. In some embodiments, the second coil comprises an amino acid sequence having at least 77%, at least 88%, or more, sequence identity to SEQ ID NO: 16. In some embodiments, the second coil comprises an amino acid sequence of SEQ ID NO: 16.

In some embodiments, the second turn of the polypeptide linker of a presently disclosed engineered meganuclease comprises 4 amino acids. In some embodiments, the second turn comprises residues corresponding to residues 180-184 of SEQ ID NO: 25. In some embodiments, the second turn comprises a non-polar amino acid at a residue corresponding to residue 180 of SEQ ID NO: 25. In some embodiments, the second turn comprises F at a residue corresponding to residue 180 of SEQ ID NO: 25. In some embodiments, the second turn comprises P at a residue corresponding to residue 181 of SEQ ID NO: 25. In some embodiments, the second turn comprises Y, Q, or L at a residue corresponding to residue 182 of SEQ ID NO: 25. In some embodiments, the second turn comprises L at a residue corresponding to residue 182 of SEQ ID NO: 25. In some embodiments, the second turn comprises a polar amino acid at a residue corresponding to residue 183 of SEQ ID NO: 25. In some embodiments, the second turn comprises a small amino acid at a residue corresponding to residue 183 of SEQ ID NO: 25. In some embodiments, the second turn comprises S. K, or G at a position corresponding to residue 183 of SEQ ID NO: 25. In some embodiments, the second turn comprises G at a position corresponding to residue 183 of SEQ ID NO: 25. In some embodiments, the second turn comprises an amino acid sequence of SEQ ID NO: 20) or an amino acid sequence that differs from SEQ ID NO: 20 by 1 amino acid residue. In some embodiments, the second turn comprises an amino acid sequence having at least 80% sequence identity to SEQ ID NO: 20. In some embodiments, the second turn comprises an amino acid sequence of SEQ ID NO: 20.

In some embodiments, the engineered meganuclease comprises a polypeptide linker comprising a first turn comprising an amino acid sequence of SEQ ID NO: 9 or an amino acid sequence that differs from SEQ ID NO: 9 by 1 amino acid residue, a first coil comprising an amino acid sequence of SEQ ID NO: 13 or an amino acid sequence that differs from SEQ ID NO: 13 by 1-3 amino acid residues, a second coil comprising an amino acid sequence of SEQ ID NO: 16 or an amino acid sequence that differs from SEQ ID NO: 16 by 1 or 2 amino acid residues, and a second turn comprising an amino acid sequence of SEQ ID NO: 20 or an amino acid sequence that differs from SEQ ID NO: 20 by 1 amino acid residue.

In some embodiments, the engineered meganuclease comprises a polypeptide linker comprising a first turn comprising an amino acid sequence of SEQ ID NO: 9, a first coil comprising an amino acid sequence of SEQ ID NO: 13, a second coil comprising an amino acid sequence of SEQ ID NO: 16, and a second turn comprising an amino acid sequence of SEQ ID NO: 20.

In some embodiments, the polypeptide linker comprises an amino acid sequence of SEQ ID NO: 7 or an amino acid sequence that differs from SEQ ID NO: 7 by 1, 2, 3, 4, 5, or 6 amino acid residues.

In some embodiments, the engineered meganuclease comprises a first subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 6-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 4-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 3-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 1. In some embodiments, the first subunit comprises a residue other than M at a position corresponding to position 1 of SEQ ID NO: 1. In some embodiments, the first subunit comprises an A residue at a position corresponding to position 1 of SEQ ID NO: 1. In some embodiments, the engineered meganuclease comprises a first subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 1. In some embodiments, the first subunit comprises a Y at a position corresponding to position 37 of SEQ ID NO: 1. In some embodiments, the first subunit comprises an A at a position corresponding to position 96 of SEQ ID NO: 1. In some embodiments, the first subunit comprises an A at a position corresponding to position 99 of SEQ ID NO: 1. In some embodiments, the first subunit comprises a D at a position corresponding to position 100 of SEQ ID NO: 1. In some embodiments, the first subunit comprises an A at a position corresponding to position 99 of SEQ ID NO: 1 and a D at a position corresponding to position 100 of SEQ ID NO: 1. In some embodiments, the first subunit comprises an A at a position corresponding to position 96 of SEQ ID NO: 1, an A at a position corresponding to position 99 of SEQ ID NO: 1, and a D at a position corresponding to position 100 of SEQ ID NO: 1. In some embodiments, the first subunit comprises a Y at a position corresponding to position 37 of SEQ ID NO: 1 and an A at a position corresponding to position 96 of SEQ ID NO: 1. In some embodiments, the first subunit comprises a Y at a position corresponding to position 37 of SEQ ID NO: 1, an A at a position corresponding to position 99 of SEQ ID NO: 1, and a D at a position corresponding to position 100 of SEQ ID NO: 1. In some embodiments, the first subunit comprises a Y at a position corresponding to position 37 of SEQ ID NO: 1, an A at a position corresponding to position 96 of SEQ ID NO: 1, an A at a position corresponding to position 99 of SEQ ID NO: 1, and a D at a position corresponding to position 100 of SEQ ID NO: 1. In some embodiments, the first subunit comprises a specificity-altering amino acid modification at one or more positions corresponding to positions 24, 26, 28, 30, 32, 33, 38, 40, 42, 44, 46, 66, 68, 70, 76, 77, 79, or 139 of SEQ ID NO: 1. In some embodiments, the first subunit comprises a specificity-altering amino acid modification at one or more positions corresponding to positions 71, 72, 73, or 74 of SEQ ID NO: 1. In some embodiments, the first subunit comprises a DNA binding affinity-altering modification at one or more positions corresponding to positions 29, 34, 48, 51, 64, 80, 81, 82, 112, 116, 137, 139, or 143 of SEQ ID NO: 1. In some embodiments, the first subunit comprises a cleavage activity-altering modification at one or more positions corresponding to positions 19, 48, and 50 of SEQ ID NO: 1.

In some embodiments, the engineered meganuclease comprises a second subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 1. In some embodiments, the engineered meganuclease comprises a second subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1. In some embodiments, the second subunit comprises a F at a position corresponding to position 53 of SEQ ID NO: 1. In some embodiments, the second subunit comprises a Y at a position corresponding to position 57 of SEQ ID NO: 1. In some embodiments, the second subunit comprises a T at a position corresponding to position 61 of SEQ ID NO: 1. In some embodiments, the second subunit comprises a Y at a position corresponding to position 57 of SEQ ID NO: 1 and a T at a position corresponding to position 61 of SEQ ID NO: 1. In some embodiments, the second subunit comprises an F at a position corresponding to position 53 of SEQ ID NO: 1, a Y at a position corresponding to position 57 of SEQ ID NO: 1, and a T at a position corresponding to position 61 of SEQ ID NO: 1. In some embodiments, the second subunit comprises a specificity-altering amino acid modification at one or more positions corresponding to positions 24, 26, 28, 30, 32, 33, 38, 40, 42, 44, 46, 66, 68, 70, 76, 77, 79, or 139 of SEQ ID NO: 1. In some embodiments, the second subunit comprises a specificity-altering amino acid modification at one or more positions corresponding to positions 71, 72, 73, or 74 of SEQ ID NO: 1. In some embodiments, the second subunit comprises a DNA binding affinity-altering modification at one or more positions corresponding to positions 29, 34, 48, 51, 64, 80, 81, 82, 112, 116, 137, 139, or 143 of SEQ ID NO: 1. In some embodiments, the second subunit comprises a cleavage activity-altering modification at one or more positions corresponding to positions 19, 48, and 50 of SEQ ID NO: 1.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 1, wherein the first subunit comprises an A at a position corresponding to position 96 of SEQ ID NO: 1, an A at a position corresponding to position 99 of SEQ ID NO: 1, and a D at a position corresponding to position 100 of SEQ ID NO: 1, and the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1, wherein the second subunit comprises a Y at a position corresponding to position 57 of SEQ ID NO: 1 and a T at a position corresponding to position 61 of SEQ ID NO: 1.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 1, wherein the first subunit comprises an A at a position corresponding to position 96 of SEQ ID NO: 1, an A at a position corresponding to position 99 of SEQ ID NO: 1, and a D at a position corresponding to position 100 of SEQ ID NO: 1, and the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1, wherein the second subunit comprises a Y at a position corresponding to position 57 of SEQ ID NO: 1 and a T at a position corresponding to position 61 of SEQ ID NO: 1.

In some embodiments, the N-terminus of the polypeptide linker is covalently bound to the first subunit at a residue corresponding to any one of positions 153-163 of SEQ ID NO: 1. In some embodiments, the N-terminus of the polypeptide linker is covalently bound to the first subunit at a D residue corresponding to position 153 of SEQ ID NO: 1. In some embodiments, the C-terminus of the polypeptide linker is covalently bound to the second subunit at a residue corresponding to any one of positions 1-9 of SEQ ID NO: 1. In some embodiments, the C-terminus of the polypeptide linker is covalently bound to the second subunit at a Y residue corresponding to position 5 of SEQ ID NO: 1.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91% at least 92%, at least 93%, at least 94%, at least 95%, at least 96%, at least 97%, at least 98%, at least 99%, or more, sequence identity to SEQ ID NO: 25.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91% at least 92%, at least 93%, at least 94%, at least 95%, at least 96%, at least 97%, at least 98%, at least 99%, or more, sequence identity to a nucleic acid sequence of SEQ ID NO: 25, wherein the polypeptide linker comprises SEQ ID NO: 7. In some of these embodiments, the first subunit of the engineered meganuclease comprises an A at position 96, an A at position 99, and a D at position 100, and the said second subunit comprises a Y at position 236 and a T at position 240, or positions corresponding to the identified positions when aligned for maximum identity across the subunit as described herein.

In some embodiments, the engineered meganuclease comprises a targeting signal, such as a nuclear localization signal (NLS) or a mitochondrial targeting signal (MTS). In some embodiments, the targeting signal is at the N-terminus of the engineered meganuclease. In some embodiments, the targeting signal is at the C-terminus of the engineered meganuclease.

Linker1814 Reference Meganuclease

In some embodiments, the first turn of the polypeptide linker of a presently disclosed engineered meganuclease comprises 4 amino acid residues. In some embodiments, the first turn comprises residues corresponding to residues 154-157 of SEQ ID NO: 26. In some embodiments, the first turn comprises a residue corresponding to residue 154 of SEQ ID NO: 26. In some embodiments, the first turn comprises a residue corresponding to residue 155 of SEQ ID NO: 26. In some embodiments, the first turn comprises a residue corresponding to residue 156 of SEQ ID NO: 26. In some embodiments, the first turn comprises a residue corresponding to residue 157 of SEQ ID NO: 26. In some embodiments, the first turn of the polypeptide linker comprises an SLPG motif, set forth as SEQ ID NO: 9. In some embodiments, the first turn comprises an amino acid sequence of SEQ ID NO: 9 or an amino acid sequence that differs from SEQ ID NO: 9 by 1 amino acid residue. In some embodiments, the first turn comprises an amino acid sequence having at least 75% sequence identity to SEQ ID NO: 9. In some embodiments, the first turn comprises an amino acid sequence of SEQ ID NO: 9.

In some embodiments, the first coil of the polypeptide linker of a presently disclosed engineered meganuclease comprises 13 amino acids. In some embodiments, the first coil comprises residues corresponding to residues 158-170 of SEQ ID NO: 26. In some embodiments, the first coil comprises a non-polar amino acid at a residue corresponding to residue 158 of SEQ ID NO: 26. In some embodiments, the first coil comprises I, V, or A at residue 158 of SEQ ID NO: 26. In some embodiments, the first coil comprises A at residue 158 of SEQ ID NO: 26. In some embodiments, the first coil comprises a polar amino acid at a residue corresponding to residue 159 of SEQ ID NO: 26. In some embodiments, the first coil comprises Q. G, or R at a residue corresponding to residue 159 of SEQ ID NO: 26. In some embodiments, the first coil comprises R at a residue corresponding to residue 159 of SEQ ID NO: 26. In some embodiments, the first coil comprises a non-polar amino acid at a residue corresponding to residue 160 of SEQ ID NO: 26. In some embodiments, the first coil comprises L, V, or P at a residue corresponding to residue 160 of SEQ ID NO: 26. In some embodiments, the first coil comprises P at a residue corresponding to residue 160 of SEQ ID NO: 26. In some embodiments, the first coil comprises N, Q, H, S, or G at a residue corresponding to residue 161 of SEQ ID NO: 26. In some embodiments, the first coil comprises G at a residue corresponding to residue 161 of SEQ ID NO: 26. In some embodiments, the first coil comprises K, V, C, Q, or G at a residue corresponding to residue 162 of SEQ ID NO: 26. In some embodiments, the first coil comprises G at a residue corresponding to residue 162 of SEQ ID NO: 26. In some embodiments, the first coil comprises E, H, P, G, or V at a residue corresponding to residue 163 of SEQ ID NO: 26. In some embodiments, the first coil comprises V at a residue corresponding to residue 163 of SEQ ID NO: 26. In some embodiments, the first coil comprises S, R, L, or A at a residue corresponding to residue 164 of SEQ ID NO: 26. In some embodiments, the first coil comprises S at a residue corresponding to residue 164 of SEQ ID NO: 26. In some embodiments, the first coil comprises a polar amino acid at a residue corresponding to residue 165 of SEQ ID NO: 26. In some embodiments, the first coil comprises N at a residue corresponding to residue 165 of SEQ ID NO: 26. In some embodiments, the first coil comprises N at a residue corresponding to residue 166 of SEQ ID NO: 26. In some embodiments, the first coil comprises a polar amino acid at a residue corresponding to residue 167 of SEQ ID NO: 26. In some embodiments, the first coil comprises N at a residue corresponding to residue 167 of SEQ ID NO: 26. In some embodiments, the first coil comprises a polar amino acid at a residue corresponding to residue 168 of SEQ ID NO: 26. In some embodiments, the first coil comprises a small amino acid at a residue corresponding to residue 168 of SEQ ID NO: 26. In some embodiments, the first coil comprises A at a residue corresponding to residue 168 of SEQ ID NO: 26.

In some embodiments, the first coil comprises a polar amino acid at a residue corresponding to residue 169 of SEQ ID NO: 26. In some embodiments, the first coil comprises S at a residue corresponding to residue 169 of SEQ ID NO: 26. In some embodiments, the first coil comprises a polar amino acid at a residue corresponding to residue 170 of SEQ ID NO: 26. In some embodiments, the first coil comprises a small amino acid at a residue corresponding to residue 170) of SEQ ID NO: 26. In some embodiments, the first coil comprises T at a residue corresponding to residue 170 of SEQ ID NO: 26. In some embodiments, the first coil of the polypeptide linker comprises an amino acid sequence of SEQ ID NO: 14 or an amino acid sequence that differs from SEQ ID NO: 14 by 1, 2, or 3 amino acid residues. In some embodiments, the first coil comprises an amino acid sequence having at least 76%, at least 84%, at least 92%, or more, sequence identity to SEQ ID NO: 14. In some embodiments, the first coil comprises an amino acid sequence of SEQ ID NO: 14.

In some embodiments, the second coil of the polypeptide linker of a presently disclosed engineered meganuclease comprises 9 amino acids. In some embodiments, the second coil comprises residues corresponding to residues 171-179 of SEQ ID NO: 26. In some embodiments, the second coil comprises a Q at a residue corresponding to residue 171 of SEQ ID NO: 26. In some embodiments, the second coil comprises R at a residue corresponding to residue 172 of SEQ ID NO: 26. In some embodiments, the second coil comprises P at a residue corresponding to residue 173 of SEQ ID NO: 26. In some embodiments, the second coil comprises a QRP motif (set forth as SEQ ID NO: 15) at residues corresponding to residues 171-173 of SEQ ID NO: 26. In some embodiments, the second coil comprises S at a residue corresponding to residue 174 of SEQ ID NO: 26. In some embodiments, the second coil comprises R at a residue corresponding to residue 175 of SEQ ID NO: 26. In some embodiments, the second coil comprises a polar amino acid at a residue corresponding to residue 176 of SEQ ID NO: 26. In some embodiments, the second coil comprises N at a residue corresponding to residue 176 of SEQ ID NO: 26. In some embodiments, the second coil comprises a non-polar amino acid at a residue corresponding to residue 177 of SEQ ID NO: 26. In some embodiments, the second coil comprises V at a residue corresponding to residue 177 of SEQ ID NO: 26. In some embodiments, the second coil comprises a polar amino acid at a residue corresponding to residue 178 of SEQ ID NO: 26. In some embodiments, the second coil comprises N at a residue corresponding to residue 178 of SEQ ID NO: 26. In some embodiments, the second coil comprises a polar amino acid at a residue corresponding to residue 179 of SEQ ID NO: 26. In some embodiments, the second coil comprises N at a residue corresponding to residue 179 of SEQ ID NO: 26. In some embodiments, the second coil comprise an amino acid sequence of SEQ ID NO: 16 or an amino acid sequence that differs from SEQ ID NO: 16 by 1 or 2 amino acid residues. In some embodiments, the second coil comprises an amino acid sequence having at least 77%, at least 88%, or more, sequence identity to SEQ ID NO: 16. In some embodiments, the second coil comprises an amino acid sequence of SEQ ID NO: 16.

In some embodiments, the second turn of the polypeptide linker of a presently disclosed engineered meganuclease comprises 5 amino acids. In some embodiments, the second turn comprises residues corresponding to residues 180-184 of SEQ ID NO: 26. In some embodiments, the second turn comprises a non-polar amino acid at a residue corresponding to residue 180 of SEQ ID NO: 26. In some embodiments, the second turn comprises F at a residue corresponding to residue 180 of SEQ ID NO: 26. In some embodiments, the second turn comprises P at a residue corresponding to residue 181 of SEQ ID NO: 26. In some embodiments, the second turn comprises Y, Q, or L at a residue corresponding to residue 182 of SEQ ID NO: 26. In some embodiments, the second turn comprises Y at a residue corresponding to residue 182 of SEQ ID NO: 26. In some embodiments, the second turn comprises a polar amino acid at a residue corresponding to residue 183 of SEQ ID NO: 26. In some embodiments, the second turn comprises a small amino acid at a residue corresponding to residue 183 of SEQ ID NO: 26. In some embodiments, the second turn comprises S, K, or G at a position corresponding to residue 183 of SEQ ID NO: 26. In some embodiments, the second turn comprises S at a position corresponding to residue 183 of SEQ ID NO: 26. In some embodiments, the second turn further comprises residues $X_{31}$ such that the polypeptide linker comprises 31 amino acid residues. In some embodiments, the second turn comprises G at a residue corresponding to residue 184 of SEQ ID NO: 26. In some embodiments, the second turn comprises an amino acid sequence of SEQ ID NO: 21 or an amino acid sequence that differs from SEQ ID NO: 21 by 1 amino acid residue. In some embodiments, the second turn comprises an amino acid sequence having at least 80% sequence identity to SEQ ID NO: 21. In some embodiments, the second turn comprises an amino acid sequence of SEQ ID NO: 21.

In some embodiments, the engineered meganuclease comprises a polypeptide linker comprising a first turn comprising an amino acid sequence of SEQ ID NO: 9 or an amino acid sequence that differs from SEQ ID NO: 9 by 1 amino acid residue, a first coil comprising an amino acid sequence of SEQ ID NO: 14 or an amino acid sequence that differs from SEQ ID NO: 14 by 1-3 amino acid residues, a second coil comprising an amino acid sequence of SEQ ID NO: 16 or an amino acid sequence that differs from SEQ ID NO: 16 by 1 or 2 amino acid residues, and a second turn comprising an amino acid sequence of SEQ ID NO: 21 or an amino acid sequence that differs from SEQ ID NO: 21 by 1 amino acid residue.

In some embodiments, the engineered meganuclease comprises a polypeptide linker comprising a first turn comprising an amino acid sequence of SEQ ID NO: 9, a first coil comprising an amino acid sequence of SEQ ID NO: 14, a second coil comprising an amino acid sequence of SEQ ID NO: 16, and a second turn comprising an amino acid sequence of SEQ ID NO: 21.

In some embodiments, the polypeptide linker comprises an amino acid sequence of SEQ ID NO: 8 or an amino acid sequence that differs from SEQ ID NO: 8 by 1, 2, 3, 4, 5, or 6 amino acid residues.

In some embodiments, the engineered meganuclease comprises a first subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 6-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 4-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 3-153 of SEQ ID NO: 1. In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO: 1. In some embodiments, the first subunit comprises a residue other than M at a position corresponding to position 1 of SEQ ID NO: 1. In some embodiments, the first subunit comprises an A residue at a position corresponding to position 1 of SEQ ID NO: 1. In some embodiments, the engineered meganuclease comprises a first subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 1. In some embodiments, the first subunit comprises a Y at a position corresponding to position 37 of SEQ ID NO: 1. In some embodiments, the first subunit comprises an A at a position corresponding to position 96 of SEQ ID NO: 1. In some embodiments, the first subunit comprises an A at a position corresponding to position 99 of SEQ ID NO: 1. In some embodiments, the first subunit comprises a D at a position corresponding to position 100 of SEQ ID NO: 1. In some embodiments, the first subunit comprises an A at a position corresponding to position 99 of SEQ ID NO: 1 and a D at a position corresponding to position 100 of SEQ ID NO: 1.

In some embodiments, the first subunit comprises an A at a position corresponding to position 96 of SEQ ID NO: 1, an A at a position corresponding to position 99 of SEQ ID NO: 1, and a D at a position corresponding to position 100 of SEQ ID NO: 1. In some embodiments, the first subunit comprises a Y at a position corresponding to position 37 of SEQ ID NO: 1 and an A at a position corresponding to position 96 of SEQ ID NO: 1. In some embodiments, the first subunit comprises a Y at a position corresponding to position 37 of SEQ ID NO: 1, an A at a position corresponding to position 99 of SEQ ID NO: 1, and a D at a position corresponding to position 100 of SEQ ID NO: 1. In some embodiments, the first subunit comprises a Y at a position corresponding to position 37 of SEQ ID NO: 1, an A at a position corresponding to position 96 of SEQ ID NO: 1, an A at a position corresponding to position 99 of SEQ ID NO: 1, and a D at a position corresponding to position 100 of SEQ ID NO: 1. In some embodiments, the first subunit comprises a specificity-altering amino acid modification at one or more positions corresponding to positions 24, 26, 28, 30, 32, 33, 38, 40, 42, 44, 46, 66, 68, 70, 76, 77, 79, or 139 of SEQ ID NO: 1. In some embodiments, the first subunit comprises a specificity-altering amino acid modification at one or more positions corresponding to positions 71, 72, 73, or 74 of SEQ ID NO: 1. In some embodiments, the first subunit comprises a DNA binding affinity-altering modification at one or more positions corresponding to positions 29, 34, 48, 51, 64, 80, 81, 82, 112, 116, 137, 139, or 143 of SEQ ID NO: 1. In some embodiments, the first subunit comprises a cleavage activity-altering modification at one or more positions corresponding to positions 19, 48, and 50 of SEQ ID NO: 1.

In some embodiments, the engineered meganuclease comprises a second subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 7-153 of SEQ ID NO: 1. In some embodiments, the engineered meganuclease comprises a second subunit comprising an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1. In some embodiments, the second subunit comprises a F at a position corresponding to position 53 of SEQ ID NO: 1. In some embodiments, the second subunit comprises a Y at a position corresponding to position 57 of SEQ ID NO: 1. In some embodiments, the second subunit comprises a T at a position corresponding to position 61 of SEQ ID NO: 1. In some embodiments, the second subunit comprises a Y at a position corresponding to position 57 of SEQ ID NO: 1 and a T at a position corresponding to position 61 of SEQ ID NO: 1. In some embodiments, the second subunit comprises an F at a position corresponding to position 53 of SEQ ID NO: 1, a Y at a position corresponding to position 57 of SEQ ID NO: 1, and a T at a position corresponding to position 61 of SEQ ID NO: 1. In some embodiments, the second subunit comprises a specificity-altering amino acid modification at one or more positions corresponding to positions 24, 26, 28, 30, 32, 33, 38, 40, 42, 44, 46, 66, 68, 70, 76, 77, 79, or 139 of SEQ ID NO: 1. In some embodiments, the second subunit comprises a specificity-altering amino acid modification at one or more positions corresponding to positions 71, 72, 73, or 74 of SEQ ID NO: 1. In some embodiments, the second subunit comprises a DNA binding affinity-altering modification at one or more positions corresponding to positions 29, 34, 48, 51, 64, 80, 81, 82, 112, 116, 137, 139, or 143 of SEQ ID NO: 1. In some embodiments, the second subunit comprises a cleavage activity-altering modification at one or more positions corresponding to positions 19, 48, and 50 of SEQ ID NO: 1.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 2-153 of SEQ ID NO:

1, wherein the first subunit comprises an A at a position corresponding to position 96 of SEQ ID NO: 1, an A at a position corresponding to position 99 of SEQ ID NO: 1, and a D at a position corresponding to position 100 of SEQ ID NO: 1, and the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1, wherein the second subunit comprises a Y at a position corresponding to position 57 of SEQ ID NO: 1 and a T at a position corresponding to position 61 of SEQ ID NO: 1.

In some embodiments, the first subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 1-153 of SEQ ID NO: 1, wherein the first subunit comprises an A at a position corresponding to position 96 of SEQ ID NO: 1, an A at a position corresponding to position 99 of SEQ ID NO: 1, and a D at a position corresponding to position 100 of SEQ ID NO: 1, and the second subunit comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to residues 5-163 of SEQ ID NO: 1, wherein the second subunit comprises a Y at a position corresponding to position 57 of SEQ ID NO: 1 and a T at a position corresponding to position 61 of SEQ ID NO: 1.

In some embodiments, the N-terminus of the polypeptide linker is covalently bound to the first subunit at a residue corresponding to any one of positions 153-163 of SEQ ID NO: 1. In some embodiments, the N-terminus of the polypeptide linker is covalently bound to the first subunit at a D residue corresponding to position 153 of SEQ ID NO: 1. In some embodiments, the C-terminus of the polypeptide linker is covalently bound to the second subunit at a residue corresponding to any one of positions 1-9 of SEQ ID NO: 1. In some embodiments, the C-terminus of the polypeptide linker is covalently bound to the second subunit at a Y residue corresponding to position 5 of SEQ ID NO: 1.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91% at least 92%, at least 93%, at least 94%, at least 95%, at least 96%, at least 97%, at least 98%, at least 99%, or more, sequence identity to SEQ ID NO: 26.

In some embodiments, the engineered meganuclease comprises an amino acid sequence having at least 80%, at least 81%, at least 82%, at least 83%, at least 84%, at least 85%, at least 86%, at least 87%, at least 88%, at least 89%, at least 90%, at least 91% at least 92%, at least 93%, at least 94%, at least 95%, at least 96%, at least 97%, at least 98%, at least 99%, or more, sequence identity to a nucleic acid sequence of SEQ ID NO: 26, wherein the polypeptide linker comprises SEQ ID NO: 8. In some of these embodiments, the first subunit of the engineered meganuclease comprises an A at position 96, an A at position 99, and a D at position 100, and the said second subunit comprises a Y at position 237 and a T at position 241, or positions corresponding to the identified positions when aligned for maximum identity across the subunit as described herein.

In some embodiments, the engineered meganuclease comprises a targeting signal, such as a nuclear localization signal (NLS) or a mitochondrial targeting signal (MTS). In some embodiments, the targeting signal is at the N-terminus of the engineered meganuclease. In some embodiments, the targeting signal is at the C-terminus of the engineered meganuclease.

Exemplary polar amino acids that can be used in the presently disclosed engineered meganucleases are serine, threonine, cysteine, asparagine, glutamine, lysine, arginine, and histidine. Exemplary non-polar amino acids that can be used in the presently disclosed engineered meganucleases are glycine, alanine, valine, leucine, methionine, phenylalanine, proline, tyrosine, tryptophan, and isoleucine. Exemplary small amino acids that can be used in the presently disclosed engineered meganucleases are alanine, cysteine, glycine, serine, and threonine.

In some embodiments of the disclosed engineered meganucleases, the N-terminus of the polypeptide linker can be covalently bound to the first subunit at a residue corresponding to any one of positions 153-163 of SEQ ID NO: 1. In particular embodiments, the N-terminus of the polypeptide linker is covalently bound to the first subunit at a D residue corresponding to position 153 of SEQ ID NO: 1. In some embodiments of the disclosed engineered meganucleases, the C-terminus of the polypeptide linker is covalently bound to the second subunit at a residue corresponding to any one of positions 1-9 of SEQ ID NO: 1. In particular embodiments, the C-terminus of the polypeptide linker is covalently bound to the second subunit at a Y residue corresponding to position 5 of SEQ ID NO: 1.

In some embodiments, the disclosed engineered meganucleases comprise (i) an inactivating amino acid in the first subunit that reduces or abolishes cleavage activity; (ii) an inactivating amino acid in the second subunit that reduces or abolishes cleavage activity; or (iii) an inactivating amino acid in the first subunit that reduces or abolishes cleavage activity and an inactivating amino acid in the second subunit that reduces or abolishes cleavage activity.

As used here, an inactivating amino acid that "reduces" cleavage activity of an engineered meganuclease inactivates only the subunit comprising that amino acid, while not affecting the ability of the other subunit to cleave its DNA strand. For example, in cases where only one subunit comprises an inactivating amino acid that reduces cleavage activity, the other subunit remains active and the engineered meganuclease becomes a nickase that remains capable of cleaving one strand of the double-stranded DNA. In other cases where both subunits comprise an inactivating amino acid that reduces cleavage activity, neither subunit is active, the engineered meganuclease does not comprise any cleavage activity, and it cannot generate a single-strand or double-strand break in the DNA.

By comparison, an inactivating amino acid that "abolishes" cleavage activity of an engineered meganuclease can be present in only one subunit but will inactivate both subunits of the engineered meganuclease, such that it does not comprise any cleavage activity and cannot generate a single-strand or double-strand break in the DNA.

In some embodiments, the inactivating amino acid is an A at a position corresponding to position 20 of SEQ ID NO: 1. In some embodiments, the inactivating amino acid is an E at a position corresponding to position 47 of SEQ ID NO: 1.

In some embodiments, the first subunit and the second subunit each comprise an E at a position corresponding to position 47 of SEQ ID NO: 1, wherein the engineered meganuclease does not comprise cleavage activity (i.e., activity is abolished).

In some embodiments, the first subunit, the second subunit, or both of the first subunit and the second subunit, comprises an A at a position corresponding to position 20 of SEQ ID NO: 1, wherein the engineered meganuclease does not comprise cleavage activity (i.e., activity is abolished).

In some embodiments, the first subunit comprises an E at a position corresponding to position 47 of SEQ ID NO: 1 and the second subunit does not comprise the inactivating amino acid, wherein the engineered meganuclease is a nickase that is only capable of cleaving the antisense strand of a dsDNA target site. In some embodiments, the second subunit comprises an E at a position corresponding to position 47 of SEQ ID NO: 1 the first subunit does not comprise the inactivating amino acid, wherein the engineered meganuclease is a nickase that is only capable of cleaving the sense strand of a dsDNA target site.

In some embodiments of the disclosed meganucleases, DNA binding affinity-altering modification. Non-limiting examples of such DNA binding affinity-altering modifications that can be introduced into I-CreI-derived meganucleases are disclosed, for example, in WO2007047859 (which is incorporated by reference in its entirety), and can include, without limitation, modifications at one or more positions corresponding to positions 29, 34, 48, 51, 64, 80, 81, 82, 112, 116, 137, 139, or 143 of SEQ ID NO: 1. In some embodiments, the first subunit comprises a cleavage activity-altering modification. Non-limiting examples of such cleavage activity-altering modifications that can be introduced into I-CreI-derived meganucleases are disclosed, for example, in WO2020227534 (which is incorporated by reference in its entirety), and can include, without limitation, modifications at one or more positions corresponding to positions 19, 48, and 50 of SEQ ID NO: 1.

2.3 Methods for Delivering Engineered Meganucleases and Encoding Polynucleotides The disclosure provides methods for utilizing the disclosed engineered meganucleases to target, bind, and in some embodiments cleave double-stranded DNA recognition sequences in cells. Thus, in some cases, the disclosed methods generate genetically-modified cells and populations thereof. Such cells can be, for example, eukaryotic cells, such as human cells or plant cells. In certain embodiments of the present disclosure, any number of cell lines available in the art may be used.

The engineered meganucleases described herein are capable of generating a genetically-modified cell, for example, by introduction of an insertion or deletion via non-homologous end joining at a nuclease cleavage site (e.g., in a chromosome, in mitochondrial DNA, or in episomal DNA), through introduction of a donor template encoding an exogenous sequence of interest (e.g., encoding a transgene) into a cleavage site, or by using pairs of engineered meganucleases to excise specific regions of DNA. Cells can also be modified by the engineered meganucleases described herein by cleavage of a dsDNA target comprising a recognition sequence (e.g., mitochondrial DNA or episomal DNA) and subsequent degradation of the dsDNA. Further, in cases where the catalytic activity of the engineered meganuclease is altered, either by generating a nickase or by eliminating catalytic activity entirely, a cell may be modified by various gene editing methods that can utilize such a nuclease (e.g., base editing or epigenetic editing).

Engineered meganucleases described herein can be delivered into a cell in the form of protein or, preferably, as a nucleic acid encoding the engineered meganuclease. Such nucleic acid can be DNA (e.g., circular or linearized plasmid DNA or PCR products) or RNA (e.g., mRNA).

For embodiments in which the engineered meganuclease coding sequence is delivered in DNA form, it should be operably linked to a promoter to facilitate transcription of the gene. Mammalian promoters suitable for the embodiments of the disclosure include constitutive promoters such as the cytomegalovirus early (CMV) promoter (Thomsen et al. (1984). Proc Natl Acad Sci USA. 81(3):659-63) or the SV40 early promoter (Benoist and Chambon (1981), Nature. 290 (5804):304-10) as well as inducible promoters such as the tetracycline-inducible promoter (Dingermann et al. (1992). Mol Cell Biol. 12(9):4038-45). An engineered meganuclease of the disclosure can also be operably linked to a synthetic promoter. Synthetic promoters can include, without limitation, the JeT promoter (WO 2002/012514). In a some embodiments, engineered meganuclease genes are operably linked to a promoter that drives gene expression preferentially in a target cell or tissue.

In some embodiments, mRNA encoding the engineered meganuclease is delivered to the cell because this reduces the likelihood that the gene encoding the engineered meganuclease will integrate into the genome of the cell. Such mRNA encoding an engineered meganuclease can be produced using methods known in the art such as in vitro transcription. In some embodiments, the mRNA is 5' capped using 7-methyl-guanosine, anti-reverse cap analogs (ARCA) (U.S. Pat. No. 7,074,596). CleanCap® analogs such as Cap 1 analogs (Trilink. San Diego. CA), or enzymatically capped using vaccinia capping enzyme or similar. In some embodiments, the mRNA may be polyadenylated. The mRNA may contain various 5' and 3' untranslated sequence elements to enhance expression of the encoded engineered meganuclease and/or stability of the mRNA itself. Such elements can include, for example, posttranslational regulatory elements such as a woodchuck hepatitis virus posttranslational regulatory element. The mRNA may contain nucleoside analogs or naturally-occurring nucleosides, such as pseudouridine, 5-methylcytidine. N6-methyladenosine. 5-methyluridine, or 2-thiouridine. Additional nucleoside analogs include, for example, those described in U.S. Pat. No. 8,278,036.

In particular embodiments, an mRNA encoding an engineered meganuclease described herein can be a polycistronic mRNA encoding two or more meganucleases that are simultaneously expressed in the cell. A polycistronic mRNA can encode two or more meganucleases that target different recognition sequences in the same target gene. Alternatively, a polycistronic mRNA can encode at least one meganuclease described herein and at least one additional nuclease targeting a separate recognition sequence positioned in the same gene, or targeting a second recognition sequence positioned in a second gene such that cleavage sites are produced in both genes. A polycistronic mRNA can comprise any element known in the art to allow for the translation of two or more genes (i.e., cistrons) from the same mRNA molecule including, but not limited to, an IRES element, a T2A element, a P2A element, an E2A element, and an F2A element.

In another particular embodiment, a nucleic acid encoding an engineered meganuclease described herein can be introduced into the cell using a single-stranded DNA template. The single-stranded DNA can further comprise a 5' and/or a 3' AAV inverted terminal repeat (ITR) upstream and/or downstream of the sequence encoding the engineered meganuclease. In other embodiments, the single-stranded DNA can further comprise a 5' and/or a 3' homology arm upstream and/or downstream of the sequence encoding the engineered meganuclease.

In another particular embodiment, a gene encoding an engineered meganuclease described herein can be introduced into a cell using a linearized DNA template. Such linearized DNA templates can be produced by methods known in the art. In some examples, a plasmid DNA encoding an engineered meganuclease can be digested by one or more restriction enzymes such that the circular plasmid DNA is linearized prior to being introduced into a cell.

Purified engineered meganuclease proteins can be delivered into cells by a variety of different mechanisms known in the art, including those further detailed herein below.

In some embodiments, engineered meganuclease proteins are coupled to a cell penetrating peptide or targeting ligand to facilitate cellular uptake. Examples of cell penetrating peptides known in the art include poly-arginine (Jearawiriyapaisarn, et al. (2008) Mol Ther. 16:1624-9), TAT peptide from the HIV virus (Hudecz et al. (2005), Med. Res. Rev. 25:679-736), MPG (Simeoni, et al. (2003) Nucleic Acids Res. 31:2717-2724), Pep-1 (Deshayes et al. (2004) Biochemistry 43:7698-7706), and HSV-1 VP-22 (Deshayes et al. (2005) Cell Mol Life Sci. 62:1839-49).

In an alternative embodiment, engineered meganuclease proteins, or DNA/mRNA encoding meganucleases, are coupled covalently or non-covalently to an antibody that recognizes a specific cell-surface receptor expressed on target cells such that the engineered meganuclease protein/DNA/mRNA binds to and is internalized by the target cells. Alternatively, engineered meganuclease protein/DNA/mRNA can be coupled covalently or non-covalently to the natural ligand (or a portion of the natural ligand) for such a cell-surface receptor. (McCall, et al. (2014) Tissue Barriers. 2 (4): e944449; Dinda, et al. (2013) Curr Pharm Biotechnol. 14:1264-74; Kang, et al. (2014) Curr Pharm Biotechnol. 15 (3): 220-30; Qian et al. (2014) Expert Opin Drug Metab Toxicol. 10 (11): 1491-508).

In some embodiments, engineered meganuclease proteins, or DNA/mRNA encoding engineered meganucleases, are coupled covalently or non-covalently to a nanoparticle or encapsulated within such a nanoparticle using methods known in the art (Sharma, et al. (2014) Biomed Res Int. 2014). A nanoparticle is a nanoscale delivery system whose length scale is <1 μm, preferably <100 nm. Such nanoparticles may be designed using a core composed of metal, lipid, polymer, or biological macromolecule, and multiple copies of the recombinant meganuclease protein, mRNA, or DNA can be attached to or encapsulated with the nanoparticle core. This increases the copy number of the protein/mRNA/DNA that is delivered to each cell and, so, increases the intracellular expression of each engineered meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) Biomaterials. 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell surface receptors and the natural ligands (or portions of the natural ligands) for cell surface receptors.

In some embodiments, the engineered meganuclease proteins or DNA/mRNA encoding the engineered meganucleases are encapsulated within liposomes or complexed using cationic lipids (see, e.g., Lipofectamine™, Life Technologies Corp., Carlsbad, CA: Zuris et al. (2015) Nat Biotechnol. 33:73-80; Mishra et al. (2011) J Drug Deliv. 2011:863734). The liposome and lipoplex formulations can protect the payload from degradation, and facilitate cellular uptake and delivery efficiency through fusion with and/or disruption of the cellular membranes of the target cells.

In some embodiments, engineered meganuclease proteins, or DNA/mRNA encoding engineered meganucleases, are encapsulated within polymeric scaffolds (e.g., PLGA) or complexed using cationic polymers (e.g., PEI, PLL) (Tamboli et al. (2011) Ther Deliv. 2 (4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, engineered meganuclease proteins, or DNA/mRNA encoding engineered meganucleases, are combined with amphiphilic molecules that self-assemble into micelles (Tong et al. (2007) J Gene Med. 9 (11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, engineered meganuclease proteins, or DNA/mRNA encoding engineered meganucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015, 832, 6,506,803, 6,635,676, and 6,559,189, each of which is incorporated herein by reference in its entirety.

In some embodiments, engineered meganuclease proteins, or DNA/mRNA encoding engineered meganucleases, are covalently attached to, or non-covalently associated with, multifunctional polymer conjugates. DNA dendrimers, and polymeric dendrimers (Mastorakos et al. (2015) Nanoscale. 7(9): 3845-56; Cheng et al. (2008) J Pharm Sci. 97(1): 123-43). The dendrimer generation can control the payload capacity and size, and can provide a high drug payload capacity. Moreover, display of multiple surface groups can be leveraged to improve stability, reduce non-specific interactions, and enhance cell-specific targeting and drug release.

In some embodiments, genes encoding an engineered meganuclease are delivered using a recombinant virus. Such recombinant viruses are known in the art and include, for example, retroviruses, lentiviruses, adenoviruses, and adeno-associated viruses (AAVs) (reviewed in Vannucci, et al. (2013 New Microbiol. 36:1-22). Recombinant AAVs useful in the embodiments of the disclosure can have any serotype (i.e., capsid) that allows for transduction of the virus into a target cell type and expression of the meganuclease gene, whether the target cell is transduced ex vivo or in vivo. Recombinant AAVs useful with the engineered meganucleases described herein can include, without limitation, serotypes AAV1, AAV2, AAV3, AAV4, AAV5, AAV6, AAV7, AAV8, AAV9), AAV10, AAV11, AAV12, AAVrh10, AAVrh74, AAVrh79, and AAVhu68, among others. AAVs can also be self-complementary such that they do not require second-strand DNA synthesis in the host cell (McCarty, et al. (2001) Gene Ther. 8:1248-54). Polynucleotides delivered by recombinant AAVs can include left (5') and right (3') ITRs as part of the viral genome. In some embodiments, the recombinant viruses are injected directly into target tissues for in vivo delivery of the engineered meganuclease gene. In alternative embodiments, recombinant viruses are delivered systemically via the circulatory system for in vivo delivery of the engineered meganuclease gene. If the meganuclease gene is delivered via a recombinant virus (e.g., AAV) it can be operably linked to a promoter. In some embodiments, meganuclease genes delivered by recombinant viruses are operably linked to a promoter that drives gene expression preferentially in a target cell.

In some embodiments, a recombinant virus used for delivery of an engineered meganuclease gene is a self-limiting recombinant virus. A self-limiting virus can have limited persistence time in a cell or organism due to the presence of a recognition sequence for an engineered meganuclease within the viral genome. Thus, a self-limiting recombinant virus can be engineered to provide a coding sequence for a promoter, an engineered meganuclease described herein, and a meganuclease recognition site within the ITRs. The self-limiting recombinant virus delivers the meganuclease gene to a cell, tissue, or organism, such that the meganuclease is expressed and able to cut the genome of the cell at an endogenous recognition sequence within the genome. The delivered meganuclease will also find its target site within the self-limiting recombinant viral genome, and cut the recombinant viral genome at this target site. Once cut, the 5' and 3' ends of the viral genome will be exposed and degraded by exonucleases, thus killing the virus and ceasing production of the meganuclease.

In some embodiments, engineered meganuclease proteins, or DNA/mRNA encoding engineered meganucleases, are introduced into cells by lipid nanoparticles. In various embodiments, such lipid nanoparticles can be formulated to encapsulate an engineered meganuclease protein or, alternatively, a nucleic acid (e.g., an mRNA) encoding the engineered meganuclease.

Some lipid nanoparticles contemplated for use in the embodiments of the disclosure comprise at least one cationic lipid, at least one non-cationic lipid, and at least one conjugated lipid. In more particular examples, lipid nanoparticles can comprise from about 50 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology. In other particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate and are produced in such a manner as to have a non-lamellar (i.e., non-bilayer) morphology.

Cationic lipids can include, for example, one or more of the following: palmitovi-oleoyl-nor-arginine (PONA), MPDACA, GUADACA, ((6Z,9Z,28Z,31Z)-heptatriaconta-6,9,28,31-tetraen-19-yl 4-(dimethylamino) butanoate) (MC3), LenMC3, CP-LenMC3, γ-LenMC3. CP-γ-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N, N-dimethylaminopropane (DLenDMA), 2,2-dilinoleyl-4-(2-dimethylaminoethyl)-|1.3]-dioxolane (DLin-K-C2-DMA; "XTC2"), 2,2-dilinoleyl-4-(3-dimethylaminopropyl)-[1.3]-dioxolane (DLin-K-C3-DMA), 2,2-dilinoleyl-4-(4-dimeth-ylaminobutyl)-[1.3]-dioxolane (DLin-K-C4-DMA), 2,2-dilinoleyl-5-dimethylaminomethyl-|1,3]-dioxane (DLin-K6-DMA), 2,2-dilinoleyl-4-N-methylpepiazino-[1.3]-dioxolane (DLin-K-MPZ), 2,2-dilinoleyl-4-dimethylaminomethyl-[1.3]-dioxolane (DLin-K-DMA), 1,2-dilinoleylcarbamoyloxy-3-dimethylaminopropane (DLin-C-DAP), 1,2-dilinoleyoxy-3-(dimethylamino)ac-etoxypropane (DLin-DAC), 1,2-dilinoleyoxy-3-mor-pholinopropane (DLin-MA), 1,2-dilinoleoyl-3-dimethyl-aminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-meth-ylpiperazino) propane (DLin-MPZ), 3-(N,N-dilinoley-lamino)-1,2-propanediol (DLinAP), 3-(N,N-dioleylamino)-1,2-propanedio (DOAP), 1,2-dilinoleyloxo-3-(2-N,N-dimethylamino) ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammo-nium bromide (DDAB), N-(1-(2,3-dioleoyloxy)propyl)-N, N,N-trimethylammonium chloride (DOTAP), 3-(N-(N',N'-dimethylaminoethane)-carbamoyl)cholesterol (DC-Chol), N-(1,2-dimyristyloxyprop-3-yl)-N,N-dimethyl-N-hydroxy-ethyl ammonium bromide (DMRIE), 2,3-dioleyloxy-N-|2 (spermine-carboxamido)ethyl]-N,N-dimethyl-1-propan-aminiumtrifluoroacetate (DOSPA), dioctadecylamidoglycyl spermine (DOGS), 3-dimethylamino-2-(cholest-5-en-3-beta-oxy butan-4-oxy)-1-(cis,cis-9,12-octadecadienoxy) propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. The cationic lipid can also be DLinDMA. DLin-K-C2-DMA ("XTC2"). MC3. LenMC3. CP-LenMC3, γ-LenMC3, CP-γ-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid may comprise from about 50 mol % to about 90) mol %, from about 50 mol % to about 85 mol %, from about 50 mol % to about 80 mol %, from about 50) mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid may comprise from about 40 mol % to about 90) mol %, from about 40) mol % to about 85 mol %, from about 40 mol % to about 80 mol %, from about 40) mol % to about 75 mol %, from about 40) mol % to about 70) mol %, from about 40 mol % to about 65 mol %, or from about 40 mol % to about 60 mol % of the total lipid present in the particle.

The non-cationic lipid may comprise, e.g., one or more anionic lipids and/or neutral lipids. In particular embodiments, the non-cationic lipid comprises one of the following neutral lipid components: (1) cholesterol or a derivative thereof; (2) a phospholipid; or (3) a mixture of a phospho-lipid and cholesterol or a derivative thereof. Examples of cholesterol derivatives include, but are not limited to, cholestanol, cholestanone, cholestenone, coprostanol, cho-lesteryl-2'-hydroxyethyl ether, cholesteryl-4'-hydroxy butyl ether, and mixtures thereof. The phospholipid may be a neutral lipid including, but not limited to, dipalmitoylphos-phatidylcholine (DPPC), distearoylphosphatidylcholine (DSPC), dioleoylphosphatidylethanolamine (DOPE), palmi-toyloleovl-phosphatidylcholine (POPC), palmitoyloleovl-phosphatidylethanolamine (POPE), palmitoyloleyol-phos-phatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatid-ylethanolamine, dielaidoyl-phosphatidylethanolamine (DEPE), stearoyloleoyl-phosphatidylethanolamine (SOPE), egg phosphatidylcholine (EPC), and mixtures thereof. In certain embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60) mol %, from about 20 mol % to about 60 mol %, from about 25 mol % to about 60 mol %, from about 30 mol % to about 60) mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cho-lesterol or a cholesterol derivative, the mixture may com-prise up to about 40, 50, or 60 mol % of the total lipid present in the particle.

The conjugated lipid that inhibits aggregation of particles may comprise, e.g., one or more of the following: a poly-ethyleneglycol (PEG)-lipid conjugate, a polyamide (ATTA)-lipid conjugate, a cationic-polymer-lipid conjugates (CPLs), or mixtures thereof. In one particular embodiment, the nucleic acid-lipid particles comprise either a PEG-lipid conjugate or an ATTA-lipid conjugate. In certain embodi-ments, the PEG-lipid conjugate or ATTA-lipid conjugate is used together with a CPL. The conjugated lipid that inhibits aggregation of particles may comprise a PEG-lipid includ-ing, e.g., a PEG-diacylglycerol (DAG), a PEG dialkyloxy-propyl (DAA), a PEG-phospholipid, a PEG-ceramide (Cer), or mixtures thereof. The PEG-DAA conjugate may be PEG-dilauryloxypropyl (C12), a PEG-dimyristyloxypropyl (C14), a PEG-dipalmityloxypropyl (C16), a PEG-disteary-loxypropyl (C18), or mixtures thereof.

Additional PEG-lipid conjugates suitable for use in the embodiments of the disclosure include, but are not limited to, mPEG2000-1,2-di-O-alkyl-sn3-carbomoylglyceride (PEG-C-DOMG). The synthesis of PEG-C-DOMG is described in PCT Application No. PCT/US08/88676. Yet additional PEG-lipid conjugates suitable for use in the embodiments of the disclosure include, without limitation, 1-[8'-(1,2-dimyristov1-3-propanoxy)-carboxamido-3',6'-di-oxaoctanyl]carbamoyl-ω-methyl-poly(ethylene glycol) (2KPEG-DMG). The synthesis of 2KPEG-DMG is described in U.S. Pat. No. 7,404,969.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In other embodiments, the composition may comprise amphoteric liposomes, which contain at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

Cationic compounds useful for amphoteric liposomes include those cationic compounds previously described herein above. Without limitation, strongly cationic compounds can include, for example: DC-Chol 3-β-[N-(N',N'-dimethylmethane)carbamoyl] cholesterol. TC-Chol 3-β-[N-(N',N',N'-trimethylaminoethane) carbamoyl cholesterol. BGSC bisguanidinium-spermidine-cholesterol. BGTC bisguadinium-tren-cholesterol. DOTAP (1,2-dioleoyloxypropyl)-N,N,N-trimethylammonium chloride. DOSPER (1,3-dioleoyloxy-2-(6-carboxy-spermyl)-propylarnide. DOTMA (1,2-dioleoyloxypropyl)-N,N,N-trimethylamronium chloride) (Lipofectin®), DORIE 1,2-dioleoyloxypropyl)-3-dimethylhydroxyethylammonium bromide. DOSC (1,2-dioleoyl-3-succinyl-sn-glyceryl choline ester). DOGSDSO (1,2-dioleoyl-sn-glycero-3-succinyl-2-hydroxyethyl disulfide omithine). DDAB dimethyldioctadecylammonium bromide. DOGS ((C18)2GlySper3+) N,N-dioctadecylamido-glycol-spermin (Transfectam®) (C18) 2Gly+N,N- dioctadecylamido-glycine. CTAB cetyltrimethylarnmonium bromide, CpyC cetylpyridinium chloride, DOEPC 1,2-dioleoly-sn-glycero-3-ethylphosphocholine or other O-alkyl-phosphatidylcholine or ethanolamines, amides from lysine, arginine or ornithine and phosphatidyl ethanolamine.

Examples of weakly cationic compounds include, without limitation; His-Chol (histaminyl-cholesterol hemisuccinate), Mo-Chol (morpholine-N-ethylamino-cholesterol hemisuccinate), or histidinyl-PE.

Examples of neutral compounds include, without limitation; cholesterol, ceramides, phosphatidyl cholines, phosphatidyl ethanolamines, tetraether lipids, or diacyl glycerols.

Anionic compounds useful for amphoteric liposomes include those non-cationic compounds previously described herein. Without limitation, examples of weakly anionic compounds can include: CHEMS (cholesterol hemisuccinate), alkyl carboxylic acids with 8 to 25 carbon atoms, or diacyl glycerol hemisuccinate. Additional weakly anionic compounds can include the amides of aspartic acid, or glutamic acid and PE as well as PS and its amides with glycine, alanine, glutamine, asparagine, serine, cysteine, threonine, tyrosine, glutamic acid, aspartic acid or other amino acids or aminodicarboxylic acids. According to the same principle, the esters of hydroxycarboxylic acids or hydroxy dicarboxylic acids and PS are also weakly anionic compounds.

In some embodiments, amphoteric liposomes may contain a conjugated lipid, such as those described herein above. Particular examples of useful conjugated lipids include, without limitation, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particular examples are PEG-modified diacylglycerols and dialkylglycerols.

In some embodiments, the neutral lipids may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50) mol % of the total lipid present in the particle.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9) mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

Considering the total amount of neutral and conjugated lipids, the remaining balance of the amphoteric liposome can comprise a mixture of cationic compounds and anionic compounds formulated at various ratios. The ratio of cationic to anionic lipid may selected in order to achieve the desired properties of nucleic acid encapsulation, zeta potential, pKa, or other physicochemical property that is at least in part dependent on the presence of charged lipid components.

The present disclosure further provides for the introduction of an exogenous sequence of interest into a targeted gene of interest. Such an exogenous sequence of interest can be introduced into the cell in a donor/repair template. In some embodiments, the exogenous sequence of interest comprises a 5' homology arm and a 3' homology arm flanking the elements of the insert. Such homology arms have sequence homology to corresponding sequences 5' upstream and 3' downstream of the meganuclease recognition sequence where a cleavage site is produced. In general, homology arms can have a length of at least 50 base pairs, preferably at least 100 base pairs, and up to 2000 base pairs or more, and can have at least 90%, preferably at least 95%, or more, sequence homology to their corresponding sequences in the genome.

An exogenous sequence of interest may be introduced into the cell by any of the means previously discussed. In a particular embodiment, the exogenous sequence of interest is introduced by way of a recombinant virus, such as a lentivirus, retrovirus, adenovirus, or preferably a recombinant AAV. Recombinant AAVs useful for introducing an exogenous nucleic acid can have any serotype that allows for transduction of the virus into the cell and insertion of the exogenous nucleic acid sequence into the cell genome. The recombinant AAV can also be self-complementary such that it does not require second-strand DNA synthesis in the host cell. Exogenous nucleic acid molecules introduced using a recombinant AAV can be flanked by a 5' (left) and 3' (right) inverted terminal repeat in the viral genome.

In another particular embodiment, the exogenous sequence of interest can be introduced into the cell using a single-stranded DNA template. The single-stranded DNA can comprise the exogenous sequence of interest and, in some embodiments, can comprise 5' and 3' homology arms to promote insertion of the nucleic acid sequence into the meganuclease cleavage site by homologous recombination. The single-stranded DNA can further comprise a 5' AAV inverted terminal repeat (ITR) sequence 5' upstream of the 5' homology arm, and a 3' AAV ITR sequence 3' downstream of the 3' homology arm.

2.4 Pharmaceutical Compositions

In some embodiments, the disclosure provides a pharmaceutical composition comprising a pharmaceutically acceptable carrier and an engineered meganuclease described herein, or a pharmaceutically acceptable carrier and a polynucleotide described herein that comprises a nucleic acid sequence encoding an engineered meganuclease described herein. Such polynucleotides can be, for example, mRNA or DNA as described herein. In some such examples, the polynucleotide in the pharmaceutical composition can be comprised by a lipid nanoparticle or can be comprised by a recombinant virus (e.g., a recombinant AAV). Such pharmaceutical compositions are formulated, for example, for systemic administration, or administration to target tissues. Pharmaceutical compositions of the disclosure can be useful for treating a subject having a disease. A subject who may be particularly receptive to treatment with the engineered meganucleases disclosed herein may be identified by ascertaining the presence or absence of one or more risk factors, diagnostic, or prognostic indicators.

Such pharmaceutical compositions can be prepared in accordance with known techniques. See, e.g., Remington, The Science And Practice of Pharmacy (21st ed., Philadelphia, Lippincott, Williams & Wilkins, 2005). In the manufacture of a pharmaceutical formulation according to the disclosure, engineered meganucleases described herein, polynucleotides encoding the same, or cells expressing the same, are typically admixed with a pharmaceutically acceptable carrier and the resulting composition is administered to a subject. The carrier must be acceptable in the sense of being compatible with any other ingredients in the formulation and must not be deleterious to the subject. The carrier can be a solid or a liquid, or both, and can be formulated with the compound as a unit-dose formulation.

In some embodiments, pharmaceutical compositions of the disclosure can further comprise one or more additional agents or biological molecules useful in the treatment of a disease in the subject. Likewise, the additional agent(s) and/or biological molecule(s) can be co-administered as a separate composition.

The pharmaceutical compositions described herein can include a therapeutically effective amount of any engineered meganuclease disclosed herein, or any polynucleotide described herein encoding any engineered meganuclease described herein. A "therapeutically effective amount" refers to an amount effective, at dosages and for periods of time necessary, to achieve a desired therapeutic result. The therapeutically effective amount may vary according to factors such as the age, sex, and weight of the individual, and the ability of the polypeptide, nucleic acid, or vector to elicit a desired response in the individual.

In some embodiments, the pharmaceutical composition can comprise a recombinant virus (e.g., a recombinant AAV) comprising a polynucleotide encoding an engineered meganuclease described herein. In other embodiments, the pharmaceutical composition can comprise an engineered meganuclease described herein, or mRNA encoding the same, encapsulated within lipid nanoparticles. In some embodiments, the pharmaceutical composition can comprise a dose of about $1\times10^{10}$ gc/kg to about $1\times10^{14}$ gc/kg (e.g., $1\times10^{10}$ gc/kg, $1\times10^{11}$ gc/kg, $1\times10^{12}$ gc/kg, $1\times10^{13}$ gc/kg, or $1\times10^{14}$ gc/kg) of a nucleic acid encoding an engineered meganuclease.

The present disclosure also provides engineered meganucleases described herein, or polynucleotides described herein encoding the same, or cells described herein expressing engineered meganucleases described herein, for use as a medicament.

2.5 Methods of Administering Engineered Meganucleases

In some embodiments, engineered meganucleases described herein, or polynucleotides encoding the same, are delivered to a cell in vitro. In some embodiments, engineered meganucleases described herein, or polynucleotides encoding the same, are delivered to a cell in a subject in vivo. As discussed herein, the disclosed engineered meganucleases can be delivered as purified protein or as a polynucleotide (e.g., RNA or DNA) comprising a nucleic acid sequence encoding the meganuclease. In some embodiments, meganuclease proteins, or polynucleotides encoding meganucleases, are supplied to target cells via injection directly to the target tissue. Alternatively, meganuclease proteins, or polynucleotides encoding meganucleases, can be delivered systemically via the circulatory system.

In various embodiments of the methods, compositions described herein, such as the engineered meganucleases described herein, polynucleotides encoding the same, recombinant viruses comprising such polynucleotides, or lipid nanoparticles comprising such engineered meganuclease or polynucleotides, can be administered via any suitable route of administration known in the art. Such routes of administration can include, for example, intravenous, intramuscular, intraperitoneal, subcutaneous, intrahepatic, transmucosal, transdermal, intraarterial, and sublingual. In some embodiments, the engineered meganuclease proteins, polynucleotides encoding the same, recombinant viruses, or lipid nanoparticles, are supplied to target cells via injection directly to the target tissue. Other suitable routes of administration can be readily determined by the treating physician as necessary.

In some embodiments, a therapeutically effective amount of an engineered meganuclease described herein, or a polynucleotide encoding the same, is administered to a subject in need thereof for the treatment of a disease. As appropriate, the dosage or dosing frequency of the engineered meganuclease, or the polynucleotide encoding the same, may be adjusted over the course of the treatment, based on the judgment of the administering physician. Appropriate doses will depend, among other factors, on the specifics of any AAV chosen (e.g., serotype), any lipid nanoparticle chosen, on the route of administration, on the subject being treated (i.e., age, weight, sex, and general condition of the subject), and the mode of administration. Thus, the appropriate dosage may vary from patient to patient. An appropriate effective amount can be readily determined by one of skill in the art or treating physician. Dosage treatment may be a single dose schedule or, if multiple doses are required, a multiple dose schedule. Moreover, the subject may be administered as many doses as appropriate. One of skill in the art can readily determine an appropriate number of doses. The dosage may need to be adjusted to take into consideration an alternative route of administration or balance the therapeutic benefit against any side effects.

In some embodiments, a subject is administered a pharmaceutical composition comprising a polynucleotide comprising a nucleic acid sequence encoding an engineered meganuclease described herein, wherein the encoding polynucleotide is administered at a dose of about $1\times10^{10}$ gc/kg to about $1\times10^{14}$ gc/kg (e.g., about $1\times10^{10}$ gc/kg, about $1\times10^{11}$ gc/kg, about $1\times10^{12}$ gc/kg, about $1\times10^{13}$ gc/kg, or about $1\times10^{14}$ gc/kg).

In some embodiments, a subject is administered a lipid nanoparticle formulation comprising an mRNA comprising a nucleic acid sequence encoding an engineered meganuclease described herein, wherein the dose of the mRNA is about 0.1 mg/kg to about 3 mg/kg (e.g., about 0.1 mg/kg, about 0.25 mg/kg, about 0.5 mg/kg, about 0.75 mg/kg, about 1.0 mg/kg, about 1.5 mg/kg, about 2.0 mg/kg, about 2.5 mg/kg, or about 3.0 mg/kg).

2.6 Engineered Nuclease Variants

Embodiments disclosed herein encompass the engineered meganucleases described herein, and variants thereof. Further embodiments of the disclosure encompass polynucleotides comprising a nucleic acid sequence encoding the meganucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to bind to and/or cleave a recognition sequence, and in some embodiments, exhibit at least one improved property over previously developed engineered meganucleases comprising longer linker polypeptides. Such variants may result, for example, from human manipulation. Biologically active variants of a native polypeptide of the embodiments (e.g., SEQ ID NOs: 4-26), or biologically active variants of the recognition half-site binding subunits described herein, will have at least about 40%, about 45%, about 50%, about 55%, about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, sequence identity to the amino acid sequence of the native polypeptide or native subunit, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example. Kunkel (1985) Proc. Natl. Acad. Sci. USA 82:488-492; Kunkel et al. (1987) Methods in Enzymol. 154:367-382: U.S. Pat. No. 4,873,192: Walker and Gaastra, eds. (1983) Techniques in Molecular Biology (MacMillan Publishing Company. New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

Engineered meganucleases of the disclosure comprise variants of the hypervariable (HVR) regions of the reference meganucleases disclosed herein. Variant HVR regions can comprise variants of, for example, residues 24-79 and/or residues 204-259 of the reference meganucleases disclosed in SEQ ID NOs: 22, 23, and 26, or residues 24-79 and/or residues 203-258 of the reference meganucleases disclosed in SEQ ID NOs: 24 and 25. Thus, variant HVRs can comprise an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to an amino acid sequence corresponding to the HVR regions of the reference meganucleases exemplified herein, such that the variant HVR regions allow for the binding of and/or cleaving a recognition sequence. Further, in some embodiments of the disclosure, a variant HVR can comprise residues corresponding to the amino acid residues found at specific positions within the parental HVR. In this context. "corresponding to" means that an amino acid residue in the variant HVR is the same amino acid residue (i.e., a separate identical residue) present in the parental HVR sequence in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative (i.e., corresponding) to parental position 26.

In particular embodiments, engineered meganucleases disclosed herein comprise an HVR region that has at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 24-79 of any one of SEQ ID NOs: 22-26.

In certain embodiments, engineered meganucleases disclosed herein comprise an HVR region that has at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 204-259 of any one of SEQ ID NOs: 22, 23, or 26, or residues 203-258 of any one of SEQ ID NOs: 24 or 25.

A substantial number of amino acid modifications to the DNA recognition domain of the wild-type I-CreI meganuclease have previously been identified (e.g., U.S. Pat. No. 8,021,867) which, singly or in combination, result in recombinant meganucleases with specificities altered at individual bases within the DNA recognition sequence half-site, such that the resulting rationally-designed meganucleases have half-site specificities different from the wild-type enzyme. Table 1 provides potential substitutions that can be made in an engineered meganuclease monomer or subunit to enhance specificity based on the base present at each half-site position (-1 through-9) of a recognition half-site.

TABLE 1

| | Favored Sense-Strand Base | | | | | | | | | | |
|---|---|---|---|---|---|---|---|---|---|---|---|
| Posn. | A | C | G | T | A/T | A/C | A/G | C/T | G/T | A/G/T | A/C/G/T |
| −1 | Y75<br>L75*<br>C75*<br>Y139*<br>C46*<br>A46* | R70*<br>H75*<br>R75*<br>H46*<br>K46*<br>R46* | K70<br>E70*<br>E75*<br>E46*<br>D46* | Q70*<br>C70<br>L70<br>Y75*<br>Q75*<br>H75*<br>H139<br>Q46*<br>H46* | | | | T46* | | | G70<br>A70<br>S70<br>G46* |
| −2 | Q70<br>T44*<br>A44*<br>V44*<br>I44*<br>L44*<br>N44* | E70<br>D70<br>K44*<br>R44* | H70<br>D44*<br>E44* | Q44* | C44* | | | | | | |
| −3 | Q68<br>C24*<br>I24* | E68<br>F68<br>K24*<br>R24* | R68 | M68<br>C68<br>L68<br>F68 | | H68 | | Y68 | K68 | | |
| −4 | A26*<br>Q77 | E77<br>K26* | R77<br>E26* | | | | | S77<br>Q26* | | | S26* |
| −5 | | E42 | R42 | | | | K28* | C28*<br>Q42 | | | M66<br>K66 |
| −6 | Q40<br>C28* | E40<br>R28* | R40 | C40<br>I40<br>V40<br>C79<br>I79<br>V79<br>Q28* | A40<br>A79<br>A28*<br>H28* | | | | | | S40<br>S28* |
| −7 | N30*<br>Q38 | E38<br>K30*<br>R30* | K38<br>R38<br>E30* | I38<br>L38 | | | C38 | | | | H38<br>N38<br>Q30* |
| −8 | F33<br>Y33 | E33<br>D33 | F33<br>H33 | L33<br>V33<br>I33<br>F33<br>C33 | | R32* | R33 | | | | |
| −9 | | E32 | R32<br>K32 | L32<br>V32<br>A32<br>C32 | | | | | D32<br>I32 | | S32<br>N32<br>H32<br>Q32<br>T32 |

Bold entries are wild-type contact residues and do not constitute "modifications" as used herein. An asterisk indicates that the residue contacts the base on the antisense strand.

Certain modifications can be made in an engineered meganuclease monomer or subunit to modulate DNA-binding affinity and/or activity. For example, an engineered meganuclease monomer or subunit described herein can comprise a G, S, or A at a residue corresponding to position 19 of I-CreI (WO 2009/001159), a Y, R, K, or D at a residue corresponding to position 66 of I-CreI, and/or an E, Q, or K at a residue corresponding to position 80 of I-CreI (U.S. Pat. No. 8,021,867).

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a recombinant nuclease of the embodiments. Generally, variants of a particular polynucleotide of the embodiments will have at least about 40%, about 45%, about 50%, about 55%, about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the variant protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its ability to preferentially bind to and/or cleave a recognition sequence.

EXAMPLES

The embodiments of the disclosure is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Selection and Identification of Novel Polypeptide Linkers for I-CreI-Based Engineered Meganucleases 1. Methods These experiments were designed to identify and evaluate novel polypeptide linkers useful for connecting the first (N-terminal) and second (C-terminal) subunits of single-chain I-CreI-based engineered meganucleases. A principal goal was to identify linkers that were shorter, and potentially more active, than those currently utilized in I-CreI-based meganucleases.

These studies utilized a scaffold meganuclease comprising several different libraries of polypeptide linkers, which were evaluated for nuclease activity against a known recognition sequence. Here, the scaffold meganuclease was the HBV 11-12L.520 meganuclease (SEQ ID NO: 96), which was previously described in WO2021/113765 (which is incorporated by reference in its entirety), and which binds and cleaves a recognition sequence referred to as HBV 11-12 (SEQ ID NO: 97).

This parental HBV 11-12L.520 meganuclease comprises an N-terminal nuclear localization signal derived from SV40 (SEQ ID NO: 95), an N-terminal I-CreI-based meganuclease subunit that is truncated after position 153, a polypeptide linker sequence referred to as Linker1 (SEQ ID NO: 27), and a C-terminal I-CreI-based meganuclease subunit that lacks amino acids 1~4 of I-CreI. The N-terminal and C-terminal subunits each bind to one 9 basepair half-site of the 22 basepair recognition sequence. In this parental meganuclease, the N-terminus of Linker1 is fused to position 153 of the N-terminal subunit, while the C-terminus of Linker1 is fused to a position in the C-terminal subunit (i.e., a Y residue) that corresponds to position 5 of I-CreI (SEQ ID NO: 1). All parental meganucleases used as scaffolds in the examples have the same general structure described here.

To identify and evaluate novel polypeptide linkers that are smaller in size and potentially provide improved characteristics, the Linker1 sequence of the HBV 11-12L.520 meganuclease was substituted with two different libraries of polypeptide linkers. Library linkers were inserted into the scaffold meganuclease using the same fusion points used by Linker1. In addition to altering the linker, certain mutations to the scaffold structure of the HBV 11-12L.520 meganuclease were also introduced. In the N-terminal subunit, the following positions were mutated from the corresponding wild-type I-CreI residues; H37Y, K96A, Q99A, and K100D. In the C-terminal subunit, the following positions were mutated from the corresponding wild-type I-CreI residues; W53F, K57Y, and E6IT. Substitutions at these positions were identified in two ways; amino acids that would potentially get in the way of the new shorter linker either by being large (W53F, H37Y) or having interactions between the monomers where the linker should run (K96A, K57Y, E6IT are in a hydrogen bond network between monomers) and amino acids that were chosen to maintain a potential hydrogen bond between the scaffold and the linker (Q99A, K100D).

The first library of novel linkers was based on a parental amino acid sequence PGSVGGLSPNNNAS-TQRPSRNVNNFPG (SEQ ID NO: 28), which is referred to herein as an "Flinker" sequence due to the presence of a phenylalanine residue (F) near the C-terminus. Libraries based on this Flinker sequence were generated by randomizing (as shown by an X) five N-terminal amino acid positions of the parental linker sequence; PXXXXXL-SPNNNASTQRPSRNVNNFPG (SEQ ID NO: 29).

The second library of novel linkers was based on a parental amino acid sequence PGSVGGL-SPSLNSSTQRPIVNWNNLPG (SEQ ID NO: 30), which is referred to herein as a "Wlinker" sequence due to the presence of a tryptophan residue (W) near the C-terminus. Libraries based on this Wlinker sequence were generated by randomizing (as shown by an X) five N-terminal amino acid positions of the parental linker sequence; PGSVXXXXXSLNSSTQRPIVNWNNLPG (SEQ ID NO: 31).

Both libraries were constructed by generating an HBV 11-12L.520 scaffold that contained a pair of BsaI sites which cut outside of the recognition site. The BsaI sites were positioned on either side of the linker position so that the recognition site was in the cut out intervening sequence. This allowed for insertion of a variety of linkers into the scaffold while removing the BsaI sites so a restriction site did not need to be incorporated into the linker sequence. This method is also very efficient for library assembly. Different linker sequences were assembled by overlapping PCR, digested with BsaI, and ligated into the cut scaffold. The resulting libraries were electroporated into a bacterial system designed to select active nuclease/linker combinations from the libraries through multiple rounds of nuclease induction and selection.

A strong survival of bacteria at the 3-hour induction in round 2 was observed, with less survival in subsequent rounds with 2-hour inductions. For this reason, representative clones of different answers from round 2 and 4 for the Flinker and Wlinker selections were chosen for further characterization.

Meganucleases selected from the libraries were evaluated for activity using a previously described CHO cell reporter assay (see. WO 2012/167192, which is incorporated by reference in its entirety). To perform the assays. CHO cell reporter lines were produced, which carried a non-functional Green Fluorescent Protein (GFP) gene expression cassette integrated into the genome of the cells. The GFP gene in each cell line was interrupted by a pair of recognition sequences such that intracellular cleavage of either recognition sequence by a meganuclease would stimulate a homologous recombination event resulting in a functional GFP gene. In CHO reporter cell lines developed for this study, one recognition sequence inserted into the GFP gene was the human HBV 11-12 recognition sequence. The second recognition sequence inserted into the GFP gene was a CHO-23/24 recognition sequence, which is recognized and cleaved by a control meganuclease called "CHO-23/24."

CHO reporter cells were transfected with mRNA encoding individual clones isolated from the selections of the two libraries of meganucleases containing the two linker libraries. In 1 well out of 96, CHO reporter cells were also transfected with mRNA encoding the CHO-23/24 meganuclease. As a positive control, mRNA for HBV 11-12L.520 was also transfected into an individual well of CHO-23/24. In each assay, 5e4 CHO reporter cells were transfected with 90 ng of mRNA in a 96-well plate using Lipofectamine® MessengerMAX™ (THERMO FISHER®) according to the manufacturer's instructions. The transfected CHO cells were evaluated by flow cytometry at 2 days, 5 days, and 7 days post transfection to determine the percentage of GFP-positive cells compared to an untransfected negative control. Data obtained at each time point was normalized to the % GFP positive cells observed using the CHO 23-24 meganuclease to determine an "activity score," and the normalized data from the earliest time point was subtracted from that of the latest time point to determine a "toxicity score." The activity and toxicity scores were then added together to determine an "activity index," which was then normalized to the activity index of the CHO 23-24 meganuclease to compare data between cell lines ("normalized activity index").

Meganucleases identified in the CHO reporter assay as having a sufficient amount of activity relative to the CHO 23-24 control and the HBV 11-12L.520 control were subsequently sequenced to determine amino acid modifications introduced by the libraries and selection.

2. Results

Figures 5A, 5B:
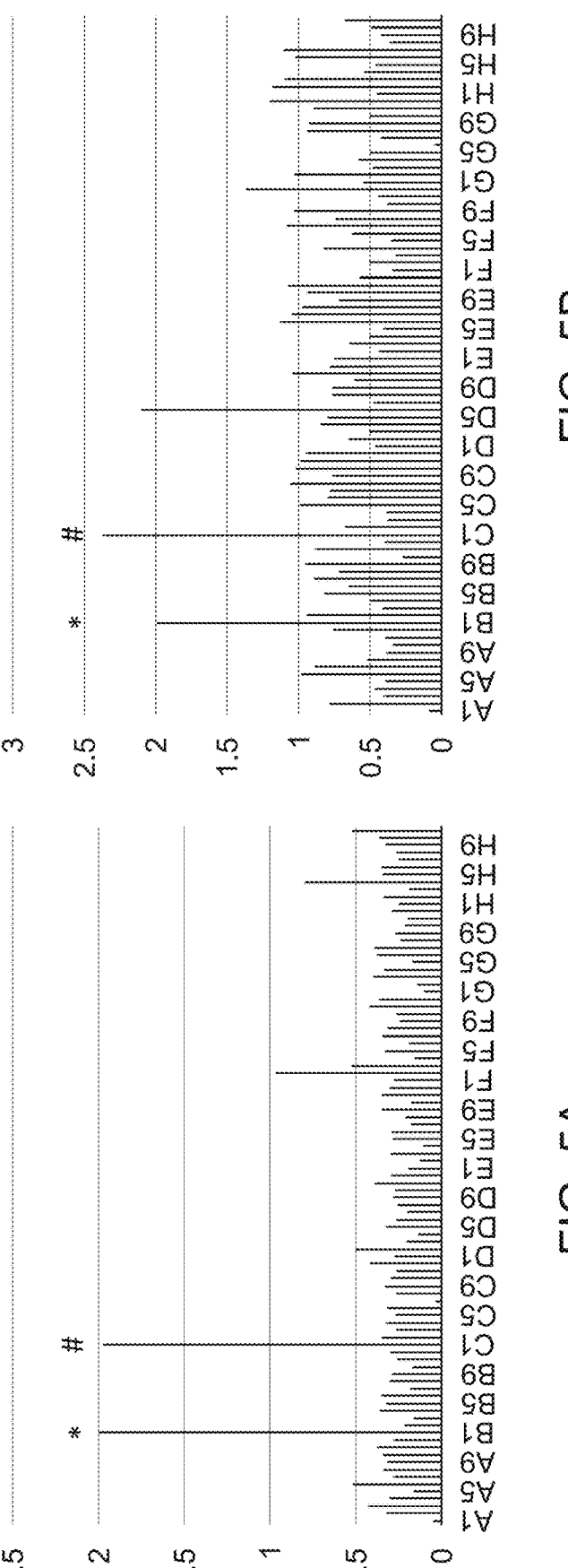
FIG. 5A provides the results of clones after two rounds of selection.
FIG. 5B provides the results of clones after four rounds of selection. Results for the positive control CHO 23-24 meganuclease is marked as "#" and the parental meganuclease is marked as "*".

As shown in FIGS. 5A and 5B, 92 clones from the first library of linkers (i.e., Flinkers) were subcloned and evaluated in the CHO cell reporter assay for activity. Of these, only certain clones were sequenced based on their ability to bind and cleave the target recognition sequence with acceptable levels of activity relative to the positive control CHO 23-24 meganuclease (marked as "#") and the parental meganuclease (marked as "*").

Of the clones evaluated after round 2 of selection (FIG. 5A), only two were sequenced. Both of these clones comprised a linker sequence of PGMKLSLSPNNNAS-TQRPSRNVNNFPG (SEQ ID NO: 32), with the underlined GMKLS (SEQ ID NO: 33) sequence appearing in each. Of the clones evaluated after round 4 of selection (FIG. 5B), only 4 were sequenced. Two of these also comprised the PGMKLSLSPNNNASTQRPSRNVNNFPG linker observed in round 2. One clone comprised a linker sequence of PGMSSQLSPNNNASTQRPSRNVNNFPG (SEQ ID NO: 34) with the underlined GMSSQ (SEQ ID NO: 35) sequence, while the other clone comprised a linker sequence of PGVKGTLSPNNNASTQRPSRNVNNFPG (SEQ ID NO: 36) with the underlined GVKGT (SEQ ID NO: 37) sequence. The clone comprising the GVKGT linker exhibited the highest level of activity, which was comparable to that of the parental meganuclease (FIG. 5B, clone D6).

Figures 6A, 6B:
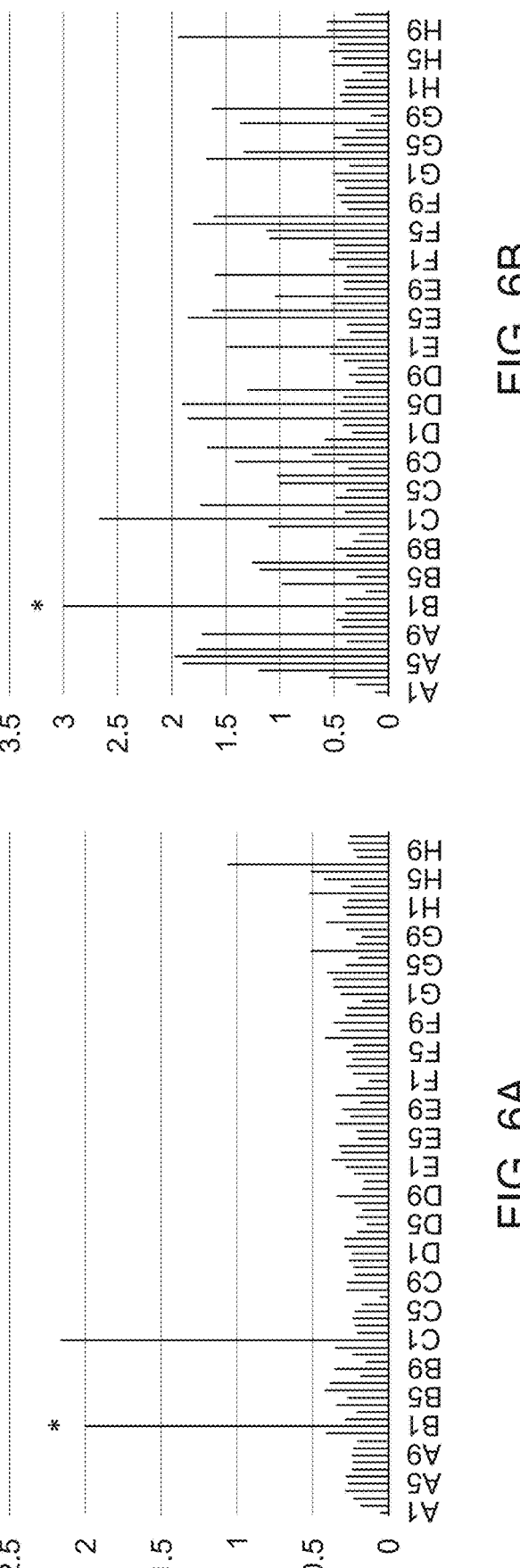
FIG. 6A provides the results of clones after two rounds of selection.
FIG. 6B provides the results of clones after four rounds of selection. Results for the parental meganuclease is marked as "*".

As shown in FIGS. 6A and 6B. 92 clones from the second library of linkers (i.e., Wlinkers) were also subcloned and evaluated in the CHO cell reporter assay for activity. Again, only certain clones were sequenced based on their ability to bind and cleave the target recognition sequence with acceptable levels of activity relative to the parental meganuclease (marked as "*").

Of the clones evaluated after round 2 of selection (Figure (A), only one was sequenced. This clone comprised a linker sequence of PGSVRGKNGSLNSSTQRPIVNWNNLPG (SEQ ID NO: 38), with the underlined RGKNG (SEQ ID NO: 39) arising from the library and selection. Of the clones evaluated after round 4 of selection (FIG. 6B). 16 were sequenced. All 16 of these sequenced clones comprised a PGSVPGGVSSLNSSTQRPIVNWNNLPG linker (SEQ ID NO: 40) with the underlined PGGVS (SEQ ID NO: 41) sequence arising from the library and selection.

3. Conclusions

The Flinker at round 2 with the 3-hour induction generated a 21.3% survival rate in the selection screen but there were only two results worth sequencing and both were still considerably lower than the CHO or HBV parental controls. The round 4 results with additional rounds of 2-hour inductions resulted in clones with better activity and importantly, one clone that was approaching the original linker activity. Similarly, the round 2 results for the Wlinker were low with only one clone reaching about half of the original linker while the round 4 yielded far more results that approached the original linker activity. Considering both libraries contained a theoretical size exceeding one hundred million possibilities, it was very surprising that the Flinker library only yielded three unique sequences and the Wlinker library only yielded one unique sequence. Clearly, fusing the two monomers in a functional single polypeptide with a shorter linker was challenging and needed to be more precise than originally anticipated. At this size, the linker is hypothesized to have to run along the protein in order to connect the two fusion points and does not have as much slack as in the original linker to exist away from the monomer subunits. This need to run along the protein most likely required a more precise fit which probably limited the amino acid sequence.

Example 2

Further Selection and Identification of Novel Polypeptide Linkers

1. Methods

Following the identification of Flinker and Wlinker sequences in Example 1, further libraries, selections, and sequencing were performed in an attempt to generate additional polypeptide linkers with greater activity.

To further improve upon the linkers identified in the first library (i.e., Flinkers), additional libraries were designed that utilized the GVKGT (SEQ ID NO: 37), GMKLS (SEQ ID NO: 33), and GMSSQ (SEQ ID NO: 35) sequences that were previously identified. These sequences were incorporated into further libraries based on the parental Flinker sequence as follows:

```
                                    (SEQ ID NO: 42)
       PGVKGTXXXNNNASTQRPSRNVNNFPG (SEQ ID NO: 43)
       PGMKLSXXXNNNASTQRPSRNVNNFPG (SEQ ID NO: 44)
       PGMSSQXXXNNNASTQRPSRNVNNFPG (SEQ ID NO: 45)
       PGVKGTXXXNNNASTQRPSRNVNNFPXG (SEQ ID NO: 46)
       PGMKLSXXXNNNASTQRPSRNVNNFPXG (SEQ ID NO: 47)
       PGMSSQXXXNNNASTQRPSRNVNNFPXG (SEQ ID NO: 48)
       PGVKGTXXXNNNASTQRPSRNVNNFPXXG (SEQ ID NO: 49)
       PGMKLSXXXNNNASTQRPSRNVNNFPXXG (SEQ ID NO: 50)
       PGMSSQXXXNNNASTQRPSRNVNNFPXXG
```

These libraries are referred to in this example as Flinker Library 2.1. As shown, three amino acids C-terminal to the sequences identified in Example 1 were randomized in these libraries. Additional libraries were generated wherein one or two additional randomized amino acids were added to the C-terminus of the linker as follows.

To further improve upon the linkers identified in the second library (i.e., Wlinkers), additional libraries were designed that utilized the PGGVS (SEQ ID NO: 41) sequence that was previously identified. This sequence was incorporated into further libraries based on the parental Wlinker sequence as follows:

```
                                    (SEQ ID NO: 51)
       PXXXPGGVSSLNSSTQRPIVNWNNLPG (SEQ ID NO: 52)
       PXXXPGGVSSLNSSTQRPIVNWNNLPXG (SEQ ID NO: 53)
       PXXXPGGVSSLNSSTQRPIVNWNNLPXXG
```

These libraries are referred to in this example as Wlinker Library 2.1. As shown, three amino acids N-terminal to the sequence identified in Example 1 were randomized in these libraries. Additional libraries were generated wherein one or two additional randomized amino acids were added to the C-terminus of the linker.

Further libraries were generated by exchanging the C-terminal and N-terminal regions of the Flinker and Wlinker library sequences as follows. A first set of combined library sequences included the N-terminal region of the Wlinker libraries and a conserved C-terminal region of the Flinker libraries NNNASTQRPSRNVNNFP (SEQ ID NO: 54; bolded):

```
                                    (SEQ ID NO: 55)
       PXXXPGGVSNNNASTQRPSRNVNNFPG (SEQ ID NO: 56)
       PXXXPGGVSNNNASTQRPSRNVNNFPXG (SEQ ID NO: 57)
       PXXXPGGVSNNNASTQRPSRNVNNFPXXG
```

These libraries are referred to in this example as Flinker Library 2.2. A second set of combined library sequences included the N-terminal region of the Flinker libraries and a conserved C-terminal region of the Wlinker libraries SLNSSTQRPIVNWNNLP (SEQ ID NO: 58; bolded):

```
                                    (SEQ ID NO: 59)
       PGVKGTXXXSLNSSTQRPIVNWNNLPG (SEQ ID NO: 60)
       PGMKLSXXXSLNSSTQRPIVNWNNLPG (SEQ ID NO: 61)
       PGMSSQXXXSLNSSTQRPIVNWNNLPG (SEQ ID NO: 62)
       PGVKGTXXXSLNSSTQRPIVNWNNLPXG (SEQ ID NO: 63)
       PGMKLSXXXSLNSSTQRPIVNWNNLPXG (SEQ ID NO: 64)
       PGMSSQXXXSLNSSTQRPIVNWNNLPXG (SEQ ID NO: 65)
       PGVKGTXXXSLNSSTQRPIVNWNNLPXXG (SEQ ID NO: 66)
       PGMKLSXXXSLNSSTQRPIVNWNNLPXXG (SEQ ID NO: 67)
       PGMSSQXXXSLNSSTQRPIVNWNNLPXXG
```

These libraries are referred to in this example as Wlinker Library 2.2. In all of the libraries described above, X represents all 20 amino acids. Each of these linker libraries was incorporated into the HBV 11-12L.520 meganuclease scaffold as previously described in Example 1, including the introduction of the seven subunit modifications (i.e., H37Y, K96A, Q99A, and K100D in the first subunit and W53F, K57Y, and E61T in the second subunit, with numbering relative to the wild-type I-CreI sequence) previously described. These libraries were subjected to the screening and selection processes described in Example 1, as well as the CHO cell reporter assay to characterize meganuclease activity.

The linker library sizes and screening conditions are provided in Table 2 below.

TABLE 2

| Linker Library | Lib. Size | R1 (4H) | R2(3H) | R3 | R4(2h) | R5 |
|---|---|---|---|---|---|---|
| Flinker 2.1 | 3.75E+08 | 0.17% | 0.58% | 2 h: 0.25% | 0.57% | 2 h: 3.1% |
| Flinker 2.2 | 6.75E+08 | | | 3 h: 4.9% | | 3 h: 25.9% |
| Wlinker 2.1 | 7.50E+08 | 0.01% | 11% | 2 h 0.43% | 4% | 2 h 8%% |
| Wlinker 2.2 | 6.75E+08 | | | 3 h: 8.1% | | 3 h: 91.7% |

Each of the Flinker and Wlinker libraries underwent five rounds of selection, followed by analysis of selected clones by the CHO reporter assay described in Example 1 for activity, and subsequent sequencing of specific clones.

2. Results

Figure 7:
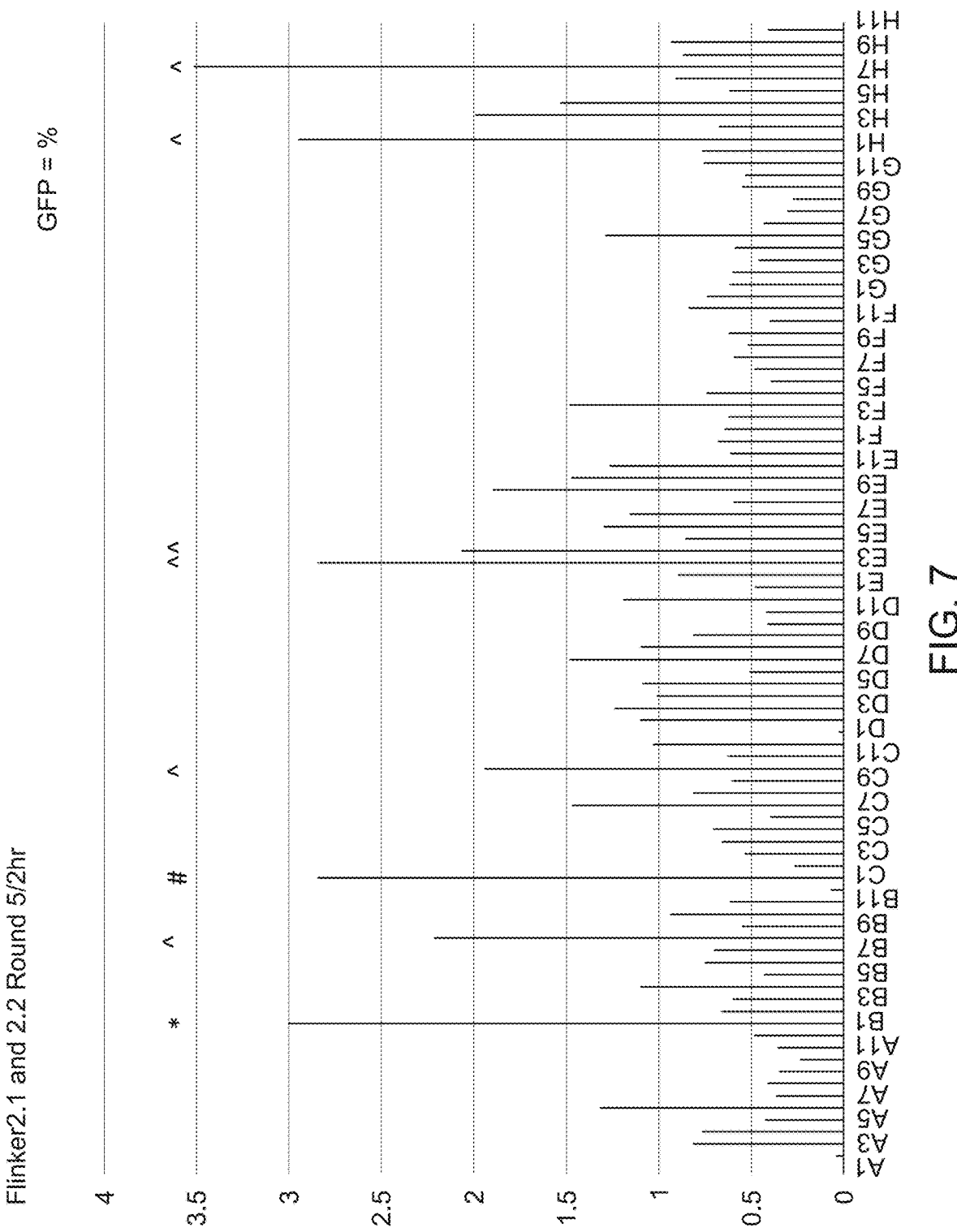
FIG. 7. Results from a CHO reporter cell assay of clones from the Flinker2.1 and Flinker2.2 libraries in the HBV 11-12L.520 engineered meganuclease scaffold after five rounds of selection with 2 hours of induction during the selection process. Clones exhibiting high levels of activity relative to the positive control CHO 23-24 meganuclease (marked as "#") and the parental meganuclease (marked as "*") were selected for sequencing and marked as "^".
Figure 8:
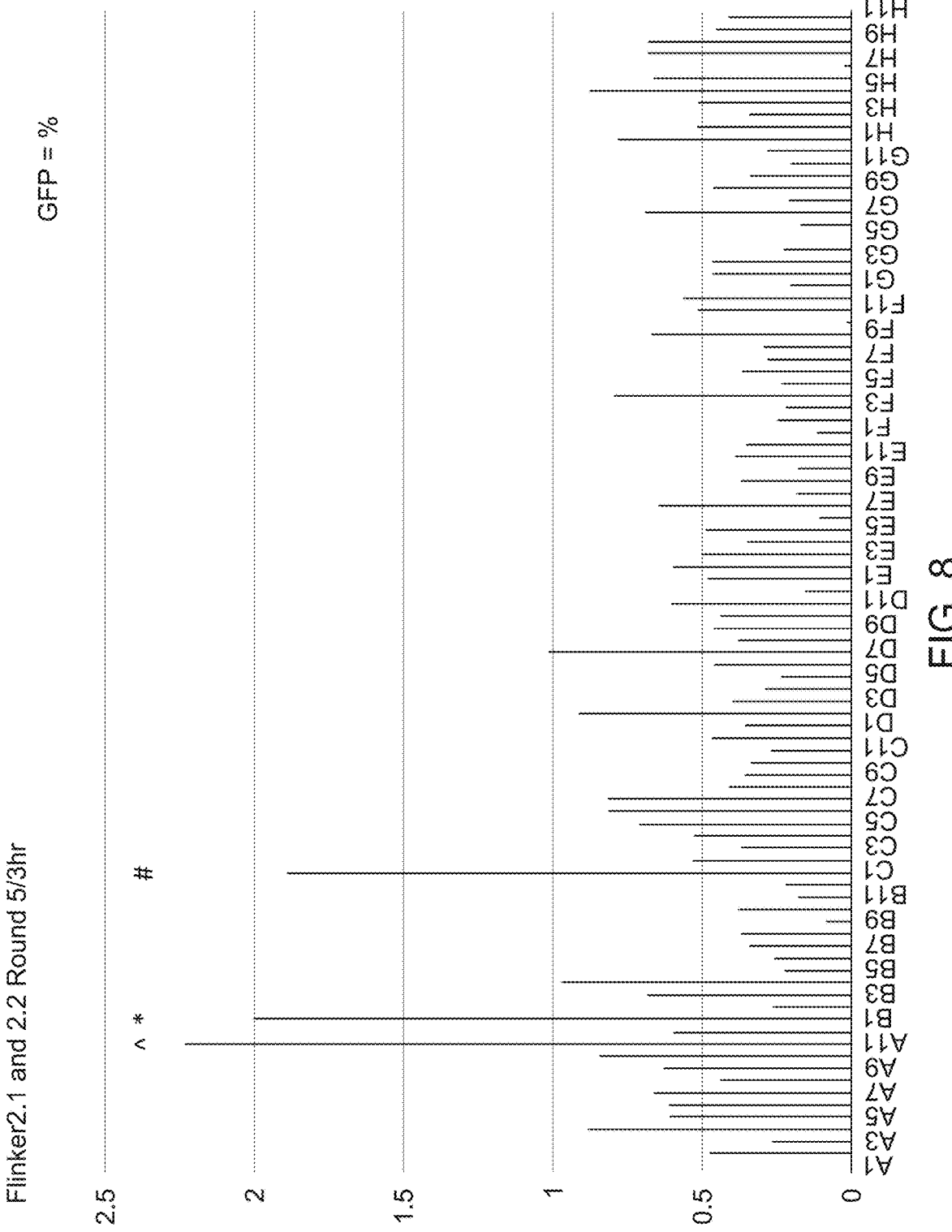
FIG. 8. Results from a CHO reporter cell assay of clones from the Flinker2.1 and Flinker2.2 libraries in the HBV 11-12L.520 engineered meganuclease scaffold after five rounds of selection with 3 hours of induction during the selection process. Clones exhibiting high levels of activity relative to the positive control CHO 23-24 meganuclease (marked as "#") and the parental meganuclease (marked as "*") were selected for sequencing and marked as "A".

Following library screening of the Flinker2.1 and Flinker2.2 libraries, clones were selected for activity analysis by the CHO reporter assay, with results shown in FIGS. 7 and 8. These figures represent activity of clones from both the Flinker2.1 and Flinker2.2 libraries after five rounds of selection, and with either 2 hours (FIG. 7) or 3 hours (FIG. 8) of induction during the selection process.

Clones exhibiting high levels of activity relative to the positive control CHO 23-24 meganuclease (marked as "#") and the parental meganuclease (marked as "*") were selected for sequencing. These selected clones are marked in each figure with an "^". Six clones were sequenced from the round 5/2 hr selection, and one clone was sequenced from the round 5/3 hr selection. The selected clones comprised the linker sequences shown in Table 3 below.

TABLE 3

Linker Sequences Identified from Flinker2.1 and Flinker2.2 Libraries

| Linker | Activity Score | Sequence | SEQ ID NO: |
|---|---|---|---|
| HBV 11-12L. 1766 | 2.95 | GIGVQVHRNNNASTQRPS RNVNNFPYKG | 116 |
| HBV 11-12L. 1771 | 2.84 | GVRLHCPLNNNASTQRPS RNVNNFPQG | 117 |
| HBV 11-12L. 1779 | 2.06 | GSVPGGVSSLNSSTQRPI VNWNNLPGSVSPSRPSLN SSTQRPIVNWNNLPG | 68 |
| HBV 11-12L. 1808 | 2.22 | GIRLSQGANNNASTQRPS RNVNNFPLG | 118 |
| HBV 11-12L. 1814 | 3.51 | GARPGGVSNNNASTQRPS RNVNNFPYSG | 119 |
| HBV 11-12L. 1825 | 1.94 | GVGRRKCANNNASTQRPS RNVNNFPLNG | 69 |
| HBV 11-12L. 1923 | 3.37 | GIQLNKESNNNASTQRPS RNVNNFPYSG | 120 |

As shown, all but one of the sequenced linkers (excluding HBV 11-12L.1779) comprised the conserved Flinker C-terminal sequence NNNASTQRPSRNVNNFP (SEQ ID NO: 54, bolded), with variable sequences introduced at both the N-terminus and the C-terminus where amino acids were randomized in the libraries (underlined).

Certain clones exhibited comparable or greater activity relative to the CHO 23-24 positive control or the parental meganuclease, with the HBV 11-12L.1923 and HBV 11-12L.1814 clones exhibiting the highest activity scores.

Surprisingly, most of the linkers generated by the libraries and selections were not predicted by the library design. For example, it would be predicted from the library design that linkers would comprise either "GT" or "PG" at the fourth and fifth positions. However, none of the sequenced linkers comprise these pairs at positions four and five. Similarly, it would be predicted from the library design that linkers would either comprise VKGT at positions 2-5 or GVS at positions 6-8. However, only one of the sequenced linkers (HBV 11-12L.1814) comprises one of these sets of amino acids (GVS). This surprising result is potentially due to the way the libraries were constructed by overlapping PCR and mixed for cloning into the HBV scaffold, possibly allowing cross pollination between libraries and additional mutations from PCR to fortunately isolate these results.

Figure 9:
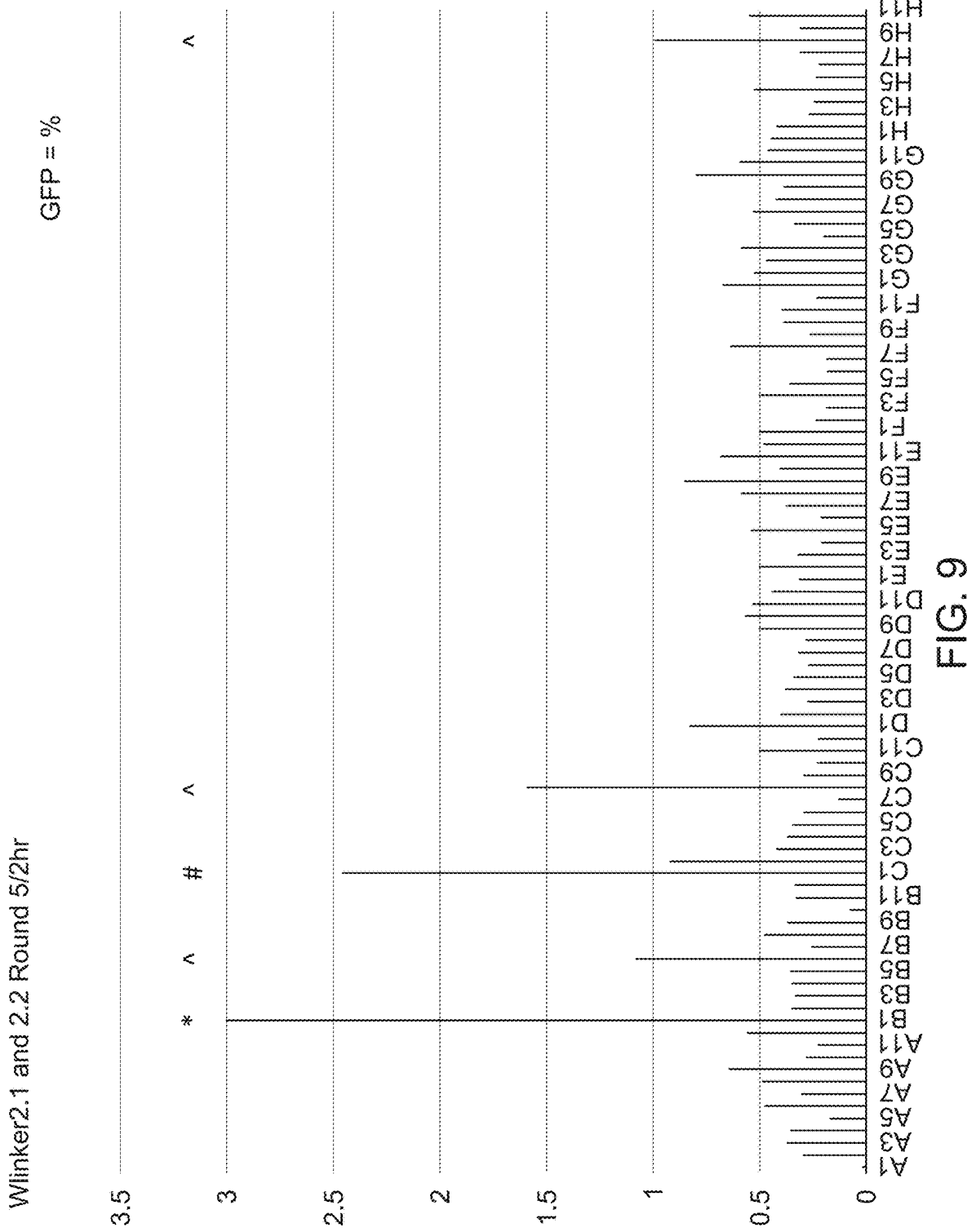
FIG. 9. Results from a CHO reporter cell assay of clones from the Wlinker2.1 and Wlinker2.2 libraries in the HBV 11-12L.520 engineered meganuclease scaffold after five rounds of selection with 2 hours of induction during the selection process. Clones exhibiting high levels of activity relative to the positive control CHO 23-24 meganuclease (marked as "#") and the parental meganuclease (marked as "*") were selected for sequencing and marked as "^".
Figure 10:
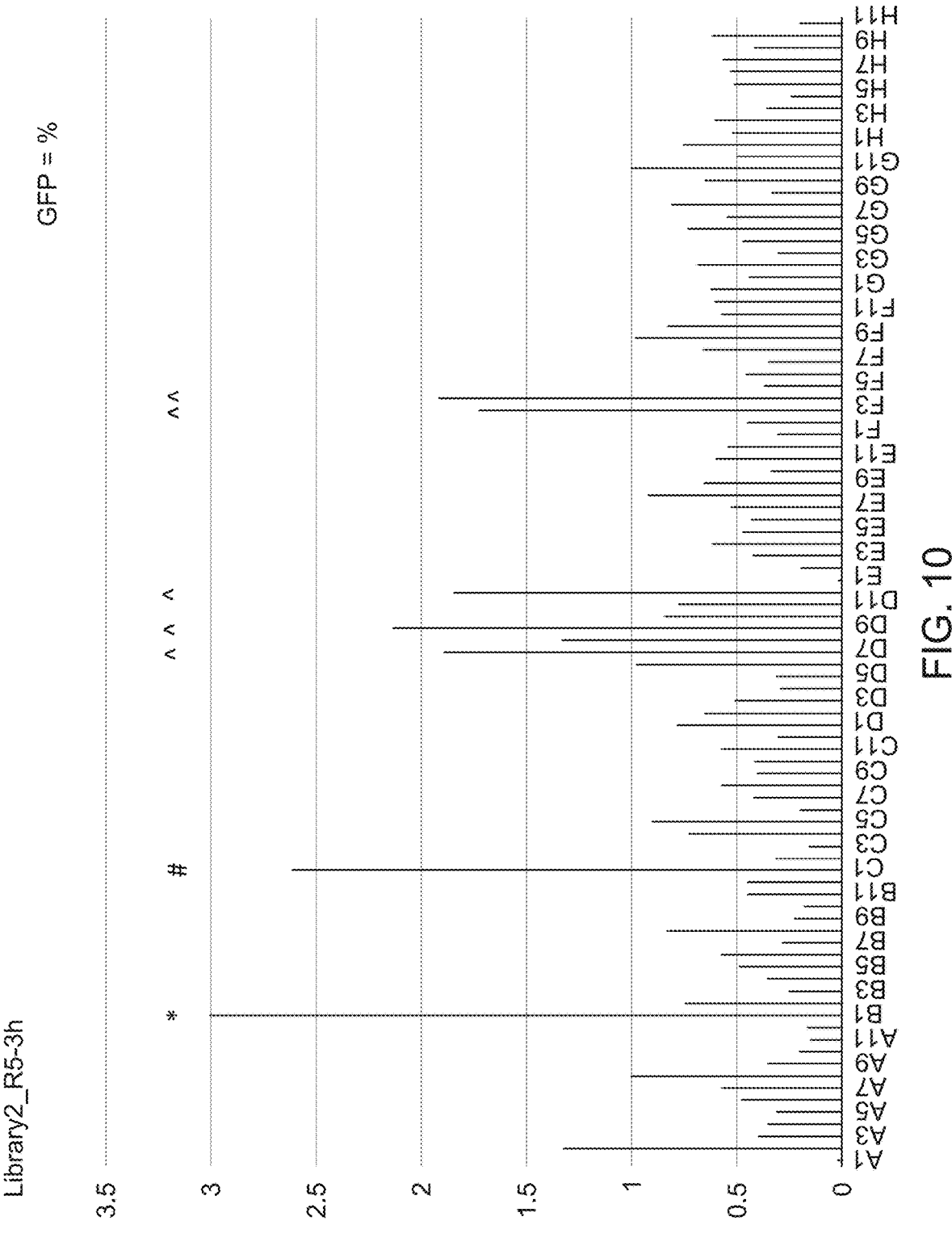
FIG. 10. Results from a CHO reporter cell assay of clones from the Wlinker2.1 and Wlinker2.2 libraries in the HBV 11-12L.520 engineered meganuclease scaffold after five rounds of selection with 3 hours of induction during the selection process. Clones exhibiting high levels of activity relative to the positive control CHO 23-24 meganuclease (marked as "#") and the parental meganuclease (marked as "*") were selected for sequencing and marked as "^".

Similarly, following library screening of the Wlinker2.1 and Wlinker2.2 libraries, clones were selected for activity analysis by the CHO reporter assay, with results shown in FIGS. 9 and 10. These figures represent activity of clones from both the Wlinker2.1 and Wlinker2.2 libraries after five rounds of selection, and with either 2 hours (FIG. 9) or 3 hours (FIG. 10) of induction during the selection process.

Clones exhibiting high levels of activity relative to the positive control CHO 23-24 meganuclease (marked as "#") and the parental meganuclease (marked as "*") were selected for sequencing. These selected clones are marked in each figure with an "A".

Three clones were sequenced from the round 5/2 hr selection, and five clones were sequenced from the round 5/3 hr selection. The selected clones comprised the linker sequences shown in Table 4 below.

TABLE 4

Linker Sequences Identified from Wlinker2.1 and Wlinker2.2 Libraries

| Linker | Activity Score | Sequence | SEQ ID NO: |
|---|---|---|---|
| HBV 11-12L. 1976 | 1.08 | GFNGHLSMSLNSSTQRPIVNWNNL PGEG | 70 |
| HBV 11-12L. 1993 | 1.59 | GSVPGGVSSLNSSTQRPIVNWNNL PGSVSPSRPSLNSSTQRPIVNWNN LPG | 71 |
| HBV 11-12L. 2006 | 0.99 | GVHLPLPLSLNSSTQRPIVNWNNL PGAG | 72 |
| HBV 11-12L. 2048 | 1.72 | GSVPGGVSSLNSSTQRPIVNWNNL PGSVSPSRPSLNSSTQRPIVNWNN LPG | 73 |

TABLE 4-continued

Linker Sequences Identified from Wlinker2.1
and Wlinker2.2 Libraries

| Linker | Activity Score | Sequence | SEQ ID NO: |
|---|---|---|---|
| HBV 11-12L. 2056 | 1.91 | GSVPGGVSSLNSSTQRPIVNWNNL PGSVSPSRPSLNSSTQRPIVNWNN LPG | 74 |
| HBV 11-12L. 2078 | 1.89 | GMKLSSAVSLNSSTQRPIVNWNNL PWGG | 75 |
| HBV 11-12L. 2094 | 2.13 | GSVPGGVSSLNSSTQRPIVNWNNL PGSVSPSRPSLNSSTQRPIVNWNN LPG | 76 |
| HBV 11-12L. 2118 | 1.84 | GMKVPRLESLNSSTQRPIVNWNNL PASG | 77 |

As shown, each of the shorter linkers comprised the conserved Wlinker C-terminal sequence SLNSSTQRPIV-NWNNLP (SEQ ID NO: 58, bolded), with variable sequences introduced at both the N-terminus and the C-terminus where amino acids were randomized in the libraries (underlined).

Contrary to what was observed with the clones selected in the two Flinker libraries, none of the clones selected and screened in the two Wlinker libraries achieved a level of activity comparable to the CHO 23-24 positive control or the parental meganuclease.

3. Conclusions

In these studies, additional novel linkers were generated, based on the Flinker sequences, that exhibited levels of activity comparable to, or exceeding, the activity of the parental meganuclease. The goal of these experiments was to identify a shorter linker that maintained or exceeded the activity of the original linker, so this further modification was encouraging. The selective pressure of the system was able to pull out additional answers beyond the initial design to accomplish this goal. Overall, the Flinker sequences appeared to enable greater activity for the meganuclease than Wlinker sequences that were identified: therefore, the Flinker sequences identified in these screens were pursued in further studies.

Example 3

Characterization of Engineered Meganucleases Comprising Novel Polypeptide Linkers and Subunit Modifications 1. Methods These experiments were designed to further evaluate one of the novel linkers, along with associated subunit modifications, that was identified in the library screens described in Example 2. More specifically, these studies evaluated whether one of the newly identified linkers and the subunit modifications could be utilized in a different scaffold other than the HBV 11-12L.520 meganuclease used in the libraries.

Here, the linker sequence identified as HBV 11-12L.1814 (SEQ ID NO: 8), which will be referred to as "Linker1814," was incorporated into an engineered meganuclease that was previously designed to bind and cleave a recognition sequence referred to as HAO 25-26 (SEQ ID NO: 78) in the human HAO gene. This meganuclease, referred to as the HAO 25-26L.908 meganuclease (SEQ ID NO: 79), was previously described in WO 2022/150616, which is hereby incorporated by reference in its entirety. A first variant of the HAO 25-26L.908 meganuclease was generated that comprised Linker1814 fused at the same positions as the parental Linker1 (i.e., at position 153 of the first (N-terminal) subunit and at a position in the second (C-terminal) subunit corresponding to position 5 of wild-type I-CreI). This variant, which is set forth in SEQ ID NO: 80, did not comprise any of the additional modifications in the first or second subunit. Next, a second variant of the HAO 25-26L.908 meganuclease was generated that comprised both Linker1814 as well as the modifications of H37Y, K96A, Q99A, and K100D in the first subunit, and W53F, K57Y, and E6IT in the second subunit (positions relative to wild-type I-CreI). This second variant had a sequence set forth in SEQ ID NO: 81. Each variant of the HAO 25-26L.908 meganuclease comprising Linker1814 (i.e., with or without the subunit modifications) was evaluated at two different mRNA concentrations (2.5 ng and 90 ng) in the CHO cell reporter assay described in Example 1.

2. Results

Figure 11:
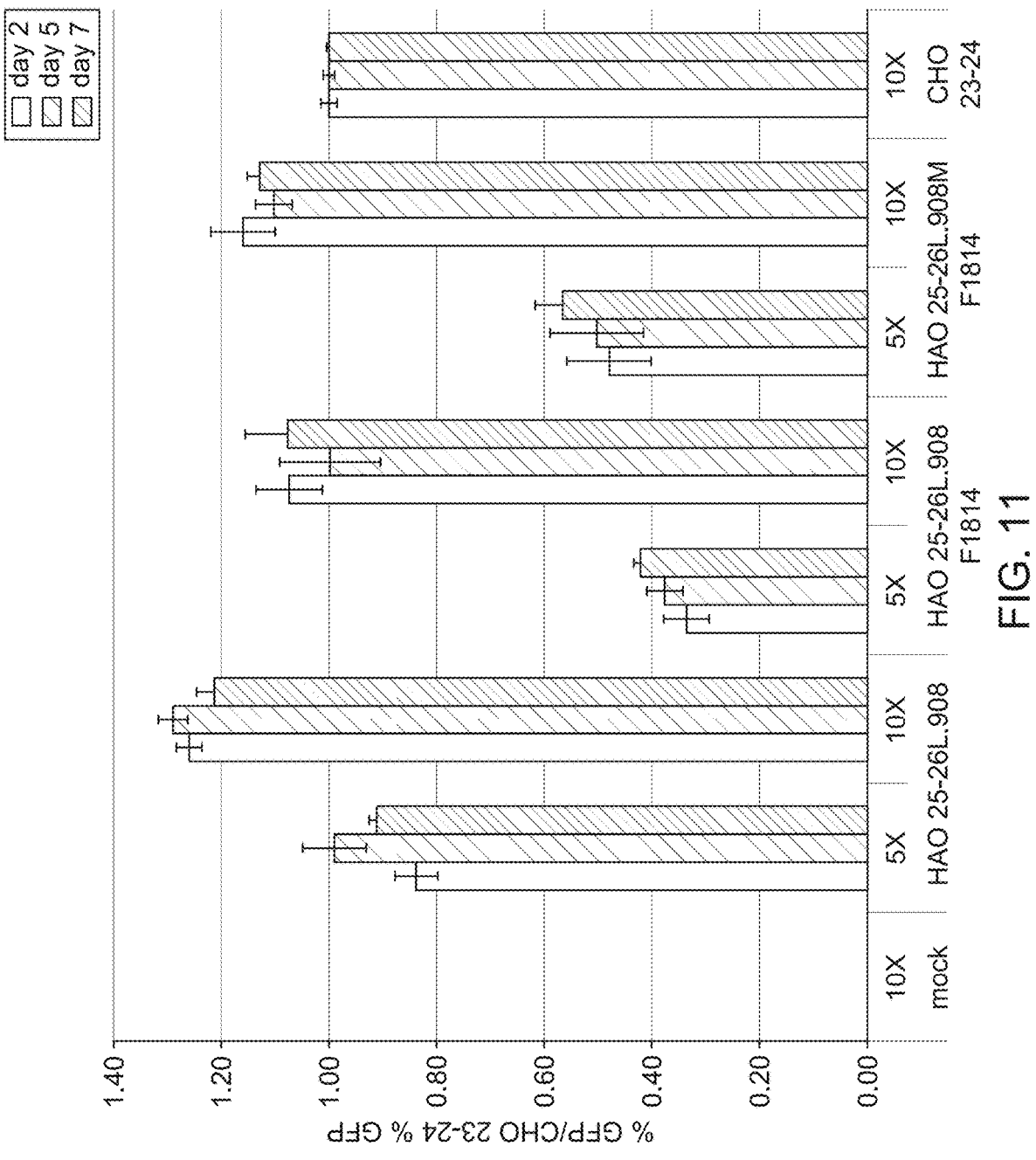
FIG. 11. Results from a CHO reporter cell assay with two different mRNA concentrations (2.5 ng, denoted as "low", and 90 ng, denoted as "high") of the HAO 25-26L.908 engineered meganuclease and two variants comprising Linker1814, one without subunit modifications, and one with subunit modifications (denoted with an "M").

The activity of the parental HAO 25-26L.908 meganuclease and the two variants comprising Linker1814 are shown in FIG. 11. The variants comprising Linker1814 are denoted with "F1814", and the variant further comprising the subunit modifications is denoted with an "M". At the high mRNA concentration, all three exhibited comparable activity to one another and to the CHO 23-24 control. However, differences were more apparent at the low mRNA concentration. Both of the variant meganucleases displayed activity, albeit lower than that of the parental meganuclease. It was also observed that the inclusion of the subunit modifications increased the activity of the variant comprising Linker1814 compared to the variant that did not comprise those subunit modifications.

3. Conclusions

These studies demonstrated that one of the novel linkers identified in the library screens (Linker1814) could be successfully adapted for use in another engineered meganuclease scaffold, in this case an engineered meganuclease targeting a recognition sequence in the human HAO gene. Although inclusion of Linker1814 alone reduced overall activity of the meganuclease relative to the parent version, it was notable that inclusion of the seven subunit modifications substantially improved the activity of the variant.

Example 4

Further Characterization of Engineered Meganucleases Comprising Novel Polypeptide Linkers and Subunit Modifications 1. Methods Following evaluation of Linker1814 in Example 3, these studies were designed to evaluate other novel linkers and subunit modifications identified in the library screens in Example 2.

Similar to Example 3, the HAO 25-26L.908 meganuclease was again used as a scaffold to evaluate the linker sequences of Example 2 identified as HBV 11-12L.1766 (SEQ ID NO: 5; Linker1766), HBV 11-12L.1771 (SEQ ID NO: 6; Linker1771), HBV 11-12L.1808 (SEQ ID NO: 7; Linker1808), HBV 11-12L.1814 (SEQ ID NO: 8; Linker1814), and HBV 11-12L.1923 (SEQ ID NO: 4; Linker1923). Consistent with the experimental design of Example 3, a first variant meganuclease was generated with each linker that did not comprise any of the subunit modifications, and a second variant meganuclease was generated that comprised the full set of seven subunit modifications at positions H37Y, K96A, Q99A, and K100D of the first subunit and positions W53F, K57Y, and E61T of the second subunit (corresponding to residue positions of the wild-type I-CreI meganuclease). The sequences of the parental meganuclease and each variant are as follows:

HAO 25-26L.908 parental: SEQ ID NO: 79

HAO 25-26L.908 Linker1766: SEQ ID NO: 82

HAO 25-26L.908 Linker1766 with subunit modifications (M): SEQ ID NO: 83

HAO 25-26L.908 Linker1771: SEQ ID NO: 84

HAO 25-26L.908 Linker1771 with subunit modifications (M): SEQ ID NO: 85

HAO 25-26L.908 Linker1808: SEQ ID NO: 86

HAO 25-26L.908 Linker1808 with subunit modifications (M): SEQ ID NO: 87

HAO 25-26L.908 Linker1814: SEQ ID NO: 80

HAO 25-26L.908 Linker1814 with subunit modifications (M): SEQ ID NO: 81

HAO 25-26L.908 Linker1923: SEQ ID NO: 88

HAO 25-26L.908 Linker1923 with subunit modifications (M): SEQ ID NO: 89

The parental HAO 25-26L.908 meganuclease and each variant was tested at two mRNA concentrations (2.5 ng and 90 ng) in the Fulk assay as described in Example 1.

2. Results

Figure 12:
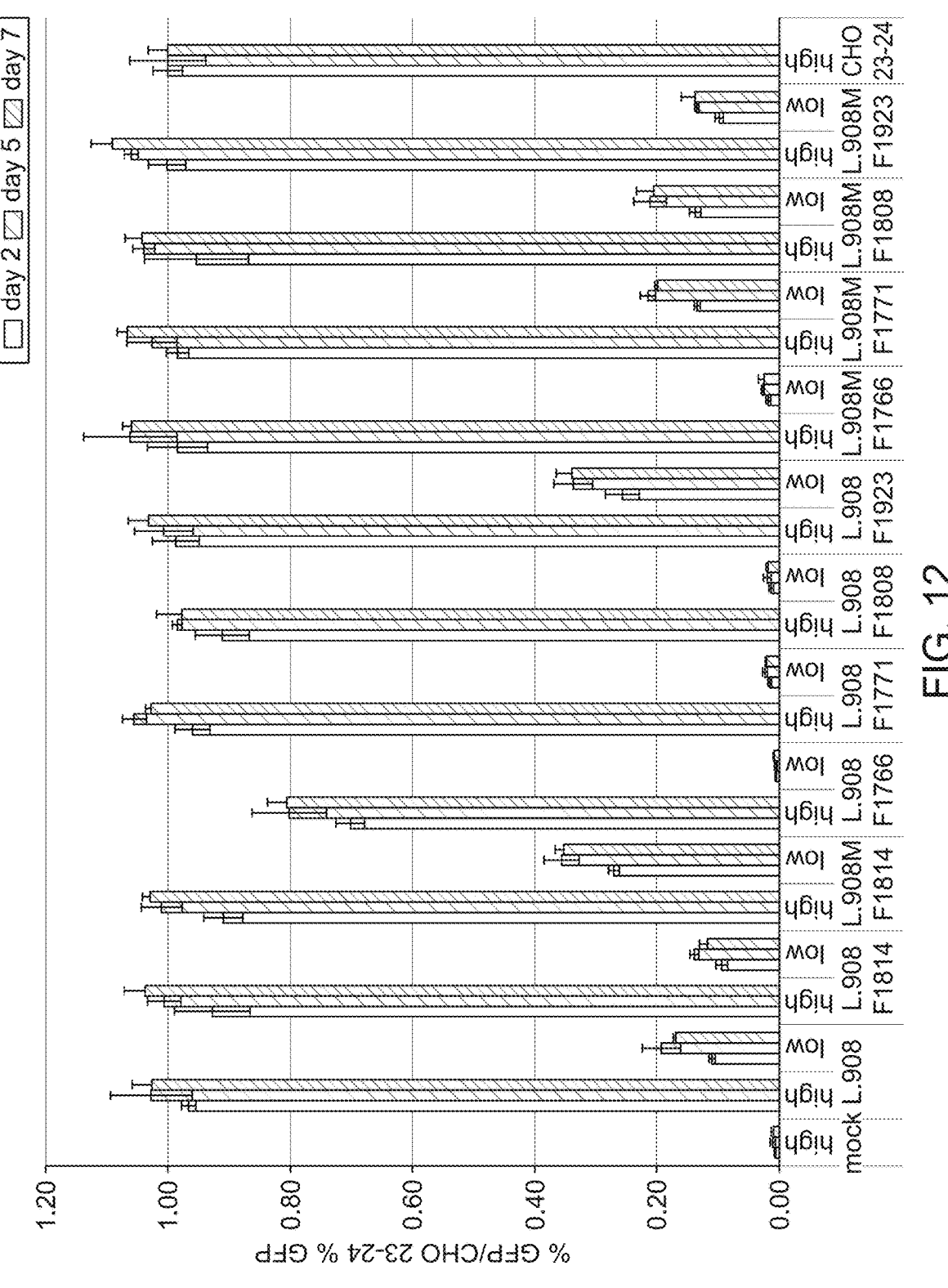
FIG. 12. Results from a CHO reporter cell assay with two different mRNA concentrations (2.5 ng, denoted as "low", and 90 ng, denoted as "high") of the HAO 25-26L.908 engineered meganuclease and two variants comprising Linker1766, two variants comprising Linker1771, two variants comprising Linker1808, two variants comprising Linker1814, and two variants comprising Linker1923, wherein each of the variant pairs comprised one without subunit modifications, and one with subunit modifications (denoted with an "M").

The activity of the parental HAO 25-26L.908 meganuclease and each variant are shown in FIG. 12. The variants comprising the subunit modifications are denoted with an "M".

The parent meganuclease and nearly all of the variants exhibited similar activity at the high concentration of mRNA, with the exception of Linker1766 with no subunit modifications, which exhibited somewhat lower activity. However, differences were discernable at the lower concentration.

At low concentrations, variants comprising Linker1814 with no subunit modifications exhibited activity slightly lower than that of the parental nuclease. However, addition of the subunit modifications significantly improved activity of the Linker1814 variant to more than twice that of the variant lacking the subunit modifications, and approximately twice that of the parental meganuclease.

At low concentrations, variants comprising Linker1766, Linker1771, or Linker1808, each without the subunit modifications, exhibited little activity and substantially less than the parental meganuclease nuclease. However, for each of these linkers, the addition of the subunit modifications improved activity of the variant. For Linker1766, the subunit modifications increased activity, though not to the level of the parental meganuclease. By contrast, addition of the subunit modifications to the variants comprising Linker1771 or Linker1808 increased activity to a similar, or slightly higher, level as the parental meganuclease.

At low concentrations, variants comprising Linker1923 without the subunit modifications exhibited approximately double the activity of the parental meganuclease, and was the highest for any linker in the absence of the subunit modifications. However, the addition of the full set of seven subunit modifications reduced activity of this variant to levels similar to, or slightly below, that of the parental meganuclease.

3. Conclusions

These experiments demonstrated that at least four of the novel polypeptide linkers identified in the earlier library screens could be introduced into new meganuclease scaffolds and allow those meganucleases to either retain a level of activity comparable to the parental meganuclease, or exceed that level of activity. These experiments further demonstrated that the inclusion of the full set of seven subunit modifications produced either a positive or negative effect on the activity of the meganuclease based on the polypeptide linker that is incorporated. It was reasoned that different subsets of amino acid modifications within the set of seven subunit modifications could be having positive and negative effects and that this balance between the positive and negative impacts could be causing the different results with different linkers.

Example 5

Evaluation of Subunit Substitution Combinations in Engineered Meganucleases Comprising Novel Polypeptide Linkers 1. Methods This experiment was designed to test the effects of introducing various combinations of the subunit modifications into different meganucleases and the corresponding effect on meganuclease activity. The combinations of subunit modifications shown in Table 5 below were introduced in conjunction with Linker1923, Linker1766, Linker1771, Linker1808, and Linker1814, which were introduced into two different meganuclease scaffolds. The activity of each meganuclease variant was tested in the CHO reporter cell assay according to Example 1 with analysis performed on day 2.

TABLE 5

| | | Subunit Modification Groupings | |
|---|---|---|
| Mutation Group | Mutations within Subunit 1 (N-terminal) | Mutations within Subunit 2 (C-terminal) |
| 1 | K96A | K57Y, E61T |
| 2 | Q99A, K100D | |
| 3 | H37Y | W53F |
| 1 + 2 | K96A, Q99A, K100D | K57Y, E61T |
| 1 + 3 | H37Y, K96A | W53F, K57Y, E61T |
| 2 + 3 | H37Y, Q99A, K100D | W53F |
| 1 + 2 + 3 | H37Y, K96A, Q99A, K100D | W53F, K57Y, E61T |

The first scaffold was the HBV 11-12L.1090 meganuclease (SEQ ID NO: 101), which targets a recognition sequence in the hepatitis B virus genome and was previously described in WO2021113765, which is incorporated herein by reference in its entirety. The HBV 11-12L.1090 meganuclease variants prepared for this experiment are shown in Table 6 below:

TABLE 6

| Scaffold Nuclease | Linker | Subunit Modifications | SEQ ID NO: |
|---|---|---|---|
| HBV 11-12L.1090 | Linker 1 | None | 101 |
| HBV 11-12L.1090 | Linker1923 | None | 121 |
| HBV 11-12L.1090 | Linker1923 | Group 1 | 122 |
| HBV 11-12L.1090 | Linker1923 | Group 2 | 123 |
| HBV 11-12L.1090 | Linker1923 | Group 3 | 124 |
| HBV 11-12L.1090 | Linker1923 | Group 1 + 2 | 100 |

TABLE 6-continued

| Scaffold Nuclease | Linker | Subunit Modifications | SEQ ID NO: |
|---|---|---|---|
| HBV 11-12L.1090 | Linker1923 | Group 1 + 3 | 125 |
| HBV 11-12L.1090 | Linker1923 | Group 2 + 3 | 126 |
| HBV 11-12L.1090 | Linker1923 | Group 1 + 2 + 3 | 127 |
| HBV 11-12L.1090 | Linker1766 | None | 128 |
| HBV 11-12L.1090 | Linker1766 | Group 1 + 2 | 129 |
| HBV 11-12L.1090 | Linker1766 | Group 1 + 2 + 3 | 130 |
| HBV 11-12L.1090 | Linker1771 | None | 131 |
| HBV 11-12L.1090 | Linker1771 | Group 1 + 2 | 132 |
| HBV 11-12L.1090 | Linker1771 | Group 1 + 2 + 3 | 133 |
| HBV 11-12L.1090 | Linker1808 | None | 134 |
| HBV 11-12L.1090 | Linker1808 | Group 1 + 2 | 135 |
| HBV 11-12L.1090 | Linker1808 | Group 1 + 2 + 3 | 136 |
| HBV 11-12L.1090 | Linker1814 | None | 137 |
| HBV 11-12L.1090 | Linker1814 | Group 1 + 2 | 138 |
| HBV 11-12L.1090 | Linker1814 | Group 1 + 2 + 3 | 139 |

The second scaffold was the F8R 1-2x.9 meganuclease (SEQ ID NO: 140), which targets a recognition sequence in the human Factor VIII gene and was previously described in WO2017192741, which is incorporated herein by reference in its entirety. The F8R 1-2x.9 meganuclease variants prepared for this experiment are shown in Table 7 below.

TABLE 7

| Scaffold Nuclease | Linker | Subunit Modifications | SEQ ID NO: |
|---|---|---|---|
| F8R 1-2x.9 | Linker1 | None | 140 |
| F8R 1-2x.9 | Linker1923 | None | 141 |
| F8R 1-2x.9 | Linker1923 | Group 1 | 142 |
| F8R 1-2x.9 | Linker1923 | Group 2 | 143 |
| F8R 1-2x.9 | Linker1923 | Group 3 | 144 |
| F8R 1-2x.9 | Linker1923 | Group 1 + 2 | 145 |
| F8R 1-2x.9 | Linker1923 | Group 1 + 3 | 146 |
| F8R 1-2x.9 | Linker1923 | Group 2 + 3 | 147 |
| F8R 1-2x.9 | Linker1923 | Group 1 + 2 + 3 | 148 |
| F8R 1-2x.9 | Linker1766 | None | 149 |
| F8R 1-2x.9 | Linker1766 | Group 1 + 2 | 150 |
| F8R 1-2x.9 | Linker1766 | Group 1 + 2 + 3 | 151 |
| F8R 1-2x.9 | Linker1771 | None | 152 |
| F8R 1-2x.9 | Linker1771 | Group 1 + 2 | 153 |
| F8R 1-2x.9 | Linker1771 | Group 1 + 2 + 3 | 154 |
| F8R 1-2x.9 | Linker1808 | None | 155 |
| F8R 1-2x.9 | Linker1808 | Group 1 + 2 | 156 |
| F8R 1-2x.9 | Linker1808 | Group 1 + 2 + 3 | 157 |
| F8R 1-2x.9 | Linker1814 | None | 158 |
| F8R 1-2x.9 | Linker1814 | Group 1 + 2 | 159 |
| F8R 1-2x.9 | Linker1814 | Group 1 + 2 + 3 | 160 |

Each of the variants was tested against a mock and the CHO 23-24 meganuclease previously described as controls.

2. Results

Figure 13A:
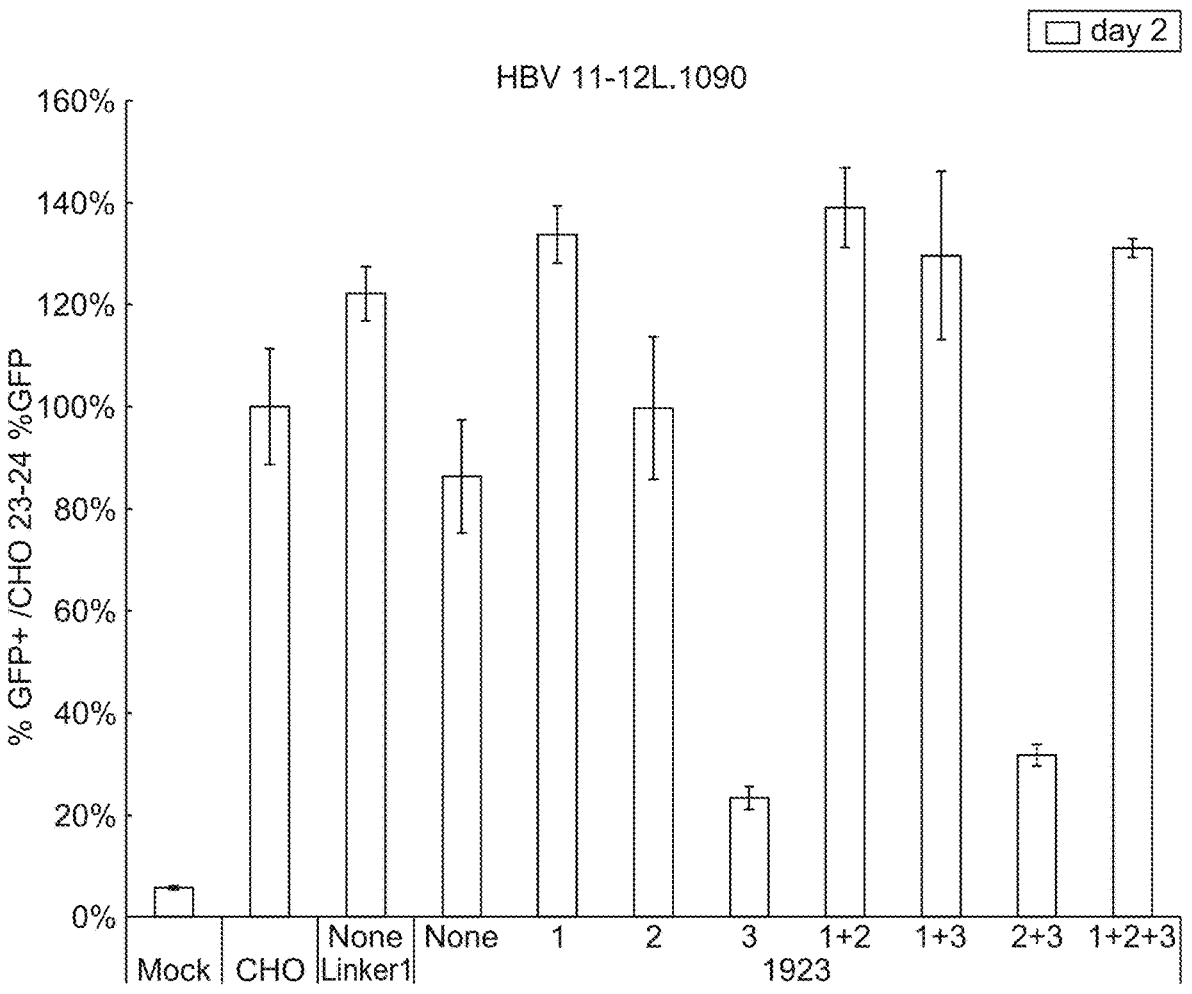
FIG. 13A-FIG. 13E. Results from a CHO reporter cell assay evaluating the activity of a parental HBV 11-12L.1090 engineered meganuclease and variants of HBV 11-12L.1090 comprising Linker1923 (FIG. 13A), Linker1766 (FIG. 13B), Linker1771 (FIG. 13C), Linker1808 (FIG. 13D), and Linker1814 (FIG. 13E), with and without various combinations of amino acid modifications in the N-terminal and C-terminal subunits, relative to mock and CHO 23-24 controls.
Figures 13B, 13C:
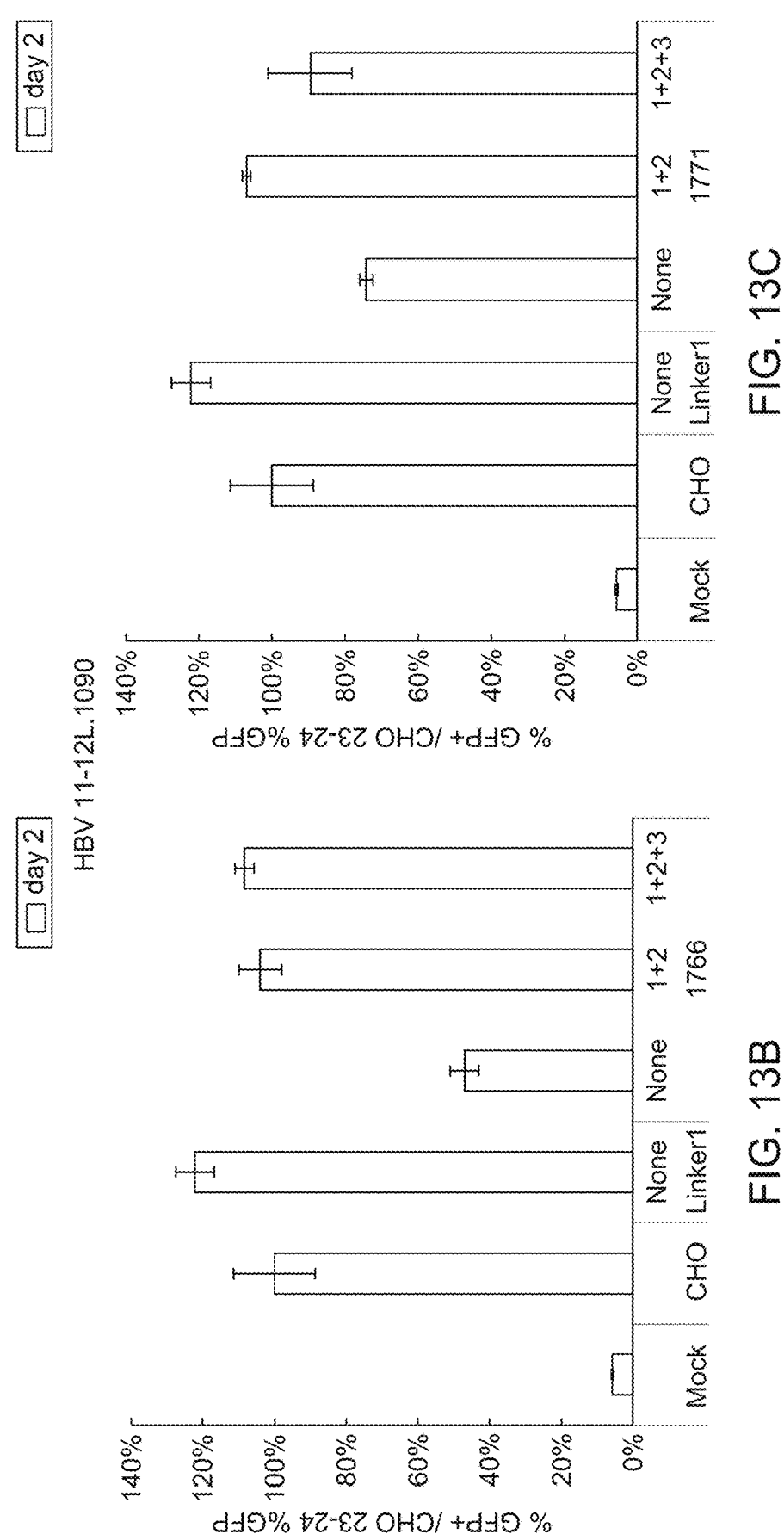
Figures 13D, 13E:
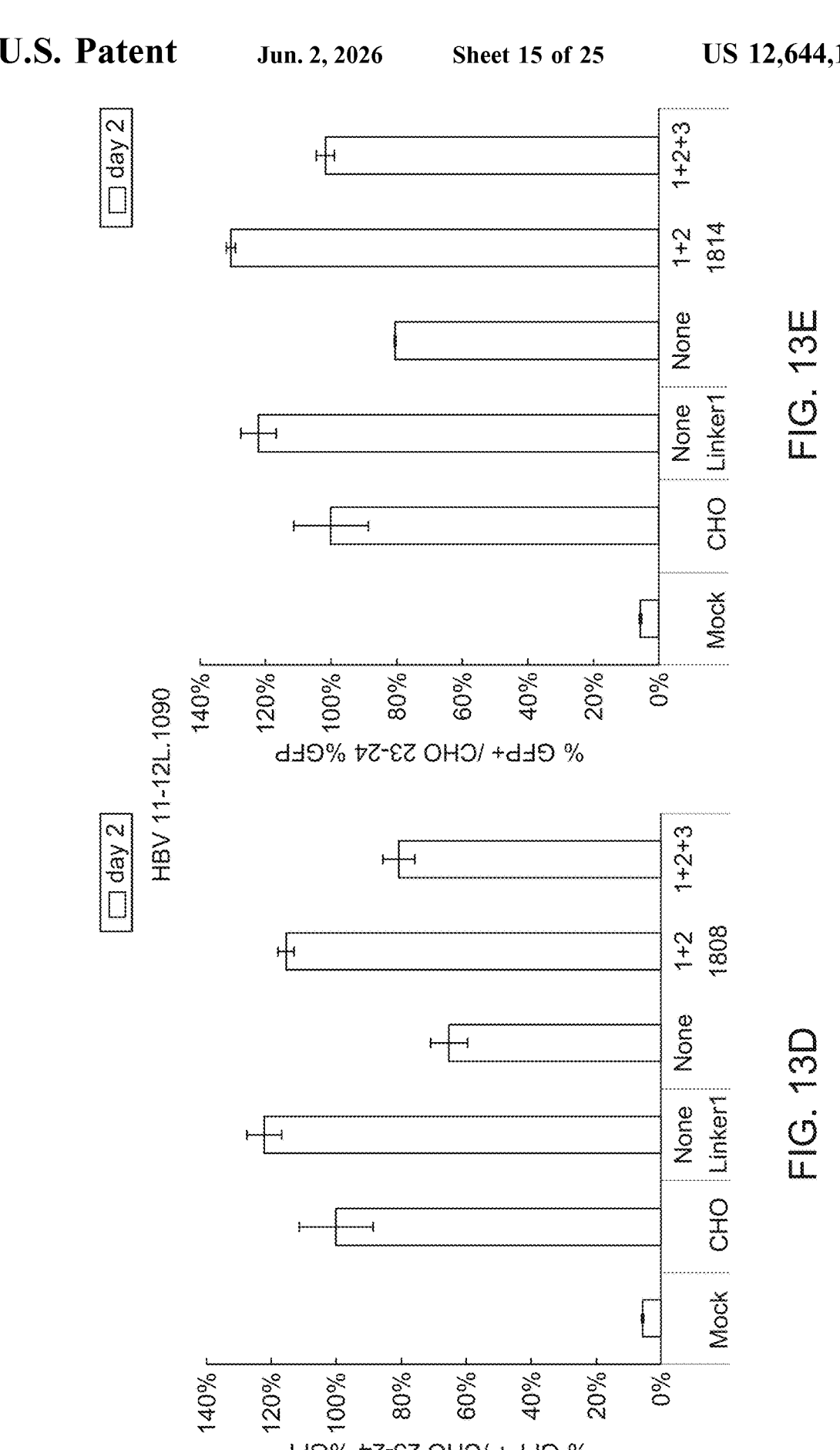
Figures 14A, 14B:
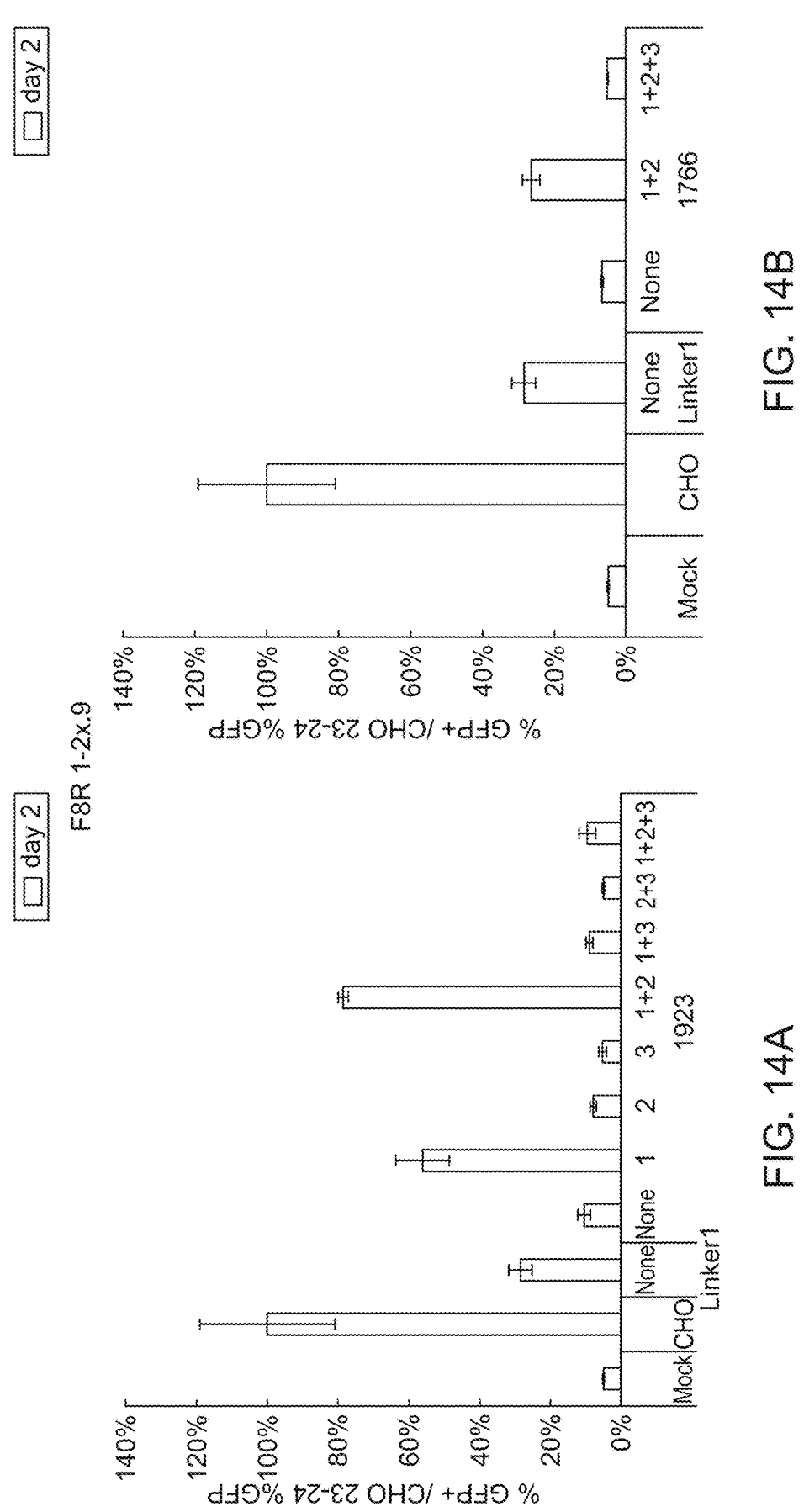
FIG. 14A-FIG. 14E. Results from a CHO reporter cell assay evaluating the activity of a parental F8R 1-2x.9 engineered meganuclease and variants of F8R 1-2x.9 comprising Linker1923 (FIG. 13A), Linker1766 (FIG. 13B), Linker1771 (FIG. 13C), Linker1808 (FIG. 13D), and Linker1814 (FIG. 13E), with and without various combinations of amino acid modifications in the N-terminal and C-terminal subunits, relative to mock and CHO 23-24 controls.
Figures 14C, 14D:
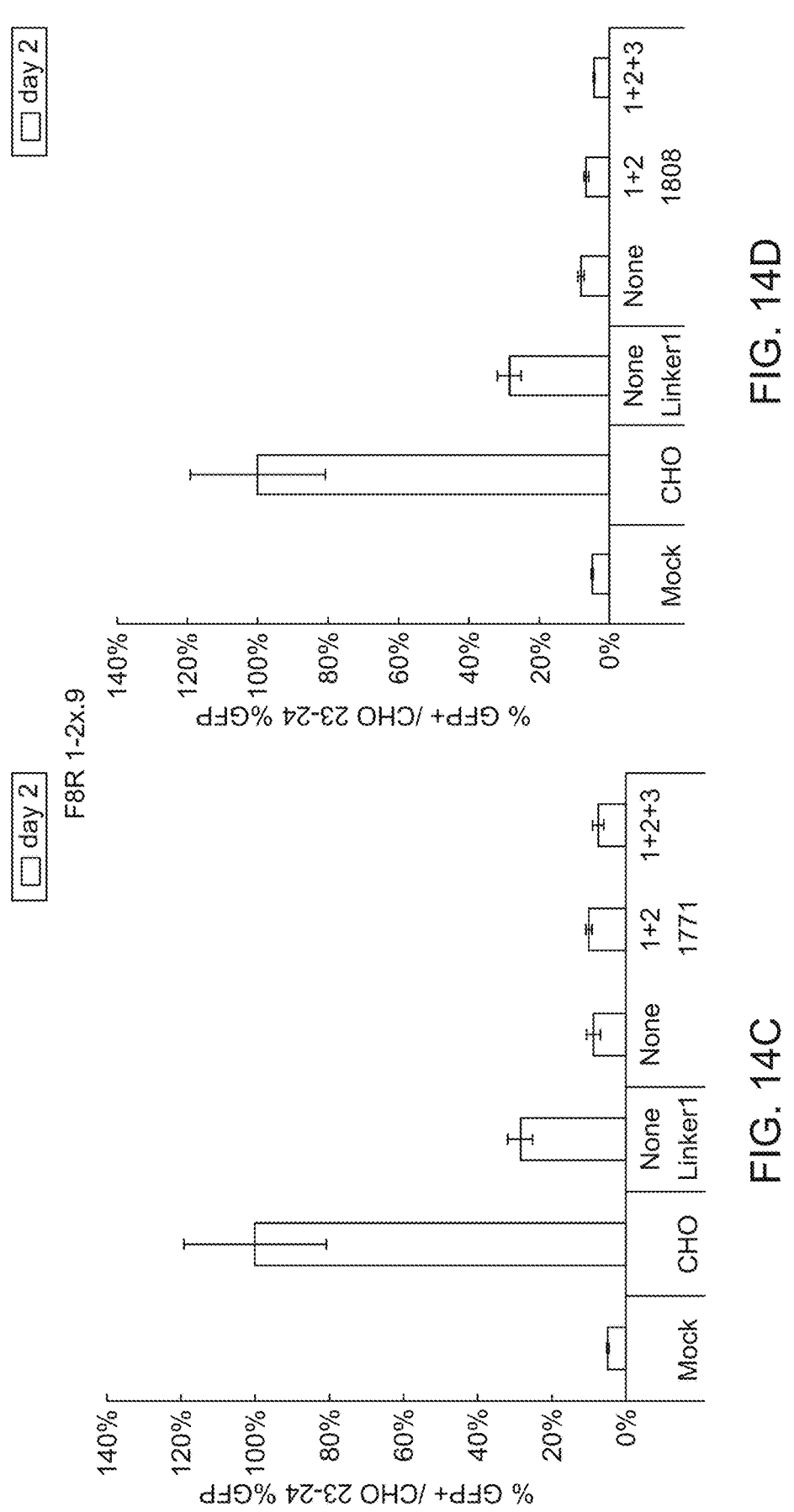
Figure 14E:
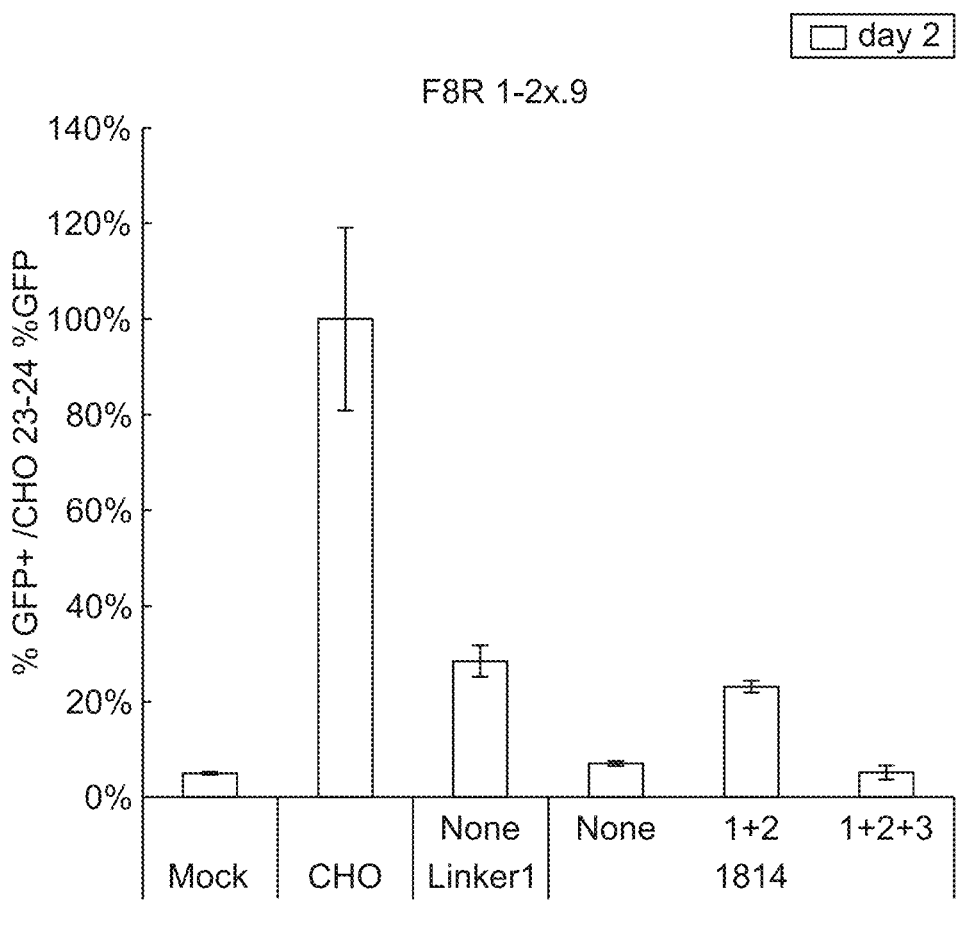

The activity results of each meganuclease variant, with the various linkers and combinations of subunit modifications, are shown in FIG. 13 (HBV 11-12L.1090) and FIG. 14 (F8R 1-2x.9). Each HBV 11-12L.1090 variant was evaluated at a low mRNA concentration (2.5 ng) due to the high level of activity of the parent meganuclease. The F8R 1-2x.9 variants were evaluated at a higher mRNA concentration (100 ng) due to the lower relative activity of the parent meganuclease. It was observed that the different combinations of subunit modifications resulted in differing levels of meganuclease activity in each scaffold.

For those variants of HBV 11-12L.1090, it was observed that replacing the parental Linker1 with any of the five novel linkers, in the absence of any subunit modifications, resulted in a significant decrease in meganuclease activity (FIGS. 13A-13E). When incorporating Linker1923 (FIG. 13A), it was observed that the addition of the Group 1 subunit modifications enhanced activity to a level above that of the parental nuclease having Linker1. The addition of the Group 2 subunit modifications also enhanced activity to a lesser degree, while the addition of the Group 3 subunit modifications substantially suppressed activity. Incorporating the Group 1 and 2 subunit modifications (1+2) together produced the highest level of meganuclease activity, whereas with the Group 1 and 3 (1+3) and Group 1, 2, and 3 combinations (1+2+3) produced a slightly lower level of activity. By comparison, the addition of the Group 2 and 3 combination (2+3) exhibited suppressed activity, suggesting that in the absence of the Group 1 modifications, the Group 3 modifications act to suppress activity.

For the remaining novel linkers used with HBV 11-12L.1090, the only variants tested were novel linker with no modifications, a combination of the Group 1 and 2 modifications (1+2), and a combination of the Group 1, 2, and 3 modifications (1+2+3). Similar to Linker1923, all remaining linkers also exhibited reduced meganuclease activity relative to the parental linker when no subunit modifications are incorporated (FIGS. 13B-13E). Also similar to Linker1923, addition of the Group 1 and 2 modifications combination (1+2) improved activity to levels near (slightly higher or lower, or comparable to) the parent meganuclease activity. The combination of Group 1, 2, and 3 modifications produced variable changes in activity depending on the linker, with little change observed with Linker1766, and reductions of various degrees for Linker1771, Linker1808, and Linker1814.

Similar to what was observed with the HBV 11-12L.1090 variants, it was observed with all variants of F8R 1-2x.9 that replacing the parental Linker1 with any of the five novel linkers, in the absence of any subunit modifications, resulted in a significant decrease in meganuclease activity (FIGS. 14A-14E). When incorporating Linker1923 (FIG. 14A), it was observed that the addition of the Group 1 subunit modifications enhanced activity to a level substantially above that of the parental nuclease having Linker1. The addition of a combination of the Group 1 and Group 2 subunit modifications (1+2) further enhanced activity. The addition of either the Group 2 or Group 3 modifications suppressed meganuclease activity, as did combinations of Groups 1 and 3 (1+3) and Groups 2 and 3 (2+3). By contrast to the HBV 11-12L.1090 variants, a combination of Groups 1, 2, and 3 (1+2+3) remained suppressed rather than exhibiting higher activity.

For the remaining novel linkers used with F8R 1-2x.9, the only variants tested were novel linker with no modifications, a combination of the Group 1 and 2 modifications (1+2), and a combination of the Group 1, 2, and 3 modifications (1+2+3). Similar to Linker1923, all remaining linkers also exhibited reduced meganuclease activity relative to the parental linker when no subunit modifications are incorporated (FIGS. 14B-14E). The combination of Group 1 and 2 combinations (1+2) enhanced meganuclease activity with Linker1766 and Linker1814, while having no apparent effect with the other two linkers. Also similar to Linker1923, a combination of Groups 1, 2, and 3 (1+2+3) remained suppressed.

3. Conclusions

It was observed in these studies that various combinations of amino acid modifications within the N-terminal and C-terminal subunits could modulate the activity of engineered meganucleases comprising the novel linkers. It was observed in both meganuclease scaffolds tested that incorporating Linker1923 with a combination of the Group 1 and Group 2 (1+2) subunit modifications produced the highest overall activity. Additionally, the combined Group 1 and 2

(1+2) modifications increased activity versus no modifications for nearly all of the linker/scaffold combinations tested. Generally, incorporation of the Group 3 modifications suppressed activity, either alone or in combination with other group modifications. Accordingly, these studies demonstrate that the activity of engineered meganucleases comprising the novel linkers can be modulated to enhance or suppress activity by incorporating different combinations of these N-terminal and C-terminal subunit modifications.

Example 6

Further Evaluation of Subunit Substitution Combinations in Engineered Meganucleases Comprising Novel Polypeptide Linkers 1. Methods This experiment was designed to evaluate the effect of introducing only a subset of subunit modifications, identified in Example 5 as group "1+2", also referred to herein as "(1/2)" along with Linker1923 in three additional meganuclease scaffolds. The first meganuclease scaffold was the HAO 25-26L.1434 meganuclease (SEQ ID NO: 90) which was previously described in WO 2022/150616, which is herein incorporated by reference in its entirety. The second meganuclease scaffold was the HBV 27-28L.385 meganuclease (SEQ ID NO: 91) designed to target a recognition sequence referred to as HBV 27-28 (SEQ ID NO: 92) in the hepatitis B virus genome. The third meganuclease scaffold was RHO2-L3-3 (SEQ ID NO: 161) which was previously described in WO2017044649, which is incorporated herein by reference in its entirety. Variants of these three meganucleases were generated that included Linker1923 (introduced as previously discussed) and the subunit modifications identified in Example 5 as "(1/2)", which included K96A, Q99A, K100D in the first (N-terminal) subunit and K57Y and E61T in the second (C-terminal) subunit (with numbering corresponding to positions in wild-type I-CreI of SEQ ID NO: 1). The sequences of the HAO 25-26L.1434, HBV 27-28L.385, and RHO2-L3-3 variant meganucleases are shown below:

HAO 25-26L.1434 Linker1923 with "(1/2)" modifications: SEQ ID NO: 93

HBV 27-28L.385 Linker1923 with "(1/2)" modifications: SEQ ID NO: 94

RHO2-L3-3 Linker1923 with "(1/2)" modifications: SEQ ID NO: 162

The activity of these parental and variant meganucleases were then tested in the CHO reporter cell assay as described in Example 1. The HAO 25-26L.1434 and HBV 27-28L.385 meganucleases were evaluated at a low mRNA concentration (2.5 ng), due to the relatively high activity of the parental meganucleases, whereas the RHO2-L3-3 meganucleases were evaluated at a high mRNA concentration (100 ng) due to the relatively low activity of the parental meganuclease.

2. Results

Figure 15:
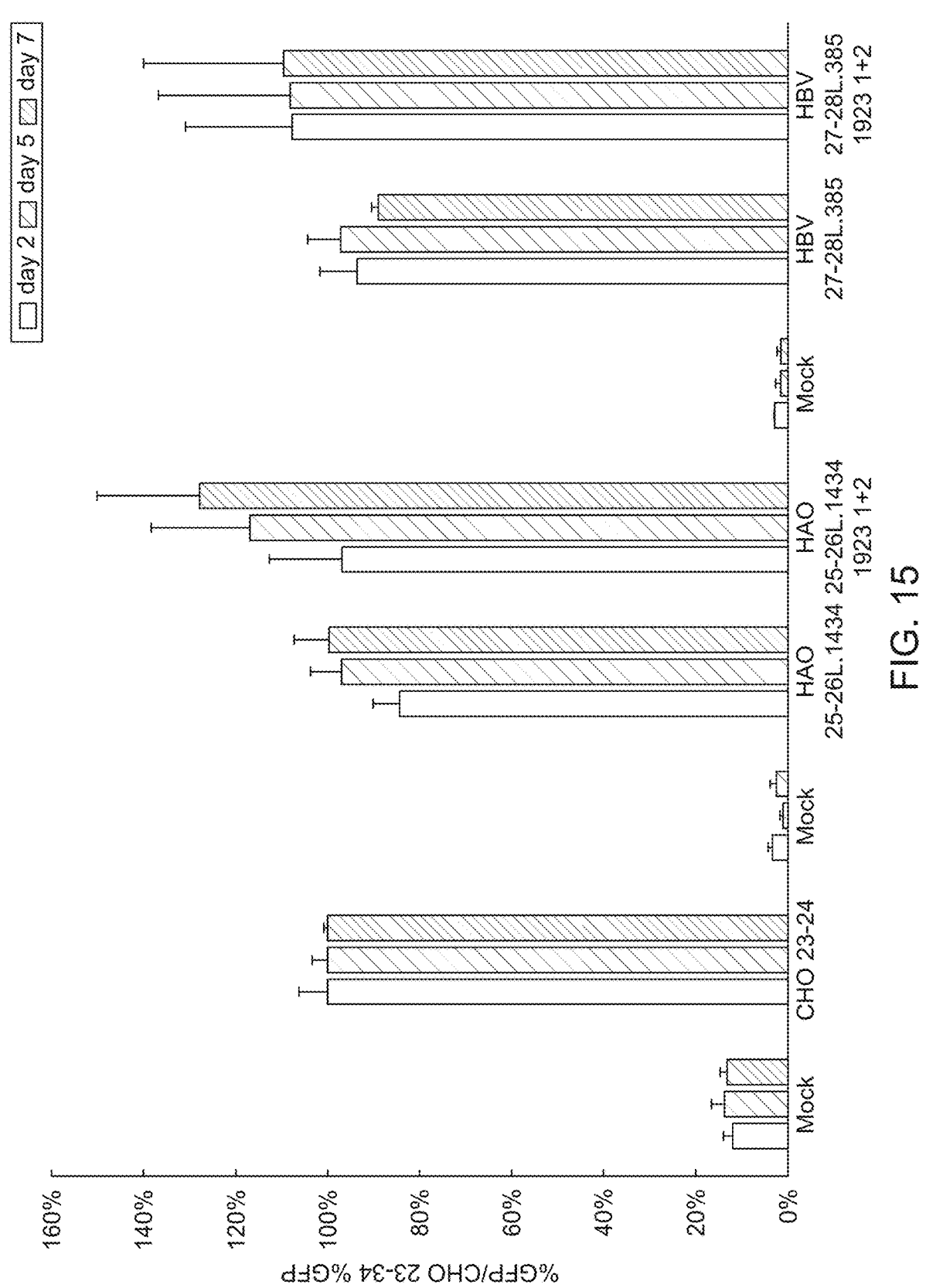
FIG. 15. Results from a CHO reporter cell assay of the HAO 25-26L.1434 engineered meganuclease and a variant thereof comprising Linker1923(1/2) and the HBV 27-28L.385 engineered meganuclease and a variant thereof comprising Linker1923(1/2).
Figure 16:
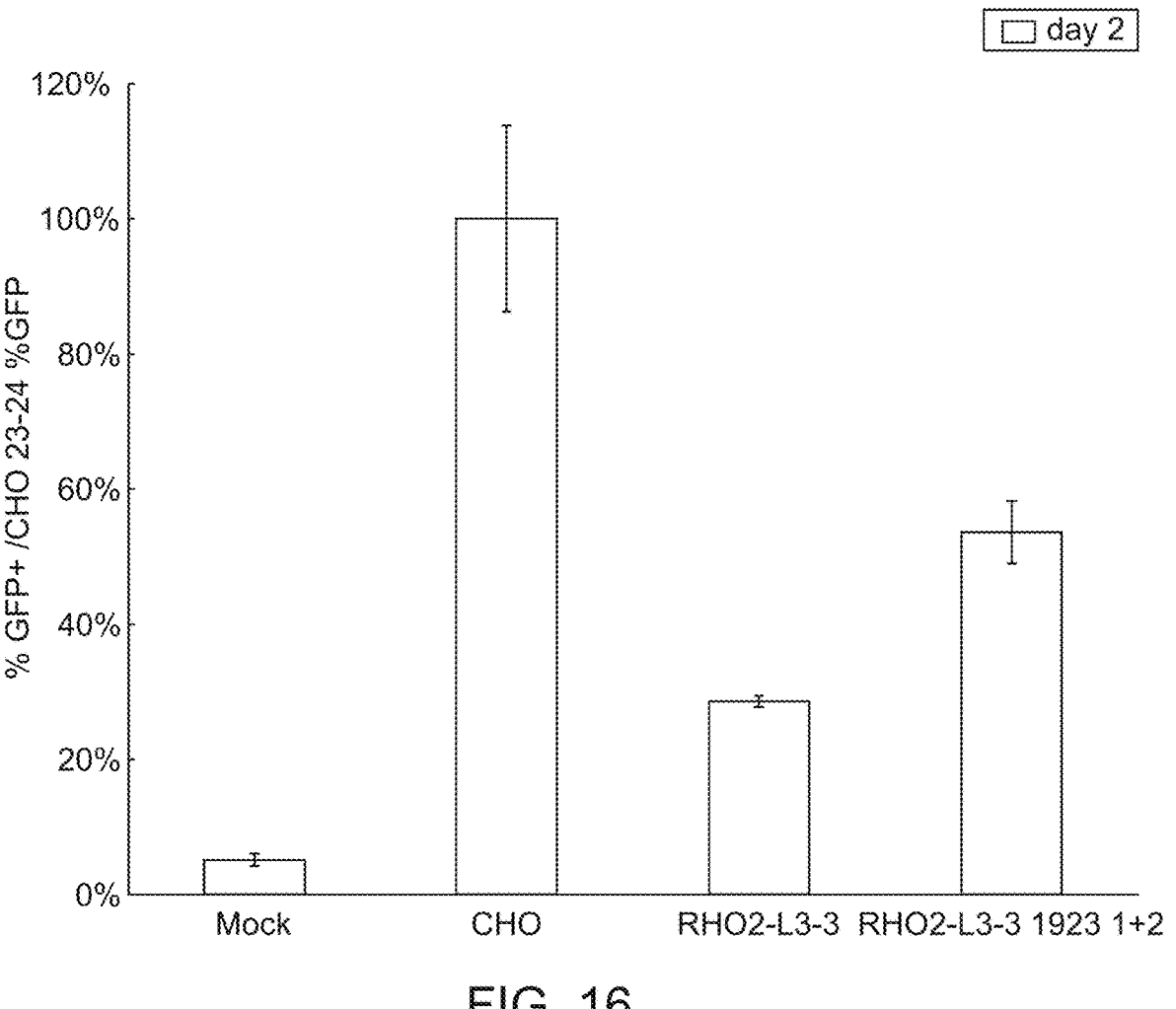
FIG. 16. Results from a CHO reporter cell assay of the RHO2-L3-3 engineered meganuclease and a variant thereof comprising Linker1923(1/2).

In a first set of experiments, the activity of the parental HAO 25-26L.1434 and HBV 27-28L.385 meganucleases and each of the Linker1923(1/2) variants is shown in FIG. 15. For both meganucleases, introduction of Linker1923 in combination with the subset of subunit modifications identified as "(1/2)" (i.e., K96A, Q99A, K100D in the first N-terminal subunit and K57Y and E61T in the second C-terminal subunit) produced a meganuclease with greater activity at all time points than the corresponding parental meganuclease and the CHO 23-24 control. Similar results were observed in a second experiment, shown in FIG. 16, which demonstrated that the introduction of Linker1923 into RHO2-L3-3, in combination with the subset of subunit modifications identified as "(1/2)", produced a meganuclease with greater activity at the evaluated day 2 time point than the corresponding parental meganuclease. While the RHO2-L3-3 1923(1/2) meganuclease did not achieve the same level of activity as the CHO 23-24 control, the parental RHO2-L3-3 meganuclease started with a low level of activity relative to CHO 23-24, whereas the parental HAO 25-26L.1434 and HBV 27-28L.385 meganucleases had either equivalent or slightly lower activity than the CHO 23-24 control. Although it did not achieve the same level of activity as the CHO 23-24 control, the RHO2-L3-3 1923(1/2) variant was 86% more active that its parent meganuclease.

3. Conclusions

The results of this experiment demonstrated that incorporation of Linker1923 into three additional scaffold meganucleases (e.g., HAO 25-26L.1434, HBV 27-28L.385, and RHO2-L3-3), along with the "(1/2)" subset of subunit modifications, resulted in smaller meganucleases having higher levels of activity than their parental nucleases comprising Linker1, and in the case of HAO 25-26L.1434 and HBV 27-28L.385 higher levels of activity than the CHO 23-24 control. Compared to the data observed in Example 4, where the full set of seven subunit modifications was seen to reduce the activity of an engineered meganuclease comprising Linker1923, it was notable here to observe that removing the H37Y modification from the first subunit and the W53F modification from the second subunit not only prevented a reduction in activity, but enhanced activity relative to the parental meganuclease. These data align with the observations of Example 5, where two engineered meganuclease scaffolds comprising Linker1923 and the "(1/2)" subset of subunit modifications both exhibited higher activity than the parental meganuclease that comprised Linker1.

Overall, Examples 5 and 6 provide data for five different engineered meganuclease scaffolds that comprise Linker1923 and the subset of subunit modifications identified as "(1/2)" (i.e., K96A, Q99A, K100D in the first N-terminal subunit and K57Y and E6IT in the second C-terminal subunit), whose variability to a reference meganuclease comprising wild-type I-CreI subunits and Linker1923 (SEQ ID NO: 163) is summarized in Table 8 below:

TABLE 8

| Meganuclease | SEQ ID NO | Full Seq (1-343) % to Reference* | N-terminal Subunit (1-153) % to Reference* | C-terminal Subunit (185-343) % to Reference* |
|---|---|---|---|---|
| I-CreI 1923 Reference | 163 | 100 | 100 | 100 |
| I-CreI 1923 (1 + 2) Reference | 22 | 98.54 | 98.04 | 98.74 |
| HBV 11-12L.1090 1923 (1 + 2) | 100 | 86.88 | 85.62 | 85.53 |

TABLE 8-continued

| Meganuclease | SEQ ID NO | Full Seq (1-343) % to Reference* | N-terminal Subunit (1-153) % to Reference* | C-terminal Subunit (185-343) % to Reference* |
|---|---|---|---|---|
| F8R 1-2x.9 1923 (1 + 2) | 145 | 87.76 | 86.27 | 86.79 |
| HAO 25-26L. 1434 1923 (1 + 2) | 93 | 87.46 | 86.93 | 85.53 |
| HBV 27-28L.385 1923 (1 + 2) | 94 | 87.17 | 83.01 | 88.68 |
| RHO2-L3-3 1923 (1 + 2) | 162 | 88.05 | 84.97 | 88.68 |

*The "Reference" meganuclease is provided in SEQ ID NO: 163 and comprises, from 5' to 3': an N-terminal subunit comprising residues 1-153 of wild-type I-CreI; Linker1923; a C-terminal subunit comprising residues 5-163 of wild-type I-CreI (i.e., wild-type I-CreI is set forth in SEQ ID NO: 1).

Moreover, the Examples disclosed herein provided additional engineered meganucleases comprising Linker1923, either with or without various combinations of subunit modifications, including those shown in Table 9) below:

described HBV meganucleases, which contained the previous linker (Linker1) (SEQ ID NO: 27). In addition, amino acids within the nuclease backbone were modified to electrostatically interact with the new linker. The first (N-termi-

TABLE 9

| Meganuclease | SEQ ID NO | Full Seq (1-343) % to Reference* | N-terminal Subunit (1-153) % to Reference* | C-terminal Subunit (185-343) % to Reference* |
|---|---|---|---|---|
| I-CreI 1923 Reference | 163 | 100 | 100 | 100 |
| HAO 25-26L.908 1923 (None) | 88 | 88.92 | 89.54 | 86.16 |
| HAO 25-26L.908 1923 (1 + 2 + 3) | 89 | 86.88 | 86.93 | 84.28 |
| HBV 11-12L.1090 1923 (None) | 121 | 88.34 | 87.58 | 86.79 |
| HBV 11-12L.1090 1923 (1) | 122 | 87.46 | 86.93 | 85.53 |
| HBV 11-12L.1090 1923 (2) | 123 | 87.76 | 86.27 | 86.79 |
| HBV 11-12L.1090 1923 (3) | 124 | 87.76 | 86.93 | 86.16 |
| HBV 11-12L.1090 1923 (1 + 3) | 125 | 86.88 | 86.27 | 84.91 |
| HBV 11-12L.1090 1923 (2 + 3) | 126 | 87.17 | 85.62 | 86.16 |
| HBV 11-12L.1090 1923 (1 + 2 + 3) | 127 | 86.3 | 84.97 | 84.91 |
| F8R 1-2x.9 1923 (None) | 141 | 89.21 | 88.24 | 88.05 |
| F8R 1-2x.9 1923 (1) | 142 | 88.34 | 87.58 | 86.79 |
| F8R 1-2x.9 1923 (2) | 143 | 88.63 | 86.93 | 88.05 |
| F8R 1-2x.9 1923 (3) | 144 | 88.63 | 87.58 | 87.42 |
| F8R 1-2x.9 1923 (1 + 3) | 146 | 87.76 | 86.93 | 86.16 |
| F8R 1-2x.9 1923 (2 + 3) | 147 | 88.05 | 86.27 | 87.42 |
| F8R 1-2x.9 1923 (1 + 2 + 3) | 148 | 87.17 | 85.62 | 86.16 |

*The "Reference" meganuclease is provided in SEQ ID NO: 163 and comprises, from 5' to 3': an N-terminal subunit comprising residues 1-153 of wild-type I-CreI; Linker1923; a C-terminal subunit comprising residues 5-163 of wild-type I-CreI (i.e., wild-type I-CreI is set forth in SEQ ID NO: 1).

The variability relative to wild-type I-CreI that is observed in each of these meganuclease variants, which were all capable of binding their dsDNA target sites, is the result of amino acid modifications made at certain positions in each subunit that are necessary to alter the specificity of the meganuclease from its wild-type recognition sequence to a desired target recognition sequence (e.g., positions 24, 26, 28, 30, 32, 33, 38, 40, 42, 44, 46, 66, 68, 70, 71, 72, 73, 74, 76, 77, 79, and 139 of SEQ ID NO: 1), alter DNA-binding affinity of the meganuclease to the DNA (e.g., 29, 34, 48, 51, 64, 80, 81, 82, 112, 116, 137, 139, and 143 of SEQ ID NO: 1), alter the cleavage activity of the meganuclease (e.g., positions 19, 48, and 50), or modify other properties of the meganuclease.

Example 7

Generation of Indels at the HBV 11-12 Recognition Sequence by HBV 11-12 Meganucleases Having Novel Linker Sequences in HepG2-sAg Cells After Electroporation with HBV 11-12 mRNA 1. Methods HBV 11-12 meganucleases are linked dimers. Linker1923 (SEQ ID NO: 4) was engineered to improve upon previously nal) subunit was modified to include an A at position 96, an A at position 99, and a D at position 100. The second (C-terminal) subunit was modified to include a Y at a position corresponding to position 57 of SEQ ID NO: 1, and a T at a position corresponding to position 61 of SEQ ID NO: 1. Engineered meganucleases that include these modifications are denoted with "(1/2)". The original pRNA vector used as template for in vitro mRNA transcription (pRNA6) contained a HBA2 5' UTR, a WPRE 3' UTR and a single 5' SV40 nuclear localization signal (NLS). The pRNA6 vector was modified to use untranslated regions (UTRs) for liver expression (ALB 5' UTR and SNRPB 3' UTR), an additional SV40 NLS on the 3' end to facilitate nuclear import, and a stronger Kozak sequence. These modifications generated the pRNA8 vector. In conjunction with the pRNA8 vector, the meganuclease amino acid codon usage was modified to achieve maximum uridine depletion (MAX) to reduce immune responses and increase expression. The meganucleases assessed in this study are HBV11-12L.1090 pRNA8 MAX Linker1923(1/2) (SEQ ID NO: 100) and a previously generated meganuclease, HBV11-12L.1090 pRNA6 Linker1 (SEQ ID NO: 101) described in PCT International Patent Application Publication No. WO 2021/113765. This study was conducted to evaluate the efficacy of the described modifications within HBV11-12 meganucleases for causing insertions and/or deletions (indels) at their intended recognition sequence (i.e., the HBV 11-12 recognition sequence). Indel formation was detected in these experiments by digital PCR analysis.

To evaluate editing efficiency of the above mentioned HBV11-12 meganucleases to cleave an integrated hepatitis B sequence, we utilized an engineered HepG2 cell line (HepG2-sAg) containing a single integration of a partial HBV sequence. 1e6 HepG2-sAg cells were electroporated using the Lonza Amaxa >4D system with 100 ng, 10 ng or 1ng of mRNA encoding the HBV11-12L.1090 pRNA6 Linker1 and HBV11-12L.1090 pRNA8 MAX Linker1923 (1/2) meganucleases. 100 ng of mCherry mRNA was included as a transfection control. Cells were collected at three- and six-days post transfection for genomic DNA extraction and evaluated for transfection efficiency using a Beckman Coulter® CrtoFLEX™ flow cytometer. Transfection efficiency exceeded 90%. Genomic DNA was prepared using the Macherey Nagel NucleoSpin™ Blood QuickPure kit.

Digital droplet PCR was utilized to determine the frequency of target indels at the HBV 11-12 binding site using primers F1 and R1 and probe P1 to generate an amplicon surrounding the binding site, as well as primers F2 and R2 and probe P2 to generate a reference amplicon. Amplifications were multiplexed in a 20 µL reaction containing 1× 44DDPCR™ Supermix for Probes (no dUTP, BIO-RAD®), 250 nM of each probe, 900 nM of each primer, 5U of HindIII-HF, and ~50 ng cellular gDNA. Droplets were generated using a QX1001™ droplet generator (BIO-RAD®). Cycling conditions were as follows: 1 cycle of 95° C. (2° C./s ramp) for 10 minutes, 45 cycles of 94° C. (2° C./s ramp) for 10 seconds, 59.2° C. (2° C./s ramp) for 30 seconds, 72° C. (2° C./s ramp) for 1.5 minutes, 1 cycle of 98° C. for 10 minutes, 4° C. hold. Droplets were analyzed using a QX200™ droplet reader (BIO-RAD®) and QUANTASOFT™ analysis software (BIO-RAD®) was used to acquire and analyze data. Indel frequencies were calculated by dividing the number of positive droplets for the binding site probe by the number of positive droplets for the reference probe. The sequences for the primers and probes used in this study are provided in the table below.

TABLE 10

| Primer and probe sequences for Example 7 | |
| --- | --- |
| Primer Identifier | SEQ ID NO: |
| P1: [5'-TGCCGATCCATACTGCGGAACT-3'] | 102 |
| F1: [5'-GGTCTGTGCCAAGTGTTTG-3'] | 103 |
| R1: [5'-GCTGCGAGCAAAACAAG-3'] | 104 |
| P2: [5'-CCCGCCTGTAACACG-3'] | 105 |
| F2: [5'-CATCAGGATTCCTAGGACC-3'] | 106 |
| R2: [5'-AGTCCACCACGAGTCTA-3'] | 107 |

2. Results

HBV11-12L.1090 pRNA6 Linker1 and HBV11-12L.1090 pRNA8 MAX Linker1923(1/2) were evaluated for on-target activity in HepG2-sAg cells. In combination, Linker1923(1/2) and pRNA8 vector with MAX codon usage greatly improve efficacy in HepG2-sAg cells at 2 days post transfection (FIG. 17A). By day 6, HBV 11-12L.1090 pRNA8 MAX Linker1923(1/2) achieved saturation at the 10 ng dose with 78% on-target editing compared to 33% editing with the previous construct (FIG. 17B). HBV11-12L.1090 MAX Linker1923(1/2) shows equivalent or increased on-target editing in all doses across both timepoints.

3. Conclusions

These data demonstrate that Linker1923 and associated modifications in the nuclease backbone, in combination with the pRNA8 vector and maximal uridine depletion, give rise to higher editing rates of integrated hepatitis B sequence compared to the previously described engineered meganuclease HBV11-12L.1090 Linker1 using pRNA6.

Example 8

Generation of Indels at the HBV 11-12 Recognition Sequence by HBV 11-12 Meganucleases Having Novel Linker Sequences in HepG2-sAg Cells After Electroporation with HBV 11-12 mRNA 1 Methods Studies were conducted to evaluate the efficacy of the structural modifications to the HBV 11-12L.1090 engineered meganuclease described in Example 7 for generating indels at their intended recognition sequence (i.e., the HBV 11-12 recognition sequence). This study includes the same meganucleases as Example 7, HBV11-12L.1090 pRNA6 Linker1 and HBV11-12L.1090 pRNA8 MAX Linker1923 (1/2), with the addition of a meganuclease using the pRNA8 vector with MAX codon usage with Linker1, HBV11-12L.1090 pRNA8 MAX Linker1 to specifically evaluate the editing efficiency of Linker1923 compared to Linker 1.

To evaluate editing efficiency of an HBV11-12 meganucleases to an integrated hepatitis B sequence, we electroporated 1e6 HepG2-sAg cells using the Lonza Amaxa™ 4D system with 100 ng or 10 ng of mRNA encoding the HBV11-12 L.1090 pRNA6 Linker1, HBV11-12 L.1090 MAX Linker1, or HBV11-12 L.1090 MAX Linker1923(1/2) engineered meganuclease, or an mCherry control. Cells were collected at two- and six-days post transfection for genomic DNA extraction and evaluated for transfection efficiency using a Beckman Coulter® CytoFLEX™ S flow cytometer. Transfection efficiency exceeded 90%. Genomic DNA was prepared using the MagMAX™ DNA Multi-Sample Ultra 2.0 kit with the KingFisher™ Apex. Digital droplet PCR was performed according to Example 7.

2. Results

Figure 18:
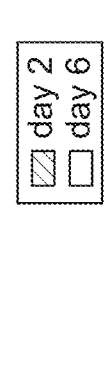
FIG. 18. Provides a bar graph that shows the percentage indels by ddDDPCRIM at day 2 and day 6 at a 100 ng and 10 ng dosage of the HBV11-12L.1090 meganuclease having either Linker 1 or Linker1923. Meganucleases that have the Max 1.0 denotation utilized the pRNA6 vector and do not include uridine depletion in the RNA coding sequence and those that contain Max 2.0 utilized a pRNA8 vector that did include uridine depletion.

The HBV11-12L.1090 pRNA6 Linker1, HBV11-12L.1090 pRNA8 MAX Linker1, and HBV11-12L.1090 pRNA8 MAX Linker1923(1/2) meganucleases were evaluated for on-target activity in HepG2-sAg cells. The pRNA8 vector with MAX codon usage in combination with Linker1 or Linker1923 improved efficacy in HepG2-sAg cells. By day 6 at the 10 ng dose, HBV 11-12L.1090 MAX Linker1923(1/2) (denoted as "HBV 11-12L.1090 MAX2.0/linker") achieved 88% on-target editing compared to 51% editing by HBV11-12L.1090 pRNA6 Linker1 (denoted as "HBV 11-12L.1090 MAX1.0") and 69% editing by HBV 11-12L.1090 MAX that comprised Linker1 and no subunit modifications (denoted as "HBV 11-12L.1090 MAX2.0") (FIG. 18).

3. Conclusions

These data demonstrate that pRNA8 vector modifications with MAX codon usage in conjunction with Linker1923 increase editing rates of an integrated hepatitis B sequence by the HBV11-12L.1090 meganuclease compared to the previously described engineered meganuclease, HBV11-

12L.1090 pRNA6 Linker1, and that Linker1923 and associated changes to the meganuclease backbone further increases editing.

Example 9

Generation of Indels at the HBV 11-12 Recognition Sequence and HBV Surface Antigen Inhibition by HBV 11-12 Meganucleases Having Novel Linker Sequences and Additional Structural Modifications in HepG2-sAg Cells 1. Methods An amino acid substitution from glutamine (Q) to glutamic acid (E) in the C-terminal subunit at a position corresponding to position 80 of I-Cre was made to determine if specificity of the HBV11-12L.1090 meganuclease could be improved. Variants generated from this substitution will subsequently be referred to as having a "QQ" to denote the presence of a Q in each subunit at a position corresponding to position 80 of I-CreI, or having a "QE" to denote the modification in the C-terminal subunit to an E at a position corresponding to position 80 of I-CreI. This study investigated how this substitution may affect the indel formation and HBV surface antigen (HBsAg) inhibition of the HBV11-12L.1090 meganuclease comprising either Linker1 or Linker1923 and the (1/2) modifications. Thus, variants evaluated in this study are referred to as HBV11-12L.1090QQ Linker1 (SEQ ID NO: 101), HBV11-12L.1090QQ Linker1923(1/2) (SEQ ID NO: 100), HBV11-12L.1090QE Linker1 (SEQ ID NO: 108), and HBV11-12L.1090QE Linker1923(1/2) (SEQ ID NO: 109). All meganucleases in this study used the pRNA8 vector with MAX codon usage. HBsAg is one of the main viral components of the envelope for infectious HBV that can be derived from cccDNA or integrations of HBV DNA in the genome. Sustained reduction of HBsAg is an important clinical endpoint for treatment of HBV disease. The engineered HepG2-sAg cells have a single integration of a partial HBV genome that contains the HBsAg ORF, which results in expression and secretion of HBsAg.

HepG2-sAg cells were electroporated according to Example 7 with 100 ng. 10 ng or Ing of mRNA encoding the four meganuclease variants, HBV11-12L.1090QQ Linker1, HBV11-12L.1090QQ Linker1923(1/2), HBV11-12L.1090QE Linker1, and HBV11-12L.1090QE Linker1923(1/2), or an mCherry control. Cells and supernatant were collected on day 2, 6 and 9 post-electroporation. Transfection efficiency was evaluated at 98%. Genomic DNA was isolated from cells using the MagMAN™ DNA Multi-Sample Ultra 2.0 kit with the KingFisher™ Apex. This experiment was done in duplicate for increased strength in the study.

To assess percent indel formation, digital droplet PCR was performed in a similar approach to Example 7 with variations in the primers, probes and cycling conditions used. Cycling conditions were as follows: 1 cycle of 95° C. (0.2° C./s ramp) for 10 minutes, 45 cycles of 94° C. (0.2°

C./s ramp) for 10 seconds, 61.1° C. (0.2° C./s ramp) for 30 seconds, 72° C. (0.2° C./s ramp) for 2 minutes, 1 cycle of 98° C., for 10 minutes, 4° C., hold. The sequences for the primers and probes used in this study are provided in the table below.

TABLE 11

Primer and probe sequences for Example 9

| Primer Identifier | SEQ ID NO: |
|---|---|
| P1: [5'-TGCCGATCCATACTGCGGAACT-3'] | 110 |
| F1: [5'-GGTCTGTGCCAAGTGTTTG-3'] | 111 |
| R1: [5'-GTATATTTCCGCGAGAGGAC-3'] | 112 |
| P2: [5'-CTTGGCCCCCAATACCACATCATC-3'] | 113 |
| F2: [5'-GGATGGAAATTGCACCTGTATTC-3'] | 114 |
| R2: [5'-GGGTTTAAATGTATACCCAGAGAC-3'] | 115 |

To assess reduction of secreted HBsAg in cell supernatants, an HBsAg-specific chemiluminescence immunoassay (CLIA) from AutoBio® was used according to the manufacturer's instructions. Luminescence was read using a SpectraMax™ i3x microplate reader. The amount of HBsAg (IU/mL) was calculated based on a real-time calibration curve.

2. Results

Figure 19A:
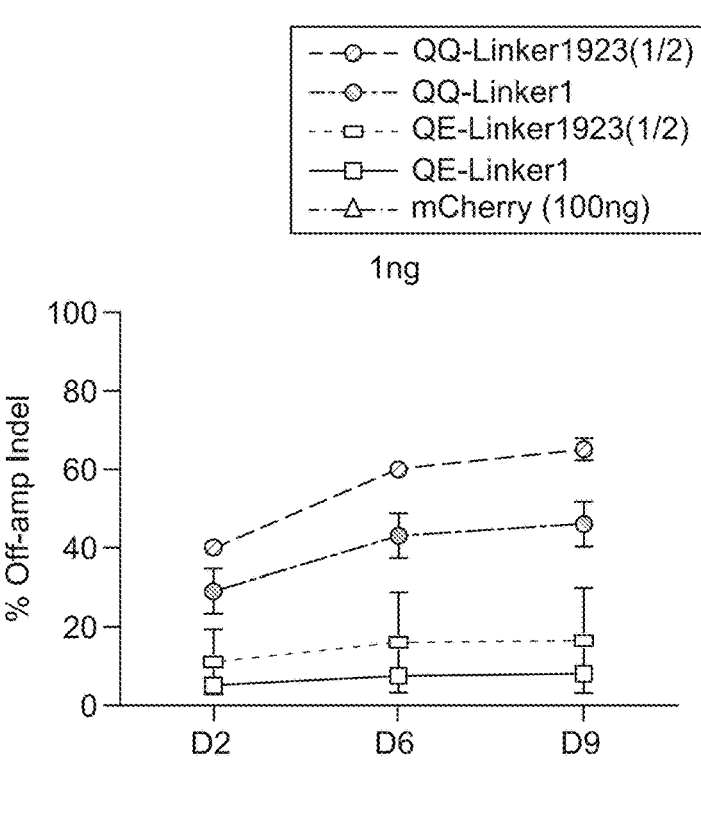
FIG. 19A-FIG. 19F. Provides line graphs showing the percentage of indels and HBsAg inhibition for the indicated meganucleases at D2, D6, and D9) post transfection at either a Ing. 10 ng, or 100 ng dosage. In each figure, four different meganucleases were tested. The first meganuclease was an HBV 11-12L.1090 meganuclease with the linker 1923 labeled as QQ-Linker1923(1/2). The second tested meganuclease was an HBV11-12L.1090 meganuclease with Linker 1 labeled as QQ Linker 1. The third tested meganuclease was the HBV11-12L.1090 meganuclease with a glutamine (Q) to glutamic acid (E) mutation in the C-terminal subunit at a position corresponding to position 80 of I-CreI with Linker1923 denoted as QE Linker1923(1/2). The fourth tested meganuclease was the HBV11-12L.1090 meganuclease with the same QE mutation but with Linker1 denoted as QE Linker 1. An mCherry control is also shown at a 100 ng transfection dosage.
Figure 19B:
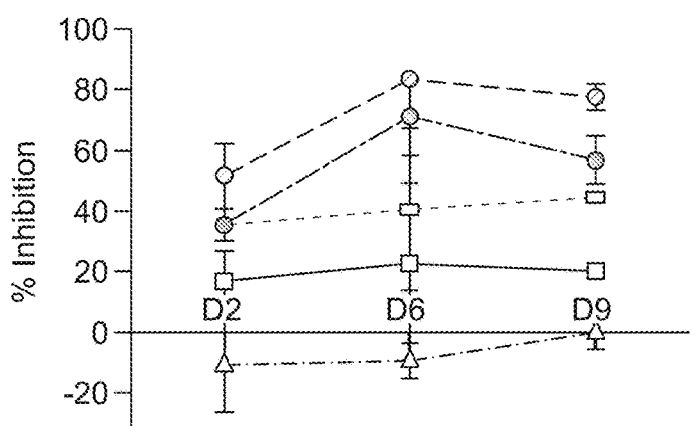
Figures 19C, 19D:
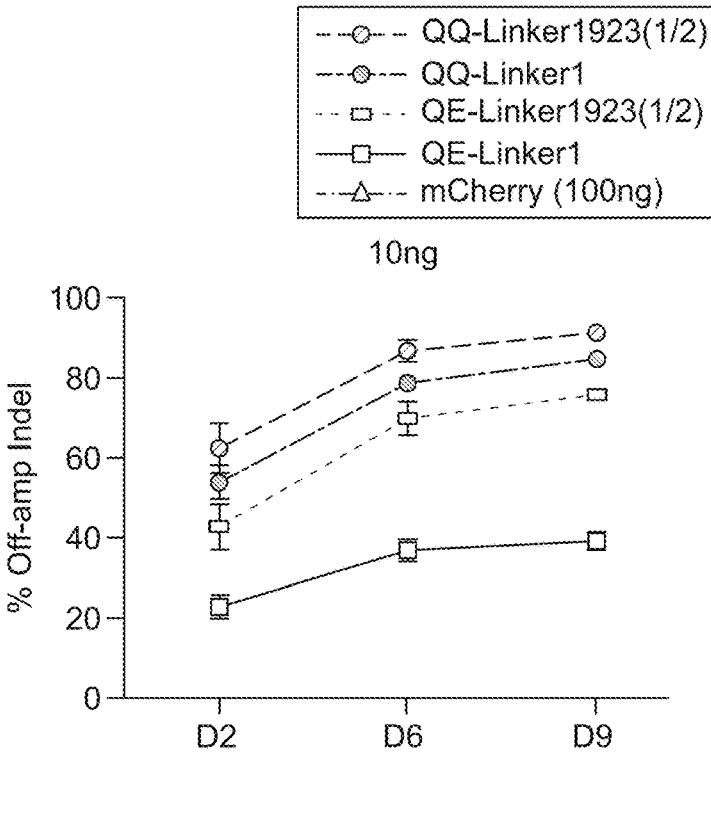
Figure 19E:
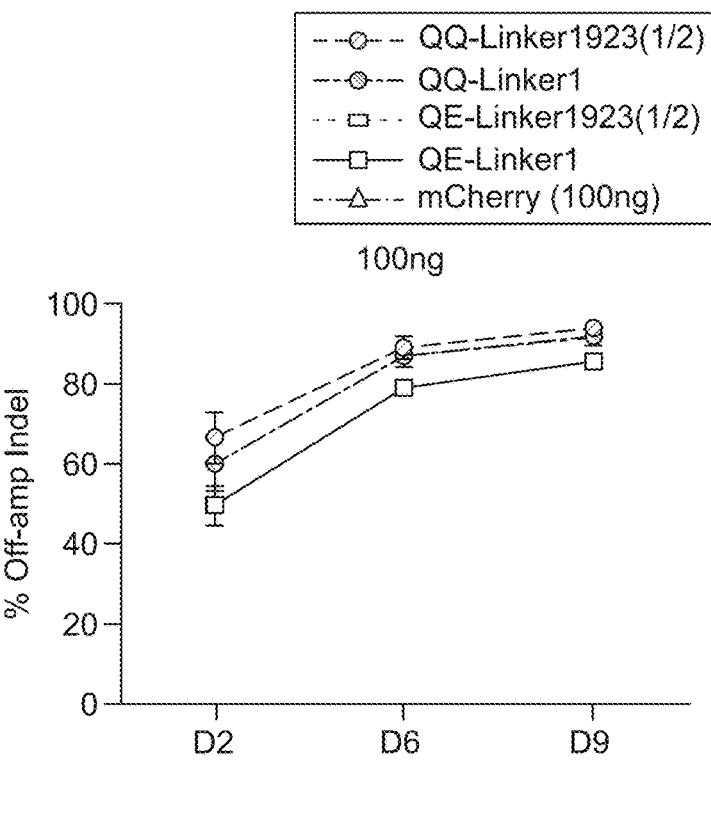
Figure 19F:
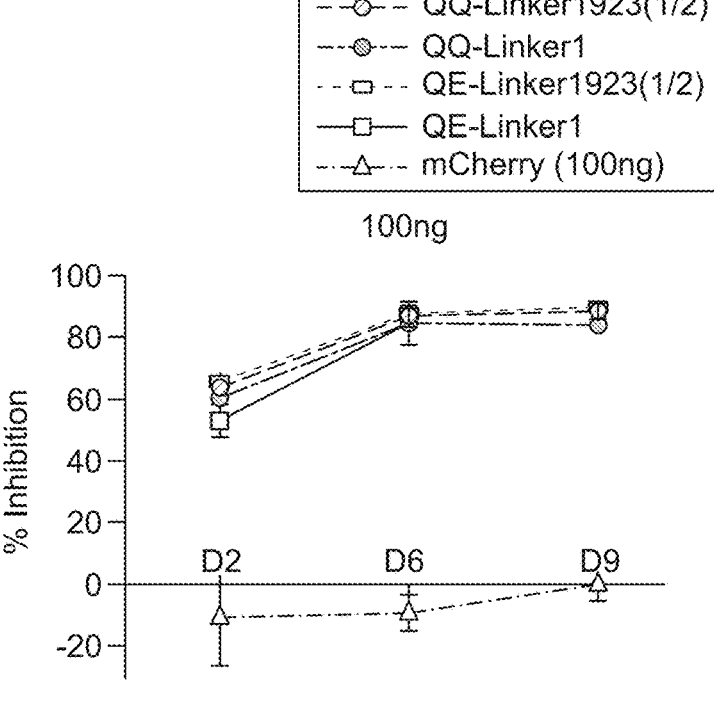

The QQ and QE variants were evaluated for indel formation and HBsAg reduction, with Linker1 or Linker1923 and the (1/2) subunit modifications, at three different dosages shown in FIG. 19A-FIG. 19F. Average indels at day 9 post-transfection increased from 46% with Linker1 to 65% with Linker1923(1/2) at the Ing dose with the QQ variant (FIG. 19A). Using the same conditions, an increase from 8% to 16.5% average indels was observed for the QE variant (FIG. 19A). A similar trend was observed at the higher 10 ng and 100 ng dosages as shown in FIG. 19C and FIG. 19E. Consistent with the indel results, the meganucleases with Linker1923(1/2) demonstrated higher levels of HBsAg inhibition in both the QQ and QE variants as shown in FIG. 19B at the Ing dose. Maximal HBsAg reduction of 90% was achieved by day 9 post-transfection using 10 ng of mRNA for both QQ and QE variants using Linker1923(1/2) (FIG. 16D). At a saturating dosage, all of the meganucleases performed similarly in reducing HBsAg as shown in FIG. 19F.

3. Conclusions

Use of Linker1923 with the (1/2) subunit modifications improved editing and HBsAg inhibition across all doses and timepoints for both variants. The QE variant is less potent than the QQ variant at creating indels at mid-low doses; however, at high doses a comparable potency is achieved, especially in variants containing Linker1923(1/2). HBsAg inhibition is equivalent in both variants with Linker1923(1/2) in mid-high doses.

SEQUENCE LISTING

SEQ ID NO: 1

MNTKYNKEFLLYLAGFVDGDGSIIAQIKPNQSYKFKHQLSLAFQVTQKTQRRWFLDKLVDEIGVGY

VRDRGSVSDYILSEIKPLHNFLTQLQPFLKLKQKQANLVLKIIWRLPSAKESPDKFLEVCTWVDQI

AALNDSKTRKTTSETVRAVLDSLSEKKKSSP

-continued

SEQ ID NO: 2

LAGLIDADG

SEQ ID NO: 3

XXXXXXXXXXXXXXXXXXXXXXXXXXXXXX

SEQ ID NO: 4

SLPGIQLNKESNNNASTQRPSRNVNNFPYSG

SEQ ID NO: 5

SLPGIGVQVHRNNNASTQRPSRNVNNFPYKG

SEQ ID NO: 6

SLPGVRLHCPLNNNASTQRPSRNVNNFPQG

SEQ ID NO: 7

SLPGIRLSQGANNNASTQRPSRNVNNFPLG

SEQ ID NO: 8

SLPGARPGGVSNNNASTQRPSRNVNNFPYSG

SEQ ID NO: 9

SLPG

SEQ ID NO: 10

IQLNKESNNNAST

SEQ ID NO: 11

IGVQVHRNNNAST

SEQ ID NO: 12

VRLHCPLNNNAST

SEQ ID NO: 13

IRLSQGANNNAST

SEQ ID NO: 14

ARPGGVSNNNAST

SEQ ID NO: 15

QRP

SEQ ID NO: 16

QRPSRNVNN

SEQ ID NO: 17

FPYSG

SEQ ID NO: 18

FPYKG

SEQ ID NO: 19

FPQG

SEQ ID NO: 20

FPLG

SEQ ID NO: 21

FPYSG

SEQ ID NO: 22
MNTKYNKEFLLYLAGFVDGDGSIIAQIKPNQSYKFKHQLSLAFQVTQKTQRRWELDKLVDEIGVGY

VRDRGSVSDYILSEIKPLHNFLTQLQPFLALKADQANLVLKIIWRLPSAKESPDKFLEVCTWVDQI

AALNDSKTRKTTSETVRAVLDSLPGIQLNKESNNNASTQRPSRNVNNFPYSGYNKEFLLYLAGFVD

GDGSIIAQIKPNQSYKFKHQLSLAFQVTQKTQRRWFLDYLVDTIGVGYVRDRGSVSDYILSEIKPL

HNFLTQLQPFLKLKQKQANLVLKIIWRLPSAKESPDKFLEVCTWVDQIAALNDSKTRKTTSETVRA

VLDSLSEKKKSSP

SEQ ID NO: 23
MNTKYNKEFLLYLAGFVDGDGSIIAQIKPNQSYKFKHQLSLAFQVTQKTQRRWFLDKLVDEIGVGY

VRDRGSVSDYILSEIKPLHNFLTQLQPFLALKADQANLVLKIIWRLPSAKESPDKFLEVCTWVDQI

AALNDSKTRKTTSETVRAVLDSLPGIGVQVHRNNNASTQRPSRNVNNFPYKGYNKEFLLYLAGFVD

GDGSIIAQIKPNQSYKFKHQLSLAFQVTQKTQRRWFLDYLVDTIGVGYVRDRGSVSDYILSEIKPL

-continued

HNFLTQLQPFLKLKQKQANLVLKIIWRLPSAKESPDKFLEVCTWVDQIAALNDSKTRKTTSETVRA

VLDSLSEKKKSSP

SEQ ID NO: 24
MNTKYNKEFLLYLAGFVDGDGSIIAQIKPNQSYKFKHQLSLAFQVTQKTQRRWFLDKLVDEIGVGY

VRDRGSVSDYILSEIKPLHNFLTQLQPFLALKADQANLVLKIIWRLPSAKESPDKFLEVCTWVDQI

AALNDSKTRKTTSETVRAVLDSLPGVRLHCPLNNNASTQRPSRNVNNFPQGYNKEFLLYLAGFVDG

DGSIIAQIKPNQSYKFKHQLSLAFQVTQKTQRRWFLDYLVDTIGVGYVRDRGSVSDYILSEIKPLH

NFLTQLQPFLKLKQKQANLVLKIIWRLPSAKESPDKFLEVCTWVDQIAALNDSKTRKTTSETVRAV

LDSLSEKKKSSP

SEQ ID NO: 25
MNTKYNKEFLLYLAGFVDGDGSIIAQIKPNQSYKFKHQLSLAFQVTQKTQRRWFLDKLVDEIGVGY

VRDRGSVSDYILSEIKPLHNFLTQLQPFLALKADQANLVLKIIWRLPSAKESPDKFLEVCTWVDQI

AALNDSKTRKTTSETVRAVLDSLPGIRLSQGANNNASTQRPSRNVNNFPLGYNKEFLLYLAGFVDG

DGSIIAQIKPNQSYKFKHQLSLAFQVTQKTQRRWFLDYLVDTIGVGYVRDRGSVSDYILSEIKPLH

NFLTQLQPFLKLKQKQANLVLKIIWRLPSAKESPDKFLEVCTWVDQIAALNDSKTRKTTSETVRAV

LDSLSEKKKSSP

SEQ ID NO: 26
MNTKYNKEFLLYLAGFVDGDGSIIAQIKPNQSYKFKHQLSLAFQVTQKTQRRWELDKLVDEIGVGY

VRDRGSVSDYILSEIKPLHNFLTQLQPFLALKADQANLVLKIIWRLPSAKESPDKFLEVCTWVDQI

AALNDSKTRKTTSETVRAVLDSLPGARPGGVSNNNASTQRPSRNVNNFPYSGYNKEFLLYLAGFVD

GDGSIIAQIKPNQSYKFKHQLSLAFQVTQKTQRRWFLDYLVDTIGVGYVRDRGSVSDYILSEIKPL

HNFLTQLQPFLKLKQKQANLVLKIIWRLPSAKESPDKFLEVCTWVDQIAALNDSKTRKTTSETVRA

VLDSLSEKKKSSP

SEQ ID NO: 27
SLPGSVGGLSPSQASSAASSASSSPGSGISEALRAGAGSGTG

SEQ ID NO: 28
PGSVGGLSPNNNASTQRPSRNVNNFPG

SEQ ID NO: 29
PXXXXXLSPNNNASTQRPSRNVNNFPG

SEQ ID NO: 30
PGSVGGLSPSLNSSTQRPIVNWNNLPG

SEQ ID NO: 31
PGSVXXXXXSLNSSTQRPIVNWNNLPG

SEQ ID NO: 32
PGMKLSLSPNNNASTQRPSRNVNNFPG

SEQ ID NO: 33
GMKLS

SEQ ID NO: 34
PGMSSQLSPNNNASTQRPSRNVNNFPG

SEQ ID NO: 35
GMSSQ

SEQ ID NO: 36
PGVKGTLSPNNNASTQRPSRNVNNFPG

SEQ ID NO: 37
GVKGT

SEQ ID NO: 38
PGSVRGKNGSLNSSTQRPIVNWNNLPG

-continued

```
                                            SEQ ID NO: 39
RGKNG

SEQ ID NO: 40
PGSVPGGVSSLNSSTQRPIVNWNNLPG

SEQ ID NO: 41
PGGVS

SEQ ID NO: 42
PGVKGTXXXNNNASTQRPSRNVNNFPG

SEQ ID NO: 43
PGMKLSXXXNNNASTQRPSRNVNNFPG

SEQ ID NO: 44
PGMSSQXXXNNNASTQRPSRNVNNFPG

SEQ ID NO: 45
PGVKGTXXXNNNASTQRPSRNVNNFPXG

SEQ ID NO: 46
PGMKLSXXXNNNASTQRPSRNVNNFPXG

SEQ ID NO: 47
PGMSSQXXXNNNASTQRPSRNVNNFPXG

SEQ ID NO: 48
PGVKGTXXXNNNASTQRPSRNVNNFPXXG

SEQ ID NO: 49
PGMKLSXXXNNNASTQRPSRNVNNFPXXG

SEQ ID NO: 50
PGMSSQXXXNNNASTQRPSRNVNNFPXXG

SEQ ID NO: 51
PXXXPGGVSSLNSSTQRPIVNWNNLPG

SEQ ID NO: 52
PXXXPGGVSSLNSSTQRPIVNWNNLPXG

SEQ ID NO: 53
PXXXPGGVSSLNSSTQRPIVNWNNLPXXG

SEQ ID NO: 54
NNNASTQRPSRNVNNFP

SEQ ID NO: 55
PXXXPGGVSNNNASTQRPSRNVNNFPG

SEQ ID NO: 56
PXXXPGGVSNNNASTQRPSRNVNNFPXG

SEQ ID NO: 57
PXXXPGGVSNNNASTQRPSRNVNNFPXXG

SEQ ID NO: 58
SLNSSTQRPIVNWNNLP

SEQ ID NO: 59
PGVKGTXXXSLNSSTQRPIVNWNNLPG

SEQ ID NO: 60
PGMKLSXXXSLNSSTQRPIVNWNNLPG

SEQ ID NO: 61
PGMSSQXXXSLNSSTQRPIVNWNNLPG

SEQ ID NO: 62
PGVKGTXXXSLNSSTQRPIVNWNNLPXG

SEQ ID NO: 63
PGMKLSXXXSLNSSTQRPIVNWNNLPXG

SEQ ID NO: 64
PGMSSQXXXSLNSSTQRPIVNWNNLPXG

SEQ ID NO: 65
PGVKGTXXXSLNSSTQRPIVNWNNLPXXG
```

-continued

SEQ ID NO: 66
PGMKLSXXXSLNSSTQRPIVNWNNLPXXG

SEQ ID NO: 67
PGMSSQXXXSLNSSTQRPIVNWNNLPXXG

SEQ ID NO: 68
GSVPGGVSSLNSSTQRPIVNWNNLPGSVSPSRPSLNSSTQRPIVNWNNLPG

SEQ ID NO: 69
GVGRRKCANNNASTQRPSRNVNNFPLNG

SEQ ID NO: 70
GFNGHLSMSLNSSTQRPIVNWNNLPGEG

SEQ ID NO: 71
GSVPGGVSSLNSSTQRPIVNWNNLPGSVSPSRPSLNSSTQRPIVNWNNLPG

SEQ ID NO: 72
GVHLPLPLSLNSSTQRPIVNWNNLPGAG

SEQ ID NO: 73
GSVPGGVSSLNSSTQRPIVNWNNLPGSVSPSRPSLNSSTQRPIVNWNNLPG

SEQ ID NO: 74
GSVPGGVSSLNSSTQRPIVNWNNLPGSVSPSRPSLNSSTQRPIVNWNNLPG

SEQ ID NO: 75
GMKLSSAVSLNSSTQRPIVNWNNLPWGG

SEQ ID NO: 76
GSVPGGVSSLNSSTQRPIVNWNNLPGSVSPSRPSLNSSTQRPIVNWNNLPG

SEQ ID NO: 77
GMKVPRLESLNSSTQRPIVNWNNLPASG

SEQ ID NO: 78
ATGGAAGCTGTATCCAAGGATG

SEQ ID NO: 79
MNTKYNKEFLLYLAGFVDSDGSIWAFIEPCQTVKFKHRLRLSLNVTQKTQRRWELDKLVDEIGVGY

VRDTGSVSQYILSEIKPLHNFLTQLQPFLKLKQKQANLVLKIIEQLPSAKESPDKFLEVCTWVDQI

AALNDSKTRKTTSETVRAVLDSLPGSVGGLSPSQASSAASSASSSPGSGISEALRAGAGSGTGYNK

EFLLYLAGFVDGDGSIYAKIRPQQASKFKHVLELVFEVTQSTQRRWELDKLVDEIGVGYVYDWKQA

SMYRLSQIKPLHNFLTQLQPFLKLKQKQANLVLKIIEQLPSAKESPDKFLEVCTWVDQIAALNDSR

TRKTTSETVRAVLDSLSEKKKSSP

SEQ ID NO: 80
MNTKYNKEFLLYLAGFVDSDGSIWAFIEPCQTVKFKHRLRLSLNVTQKTQRRWELDKLVDEIGVGY

VRDTGSVSQYILSEIKPLHNFLTQLQPFLKLKQKQANLVLKIIEQLPSAKESPDKFLEVCTWVDQI

AALNDSKTRKTTSETVRAVLDSLPGARPGGVSNNNASTQRPSRNVNNFPYSGYNKEFLLYLAGFVD

GDGSIYAKIRPQQASKFKHVLELVFEVTQSTQRRWELDKLVDEIGVGYVYDWKQASMYRLSQIKPL

HNFLTQLQPFLKLKQKQANLVLKIIEQLPSAKESPDKFLEVCTWVDQIAALNDSRTRKTTSETVRA

VLDSLSEKKKSSP

SEQ ID NO: 81
MNTKYNKEFLLYLAGFVDSDGSIWAFIEPCQTVKFKYRLRLSLNVTQKTQRRWFLDKLVDEIGVGY

VRDTGSVSQYILSEIKPLHNELTQLQPFLALKADQANLVLKIIEQLPSAKESPDKFLEVCTWVDQI

AALNDSKTRKTTSETVRAVLDSLPGARPGGVSNNNASTQRPSRNVNNFPYSGYNKEFLLYLAGFVD

GDGSIYAKIRPQQASKFKHVLELVFEVTQSTQRRFFLDYLVDTIGVGYVYDWKQASMYRLSQIKPL

HNFLTQLQPFLKLKQKQANLVLKIIEQLPSAKESPDKFLEVCTWVDQIAALNDSRTRKTTSETVRA

VLDSLSEKKKSSP

-continued

```
                                              SEQ ID NO: 82
MNTKYNKEFLLYLAGFVDSDGSIWAFIEPCQTVKFKHRLRLSLNVTQKTQRRWELDKLVDEIGVGY

VRDTGSVSQYILSEIKPLHNFLTQLQPFLKLKQKQANLVLKIIEQLPSAKESPDKFLEVCTWVDQI

AALNDSKTRKTTSETVRAVLDSLPGIGVQVHRNNNASTQRPSRNVNNEPYKGYNKEFLLYLAGFVD

GDGSIYAKIRPQQASKFKHVLELVFEVTQSTQRRWELDKLVDEIGVGYVYDWKQASMYRLSQIKPL

HNFLTQLQPFLKLKQKQANLVLKIIEQLPSAKESPDKFLEVCTWVDQIAALNDSRTRKTTSETVRA

VLDSLSEKKKSSP

SEQ ID NO: 83
MNTKYNKEFLLYLAGFVDSDGSIWAFIEPCQTVKFKYRLRLSLNVTQKTQRRWELDKLVDEIGVGY

VRDTGSVSQYILSEIKPLHNFLTQLQPFLALKADQANLVLKIIEQLPSAKESPDKFLEVCTWVDQI

AALNDSKTRKTTSETVRAVLDSLPGIGVQVHRNNNASTQRPSRNVNNFPYKGYNKEFLLYLAGFVD

GDGSIYAKIRPQQASKFKHVLELVFEVTQSTQRRFFLDYLVDTIGVGYVYDWKQASMYRLSQIKPL

HNFLTQLQPFLKLKQKQANLVLKIIEQLPSAKESPDKFLEVCTWVDQIAALNDSRTRKTTSETVRA

VLDSLSEKKKSSP

SEQ ID NO: 84
MNTKYNKEFLLYLAGFVDSDGSIWAFIEPCQTVKFKHRLRLSLNVTQKTQRRWELDKLVDEIGVGY

VRDTGSVSQYILSEIKPLHNFLTQLQPFLKLKQKQANLVLKIIEQLPSAKESPDKFLEVCTWVDQI

AALNDSKTRKTTSETVRAVLDSLPGVRLHCPLNNNASTQRPSRNVNNFPQGYNKEFLLYLAGFVDG

DGSIYAKIRPQQASKFKHVLELVFEVTQSTQRRWFLDKLVDEIGVGYVYDWKQASMYRLSQIKPLH

NFLTQLQPFLKLKQKQANLVLKIIEQLPSAKESPDKFLEVCTWVDQIAALNDSRTRKTTSETVRAV

LDSLSEKKKSSP

SEQ ID NO: 85
MNTKYNKEFLLYLAGFVDSDGSIWAFIEPCQTVKFKYRLRLSLNVTQKTQRRWELDKLVDEIGVGY

VRDTGSVSQYILSEIKPLHNFLTQLQPFLALKADQANLVLKIIEQLPSAKESPDKFLEVCTWVDQI

AALNDSKTRKTTSETVRAVLDSLPGVRLHCPLNNNASTQRPSRNVNNFPQGYNKEFLLYLAGFVDG

DGSIYAKIRPQQASKFKHVLELVFEVTQSTQRRFFLDYLVDTIGVGYVYDWKQASMYRLSQIKPLH

NFLTQLQPFLKLKQKQANLVLKIIEQLPSAKESPDKFLEVCTWVDQIAALNDSRTRKTTSETVRAV

LDSLSEKKKSSP

SEQ ID NO: 86
MNTKYNKEFLLYLAGFVDSDGSIWAFIEPCQTVKFKHRLRLSLNVTQKTQRRWELDKLVDEIGVGY

VRDTGSVSQYILSEIKPLHNFLTQLQPFLKLKQKQANLVLKIIEQLPSAKESPDKFLEVCTWVDQI

AALNDSKTRKTTSETVRAVLDSLPGIRLSQGANNNASTQRPSRNVNNFPLGYNKEFLLYLAGFVDG

DGSIYAKIRPQQASKFKHVLELVFEVTQSTQRRWFLDKLVDEIGVGYVYDWKQASMYRLSQIKPLH

NFLTQLQPFLKLKQKQANLVLKIIEQLPSAKESPDKFLEVCTWVDQIAALNDSRTRKTTSETVRAV

LDSLSEKKKSSP

SEQ ID NO: 87
MNTKYNKEFLLYLAGFVDSDGSIWAFIEPCQTVKFKYRLRLSLNVTQKTQRRWFLDKLVDEIGVGY

VRDTGSVSQYILSEIKPLHNFLTQLQPFLALKADQANLVLKIIEQLPSAKESPDKFLEVCTWVDQI

AALNDSKTRKTTSETVRAVLDSLPGIRLSQGANNNASTQRPSRNVNNFPLGYNKEFLLYLAGFVDG

DGSIYAKIRPQQASKFKHVLELVFEVTQSTQRRFFLDYLVDTIGVGYVYDWKQASMYRLSQIKPLH

NFLTQLQPFLKLKQKQANLVLKIIEQLPSAKESPDKFLEVCTWVDQIAALNDSRTRKTTSETVRAV

LDSLSEKKKSSP
```

-continued

```
                                                    SEQ ID NO: 88
MNTKYNKEFLLYLAGFVDSDGSIWAFIEPCQTVKFKHRLRLSLNVTQKTQRRWFLDKLVDEIGVGY

VRDTGSVSQYILSEIKPLHNFLTQLQPFLKLKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIYAKIRPQQASKFKHVLELVFEVTQSTQRRWELDKLVDEIGVGYVYDWKQASMYRLSQIKPL

HNFLTQLQPFLKLKQKQANLVLKIIEQLPSAKESPDKFLEVCTWVDQIAALNDSRTRKTTSETVRA

VLDSLSEKKKSSP

SEQ ID NO: 89
MNTKYNKEFLLYLAGFVDSDGSIWAFIEPCQTVKFKYRLRLSLNVTQKTQRRWFLDKLVDEIGVGY

VRDTGSVSQYILSEIKPLHNFLTQLQPFLALKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIYAKIRPQQASKFKHVLELVFEVTQSTQRRFFLDYLVDTIGVGYVYDWKQASMYRLSQIKPL

HNFLTQLQPFLKLKQKQANLVLKIIEQLPSAKESPDKFLEVCTWVDQIAALNDSRTRKTTSETVRA

VLDSLSEKKKSSP

SEQ ID NO: 90
MNTKYNKEFLLYLAGFVDADGSIWAYIEPCQWVKFKHRLKLQLNVTQKTQRRWFLDKLVDEIGVGY

VRDTGSVSQYMLSEIKPLHNFLTQLQPFLKLKQKQANLVLKIIEQLPSAKESPDKFLEVCTWVDQI

AALNDSKTRKTTSETVRAVLDSLPGSVGGLSPSQASSAASSASSSPGSGISEALRAGAGSGTGYNK

EFLLYLAGFVDGDGSIYAKIRPQQASKFKHVLELVFEVTQSTQRRWFLDKLVDEIGVGYVYDWKQA

SMYRLSQIKPLHNFLTQLQPFLKLKQKQANLVLKIIEQLPSAKESPDKFLEVCTWVDQIAALNDSK

TRKTTSETVRAVLDSLSEKKKSSP

SEQ ID NO: 91
MNTKYNKEFLLYLAGFVDADGSIYARIRPQQDVKFKHRLELVFTVYQDTRRRWELDKLVDEIGVGY

VYDSKKVSRYHLSEIKPLHNFLTQLQPFLKLKQKQANLVLKIIEQLPSAKESPDKFLEVCTWVDQI

AALNDSRTRKTTSETVRAVLDSLPGSVGGLSPSQASSAASSASSSPGSGISEALRAGAGSGTGYNK

EFLLYLAGFVDGDGSIYAHIKPKQVAKFKHELNLAFRVFQKTQRRWFLDKLVDEIGVGYVSDKGSV

SYYGLSEIKPLHNFLTQLQPFLKLKQKQANLVLKIIEQLPSAKESPDKFLEVCTWVDQIAALNDSH

TRKTTSETVRAVLDSLSEKKKSSP

SEQ ID NO: 92
CTGCTCGTGTTACAGGCGGGGT

SEQ ID NO: 93
MNTKYNKEFLLYLAGFVDADGSIWAYIEPCQWVKFKHRLKLQLNVTQKTQRRWFLDKLVDEIGVGY

VRDTGSVSQYMLSEIKPLHNFLTQLQPFLALKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIYAKIRPQQASKFKHVLELVFEVTQSTQRRWFLDYLVDTIGVGYVYDWKQASMYRLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 94
MNTKYNKEFLLYLAGFVDADGSIYARIRPQQDVKFKHRLELVFTVYQDTRRRWELDKLVDEIGVGY

VYDSKKVSRYHLSEIKPLHNFLTQLQPFLALKADQANLVLKIIEQLPSAKESPDKFLEVCTWVDQI

AALNDSRTRKTTSETVRAVLDSLPGIQLNKESNNNASTQRPSRNVNNFPYSGYNKEFLLYLAGFVD

GDGSIYAHIKPKQVAKFKHELNLAFRVFQKTQRRWFLDYLVDTIGVGYVSDKGSVSYYGLSEIKPL

HNFLTQLQPFLKLKQKQANLVLKIIEQLPSAKESPDKFLEVCTWVDQIAALNDSHTRKTTSETVRA

VLDSLSEKKKSSP
```

-continued

```
                                                    SEQ ID NO: 95
MAPKKKRKVH

SEQ ID NO: 96
MNTKYNKEFLLYLAGFVDGDGSINASIAPRQSFKFKHGLKLRFEVGQKTQRRWELDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGSVGGLSPSQASSAASSASSSPGSGISEALRAGAGSGTGYNK

EFLLYLAGFVDGDGSIFASIRPRQMAKFKHDLELCENVRQKTQRRWFLDKLVDEIGVGYVHDWGSV

STYKLSEIKPLHNFLTQLQPFLKLKQKQANLVLKIIEQLPSAKESPDKFLEVCTWVDQIAALNDSK

TRKTTSETVRAVLDSLSEKKKSSP

SEQ ID NO: 97
TGCCGATCCATACTGCGGAACT

SEQ ID NO: 98
VLDXXXXXXXXXXXXXXXXXXXXXXXXXXXXXXXXYNK

SEQ ID NO: 99
VLDXXXXXXXXXXXXXXXXXXXXXXXXXXXXXXXXXYNK

SEQ ID NO: 100
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCENVRQKTQRRWFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 101
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGSVGGLSPSQASSAASSASSSPGSGISEALRAGAGSGTGYNK

EFLLYLAGFVDGDGSIFASIRPRQHAKFKHDLELCFNVRQKTQRRWFLDKLVDEIGVGYVIDWRGA

STYKLSQIKPLHNFLTQLQPFLKLKQKQANLVLKIIEQLPSAKESPDKFLEVCTWVDQIAALNDSK

TRKTTSETVRAVLDSLSEKKKSSP

SEQ ID NO: 102
TGCCGATCCATACTGCGGAACT

SEQ ID NO: 103
GGTCTGTGCCAAGTGTTTG

SEQ ID NO: 104
GCTGCGAGCAAAACAAG

SEQ ID NO: 105
CCCGCCTGTAACACG

SEQ ID NO: 106
CATCAGGATTCCTAGGACC

SEQ ID NO: 107
AGTCCACCACGAGTCTA

SEQ ID NO: 108
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGSVGGLSPSQASSAASSASSSPGSGISEALRAGAGSGTGYNK

EFLLYLAGFVDGDGSIFASIRPRQHAKFKHDLELCFNVRQKTQRRWELDKLVDEIGVGYVIDWRGA
```

118

-continued

STYKLSEIKPLHNFLTQLQPFLKLKQKQANLVLKIIEQLPSAKESPDKFLEVCTWVDQIAALNDSK

TRKTTSETVRAVLDSLSEKKKSSP

SEQ ID NO: 109
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCENVRQKTQRRWFLDYLVDTIGVGYVIDWRGASTYKLSEIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 110
TGCCGATCCATACTGCGGAACT

SEQ ID NO: 111
GGTCTGTGCCAAGTGTTTG

SEQ ID NO: 112
GTATATTTCCGCGAGAGGAC

SEQ ID NO: 113
CTTGGCCCCCAATACCACATCATC

SEQ ID NO: 114
GGATGGAAATTGCACCTGTATTC

SEQ ID NO: 115
GGGTTTAAATGTATACCCAGAGAC

SEQ ID NO: 116
GIGVQVHRNNNASTQRPSRNVNNFPYKG

SEQ ID NO: 117
GVRLHCPLNNNASTQRPSRNVNNFPQG

SEQ ID NO: 118
GIRLSQGANNNASTQRPSRNVNNFPLG

SEQ ID NO: 119
GARPGGVSNNNASTQRPSRNVNNFPYSG

SEQ ID NO: 120
GIQLNKESNNNASTQRPSRNVNNFPYSG

SEQ ID NO: 121
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCFNVRQKTQRRWFLDKLVDEIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 122
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCFNVRQKTQRRWFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 123
MNTKYNKEFLLYLAGFVDSDGSINASISPRQSFKFKHGLKLRFEVGQKTQHRWFLDKLVDEIGVGY

VYDNGSVSVYSLSQIKPLHNELTQLQPFLKLKADQANLVLKIIEQLPSAKESPDKFLEVCTWVDQI

-continued

AALNDSKTRKTTSETVRAVLDSLPGIQLNKESNNNASTQRPSRNVNNFPYSGYNKEFLLYLAGFVD

GDGSIFASIRPRQHAKFKHDLELCFNVRQKTQRRWFLDKLVDEIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 124
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCENVRQKTQRRFFLDKLVDEIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 125
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLALKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCENVRQKTQRRFFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 126
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLKLKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCFNVRQKTQRRFFLDKLVDEIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 127
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFASIRPRQHAKFKHDLELCFNVRQKTQRRFFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 128
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGIGVQVHRNNNASTQRPSRNVNNFPYKGYNKEFLLYLAGFVD

GDGSIFASIRPRQHAKFKHDLELCFNVRQKTQRRWFLDKLVDEIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 129
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIGVQVHRNNNASTQRPSRNVNNEPYKGYNKEFLLYLAGFVD

-continued

GDGSIFASIRPRQHAKFKHDLELCFNVRQKTQRRWFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 130
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIGVQVHRNNNASTQRPSRNVNNFPYKGYNKEFLLYLAGFVD

GDGSIFASIRPRQHAKFKHDLELCFNVRQKTQRRFFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 131
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGVRLHCPLNNNASTQRPSRNVNNFPQGYNKEFLLYLAGFVDG

DGSIFASIRPRQHAKFKHDLELCFNVRQKTQRRWELDKLVDEIGVGYVIDWRGASTYKLSQIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 132
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGVRLHCPLNNNASTQRPSRNVNNFPQGYNKEFLLYLAGFVDG

DGSIFASIRPRQHAKFKHDLELCENVRQKTQRRWFLDYLVDTIGVGYVIDWRGASTYKLSQIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 133
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGVRLHCPLNNNASTQRPSRNVNNFPQGYNKEFLLYLAGFVDG

DGSIFASIRPRQHAKFKHDLELCFNVRQKTQRRFFLDYLVDTIGVGYVIDWRGASTYKLSQIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 134
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLKLKQKQANLVLKIIEQLPSAKESPDKFLEVCTWVDQI

AALNDSKTRKTTSETVRAVLDSLPGIRLSQGANNNASTQRPSRNVNNFPLGYNKEFLLYLAGFVDG

DGSIFASIRPRQHAKFKHDLELCENVRQKTQRRWFLDKLVDEIGVGYVIDWRGASTYKLSQIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 135
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIRLSQGANNNASTQRPSRNVNNFPLGYNKEFLLYLAGFVDG

DGSIFASIRPRQHAKFKHDLELCENVRQKTQRRWFLDYLVDTIGVGYVIDWRGASTYKLSQIKPLH

-continued

```
NFLTQLQPFLKLKQKQANLVLKIIEQLPSAKESPDKFLEVCTWVDQIAALNDSKTRKTTSETVRAV

LDSLSEKKKSSP
```

```
                                                         SEQ ID NO: 136
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGIRLSQGANNNASTQRPSRNVNNFPLGYNKEFLLYLAGFVDG

DGSIFASIRPRQHAKFKHDLELCFNVRQKTQRRFFLDYLVDTIGVGYVIDWRGASTYKLSQIKPLH

NFLTQLQPFLKLKQKQANLVLKIIEQLPSAKESPDKFLEVCTWVDQIAALNDSKTRKTTSETVRAV

LDSLSEKKKSSP
```

```
                                                         SEQ ID NO: 137
MNTKYNKEFLLYLAGFVDSDGSINASISPRQSFKFKHGLKLRFEVGQKTQHRWFLDKLVDEIGVGY

VYDNGSVSVYSLSQIKPLHNELTQLQPFLKLKQKQANLVLKIIEQLPSAKESPDKFLEVCTWVDQI

AALNDSKTRKTTSETVRAVLDSLPGARPGGVSNNNASTQRPSRNVNNFPYSGYNKEFLLYLAGFVD

GDGSIFASIRPRQHAKFKHDLELCFNVRQKTQRRWFLDKLVDEIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP
```

```
                                                         SEQ ID NO: 138
MNTKYNKEFLLYLAGFVDSDGSINASISPRQSFKFKHGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGARPGGVSNNNASTQRPSRNVNNFPYSGYNKEFLLYLAGFVD

GDGSIFASIRPRQHAKFKHDLELCFNVRQKTQRRWFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP
```

```
                                                         SEQ ID NO: 139
MNTKYNKEFLLYLAGFVDSDGSINASISPRQSFKFKYGLKLRFEVGQKTQHRWFLDKLVDEIGVGY

VYDNGSVSVYSLSQIKPLHNFLTQLQPFLALKADQANLVLKIIEQLPSAKESPDKFLEVCTWVDQI

AALNDSKTRKTTSETVRAVLDSLPGARPGGVSNNNASTQRPSRNVNNFPYSGYNKEFLLYLAGFVD

GDGSIFASIRPRQHAKFKHDLELCENVRQKTQRRFFLDYLVDTIGVGYVIDWRGASTYKLSQIKPL

HNFLTQLQPFLKLKQKQANLVLKIIEQLPSAKESPDKFLEVCTWVDQIAALNDSKTRKTTSETVRA

VLDSLSEKKKSSP
```

```
                                                         SEQ ID NO: 140
MNTKYNKEFLLYLAGFVDGDGSIHACISPDQACKFKHYLRLRENVAQKTQRRWELDKLVDEIGVGY

VHDQGSVSYYQLSQIKPLHNFLTQLQPFLKLKQKQANLVLKIIEQLPSAKESPDKFLEVCTWVDQI

AALNDSKTRKTTSETVRAVLDSLPGSVGGLSPSQASSAASSASSSPGSGISEALRAGAGSGTGYNK

EFLLYLAGFVDGDGSIFACIQPRQQSKFKHSLQLWFYVTQKTQRRWELDKLVDEIGAGYVNDWGGA

SQYRLSEIKPLHNFLTQLQPFLKLKQKQANLVLKIIEQLPSAKESPDKFLEVCTWVDQIAALNDSK

TRKTTSETVRAVLDSLSEKKKSSP
```

```
                                                         SEQ ID NO: 141
MNTKYNKEFLLYLAGFVDGDGSIHACISPDQACKFKHYLRLRENVAQKTQRRWELDKLVDEIGVGY

VHDQGSVSYYQLSQIKPLHNFLTQLQPFLKLKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD
```

-continued

```
GDGSIFACIQPRQQSKFKHSLQLWFYVTQKTQRRWFLDKLVDEIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP
```

```
                                                    SEQ ID NO: 142
MNTKYNKEFLLYLAGFVDGDGSIHACISPDQACKFKHYLRLRENVAQKTQRRWFLDKLVDEIGVGY

VHDQGSVSYYQLSQIKPLHNFLTQLQPFLALKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFACIQPRQQSKFKHSLQLWFYVTQKTQRRWFLDYLVDTIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP
```

```
                                                    SEQ ID NO: 143
MNTKYNKEFLLYLAGFVDGDGSIHACISPDQACKFKHYLRLRENVAQKTQRRWELDKLVDEIGVGY

VHDQGSVSYYQLSQIKPLHNFLTQLQPFLKLKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFACIQPRQQSKFKHSLQLWFYVTQKTQRRWFLDKLVDEIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP
```

```
                                                    SEQ ID NO: 144
MNTKYNKEFLLYLAGFVDGDGSIHACISPDQACKFKYYLRLRENVAQKTQRRWFLDKLVDEIGVGY

VHDQGSVSYYQLSQIKPLHNFLTQLQPFLKLKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFACIQPRQQSKFKHSLQLWFYVTQKTQRRFFLDKLVDEIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP
```

```
                                                    SEQ ID NO: 145
MNTKYNKEFLLYLAGFVDGDGSIHACISPDQACKFKHYLRLRENVAQKTQRRWFLDKLVDEIGVGY

VHDQGSVSYYQLSQIKPLHNFLTQLQPFLALKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFACIQPRQQSKFKHSLQLWFYVTQKTQRRWFLDYLVDTIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP
```

```
                                                    SEQ ID NO: 146
MNTKYNKEFLLYLAGFVDGDGSIHACISPDQACKFKYYLRLRENVAQKTQRRWELDKLVDEIGVGY

VHDQGSVSYYQLSQIKPLHNFLTQLQPFLALKQKQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFACIQPRQQSKFKHSLQLWFYVTQKTQRRFFLDYLVDTIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP
```

```
                                                    SEQ ID NO: 147
MNTKYNKEFLLYLAGFVDGDGSIHACISPDQACKFKYYLRLRENVAQKTQRRWFLDKLVDEIGVGY

VHDQGSVSYYQLSQIKPLHNELTQLQPFLKLKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFACIQPRQQSKFKHSLQLWFYVTQKTQRRFFLDKLVDEIGAGYVNDWGGASQYRLSEIKPL
```

-continued

HNFLTQLQPFLKLKQKQANLVLKIIEQLPSAKESPDKFLEVCTWVDQIAALNDSKTRKTTSETVRA

VLDSLSEKKKSSP

SEQ ID NO: 148
MNTKYNKEFLLYLAGFVDGDGSIHACISPDQACKFKYYLRLRENVAQKTQRRWFLDKLVDEIGVGY

VHDQGSVSYYQLSQIKPLHNFLTQLQPFLALKADQANLVLKIIEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIFACIQPRQQSKFKHSLQLWFYVTQKTQRRFFLDYLVDTIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 149
MNTKYNKEFLLYLAGFVDGDGSIHACISPDQACKFKHYLRLRENVAQKTQRRWFLDKLVDEIGVGY

VHDQGSVSYYQLSQIKPLHNFLTQLQPFLKLKQKQANLVLKIIEQLPSAKESPDKFLEVCTWVDQI

AALNDSKTRKTTSETVRAVLDSLPGIGVQVHRNNNASTQRPSRNVNNEPYKGYNKEFLLYLAGFVD

GDGSIFACIQPRQQSKFKHSLQLWFYVTQKTQRRWELDKLVDEIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 150
MNTKYNKEFLLYLAGFVDGDGSIHACISPDQACKFKHYLRLRFNVAQKTQRRWELDKLVDEIGVGY

VHDQGSVSYYQLSQIKPLHNFLTQLQPFLALKADQANLVLKITEQLPSAKESPDKFLEVCTWVDQI

AALNDSKTRKTTSETVRAVLDSLPGIGVQVHRNNNASTQRPSRNVNNFPYKGYNKEFLLYLAGFVD

GDGSIFACIQPRQQSKFKHSLQLWFYVTQKTQRRWFLDYLVDTIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 151
MNTKYNKEFLLYLAGFVDGDGSIHACISPDQACKFKYYLRLRFNVAQKTQRRWELDKLVDEIGVGY

VHDQGSVSYYQLSQIKPLHNFLTQLQPFLALKADQANLVLKIIEQLPSAKESPDKFLEVCTWVDQI

AALNDSKTRKTTSETVRAVLDSLPGIGVQVHRNNNASTQRPSRNVNNEPYKGYNKEFLLYLAGFVD

GDGSIFACIQPRQQSKFKHSLQLWFYVTQKTQRRFFLDYLVDTIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 152
MNTKYNKEFLLYLAGFVDGDGSIHACISPDQACKFKHYLRLRENVAQKTQRRWFLDKLVDEIGVGY

VHDQGSVSYYQLSQIKPLHNFLTQLQPFLKLKQKQANLVLKIIEQLPSAKESPDKFLEVCTWVDQI

AALNDSKTRKTTSETVRAVLDSLPGVRLHCPLNNNASTQRPSRNVNNFPQGYNKEFLLYLAGFVDG

DGSIFACIQPRQQSKFKHSLQLWFYVTQKTQRRWFLDKLVDEIGAGYVNDWGGASQYRLSEIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 153
MNTKYNKEFLLYLAGFVDGDGSIHACISPDQACKFKHYLRLRENVAQKTQRRWFLDKLVDEIGVGY

VHDQGSVSYYQLSQIKPLHNFLTQLQPFLALKADQANLVLKIIEQLPSAKESPDKFLEVCTWVDQI

AALNDSKTRKTTSETVRAVLDSLPGVRLHCPLNNNASTQRPSRNVNNFPQGYNKEFLLYLAGFVDG

DGSIFACIQPRQQSKFKHSLQLWFYVTQKTQRRWFLDYLVDTIGAGYVNDWGGASQYRLSEIKPLH

NFLTQLQPFLKLKQKQANLVLKIIEQLPSAKESPDKFLEVCTWVDQIAALNDSKTRKTTSETVRAV

LDSLSEKKKSSP

-continued

SEQ ID NO: 154
MNTKYNKEFLLYLAGFVDGDGSIHACISPDQACKFKYYLRLRENVAQKTQRRWELDKLVDEIGVGY

VHDQGSVSYYQLSQIKPLHNFLTQLQPFLALKADQANLVLKIIEQLPSAKESPDKFLEVCTWVDQI

AALNDSKTRKTTSETVRAVLDSLPGVRLHCPLNNNASTQRPSRNVNNFPQGYNKEFLLYLAGFVDG

DGSIFACIQPRQQSKFKHSLQLWFYVTQKTQRRFFLDYLVDTIGAGYVNDWGGASQYRLSEIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 155
MNTKYNKEFLLYLAGFVDGDGSIHACISPDQACKFKHYLRLRENVAQKTQRRWFLDKLVDEIGVGY

VHDQGSVSYYQLSQIKPLHNFLTQLQPFLKLKQKQANLVLKIIEQLPSAKESPDKFLEVCTWVDQI

AALNDSKTRKTTSETVRAVLDSLPGIRLSQGANNNASTQRPSRNVNNFPLGYNKEFLLYLAGFVDG

DGSIFACIQPRQQSKFKHSLQLWFYVTQKTQRRWFLDKLVDEIGAGYVNDWGGASQYRLSEIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 156
MNTKYNKEFLLYLAGFVDGDGSIHACISPDQACKFKHYLRLRENVAQKTQRRWFLDKLVDEIGVGY

VHDQGSVSYYQLSQIKPLHNFLTQLQPFLALKADQANLVLKIIEQLPSAKESPDKFLEVCTWVDQI

AALNDSKTRKTTSETVRAVLDSLPGIRLSQGANNNASTQRPSRNVNNFPLGYNKEFLLYLAGFVDG

DGSIFACIQPRQQSKFKHSLQLWFYVTQKTQRRWFLDYLVDTIGAGYVNDWGGASQYRLSEIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 157
MNTKYNKEFLLYLAGFVDGDGSIHACISPDQACKFKYYLRLRENVAQKTQRRWFLDKLVDEIGVGY

VHDQGSVSYYQLSQIKPLHNFLTQLQPFLALKADQANLVLKIIEQLPSAKESPDKFLEVCTWVDQI

AALNDSKTRKTTSETVRAVLDSLPGIRLSQGANNNASTQRPSRNVNNFPLGYNKEFLLYLAGFVDG

DGSIFACIQPRQQSKFKHSLQLWFYVTQKTQRRFFLDYLVDTIGAGYVNDWGGASQYRLSEIKPLH

NFLTQLQPFLKLKQKQANLVLKIIEQLPSAKESPDKFLEVCTWVDQIAALNDSKTRKTTSETVRAV

LDSLSEKKKSSP

SEQ ID NO: 158
MNTKYNKEFLLYLAGFVDGDGSIHACISPDQACKFKHYLRLRENVAQKTQRRWELDKLVDEIGVGY

VHDQGSVSYYQLSQIKPLHNFLTQLQPFLKLKQKQANLVLKIIEQLPSAKESPDKFLEVCTWVDQI

AALNDSKTRKTTSETVRAVLDSLPGARPGGVSNNNASTQRPSRNVNNFPYSGYNKEFLLYLAGFVD

GDGSIFACIQPRQQSKFKHSLQLWFYVTQKTQRRWFLDKLVDEIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 159
MNTKYNKEFLLYLAGFVDGDGSIHACISPDQACKFKHYLRLRENVAQKTQRRWFLDKLVDEIGVGY

VHDQGSVSYYQLSQIKPLHNFLTQLQPFLALKADQANLVLKIIEQLPSAKESPDKFLEVCTWVDQI

AALNDSKTRKTTSETVRAVLDSLPGARPGGVSNNNASTQRPSRNVNNFPYSGYNKEFLLYLAGFVD

GDGSIFACIQPRQQSKFKHSLQLWFYVTQKTQRRWFLDYLVDTIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP

-continued

```
                                                 SEQ ID NO: 160
MNTKYNKEFLLYLAGFVDGDGSIHACISPDQACKFKYYLRLRENVAQKTQRRWELDKLVDEIGVGY

VHDQGSVSYYQLSQIKPLHNFLTQLQPFLALKADQANLVLKIIEQLPSAKESPDKFLEVCTWVDQI

AALNDSKTRKTTSETVRAVLDSLPGARPGGVSNNNASTQRPSRNVNNFPYSGYNKEFLLYLAGFVD

GDGSIFACIQPRQQSKFKHSLQLWFYVTQKTQRRFFLDYLVDTIGAGYVNDWGGASQYRLSEIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 161
MNTKYNKEFLLYLAGFVDGDGSIFARIFKGQHWKFKHHIRLTFNVSQKTQRRWELDKLVDEIGVGY

VNDYGSTSNYYLSEIKPLHNFLTQLQPFLKLKQKQANLVLKIIEQLPSAKESPDKFLEVCTWVDQI

AALNDSKTRKTTSETVRAVLDSLPGSVGGLSPSQASSAASSASSSPGSGISEALRAGAGSGTGYNK

EFLLYLAGFVDGDGSIWASIIPEQGYKFKHRLRLSFTVAQKTQRRWFLDKLVDEIGVGYVVDQGSV

SEYRLSEIKPLHNFLTQLQPFLKLKQKQANLVLKIIEQLPSAKESPDKFLEVCTWVDQIAALNDSK

TRKTTSETVRAVLDSLSEKKKSSP

SEQ ID NO: 162
MNTKYNKEFLLYLAGFVDGDGSIFARIFKGQHWKFKHHIRLTFNVSQKTQRRWFLDKLVDEIGVGY

VNDYGSTSNYYLSEIKPLHNFLTQLQPFLALKADQANLVLKITEQLPSAKESPDKFLEVCTWVDQI

AALNDSKTRKTTSETVRAVLDSLPGIQLNKESNNNASTQRPSRNVNNFPYSGYNKEFLLYLAGFVD

GDGSIWASIIPEQGYKFKHRLRLSFTVAQKTQRRWFLDYLVDTIGVGYVVDQGSVSEYRLSEIKPL

HNFLTQLQPFLKLKQKQANLVLKIIEQLPSAKESPDKFLEVCTWVDQIAALNDSKTRKTTSETVRA

VLDSLSEKKKSSP

SEQ ID NO: 163
MNTKYNKEFLLYLAGFVDGDGSIIAQIKPNQSYKFKHQLSLAFQVTQKTQRRWELDKLVDEIGVGY

VRDRGSVSDYILSEIKPLHNFLTQLQPFLKLKQKQANLVLKIIWRLPSAKESPDKFLEVCTWVDQI

AALNDSKTRKTTSETVRAVLDSLPGIQLNKESNNNASTQRPSRNVNNFPYSGYNKEFLLYLAGFVD

GDGSIIAQIKPNQSYKFKHQLSLAFQVTQKTQRRWFLDKLVDEIGVGYVRDRGSVSDYILSEIKPL

HNFLTQLQPFLKLKQKQANLVLKIIWRLPSAKESPDKFLEVCTWVDQIAALNDSKTRKTTSETVRA

VLDSLSEKKKSSP
(For all sequences, X = any amino acid)
```

The invention claimed is:

1. A polypeptide comprising a polypeptide linker, wherein said polypeptide linker comprises the amino acid sequence of SEQ ID NO: 4.

2. A polynucleotide comprising a nucleic acid sequence encoding a polypeptide linker, wherein said polypeptide linker comprises the amino acid sequence of SEQ ID NO: 4.

3. The polynucleotide of claim 2, wherein said polynucleotide is an mRNA.

4. A recombinant DNA construct comprising said polynucleotide of claim 2.

5. The recombinant DNA construct of claim 4, wherein said recombinant DNA construct is a plasmid DNA.

6. The recombinant DNA construct of claim 4, wherein said recombinant DNA construct encodes a recombinant virus comprising said polynucleotide.

7. The recombinant DNA construct of claim 6, wherein said recombinant virus is a recombinant adenovirus, a recombinant lentivirus, a recombinant retrovirus, or a recombinant adeno-associated virus (AAV).

8. The recombinant DNA construct of claim 6, wherein said recombinant virus is a recombinant AAV.

9. A recombinant virus comprising said polynucleotide of claim 2.

10. The recombinant virus of claim 9, wherein said recombinant virus is a recombinant adenovirus, a recombinant lentivirus, a recombinant retrovirus, or a recombinant AAV.

11. The recombinant virus of claim 10, wherein said recombinant virus is a recombinant AAV.

12. A lipid nanoparticle composition comprising lipid nanoparticles comprising said polynucleotide of claim 2.

13. The lipid nanoparticle composition of claim 12, wherein said polynucleotide is an mRNA.

* * * * *

SEQUENCE LISTING

```
Sequence total quantity: 163
SEQ ID NO: 1             moltype = AA  length = 163
FEATURE                  Location/Qualifiers
source                   1..163
                         mol_type = protein
                         organism = Chlamydomonas reinhardtii
SEQUENCE: 1
MNTKYNKEFL LYLAGFVDGD GSIIAQIKPN QSYKFKHQLS LAFQVTQKTQ RRWFLDKLVD  60
EIGVGYVRDR GSVSDYILSE IKPLHNFLTQ LQPFLKLKQK QANLVLKIIW RLPSAKESPD  120
KFLEVCTWVD QIAALNDSKT RKTTSETVRA VLDSLSEKKK SSP                     163

SEQ ID NO: 2             moltype = AA  length = 9
FEATURE                  Location/Qualifiers
source                   1..9
                         mol_type = protein
                         organism = Chlamydomonas reinhardtii
SEQUENCE: 2
LAGLIDADG                                                            9

SEQ ID NO: 3             moltype =   length =
SEQUENCE: 3
```

```
000

SEQ ID NO: 4              moltype = AA   length = 31
FEATURE                   Location/Qualifiers
source                    1..31
                          mol_type = protein
                          organism = synthetic construct
SEQUENCE: 4
SLPGIQLNKE SNNNASTQRP SRNVNNFPYS G                                 31

SEQ ID NO: 5              moltype = AA   length = 31
FEATURE                   Location/Qualifiers
source                    1..31
                          mol_type = protein
                          organism = synthetic construct
SEQUENCE: 5
SLPGIGVQVH RNNNASTQRP SRNVNNFPYK G                                 31

SEQ ID NO: 6              moltype = AA   length = 30
FEATURE                   Location/Qualifiers
source                    1..30
                          mol_type = protein
                          organism = synthetic construct
SEQUENCE: 6
SLPGVRLHCP LNNNASTQRP SRNVNNFPQG                                   30

SEQ ID NO: 7              moltype = AA   length = 30
FEATURE                   Location/Qualifiers
source                    1..30
                          mol_type = protein
                          organism = synthetic construct
SEQUENCE: 7
SLPGIRLSQG ANNNASTQRP SRNVNNFPLG                                   30

SEQ ID NO: 8              moltype = AA   length = 31
FEATURE                   Location/Qualifiers
source                    1..31
                          mol_type = protein
                          organism = synthetic construct
SEQUENCE: 8
SLPGARPGGV SNNNASTQRP SRNVNNFPYS G                                 31

SEQ ID NO: 9              moltype = AA   length = 4
FEATURE                   Location/Qualifiers
source                    1..4
                          mol_type = protein
                          organism = synthetic construct
SEQUENCE: 9
SLPG                                                              4

SEQ ID NO: 10             moltype = AA   length = 13
FEATURE                   Location/Qualifiers
source                    1..13
                          mol_type = protein
                          organism = synthetic construct
SEQUENCE: 10
IQLNKESNNN AST                                                     13

SEQ ID NO: 11             moltype = AA   length = 13
FEATURE                   Location/Qualifiers
source                    1..13
                          mol_type = protein
                          organism = synthetic construct
SEQUENCE: 11
IGVQVHRNNN AST                                                     13

SEQ ID NO: 12             moltype = AA   length = 13
FEATURE                   Location/Qualifiers
source                    1..13
                          mol_type = protein
                          organism = synthetic construct
SEQUENCE: 12
VRLHCPLNNN AST                                                     13

SEQ ID NO: 13             moltype = AA   length = 13
FEATURE                   Location/Qualifiers
source                    1..13
                          mol_type = protein
                          organism = synthetic construct
```

-continued

```
SEQUENCE: 13
IRLSQGANNN AST                                                              13

SEQ ID NO: 14          moltype = AA  length = 13
FEATURE                Location/Qualifiers
source                 1..13
                       mol_type = protein
                       organism = synthetic construct
SEQUENCE: 14
ARPGGVSNNN AST                                                             13

SEQ ID NO: 15          moltype =   length =
SEQUENCE: 15
000

SEQ ID NO: 16          moltype = AA  length = 9
FEATURE                Location/Qualifiers
source                 1..9
                       mol_type = protein
                       organism = synthetic construct
SEQUENCE: 16
QRPSRNVNN                                                                   9

SEQ ID NO: 17          moltype = AA  length = 5
FEATURE                Location/Qualifiers
source                 1..5
                       mol_type = protein
                       organism = synthetic construct
SEQUENCE: 17
FPYSG                                                                       5

SEQ ID NO: 18          moltype = AA  length = 5
FEATURE                Location/Qualifiers
source                 1..5
                       mol_type = protein
                       organism = synthetic construct
SEQUENCE: 18
FPYKG                                                                       5

SEQ ID NO: 19          moltype = AA  length = 4
FEATURE                Location/Qualifiers
source                 1..4
                       mol_type = protein
                       organism = synthetic construct
SEQUENCE: 19
FPQG                                                                        4

SEQ ID NO: 20          moltype = AA  length = 4
FEATURE                Location/Qualifiers
source                 1..4
                       mol_type = protein
                       organism = synthetic construct
SEQUENCE: 20
FPLG                                                                        4

SEQ ID NO: 21          moltype = AA  length = 5
FEATURE                Location/Qualifiers
source                 1..5
                       mol_type = protein
                       organism = synthetic construct
SEQUENCE: 21
FPYSG                                                                       5

SEQ ID NO: 22          moltype = AA  length = 343
FEATURE                Location/Qualifiers
source                 1..343
                       mol_type = protein
                       organism = synthetic construct
SEQUENCE: 22
MNTKYNKEFL LYLAGFVDGD GSIIAQIKPN QSYKFKHQLS LAFQVTQKTQ RRWFLDKLVD   60
EIGVGYVRDR GSVSDYILSE IKPLHNFLTQ LQPFLALKAD QANLVLKIIW RLPSAKESPD   120
KFLEVCTWVD QIAALNDSKT RKTTSETVRA VLDSLPGIQL NKESNNNAST QRPSRNVNNF   180
PYSGYNKEFL LYLAGFVDGD GSIIAQIKPN QSYKFKHQLS LAFQVTQKTQ RRWFLDYLVD   240
TIGVGYVRDR GSVSDYILSE IKPLHNFLTQ LQPFLKLKQK QANLVLKIIW RLPSAKESPD   300
KFLEVCTWVD QIAALNDSKT RKTTSETVRA VLDSLSEKKK SSP                     343

SEQ ID NO: 23          moltype = AA  length = 343
FEATURE                Location/Qualifiers
source                 1..343
```

```
                              mol_type = protein
                              organism = synthetic construct
SEQUENCE: 23
MNTKYNKEFL LYLAGFVDGD GSIIAQIKPN QSYKFKHQLS LAFQVTQKTQ RRWFLDKLVD    60
EIGVGYVRDR GSVSDYILSE IKPLHNFLTQ LQPFLALKAD QANLVLKIIW RLPSAKESPD   120
KFLEVCTWVD QIAALNDSKT RKTTSETVRA VLDSLPGIGV QVHRNNNAST QRPSRNVNNF   180
PYKGYNKEFL LYLAGFVDGD GSIIAQIKPN QSYKFKHQLS LAFQVTQKTQ RRWFLDYLVD   240
TIGVGYVRDR GSVSDYILSE IKPLHNFLTQ LQPFLKLKQK QANLVLKIIW RLPSAKESPD   300
KFLEVCTWVD QIAALNDSKT RKTTSETVRA VLDSLSEKKK SSP                     343

SEQ ID NO: 24              moltype = AA   length = 342
FEATURE                    Location/Qualifiers
source                     1..342
                           mol_type = protein
                           organism = synthetic construct
SEQUENCE: 24
MNTKYNKEFL LYLAGFVDGD GSIIAQIKPN QSYKFKHQLS LAFQVTQKTQ RRWFLDKLVD    60
EIGVGYVRDR GSVSDYILSE IKPLHNFLTQ LQPFLALKAD QANLVLKIIW RLPSAKESPD   120
KFLEVCTWVD QIAALNDSKT RKTTSETVRA VLDSLPGVRL HCPLNNNAST QRPSRNVNNF   180
PQGYNKEFLL YLAGFVDGDG SIIAQIKPNQ SYKFKHQLSL AFQVTQKTQR RWFLDYLVDT   240
IGVGYVRDRG SVSDYILSEI KPLHNFLTQL QPFLKLKQKQ ANLVLKIIWR LPSAKESPDK   300
FLEVCTWVDQ IAALNDSKTR KTTSETVRAV LDSLSEKKKS SP                      342

SEQ ID NO: 25              moltype = AA   length = 342
FEATURE                    Location/Qualifiers
source                     1..342
                           mol_type = protein
                           organism = synthetic construct
SEQUENCE: 25
MNTKYNKEFL LYLAGFVDGD GSIIAQIKPN QSYKFKHQLS LAFQVTQKTQ RRWFLDKLVD    60
EIGVGYVRDR GSVSDYILSE IKPLHNFLTQ LQPFLALKAD QANLVLKIIW RLPSAKESPD   120
KFLEVCTWVD QIAALNDSKT RKTTSETVRA VLDSLPGIRL SQGANNNAST QRPSRNVNNF   180
PLGYNKEFLL YLAGFVDGDG SIIAQIKPNQ SYKFKHQLSL AFQVTQKTQR RWFLDYLVDT   240
IGVGYVRDRG SVSDYILSEI KPLHNFLTQL QPFLKLKQKQ ANLVLKIIWR LPSAKESPDK   300
FLEVCTWVDQ IAALNDSKTR KTTSETVRAV LDSLSEKKKS SP                      342

SEQ ID NO: 26              moltype = AA   length = 343
FEATURE                    Location/Qualifiers
source                     1..343
                           mol_type = protein
                           organism = synthetic construct
SEQUENCE: 26
MNTKYNKEFL LYLAGFVDGD GSIIAQIKPN QSYKFKHQLS LAFQVTQKTQ RRWFLDKLVD    60
EIGVGYVRDR GSVSDYILSE IKPLHNFLTQ LQPFLALKAD QANLVLKIIW RLPSAKESPD   120
KFLEVCTWVD QIAALNDSKT RKTTSETVRA VLDSLPGARP GGVSNNNAST QRPSRNVNNF   180
PYSGYNKEFL LYLAGFVDGD GSIIAQIKPN QSYKFKHQLS LAFQVTQKTQ RRWFLDYLVD   240
TIGVGYVRDR GSVSDYILSE IKPLHNFLTQ LQPFLKLKQK QANLVLKIIW RLPSAKESPD   300
KFLEVCTWVD QIAALNDSKT RKTTSETVRA VLDSLSEKKK SSP                     343

SEQ ID NO: 27              moltype = AA   length = 42
FEATURE                    Location/Qualifiers
source                     1..42
                           mol_type = protein
                           organism = synthetic construct
SEQUENCE: 27
SLPGSVGGLS PSQASSAASS ASSSPGSGIS EALRAGAGSG TG                       42

SEQ ID NO: 28              moltype = AA   length = 27
FEATURE                    Location/Qualifiers
source                     1..27
                           mol_type = protein
                           organism = synthetic construct
SEQUENCE: 28
PGSVGGLSPN NNASTQRPSR NVNNFPG                                        27

SEQ ID NO: 29              moltype = AA   length = 27
FEATURE                    Location/Qualifiers
source                     1..27
                           mol_type = protein
                           organism = synthetic construct
SEQUENCE: 29
PXXXXXLSPN NNASTQRPSR NVNNFPG                                        27

SEQ ID NO: 30              moltype = AA   length = 27
FEATURE                    Location/Qualifiers
source                     1..27
                           mol_type = protein
                           organism = synthetic construct
SEQUENCE: 30
```

-continued

```
PGSVGGLSPS LNSSTQRPIV NWNNLPG                                          27

SEQ ID NO: 31            moltype = AA  length = 27
FEATURE                  Location/Qualifiers
source                   1..27
                         mol_type = protein
                         organism = synthetic construct
SEQUENCE: 31
PGSVXXXXXS LNSSTQRPIV NWNNLPG                                          27

SEQ ID NO: 32            moltype = AA  length = 27
FEATURE                  Location/Qualifiers
source                   1..27
                         mol_type = protein
                         organism = synthetic construct
SEQUENCE: 32
PGMKLSLSPN NNASTQRPSR NVNNFPG                                          27

SEQ ID NO: 33            moltype = AA  length = 5
FEATURE                  Location/Qualifiers
source                   1..5
                         mol_type = protein
                         organism = synthetic construct
SEQUENCE: 33
GMKLS                                                                  5

SEQ ID NO: 34            moltype = AA  length = 27
FEATURE                  Location/Qualifiers
source                   1..27
                         mol_type = protein
                         organism = synthetic construct
SEQUENCE: 34
PGMSSQLSPN NNASTQRPSR NVNNFPG                                          27

SEQ ID NO: 35            moltype = AA  length = 5
FEATURE                  Location/Qualifiers
source                   1..5
                         mol_type = protein
                         organism = synthetic construct
SEQUENCE: 35
GMSSQ                                                                  5

SEQ ID NO: 36            moltype = AA  length = 27
FEATURE                  Location/Qualifiers
source                   1..27
                         mol_type = protein
                         organism = synthetic construct
SEQUENCE: 36
PGVKGTLSPN NNASTQRPSR NVNNFPG                                          27

SEQ ID NO: 37            moltype = AA  length = 5
FEATURE                  Location/Qualifiers
source                   1..5
                         mol_type = protein
                         organism = synthetic construct
SEQUENCE: 37
GVKGT                                                                  5

SEQ ID NO: 38            moltype = AA  length = 27
FEATURE                  Location/Qualifiers
source                   1..27
                         mol_type = protein
                         organism = synthetic construct
SEQUENCE: 38
PGSVRGKNGS LNSSTQRPIV NWNNLPG                                          27

SEQ ID NO: 39            moltype = AA  length = 5
FEATURE                  Location/Qualifiers
source                   1..5
                         mol_type = protein
                         organism = synthetic construct
SEQUENCE: 39
RGKNG                                                                  5

SEQ ID NO: 40            moltype = AA  length = 27
FEATURE                  Location/Qualifiers
source                   1..27
                         mol_type = protein
                         organism = synthetic construct
```

-continued

```
SEQUENCE: 40
PGSVPGGVSS LNSSTQRPIV NWNNLPG                                            27

SEQ ID NO: 41          moltype = AA  length = 5
FEATURE                Location/Qualifiers
source                 1..5
                       mol_type = protein
                       organism = synthetic construct
SEQUENCE: 41
PGGVS                                                                    5

SEQ ID NO: 42          moltype = AA  length = 27
FEATURE                Location/Qualifiers
source                 1..27
                       mol_type = protein
                       organism = synthetic construct
SEQUENCE: 42
PGVKGTXXXN NNASTQRPSR NVNNFPG                                            27

SEQ ID NO: 43          moltype = AA  length = 27
FEATURE                Location/Qualifiers
source                 1..27
                       mol_type = protein
                       organism = synthetic construct
SEQUENCE: 43
PGMKLSXXXN NNASTQRPSR NVNNFPG                                            27

SEQ ID NO: 44          moltype = AA  length = 27
FEATURE                Location/Qualifiers
source                 1..27
                       mol_type = protein
                       organism = synthetic construct
SEQUENCE: 44
PGMSSQXXXN NNASTQRPSR NVNNFPG                                            27

SEQ ID NO: 45          moltype = AA  length = 28
FEATURE                Location/Qualifiers
source                 1..28
                       mol_type = protein
                       organism = synthetic construct
SEQUENCE: 45
PGVKGTXXXN NNASTQRPSR NVNNFPXG                                           28

SEQ ID NO: 46          moltype = AA  length = 28
FEATURE                Location/Qualifiers
source                 1..28
                       mol_type = protein
                       organism = synthetic construct
SEQUENCE: 46
PGMKLSXXXN NNASTQRPSR NVNNFPXG                                           28

SEQ ID NO: 47          moltype = AA  length = 28
FEATURE                Location/Qualifiers
source                 1..28
                       mol_type = protein
                       organism = synthetic construct
SEQUENCE: 47
PGMSSQXXXN NNASTQRPSR NVNNFPXG                                           28

SEQ ID NO: 48          moltype = AA  length = 29
FEATURE                Location/Qualifiers
source                 1..29
                       mol_type = protein
                       organism = synthetic construct
SEQUENCE: 48
PGVKGTXXXN NNASTQRPSR NVNNFPXXG                                          29

SEQ ID NO: 49          moltype = AA  length = 29
FEATURE                Location/Qualifiers
source                 1..29
                       mol_type = protein
                       organism = synthetic construct
SEQUENCE: 49
PGMKLSXXXN NNASTQRPSR NVNNFPXXG                                          29

SEQ ID NO: 50          moltype = AA  length = 29
FEATURE                Location/Qualifiers
source                 1..29
                       mol_type = protein
```

```
                              organism = synthetic construct
SEQUENCE: 50
PGMSSQXXXN NNASTQRPSR NVNNFPXXG                                              29

SEQ ID NO: 51           moltype = AA  length = 27
FEATURE                 Location/Qualifiers
source                  1..27
                        mol_type = protein
                        organism = synthetic construct
SEQUENCE: 51
PXXXPGGVSS LNSSTQRPIV NWNNLPG                                                27

SEQ ID NO: 52           moltype = AA  length = 28
FEATURE                 Location/Qualifiers
source                  1..28
                        mol_type = protein
                        organism = synthetic construct
SEQUENCE: 52
PXXXPGGVSS LNSSTQRPIV NWNNLPXG                                               28

SEQ ID NO: 53           moltype = AA  length = 29
FEATURE                 Location/Qualifiers
source                  1..29
                        mol_type = protein
                        organism = synthetic construct
SEQUENCE: 53
PXXXPGGVSS LNSSTQRPIV NWNNLPXXG                                              29

SEQ ID NO: 54           moltype = AA  length = 17
FEATURE                 Location/Qualifiers
source                  1..17
                        mol_type = protein
                        organism = synthetic construct
SEQUENCE: 54
NNNASTQRPS RNVNNFP                                                           17

SEQ ID NO: 55           moltype = AA  length = 27
FEATURE                 Location/Qualifiers
source                  1..27
                        mol_type = protein
                        organism = synthetic construct
SEQUENCE: 55
PXXXPGGVSN NNASTQRPSR NVNNFPG                                                27

SEQ ID NO: 56           moltype = AA  length = 28
FEATURE                 Location/Qualifiers
source                  1..28
                        mol_type = protein
                        organism = synthetic construct
SEQUENCE: 56
PXXXPGGVSN NNASTQRPSR NVNNFPXG                                               28

SEQ ID NO: 57           moltype = AA  length = 29
FEATURE                 Location/Qualifiers
source                  1..29
                        mol_type = protein
                        organism = synthetic construct
SEQUENCE: 57
PXXXPGGVSN NNASTQRPSR NVNNFPXXG                                              29

SEQ ID NO: 58           moltype = AA  length = 17
FEATURE                 Location/Qualifiers
source                  1..17
                        mol_type = protein
                        organism = synthetic construct
SEQUENCE: 58
SLNSSTQRPI VNWNNLP                                                           17

SEQ ID NO: 59           moltype = AA  length = 27
FEATURE                 Location/Qualifiers
source                  1..27
                        mol_type = protein
                        organism = synthetic construct
SEQUENCE: 59
PGVKGTXXXS LNSSTQRPIV NWNNLPG                                                27

SEQ ID NO: 60           moltype = AA  length = 27
FEATURE                 Location/Qualifiers
source                  1..27
```

-continued

```
                         mol_type = protein
                         organism = synthetic construct
SEQUENCE: 60
PGMKLSXXXS LNSSTQRPIV NWNNLPG                                        27

SEQ ID NO: 61            moltype = AA   length = 27
FEATURE                  Location/Qualifiers
source                   1..27
                         mol_type = protein
                         organism = synthetic construct
SEQUENCE: 61
PGMSSQXXXS LNSSTQRPIV NWNNLPG                                        27

SEQ ID NO: 62            moltype = AA   length = 28
FEATURE                  Location/Qualifiers
source                   1..28
                         mol_type = protein
                         organism = synthetic construct
SEQUENCE: 62
PGVKGTXXXS LNSSTQRPIV NWNNLPXG                                       28

SEQ ID NO: 63            moltype = AA   length = 28
FEATURE                  Location/Qualifiers
source                   1..28
                         mol_type = protein
                         organism = synthetic construct
SEQUENCE: 63
PGMKLSXXXS LNSSTQRPIV NWNNLPXG                                       28

SEQ ID NO: 64            moltype = AA   length = 28
FEATURE                  Location/Qualifiers
source                   1..28
                         mol_type = protein
                         organism = synthetic construct
SEQUENCE: 64
PGMSSQXXXS LNSSTQRPIV NWNNLPXG                                       28

SEQ ID NO: 65            moltype = AA   length = 29
FEATURE                  Location/Qualifiers
source                   1..29
                         mol_type = protein
                         organism = synthetic construct
SEQUENCE: 65
PGVKGTXXXS LNSSTQRPIV NWNNLPXXG                                      29

SEQ ID NO: 66            moltype = AA   length = 29
FEATURE                  Location/Qualifiers
source                   1..29
                         mol_type = protein
                         organism = synthetic construct
SEQUENCE: 66
PGMKLSXXXS LNSSTQRPIV NWNNLPXXG                                      29

SEQ ID NO: 67            moltype = AA   length = 29
FEATURE                  Location/Qualifiers
source                   1..29
                         mol_type = protein
                         organism = synthetic construct
SEQUENCE: 67
PGMSSQXXXS LNSSTQRPIV NWNNLPXXG                                      29

SEQ ID NO: 68            moltype = AA   length = 51
FEATURE                  Location/Qualifiers
source                   1..51
                         mol_type = protein
                         organism = synthetic construct
SEQUENCE: 68
GSVPGGVSSL NSSTQRPIVN WNNLPGSVSP SRPSLNSSTQ RPIVNWNNLP G            51

SEQ ID NO: 69            moltype = AA   length = 28
FEATURE                  Location/Qualifiers
source                   1..28
                         mol_type = protein
                         organism = synthetic construct
SEQUENCE: 69
GVGRRKCANN NASTQRPSRN VNNFPLNG                                       28

SEQ ID NO: 70            moltype = AA   length = 28
FEATURE                  Location/Qualifiers
```

-continued

```
source                    1..28
                          mol_type = protein
                          organism = synthetic construct
SEQUENCE: 70
GFNGHLSMSL NSSTQRPIVN WNNLPGEG                                             28

SEQ ID NO: 71             moltype = AA   length = 51
FEATURE                   Location/Qualifiers
source                    1..51
                          mol_type = protein
                          organism = synthetic construct
SEQUENCE: 71
GSVPGGVSSL NSSTQRPIVN WNNLPGSVSP SRPSLNSSTQ RPIVNWNNLP G                   51

SEQ ID NO: 72             moltype = AA   length = 28
FEATURE                   Location/Qualifiers
source                    1..28
                          mol_type = protein
                          organism = synthetic construct
SEQUENCE: 72
GVHLPLPLSL NSSTQRPIVN WNNLPGAG                                             28

SEQ ID NO: 73             moltype = AA   length = 51
FEATURE                   Location/Qualifiers
source                    1..51
                          mol_type = protein
                          organism = synthetic construct
SEQUENCE: 73
GSVPGGVSSL NSSTQRPIVN WNNLPGSVSP SRPSLNSSTQ RPIVNWNNLP G                   51

SEQ ID NO: 74             moltype = AA   length = 51
FEATURE                   Location/Qualifiers
source                    1..51
                          mol_type = protein
                          organism = synthetic construct
SEQUENCE: 74
GSVPGGVSSL NSSTQRPIVN WNNLPGSVSP SRPSLNSSTQ RPIVNWNNLP G                   51

SEQ ID NO: 75             moltype = AA   length = 28
FEATURE                   Location/Qualifiers
source                    1..28
                          mol_type = protein
                          organism = synthetic construct
SEQUENCE: 75
GMKLSSAVSL NSSTQRPIVN WNNLPWGG                                             28

SEQ ID NO: 76             moltype = AA   length = 51
FEATURE                   Location/Qualifiers
source                    1..51
                          mol_type = protein
                          organism = synthetic construct
SEQUENCE: 76
GSVPGGVSSL NSSTQRPIVN WNNLPGSVSP SRPSLNSSTQ RPIVNWNNLP G                   51

SEQ ID NO: 77             moltype = AA   length = 28
FEATURE                   Location/Qualifiers
source                    1..28
                          mol_type = protein
                          organism = synthetic construct
SEQUENCE: 77
GMKVPRLESL NSSTQRPIVN WNNLPASG                                             28

SEQ ID NO: 78             moltype = DNA   length = 22
FEATURE                   Location/Qualifiers
source                    1..22
                          mol_type = genomic DNA
                          organism = Homo sapiens
SEQUENCE: 78
atggaagctg tatccaagga tg                                                  22

SEQ ID NO: 79             moltype = AA   length = 354
FEATURE                   Location/Qualifiers
source                    1..354
                          mol_type = protein
                          organism = synthetic construct
SEQUENCE: 79
MNTKYNKEFL LYLAGFVDSD GSIWAFIEPC QTVKFKHRLR LSLNVTQKTQ RRWFLDKLVD   60
EIGVGYVRDT GSVSQYILSE IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
```

```
GISEALRAGA GSGTGYNKEF LLYLAGFVDG DGSIYAKIRP QQASKFKHVL ELVFEVTQST  240
QRRWFLDKLV DEIGVGYVYD WKQASMYRLS QIKPLHNFLT QLQPFLKLKQ KQANLVLKII  300
EQLPSAKESP DKFLEVCTWV DQIAALNDSR TRKTTSETVR AVLDSLSEKK KSSP        354

SEQ ID NO: 80            moltype = AA  length = 343
FEATURE                  Location/Qualifiers
source                   1..343
                         mol_type = protein
                         organism = synthetic construct
SEQUENCE: 80
MNTKYNKEFL LYLAGFVDSD GSIWAFIEPC QTVKFKHRLR LSLNVTQKTQ RRWFLDKLVD  60
EIGVGYVRDT GSVSQYILSE IKPLHNFLTQ LQPFLKLKQK QANLVLKIIE QLPSAKESPD  120
KFLEVCTWVD QIAALNDSKT RKTTSETVRA VLDSLPGARP GGVSNNNAST QRPSRNVNNF  180
PYSGYNKEFL LYLAGFVDGD GSIYAKIRPQ QASKFKHVLE LVFEVTQSTQ RRWFLDKLVD  240
EIGVGYVYDW KQASMYRLSQ IKPLHNFLTQ LQPFLKLKQK QANLVLKIIE QLPSAKESPD  300
KFLEVCTWVD QIAALNDSRT RKTTSETVRA VLDSLSEKKK SSP                   343

SEQ ID NO: 81            moltype = AA  length = 343
FEATURE                  Location/Qualifiers
source                   1..343
                         mol_type = protein
                         organism = synthetic construct
SEQUENCE: 81
MNTKYNKEFL LYLAGFVDSD GSIWAFIEPC QTVKFKYRLR LSLNVTQKTQ RRWFLDKLVD  60
EIGVGYVRDT GSVSQYILSE IKPLHNFLTQ LQPFLALKAD QANLVLKIIE QLPSAKESPD  120
KFLEVCTWVD QIAALNDSKT RKTTSETVRA VLDSLPGARP GGVSNNNAST QRPSRNVNNF  180
PYSGYNKEFL LYLAGFVDGD GSIYAKIRPQ QASKFKHVLE LVFEVTQSTQ RRFFLDYLVD  240
TIGVGYVYDW KQASMYRLSQ IKPLHNFLTQ LQPFLKLKQK QANLVLKIIE QLPSAKESPD  300
KFLEVCTWVD QIAALNDSRT RKTTSETVRA VLDSLSEKKK SSP                   343

SEQ ID NO: 82            moltype = AA  length = 343
FEATURE                  Location/Qualifiers
source                   1..343
                         mol_type = protein
                         organism = synthetic construct
SEQUENCE: 82
MNTKYNKEFL LYLAGFVDSD GSIWAFIEPC QTVKFKHRLR LSLNVTQKTQ RRWFLDKLVD  60
EIGVGYVRDT GSVSQYILSE IKPLHNFLTQ LQPFLKLKQK QANLVLKIIE QLPSAKESPD  120
KFLEVCTWVD QIAALNDSKT RKTTSETVRA VLDSLPGIGV QVHRNNNAST QRPSRNVNNF  180
PYKGYNKEFL LYLAGFVDGD GSIYAKIRPQ QASKFKHVLE LVFEVTQSTQ RRWFLDKLVD  240
EIGVGYVYDW KQASMYRLSQ IKPLHNFLTQ LQPFLKLKQK QANLVLKIIE QLPSAKESPD  300
KFLEVCTWVD QIAALNDSRT RKTTSETVRA VLDSLSEKKK SSP                   343

SEQ ID NO: 83            moltype = AA  length = 343
FEATURE                  Location/Qualifiers
source                   1..343
                         mol_type = protein
                         organism = synthetic construct
SEQUENCE: 83
MNTKYNKEFL LYLAGFVDSD GSIWAFIEPC QTVKFKYRLR LSLNVTQKTQ RRWFLDKLVD  60
EIGVGYVRDT GSVSQYILSE IKPLHNFLTQ LQPFLALKAD QANLVLKIIE QLPSAKESPD  120
KFLEVCTWVD QIAALNDSKT RKTTSETVRA VLDSLPGIGV QVHRNNNAST QRPSRNVNNF  180
PYKGYNKEFL LYLAGFVDGD GSIYAKIRPQ QASKFKHVLE LVFEVTQSTQ RRFFLDYLVD  240
TIGVGYVYDW KQASMYRLSQ IKPLHNFLTQ LQPFLKLKQK QANLVLKIIE QLPSAKESPD  300
KFLEVCTWVD QIAALNDSRT RKTTSETVRA VLDSLSEKKK SSP                   343

SEQ ID NO: 84            moltype = AA  length = 342
FEATURE                  Location/Qualifiers
source                   1..342
                         mol_type = protein
                         organism = synthetic construct
SEQUENCE: 84
MNTKYNKEFL LYLAGFVDSD GSIWAFIEPC QTVKFKHRLR LSLNVTQKTQ RRWFLDKLVD  60
EIGVGYVRDT GSVSQYILSE IKPLHNFLTQ LQPFLKLKQK QANLVLKIIE QLPSAKESPD  120
KFLEVCTWVD QIAALNDSKT RKTTSETVRA VLDSLPGVRL HCPLNNNAST QRPSRNVNNF  180
PQGYNKEFLL YLAGFVDGDG SIYAKIRPQQ ASKFKHVLEL VFEVTQSTQR RWFLDKLVDE  240
IGVGYVYDWK QASMYRLSQI KPLHNFLTQL QPFLKLKQKQ ANLVLKIIEQ LPSAKESPDK  300
FLEVCTWVDQ IAALNDSRTR KTTSETVRAV LDSLSEKKKS SP                    342

SEQ ID NO: 85            moltype = AA  length = 342
FEATURE                  Location/Qualifiers
source                   1..342
                         mol_type = protein
                         organism = synthetic construct
SEQUENCE: 85
MNTKYNKEFL LYLAGFVDSD GSIWAFIEPC QTVKFKYRLR LSLNVTQKTQ RRWFLDKLVD  60
EIGVGYVRDT GSVSQYILSE IKPLHNFLTQ LQPFLALKAD QANLVLKIIE QLPSAKESPD  120
KFLEVCTWVD QIAALNDSKT RKTTSETVRA VLDSLPGVRL HCPLNNNAST QRPSRNVNNF  180
PQGYNKEFLL YLAGFVDGDG SIYAKIRPQQ ASKFKHVLEL VFEVTQSTQR RFFLDYLVDT  240
```

```
IGVGVYDWK QASMYRLSQI KPLHNFLTQL QPFLKLKQKQ ANLVLKIIEQ LPSAKESPDK  300
FLEVCTWVDQ IAALNDSRTR KTTSETVRAV LDSLSEKKKS SP                     342

SEQ ID NO: 86            moltype = AA  length = 342
FEATURE                  Location/Qualifiers
source                   1..342
                         mol_type = protein
                         organism = synthetic construct
SEQUENCE: 86
MNTKYNKEFL LYLAGFVDSD GSIWAFIEPC QTVKFKHRLR LSLNVTQKTQ RRWFLDKLVD  60
EIGVGYVRDT GSVSQYILSE IKPLHNFLTQ LQPFLKLKQK QANLVLKIIE QLPSAKESPD  120
KFLEVCTWVD QIAALNDSKT RKTTSETVRA VLDSLPGIRL SQGANNNAST QRPSRNVNNF  180
PLGYNKEFLL YLAGFVDGDG SIYAKIRPQQ ASKFKHVLEL VFEVTQSTQR RWFLDKLVDE  240
IGVGVYDWK QASMYRLSQI KPLHNFLTQL QPFLKLKQKQ ANLVLKIIEQ LPSAKESPDK  300
FLEVCTWVDQ IAALNDSRTR KTTSETVRAV LDSLSEKKKS SP                     342

SEQ ID NO: 87            moltype = AA  length = 342
FEATURE                  Location/Qualifiers
source                   1..342
                         mol_type = protein
                         organism = synthetic construct
SEQUENCE: 87
MNTKYNKEFL LYLAGFVDSD GSIWAFIEPC QTVKFKYRLR LSLNVTQKTQ RRWFLDKLVD  60
EIGVGYVRDT GSVSQYILSE IKPLHNFLTQ LQPFLALKAD QANLVLKIIE QLPSAKESPD  120
KFLEVCTWVD QIAALNDSKT RKTTSETVRA VLDSLPGIRL SQGANNNAST QRPSRNVNNF  180
PLGYNKEFLL YLAGFVDGDG SIYAKIRPQQ ASKFKHVLEL VFEVTQSTQR RFFLDYLVDT  240
IGVGVYDWK QASMYRLSQI KPLHNFLTQL QPFLKLKQKQ ANLVLKIIEQ LPSAKESPDK  300
FLEVCTWVDQ IAALNDSRTR KTTSETVRAV LDSLSEKKKS SP                     342

SEQ ID NO: 88            moltype = AA  length = 343
FEATURE                  Location/Qualifiers
source                   1..343
                         mol_type = protein
                         organism = synthetic construct
SEQUENCE: 88
MNTKYNKEFL LYLAGFVDSD GSIWAFIEPC QTVKFKHRLR LSLNVTQKTQ RRWFLDKLVD  60
EIGVGYVRDT GSVSQYILSE IKPLHNFLTQ LQPFLKLKQK QANLVLKIIE QLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIYAKIRPQ QASKFKHVLE LVFEVTQSTQ RRWFLDKLVD  240
EIGVGVYDW KQASMYRLSQ IKPLHNFLTQ LQPFLKLKQK QANLVLKIIE QLPSAKESPD  300
KFLEVCTWVD QIAALNDSRT RKTTSETVRA VLDSLSEKKK SSP                    343

SEQ ID NO: 89            moltype = AA  length = 343
FEATURE                  Location/Qualifiers
source                   1..343
                         mol_type = protein
                         organism = synthetic construct
SEQUENCE: 89
MNTKYNKEFL LYLAGFVDSD GSIWAFIEPC QTVKFKYRLR LSLNVTQKTQ RRWFLDKLVD  60
EIGVGYVRDT GSVSQYILSE IKPLHNFLTQ LQPFLALKAD QANLVLKIIE QLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIYAKIRPQ QASKFKHVLE LVFEVTQSTQ RRFFLDYLVD  240
TIGVGVYDW KQASMYRLSQ IKPLHNFLTQ LQPFLKLKQK QANLVLKIIE QLPSAKESPD  300
KFLEVCTWVD QIAALNDSRT RKTTSETVRA VLDSLSEKKK SSP                    343

SEQ ID NO: 90            moltype = AA  length = 354
FEATURE                  Location/Qualifiers
source                   1..354
                         mol_type = protein
                         organism = synthetic construct
SEQUENCE: 90
MNTKYNKEFL LYLAGFVDAD GSIWAYIEPC QWVKFKHRLK LQLNVTQKTQ RRWFLDKLVD  60
EIGVGYVRDT GSVSQYMLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIYAKIRP QQASKFKHVL ELVFEVTQST  240
QRRWFLDKLV DEIGVGYVYD WKQASMYRLS QIKPLHNFLT QLQPFLKLKQ KQANLVLKII  300
EQLPSAKESP DKFLEVCTWV DQIAALNDSK TRKTTSETVR AVLDSLSEKK KSSP        354

SEQ ID NO: 91            moltype = AA  length = 354
FEATURE                  Location/Qualifiers
source                   1..354
                         mol_type = protein
                         organism = synthetic construct
SEQUENCE: 91
MNTKYNKEFL LYLAGFVDAD GSIYARIRPQ QDVKFKHRLE LVFTVYQDTR RRWFLDKLVD  60
EIGVGYVYDS KKVSRYHLSE IKPLHNFLTQ LQPFLKLKQK QANLVLKIIE QLPSAKESPD  120
KFLEVCTWVD QIAALNDSRT RKTTSETVRA VLDSLPGSVG GLSPSQASSA ASSASSSPGS  180
GISEALRAGA GSGTGYNKEF LLYLAGFVDG DGSIYAHIKP KQVAKFKHEL NLAFRVFQKT  240
QRRWFLDKLV DEIGVGYVSD KGSVSYYGLS EIKPLHNFLT QLQPFLKLKQ KQANLVLKII  300
```

```
EQLPSAKESP DKFLEVCTWV DQIAALNDSH TRKTTSETVR AVLDSLSEKK KSSP          354

SEQ ID NO: 92            moltype = DNA   length = 22
FEATURE                  Location/Qualifiers
source                   1..22
                         mol_type = genomic DNA
                         organism = Hepatitis B virus
SEQUENCE: 92
ctgctcgtgt tacaggcggg gt                                            22

SEQ ID NO: 93            moltype = AA   length = 343
FEATURE                  Location/Qualifiers
source                   1..343
                         mol_type = protein
                         organism = synthetic construct
SEQUENCE: 93
MNTKYNKEFL LYLAGFVDAD GSIWAYIEPC QWVKFKHRLK LQLNVTQKTQ RRWFLDKLVD   60
EIGVGYVRDT GSVSQYMLSE IKPLHNFLTQ LQPFLALKAD QANLVLKIIE QLPSAKESPD   120
KFLEVCTWVD QIAALNDSKT RKTTSETVRA VLDSLPGIQL NKESNNNAST QRPSRNVNNF   180
PYSGYNKEFL LYLAGFVDGD GSIYAKIRPQ QASKFKHVLE LVFEVTQSTQ RRWFLDYLVD   240
TIGVGYVYDW KQASMYRLSQ IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 94            moltype = AA   length = 343
FEATURE                  Location/Qualifiers
source                   1..343
                         mol_type = protein
                         organism = synthetic construct
SEQUENCE: 94
MNTKYNKEFL LYLAGFVDAD GSIYARIRPQ QDVKFKHRLE LVFTVYQDTR RRWFLDKLVD   60
EIGVGYVYDS KKVSRYHLSE IKPLHNFLTQ LQPFLALKAD QANLVLKIIE QLPSAKESPD   120
KFLEVCTWVD QIAALNDSRT RKTTSETVRA VLDSLPGIQL NKESNNNAST QRPSRNVNNF   180
PYSGYNKEFL LYLAGFVDGD GSIYAHIKPK QVAKFKHELN LAFRVFQKTQ RRWFLDYLVD   240
TIGVGYVSDK GSVSYYGLSE IKPLHNFLTQ LQPFLKLKQK QANLVLKIIE QLPSAKESPD   300
KFLEVCTWVD QIAALNDSHT RKTTSETVRA VLDSLSEKKK SSP                     343

SEQ ID NO: 95            moltype = AA   length = 10
FEATURE                  Location/Qualifiers
source                   1..10
                         mol_type = protein
                         organism = synthetic construct
SEQUENCE: 95
MAPKKKRKVH                                                          10

SEQ ID NO: 96            moltype = AA   length = 354
FEATURE                  Location/Qualifiers
source                   1..354
                         mol_type = protein
                         organism = synthetic construct
SEQUENCE: 96
MNTKYNKEFL LYLAGFVDGD GSINASIAPR QSFKFKHGLK LRFEVGQKTQ RRWFLDKLVD   60
EIGVGYVYDN GSVSVYSLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFASIRP RQMAKFKHDL ELCFNVRQKT   240
QRRWFLDKLV DEIGVGYVHD WGSVSTYKLS EIKPLHNFLT QLQPFLKLKQ KQANLVLKII   300
EQLPSAKESP DKFLEVCTWV DQIAALNDSK TRKTTSETVR AVLDSLSEKK KSSP         354

SEQ ID NO: 97            moltype = DNA   length = 22
FEATURE                  Location/Qualifiers
source                   1..22
                         mol_type = genomic DNA
                         organism = Hepatitis B virus
SEQUENCE: 97
tgccgatcca tactgcggaa ct                                           22

SEQ ID NO: 98            moltype = AA   length = 36
FEATURE                  Location/Qualifiers
source                   1..36
                         mol_type = protein
                         organism = synthetic construct
SEQUENCE: 98
VLDXXXXXXX XXXXXXXXXX XXXXXXXXXX XXXYNK                             36

SEQ ID NO: 99            moltype = AA   length = 37
FEATURE                  Location/Qualifiers
source                   1..37
                         mol_type = protein
                         organism = synthetic construct
SEQUENCE: 99
```

```
VLDXXXXXXX XXXXXXXXXX XXXXXXXXXX XXXXYNK                           37

SEQ ID NO: 100         moltype = AA   length = 343
FEATURE                Location/Qualifiers
source                 1..343
                       mol_type = protein
                       organism = synthetic construct
SEQUENCE: 100
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLALKAD QANLVLKIIE QLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIFASIRPR QHAKFKHDLE LCFNVRQKTQ RRWFLDYLVD  240
TIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                    343

SEQ ID NO: 101         moltype = AA   length = 354
FEATURE                Location/Qualifiers
source                 1..354
                       mol_type = protein
                       organism = synthetic construct
SEQUENCE: 101
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIFASIRP RQHAKFKHDL ELCFNVRQKT  240
QRRWFLDKLV DEIGVGYVID WRGASTYKLS QIKPLHNFLT QLQPFLKLKQ KQANLVLKII  300
EQLPSAKESP DKFLEVCTWV DQIAALNDSK TRKTTSETVR AVLDSLSEKK KSSP        354

SEQ ID NO: 102         moltype = DNA   length = 22
FEATURE                Location/Qualifiers
source                 1..22
                       mol_type = other DNA
                       organism = synthetic construct
SEQUENCE: 102
tgccgatcca tactgcggaa ct                                          22

SEQ ID NO: 103         moltype = DNA   length = 19
FEATURE                Location/Qualifiers
source                 1..19
                       mol_type = other DNA
                       organism = synthetic construct
SEQUENCE: 103
ggtctgtgcc aagtgtttg                                              19

SEQ ID NO: 104         moltype = DNA   length = 17
FEATURE                Location/Qualifiers
source                 1..17
                       mol_type = other DNA
                       organism = synthetic construct
SEQUENCE: 104
gctgcgagca aaacaag                                                17

SEQ ID NO: 105         moltype = DNA   length = 15
FEATURE                Location/Qualifiers
source                 1..15
                       mol_type = other DNA
                       organism = synthetic construct
SEQUENCE: 105
cccgcctgta acacg                                                  15

SEQ ID NO: 106         moltype = DNA   length = 19
FEATURE                Location/Qualifiers
source                 1..19
                       mol_type = other DNA
                       organism = synthetic construct
SEQUENCE: 106
catcaggatt cctaggacc                                              19

SEQ ID NO: 107         moltype = DNA   length = 17
FEATURE                Location/Qualifiers
source                 1..17
                       mol_type = other DNA
                       organism = synthetic construct
SEQUENCE: 107
agtccaccac gagtcta                                                17

SEQ ID NO: 108         moltype = AA   length = 354
FEATURE                Location/Qualifiers
source                 1..354
```

```
                                  mol_type = protein
                                  organism = synthetic construct
SEQUENCE: 108
MNTKYNKEFL LYLAGFVDSD GSINASISPR QSFKFKHGLK LRFEVGQKTQ HRWFLDKLVD      60
EIGVGYVYDN GSVSVYSLSQ IKPLHNFLTQ LQPFLKLKQK QANLVLKIIE QLPSAKESPD     120
KFLEVCTWVD QIAALNDSKT RKTTSETVRA VLDSLPGSVG GLSPSQASSA ASSASSSPGS     180
GISEALRAGA GSGTGYNKEF LLYLAGFVDG DGSIFASIRP RQHAKFKHDL ELCFNVRQKT     240
QRRWFLDKLV DEIGVGYVID WRGASTYKLS EIKPLHNFLT QLQPFLKLKQ KQANLVLKII     300
EQLPSAKESP DKFLEVCTWV DQIAALNDSK TRKTTSETVR AVLDSLSEKK KSSP           354

SEQ ID NO: 109              moltype = AA   length = 343
FEATURE                     Location/Qualifiers
source                      1..343
                            mol_type = protein
                            organism = synthetic construct
SEQUENCE: 109
MNTKYNKEFL LYLAGFVDSD GSINASISPR QSFKFKHGLK LRFEVGQKTQ HRWFLDKLVD      60
EIGVGYVYDN GSVSVYSLSQ IKPLHNFLTQ LQPFLALKAD QANLVLKIIE QLPSAKESPD     120
KFLEVCTWVD QIAALNDSKT RKTTSETVRA VLDSLPGIQL NKESNNNAST QRPSRNVNNF     180
PYSGYNKEFL LYLAGFVDGD GSIFASIRPR QHAKFKHDLE LCFNVRQKTQ RRWFLDYLVD     240
TIGVGYVIDW RGASTYKLSE IKPLHNFLTQ LQPFLKLKQK QANLVLKIIE QLPSAKESPD     300
KFLEVCTWVD QIAALNDSKT RKTTSETVRA VLDSLSEKKK SSP                      343

SEQ ID NO: 110              moltype = DNA   length = 22
FEATURE                     Location/Qualifiers
source                      1..22
                            mol_type = other DNA
                            organism = synthetic construct
SEQUENCE: 110
tgccgatcca tactgcggaa ct                                             22

SEQ ID NO: 111              moltype = DNA   length = 19
FEATURE                     Location/Qualifiers
source                      1..19
                            mol_type = other DNA
                            organism = synthetic construct
SEQUENCE: 111
ggtctgtgcc aagtgtttg                                                 19

SEQ ID NO: 112              moltype = DNA   length = 20
FEATURE                     Location/Qualifiers
source                      1..20
                            mol_type = other DNA
                            organism = synthetic construct
SEQUENCE: 112
gtatatttcc gcgagaggac                                                20

SEQ ID NO: 113              moltype = DNA   length = 24
FEATURE                     Location/Qualifiers
source                      1..24
                            mol_type = other DNA
                            organism = synthetic construct
SEQUENCE: 113
cttggcccccc aataccacat catc                                          24

SEQ ID NO: 114              moltype = DNA   length = 23
FEATURE                     Location/Qualifiers
source                      1..23
                            mol_type = other DNA
                            organism = synthetic construct
SEQUENCE: 114
ggatggaaat tgcacctgta ttc                                            23

SEQ ID NO: 115              moltype = DNA   length = 24
FEATURE                     Location/Qualifiers
source                      1..24
                            mol_type = other DNA
                            organism = synthetic construct
SEQUENCE: 115
gggtttaaat gtatacccag agac                                           24

SEQ ID NO: 116              moltype = AA   length = 28
FEATURE                     Location/Qualifiers
source                      1..28
                            mol_type = protein
                            organism = synthetic construct
SEQUENCE: 116
GIGVQVHRNN NASTQRPSRN VNNFPYKG                                       28
```

-continued

```
SEQ ID NO: 117          moltype = AA  length = 27
FEATURE                 Location/Qualifiers
source                  1..27
                        mol_type = protein
                        organism = synthetic construct
SEQUENCE: 117
GVRLHCPLNN NASTQRPSRN VNNFPQG                                 27

SEQ ID NO: 118          moltype = AA  length = 27
FEATURE                 Location/Qualifiers
source                  1..27
                        mol_type = protein
                        organism = synthetic construct
SEQUENCE: 118
GIRLSQGANN NASTQRPSRN VNNFPLG                                 27

SEQ ID NO: 119          moltype = AA  length = 28
FEATURE                 Location/Qualifiers
source                  1..28
                        mol_type = protein
                        organism = synthetic construct
SEQUENCE: 119
GARPGGVSNN NASTQRPSRN VNNFPYSG                                28

SEQ ID NO: 120          moltype = AA  length = 28
FEATURE                 Location/Qualifiers
source                  1..28
                        mol_type = protein
                        organism = synthetic construct
SEQUENCE: 120
GIQLNKESNN NASTQRPSRN VNNFPYSG                                28

SEQ ID NO: 121          moltype = AA  length = 343
FEATURE                 Location/Qualifiers
source                  1..343
                        mol_type = protein
                        organism = synthetic construct
SEQUENCE: 121
MNTKYNKEFL LYLAGFVDSD GSINASISPR QSFKFKHGLK LRFEVGQKTQ HRWFLDKLVD  60
EIGVGYVYDN GSVSVYSLSQ IKPLHNFLTQ LQPFLKLKQK QANLVLKIIE QLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIFASIRPR QHAKFKHDLE LCFNVRQKTQ RRWFLDKLVD  240
EIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                   343

SEQ ID NO: 122          moltype = AA  length = 343
FEATURE                 Location/Qualifiers
source                  1..343
                        mol_type = protein
                        organism = synthetic construct
SEQUENCE: 122
MNTKYNKEFL LYLAGFVDSD GSINASISPR QSFKFKHGLK LRFEVGQKTQ HRWFLDKLVD  60
EIGVGYVYDN GSVSVYSLSQ IKPLHNFLTQ LQPFLALKQK QANLVLKIIE QLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIFASIRPR QHAKFKHDLE LCFNVRQKTQ RRWFLDYLVD  240
TIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                   343

SEQ ID NO: 123          moltype = AA  length = 343
FEATURE                 Location/Qualifiers
source                  1..343
                        mol_type = protein
                        organism = synthetic construct
SEQUENCE: 123
MNTKYNKEFL LYLAGFVDSD GSINASISPR QSFKFKHGLK LRFEVGQKTQ HRWFLDKLVD  60
EIGVGYVYDN GSVSVYSLSQ IKPLHNFLTQ LQPFLKLKAD QANLVLKIIE QLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIFASIRPR QHAKFKHDLE LCFNVRQKTQ RRWFLDKLVD  240
EIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                   343

SEQ ID NO: 124          moltype = AA  length = 343
FEATURE                 Location/Qualifiers
source                  1..343
                        mol_type = protein
                        organism = synthetic construct
SEQUENCE: 124
MNTKYNKEFL LYLAGFVDSD GSINASISPR QSFKFKYGLK LRFEVGQKTQ HRWFLDKLVD  60
EIGVGYVYDN GSVSVYSLSQ IKPLHNFLTQ LQPFLKLKQK QANLVLKIIE QLPSAKESPD  120
```

```
KFLEVCTWVD QIAALNDSKT RKTTSETVRA VLDSLPGIQL NKESNNNAST QRPSRNVNNF  180
PYSGYNKEFL LYLAGFVDGD GSIFASIRPR QHAKFKHDLE LCFNVRQKTQ RRFFLDKLVD  240
EIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                     343

SEQ ID NO: 125           moltype = AA  length = 343
FEATURE                  Location/Qualifiers
source                   1..343
                         mol_type = protein
                         organism = synthetic construct
SEQUENCE: 125
MNTKYNKEFL LYLAGFVDSD GSINASISPR QSFKFKYGLK LRFEVGQKTQ HRWFLDKLVD   60
EIGVGYVYDN GSVSVYSLSQ IKPLHNFLTQ LQPFLALKQK QANLVLKIIE QLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIFASIRPR QHAKFKHDLE LCFNVRQKTQ RRFFLDYLVD  240
TIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                     343

SEQ ID NO: 126           moltype = AA  length = 343
FEATURE                  Location/Qualifiers
source                   1..343
                         mol_type = protein
                         organism = synthetic construct
SEQUENCE: 126
MNTKYNKEFL LYLAGFVDSD GSINASISPR QSFKFKYGLK LRFEVGQKTQ HRWFLDKLVD   60
EIGVGYVYDN GSVSVYSLSQ IKPLHNFLTQ LQPFLKLKQK QANLVLKIIE QLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIFASIRPR QHAKFKHDLE LCFNVRQKTQ RRFFLDKLVD  240
EIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                     343

SEQ ID NO: 127           moltype = AA  length = 343
FEATURE                  Location/Qualifiers
source                   1..343
                         mol_type = protein
                         organism = synthetic construct
SEQUENCE: 127
MNTKYNKEFL LYLAGFVDSD GSINASISPR QSFKFKYGLK LRFEVGQKTQ HRWFLDKLVD   60
EIGVGYVYDN GSVSVYSLSQ IKPLHNFLTQ LQPFLALKAD QANLVLKIIE QLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIFASIRPR QHAKFKHDLE LCFNVRQKTQ RRFFLDYLVD  240
TIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                     343

SEQ ID NO: 128           moltype = AA  length = 343
FEATURE                  Location/Qualifiers
source                   1..343
                         mol_type = protein
                         organism = synthetic construct
SEQUENCE: 128
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLKLKQK QANLVLKIIE QLPSAKESPD  120
KFLEVCTWVD QIAALNDSKT RKTTSETVRA VLDSLPGIGV QVHRNNNAST QRPSRNVNNF  180
PYKGYNKEFL LYLAGFVDGD GSIFASIRPR QHAKFKHDLE LCFNVRQKTQ RRWFLDKLVD  240
EIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                     343

SEQ ID NO: 129           moltype = AA  length = 343
FEATURE                  Location/Qualifiers
source                   1..343
                         mol_type = protein
                         organism = synthetic construct
SEQUENCE: 129
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLALKAD QANLVLKIIE QLPSAKESPD  120
KFLEVCTWVD QIAALNDSKT RKTTSETVRA VLDSLPGIGV QVHRNNNAST QRPSRNVNNF  180
PYKGYNKEFL LYLAGFVDGD GSIFASIRPR QHAKFKHDLE LCFNVRQKTQ RRWFLDYLVD  240
TIGVGYVIDW RGASTYKLSQ IKPLHNFLTQ LQPFLKLKQK QANLVLKIIE QLPSAKESPD  300
KFLEVCTWVD QIAALNDSKT RKTTSETVRA VLDSLSEKKK SSP                     343

SEQ ID NO: 130           moltype = AA  length = 343
FEATURE                  Location/Qualifiers
source                   1..343
                         mol_type = protein
                         organism = synthetic construct
SEQUENCE: 130
MNTKYNKEFL LYLAGFVDSD GSINASISPR QSFKFKYGLK LRFEVGQKTQ HRWFLDKLVD   60
EIGVGYVYDN GSVSVYSLSQ IKPLHNFLTQ LQPFLALKAD QANLVLKIIE QLPSAKESPD  120
KFLEVCTWVD QIAALNDSKT RKTTSETVRA VLDSLPGIGV QVHRNNNAST QRPSRNVNNF  180
```

```
PYKGYNKEFL LYLAGFVDGD GSIFASIRPR QHAKFKHDLE LCFNVRQKTQ RRFFLDYLVD   240
TIGVGYVIDW RGASTYKLSQ IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 131              moltype = AA   length = 342
FEATURE                     Location/Qualifiers
source                      1..342
                            mol_type = protein
                            organism = synthetic construct
SEQUENCE: 131
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLKLKQK QANLVLKIIE QLPSAKESPD   120
KFLEVCTWVD QIAALNDSKT RKTTSETVRA VLDSLPGVRL HCPLNNNAST QRPSRNVNNF   180
PQGYNKEFLL YLAGFVDGDG SIFASIRPRQ HAKFKHDLEL CFNVRQKTQR RWFLDKLVDE   240
IGVGYVIDWR GASTYKLSQI KPLHNFLTQL QPFLKLKQKQ ANLVLKIIEQ LPSAKESPDK   300
FLEVCTWVDQ IAALNDSKTR KTTSETVRAV LDSLSEKKKS SP                     342

SEQ ID NO: 132              moltype = AA   length = 342
FEATURE                     Location/Qualifiers
source                      1..342
                            mol_type = protein
                            organism = synthetic construct
SEQUENCE: 132
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLALKAD QANLVLKIIE QLPSAKESPD   120
KFLEVCTWVD QIAALNDSKT RKTTSETVRA VLDSLPGVRL HCPLNNNAST QRPSRNVNNF   180
PQGYNKEFLL YLAGFVDGDG SIFASIRPRQ HAKFKHDLEL CFNVRQKTQR RWFLDYLVDT   240
IGVGYVIDWR GASTYKLSQI KPLHNFLTQL QPFLKLKQKQ ANLVLKIIEQ LPSAKESPDK   300
FLEVCTWVDQ IAALNDSKTR KTTSETVRAV LDSLSEKKKS SP                     342

SEQ ID NO: 133              moltype = AA   length = 342
FEATURE                     Location/Qualifiers
source                      1..342
                            mol_type = protein
                            organism = synthetic construct
SEQUENCE: 133
MNTKYNKEFL LYLAGFVDSD GSINASISPR QSFKFKYGLK LRFEVGQKTQ HRWFLDKLVD   60
EIGVGYVYDN GSVSVYSLSQ IKPLHNFLTQ LQPFLALKAD QANLVLKIIE QLPSAKESPD   120
KFLEVCTWVD QIAALNDSKT RKTTSETVRA VLDSLPGVRL HCPLNNNAST QRPSRNVNNF   180
PQGYNKEFLL YLAGFVDGDG SIFASIRPRQ HAKFKHDLEL CFNVRQKTQR RFFLDYLVDT   240
IGVGYVIDWR GASTYKLSQI KPLHNFLTQL QPFLKLKQKQ ANLVLKIIEQ LPSAKESPDK   300
FLEVCTWVDQ IAALNDSKTR KTTSETVRAV LDSLSEKKKS SP                     342

SEQ ID NO: 134              moltype = AA   length = 342
FEATURE                     Location/Qualifiers
source                      1..342
                            mol_type = protein
                            organism = synthetic construct
SEQUENCE: 134
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLKLKQK QANLVLKIIE QLPSAKESPD   120
KFLEVCTWVD QIAALNDSKT RKTTSETVRA VLDSLPGIRL SQGANNNAST QRPSRNVNNF   180
PLGYNKEFLL YLAGFVDGDG SIFASIRPRQ HAKFKHDLEL CFNVRQKTQR RWFLDKLVDE   240
IGVGYVIDWR GASTYKLSQI KPLHNFLTQL QPFLKLKQKQ ANLVLKIIEQ LPSAKESPDK   300
FLEVCTWVDQ IAALNDSKTR KTTSETVRAV LDSLSEKKKS SP                     342

SEQ ID NO: 135              moltype = AA   length = 342
FEATURE                     Location/Qualifiers
source                      1..342
                            mol_type = protein
                            organism = synthetic construct
SEQUENCE: 135
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLALKAD QANLVLKIIE QLPSAKESPD   120
KFLEVCTWVD QIAALNDSKT RKTTSETVRA VLDSLPGIRL SQGANNNAST QRPSRNVNNF   180
PLGYNKEFLL YLAGFVDGDG SIFASIRPRQ HAKFKHDLEL CFNVRQKTQR RWFLDYLVDT   240
IGVGYVIDWR GASTYKLSQI KPLHNFLTQL QPFLKLKQKQ ANLVLKIIEQ LPSAKESPDK   300
FLEVCTWVDQ IAALNDSKTR KTTSETVRAV LDSLSEKKKS SP                     342

SEQ ID NO: 136              moltype = AA   length = 342
FEATURE                     Location/Qualifiers
source                      1..342
                            mol_type = protein
                            organism = synthetic construct
SEQUENCE: 136
MNTKYNKEFL LYLAGFVDSD GSINASISPR QSFKFKYGLK LRFEVGQKTQ HRWFLDKLVD   60
EIGVGYVYDN GSVSVYSLSQ IKPLHNFLTQ LQPFLALKAD QANLVLKIIE QLPSAKESPD   120
KFLEVCTWVD QIAALNDSKT RKTTSETVRA VLDSLPGIRL SQGANNNAST QRPSRNVNNF   180
PLGYNKEFLL YLAGFVDGDG SIFASIRPRQ HAKFKHDLEL CFNVRQKTQR RFFLDYLVDT   240
```

-continued

```
IGVGYVIDWR GASTYKLSQI KPLHNFLTQL QPFLKLKQKQ ANLVLKIIEQ LPSAKESPDK   300
FLEVCTWVDQ IAALNDSKTR KTTSETVRAV LDSLSEKKKS SP                        342

SEQ ID NO: 137              moltype = AA  length = 343
FEATURE                     Location/Qualifiers
source                      1..343
                            mol_type = protein
                            organism = synthetic construct
SEQUENCE: 137
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLKLKQK QANLVLKIIE QLPSAKESPD   120
KFLEVCTWVD QIAALNDSKT RKTTSETVRA VLDSLPGARP GGVSNNNAST QRPSRNVNNF   180
PYSGYNKEFL LYLAGFVDGD GSIFASIRPR QHAKFKHDLE LCFNVRQKTQ RRWFLDKLVD   240
EIGVGYVIDW RGASTYKLSQ IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 138              moltype = AA  length = 343
FEATURE                     Location/Qualifiers
source                      1..343
                            mol_type = protein
                            organism = synthetic construct
SEQUENCE: 138
MNTKYNKEFL LYLAGFVDSD GSINASISPR QSFKFKHGLK LRFEVGQKTQ HRWFLDKLVD   60
EIGVGYVYDN GSVSVYSLSQ IKPLHNFLTQ LQPFLALKAD QANLVLKIIE QLPSAKESPD   120
KFLEVCTWVD QIAALNDSKT RKTTSETVRA VLDSLPGARP GGVSNNNAST QRPSRNVNNF   180
PYSGYNKEFL LYLAGFVDGD GSIFASIRPR QHAKFKHDLE LCFNVRQKTQ RRWFLDYLVD   240
TIGVGYVIDW RGASTYKLSQ IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 139              moltype = AA  length = 343
FEATURE                     Location/Qualifiers
source                      1..343
                            mol_type = protein
                            organism = synthetic construct
SEQUENCE: 139
MNTKYNKEFL LYLAGFVDSD GSINASISPR QSFKFKYGLK LRFEVGQKTQ HRWFLDKLVD   60
EIGVGYVYDN GSVSVYSLSQ IKPLHNFLTQ LQPFLALKAD QANLVLKIIE QLPSAKESPD   120
KFLEVCTWVD QIAALNDSKT RKTTSETVRA VLDSLPGARP GGVSNNNAST QRPSRNVNNF   180
PYSGYNKEFL LYLAGFVDGD GSIFASIRPR QHAKFKHDLE LCFNVRQKTQ RRFFLDYLVD   240
TIGVGYVIDW RGASTYKLSQ IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 140              moltype = AA  length = 354
FEATURE                     Location/Qualifiers
source                      1..354
                            mol_type = protein
                            organism = synthetic construct
SEQUENCE: 140
MNTKYNKEFL LYLAGFVDGD GSIHACISPD QACKFKHYLR LRFNVAQKTQ RRWFLDKLVD   60
EIGVGYVHDQ GSVSYYQLSQ IKPLHNFLTQ LQPFLKLKQK QANLVLKIIE QLPSAKESPD   120
KFLEVCTWVD QIAALNDSKT RKTTSETVRA VLDSLPGSVG GLSPSQASSA ASSASSSPGS   180
GISEALRAGA GSGTGYNKEF LLYLAGFVDG DGSIFACIQP RQQSKFKHSL QLWFYVTQKT   240
QRRWFLDKLV DEIGAGYVND WGGASQYRLS EIKPLHNFLT QLQPFLKLKQ KQANLVLKII   300
EQLPSAKESP DKFLEVCTWV DQIAALNDSK TRKTTSETVR AVLDSLSEKK KSSP         354

SEQ ID NO: 141              moltype = AA  length = 343
FEATURE                     Location/Qualifiers
source                      1..343
                            mol_type = protein
                            organism = synthetic construct
SEQUENCE: 141
MNTKYNKEFL LYLAGFVDGD GSIHACISPD QACKFKHYLR LRFNVAQKTQ RRWFLDKLVD   60
EIGVGYVHDQ GSVSYYQLSQ IKPLHNFLTQ LQPFLKLKQK QANLVLKIIE QLPSAKESPD   120
KFLEVCTWVD QIAALNDSKT RKTTSETVRA VLDSLPGIQL NKESNNNAST QRPSRNVNNF   180
PYSGYNKEFL LYLAGFVDGD GSIFACIQPR QQSKFKHSLQ LWFYVTQKTQ RRWFLDKLVD   240
EIGAGYVNDW GGASQYRLSE IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 142              moltype = AA  length = 343
FEATURE                     Location/Qualifiers
source                      1..343
                            mol_type = protein
                            organism = synthetic construct
SEQUENCE: 142
MNTKYNKEFL LYLAGFVDGD GSIHACISPD QACKFKHYLR LRFNVAQKTQ RRWFLDKLVD   60
EIGVGYVHDQ GSVSYYQLSQ IKPLHNFLTQ LQPFLALKQK QANLVLKIIE QLPSAKESPD   120
KFLEVCTWVD QIAALNDSKT RKTTSETVRA VLDSLPGIQL NKESNNNAST QRPSRNVNNF   180
PYSGYNKEFL LYLAGFVDGD GSIFACIQPR QQSKFKHSLQ LWFYVTQKTQ RRWFLDYLVD   240
TIGAGYVNDW GGASQYRLSE IKPLHNFLTQ LQPFLKLKQK QANLVLKIIE QLPSAKESPD   300
```

-continued

```
KFLEVCTWVD QIAALNDSKT RKTTSETVRA VLDSLSEKKK SSP                     343

SEQ ID NO: 143            moltype = AA   length = 343
FEATURE                   Location/Qualifiers
source                    1..343
                          mol_type = protein
                          organism = synthetic construct
SEQUENCE: 143
MNTKYNKEFL LYLAGFVDGD GSIHACISPD QACKFKHYLR LRFNVAQKTQ RRWFLDKLVD    60
EIGVGYVHDQ GSVSYYQLSQ IKPLHNFLTQ LQPFLKLKAD QANLVLKIIE QLPSAKESPD   120
KFLEVCTWVD QIAALNDSKT RKTTSETVRA VLDSLPGIQL NKESNNNAST QRPSRNVNNF   180
PYSGYNKEFL LYLAGFVDGD GSIFACIQPR QQSKFKHSLQ LWFYVTQKTQ RRWFLDKLVD   240
EIGAGYVNDW GGASQYRLSE IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 144            moltype = AA   length = 343
FEATURE                   Location/Qualifiers
source                    1..343
                          mol_type = protein
                          organism = synthetic construct
SEQUENCE: 144
MNTKYNKEFL LYLAGFVDGD GSIHACISPD QACKFKYYLR LRFNVAQKTQ RRWFLDKLVD    60
EIGVGYVHDQ GSVSYYQLSQ IKPLHNFLTQ LQPFLKLKQK QANLVLKIIE QLPSAKESPD   120
KFLEVCTWVD QIAALNDSKT RKTTSETVRA VLDSLPGIQL NKESNNNAST QRPSRNVNNF   180
PYSGYNKEFL LYLAGFVDGD GSIFACIQPR QQSKFKHSLQ LWFYVTQKTQ RRFFLDKLVD   240
EIGAGYVNDW GGASQYRLSE IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 145            moltype = AA   length = 343
FEATURE                   Location/Qualifiers
source                    1..343
                          mol_type = protein
                          organism = synthetic construct
SEQUENCE: 145
MNTKYNKEFL LYLAGFVDGD GSIHACISPD QACKFKHYLR LRFNVAQKTQ RRWFLDKLVD    60
EIGVGYVHDQ GSVSYYQLSQ IKPLHNFLTQ LQPFLALKAD QANLVLKIIE QLPSAKESPD   120
KFLEVCTWVD QIAALNDSKT RKTTSETVRA VLDSLPGIQL NKESNNNAST QRPSRNVNNF   180
PYSGYNKEFL LYLAGFVDGD GSIFACIQPR QQSKFKHSLQ LWFYVTQKTQ RRWFLDYLVD   240
TIGAGYVNDW GGASQYRLSE IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 146            moltype = AA   length = 343
FEATURE                   Location/Qualifiers
source                    1..343
                          mol_type = protein
                          organism = synthetic construct
SEQUENCE: 146
MNTKYNKEFL LYLAGFVDGD GSIHACISPD QACKFKYYLR LRFNVAQKTQ RRWFLDKLVD    60
EIGVGYVHDQ GSVSYYQLSQ IKPLHNFLTQ LQPFLALKQK QANLVLKIIE QLPSAKESPD   120
KFLEVCTWVD QIAALNDSKT RKTTSETVRA VLDSLPGIQL NKESNNNAST QRPSRNVNNF   180
PYSGYNKEFL LYLAGFVDGD GSIFACIQPR QQSKFKHSLQ LWFYVTQKTQ RRFFLDYLVD   240
TIGAGYVNDW GGASQYRLSE IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 147            moltype = AA   length = 343
FEATURE                   Location/Qualifiers
source                    1..343
                          mol_type = protein
                          organism = synthetic construct
SEQUENCE: 147
MNTKYNKEFL LYLAGFVDGD GSIHACISPD QACKFKYYLR LRFNVAQKTQ RRWFLDKLVD    60
EIGVGYVHDQ GSVSYYQLSQ IKPLHNFLTQ LQPFLKLKAD QANLVLKIIE QLPSAKESPD   120
KFLEVCTWVD QIAALNDSKT RKTTSETVRA VLDSLPGIQL NKESNNNAST QRPSRNVNNF   180
PYSGYNKEFL LYLAGFVDGD GSIFACIQPR QQSKFKHSLQ LWFYVTQKTQ RRFFLDKLVD   240
EIGAGYVNDW GGASQYRLSE IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 148            moltype = AA   length = 343
FEATURE                   Location/Qualifiers
source                    1..343
                          mol_type = protein
                          organism = synthetic construct
SEQUENCE: 148
MNTKYNKEFL LYLAGFVDGD GSIHACISPD QACKFKYYLR LRFNVAQKTQ RRWFLDKLVD    60
EIGVGYVHDQ GSVSYYQLSQ IKPLHNFLTQ LQPFLALKAD QANLVLKIIE QLPSAKESPD   120
KFLEVCTWVD QIAALNDSKT RKTTSETVRA VLDSLPGIQL NKESNNNAST QRPSRNVNNF   180
PYSGYNKEFL LYLAGFVDGD GSIFACIQPR QQSKFKHSLQ LWFYVTQKTQ RRFFLDYLVD   240
TIGAGYVNDW GGASQYRLSE IKPLHNFLTQ LQPFLKLKQK QANLVLKIIE QLPSAKESPD   300
KFLEVCTWVD QIAALNDSKT RKTTSETVRA VLDSLSEKKK SSP                     343
```

-continued

```
SEQ ID NO: 149            moltype = AA  length = 343
FEATURE                   Location/Qualifiers
source                    1..343
                          mol_type = protein
                          organism = synthetic construct
SEQUENCE: 149
MNTKYNKEFL LYLAGFVDGD GSIHACISPD QACKFKHYLR LRFNVAQKTQ RRWFLDKLVD  60
EIGVGYVHDQ GSVSYYQLSQ IKPLHNFLTQ LQPFLKLKQK QANLVLKIIE QLPSAKESPD 120
KFLEVCTWVD QIAALNDSKT RKTTSETVRA VLDSLPGIGV QVHRNNNAST QRPSRNVNNF 180
PYKGYNKEFL LYLAGFVDGD GSIFACIQPR QQSKFKHSLQ LWFYVTQKTQ RRWFLDKLVD 240
EIGAGYVNDW GGASQYRLSE IKPLHNFLTQ LQPFLKLKQK QANLVLKIIE QLPSAKESPD 300
KFLEVCTWVD QIAALNDSKT RKTTSETVRA VLDSLSEKKK SSP                   343

SEQ ID NO: 150            moltype = AA  length = 343
FEATURE                   Location/Qualifiers
source                    1..343
                          mol_type = protein
                          organism = synthetic construct
SEQUENCE: 150
MNTKYNKEFL LYLAGFVDGD GSIHACISPD QACKFKHYLR LRFNVAQKTQ RRWFLDKLVD  60
EIGVGYVHDQ GSVSYYQLSQ IKPLHNFLTQ LQPFLALKAD QANLVLKIIE QLPSAKESPD 120
KFLEVCTWVD QIAALNDSKT RKTTSETVRA VLDSLPGIGV QVHRNNNAST QRPSRNVNNF 180
PYKGYNKEFL LYLAGFVDGD GSIFACIQPR QQSKFKHSLQ LWFYVTQKTQ RRWFLDYLVD 240
TIGAGYVNDW GGASQYRLSE IKPLHNFLTQ LQPFLKLKQK QANLVLKIIE QLPSAKESPD 300
KFLEVCTWVD QIAALNDSKT RKTTSETVRA VLDSLSEKKK SSP                   343

SEQ ID NO: 151            moltype = AA  length = 343
FEATURE                   Location/Qualifiers
source                    1..343
                          mol_type = protein
                          organism = synthetic construct
SEQUENCE: 151
MNTKYNKEFL LYLAGFVDGD GSIHACISPD QACKFKYYLR LRFNVAQKTQ RRWFLDKLVD  60
EIGVGYVHDQ GSVSYYQLSQ IKPLHNFLTQ LQPFLALKAD QANLVLKIIE QLPSAKESPD 120
KFLEVCTWVD QIAALNDSKT RKTTSETVRA VLDSLPGIGV QVHRNNNAST QRPSRNVNNF 180
PYKGYNKEFL LYLAGFVDGD GSIFACIQPR QQSKFKHSLQ LWFYVTQKTQ RRFFLDYLVD 240
TIGAGYVNDW GGASQYRLSE IKPLHNFLTQ LQPFLKLKQK QANLVLKIIE QLPSAKESPD 300
KFLEVCTWVD QIAALNDSKT RKTTSETVRA VLDSLSEKKK SSP                   343

SEQ ID NO: 152            moltype = AA  length = 342
FEATURE                   Location/Qualifiers
source                    1..342
                          mol_type = protein
                          organism = synthetic construct
SEQUENCE: 152
MNTKYNKEFL LYLAGFVDGD GSIHACISPD QACKFKHYLR LRFNVAQKTQ RRWFLDKLVD  60
EIGVGYVHDQ GSVSYYQLSQ IKPLHNFLTQ LQPFLKLKQK QANLVLKIIE QLPSAKESPD 120
KFLEVCTWVD QIAALNDSKT RKTTSETVRA VLDSLPGVRL HCPLNNNAST QRPSRNVNNF 180
PQGYNKEFL YLAGFVDGDG SIFACIQPRQ QSKFKHSLQL WFYVTQKTQR RWFLDKLVDE 240
IGAGYVNDWG GASQYRLSEI KPLHNFLTQL QPFLKLKQKQ ANLVLKIIEQ LPSAKESPDK 300
FLEVCTWVDQ IAALNDSKTR KTTSETVRAV LDSLSEKKKS SP                    342

SEQ ID NO: 153            moltype = AA  length = 342
FEATURE                   Location/Qualifiers
source                    1..342
                          mol_type = protein
                          organism = synthetic construct
SEQUENCE: 153
MNTKYNKEFL LYLAGFVDGD GSIHACISPD QACKFKHYLR LRFNVAQKTQ RRWFLDKLVD  60
EIGVGYVHDQ GSVSYYQLSQ IKPLHNFLTQ LQPFLALKAD QANLVLKIIE QLPSAKESPD 120
KFLEVCTWVD QIAALNDSKT RKTTSETVRA VLDSLPGVRL HCPLNNNAST QRPSRNVNNF 180
PQGYNKEFLL YLAGFVDGDG SIFACIQPRQ QSKFKHSLQL WFYVTQKTQR RWFLDYLVDT 240
IGAGYVNDWG GASQYRLSEI KPLHNFLTQL QPFLKLKQKQ ANLVLKIIEQ LPSAKESPDK 300
FLEVCTWVDQ IAALNDSKTR KTTSETVRAV LDSLSEKKKS SP                    342

SEQ ID NO: 154            moltype = AA  length = 342
FEATURE                   Location/Qualifiers
source                    1..342
                          mol_type = protein
                          organism = synthetic construct
SEQUENCE: 154
MNTKYNKEFL LYLAGFVDGD GSIHACISPD QACKFKYYLR LRFNVAQKTQ RRWFLDKLVD  60
EIGVGYVHDQ GSVSYYQLSQ IKPLHNFLTQ LQPFLALKAD QANLVLKIIE QLPSAKESPD 120
KFLEVCTWVD QIAALNDSKT RKTTSETVRA VLDSLPGVRL HCPLNNNAST QRPSRNVNNF 180
PQGYNKEFLL YLAGFVDGDG SIFACIQPRQ QSKFKHSLQL WFYVTQKTQR RFFLDYLVDT 240
IGAGYVNDWG GASQYRLSEI KPLHNFLTQL QPFLKLKQKQ ANLVLKIIEQ LPSAKESPDK 300
FLEVCTWVDQ IAALNDSKTR KTTSETVRAV LDSLSEKKKS SP                    342
```

-continued

```
SEQ ID NO: 155          moltype = AA   length = 342
FEATURE                 Location/Qualifiers
source                  1..342
                        mol_type = protein
                        organism = synthetic construct
SEQUENCE: 155
MNTKYNKEFL LYLAGFVDGD GSIHACISPD QACKFKHYLR LRFNVAQKTQ RRWFLDKLVD    60
EIGVGYVHDQ GSVSYYQLSQ IKPLHNFLTQ LQPFLKLKQK QANLVLKIIE QLPSAKESPD   120
KFLEVCTWVD QIAALNDSKT RKTTSETVRA VLDSLPGIRL SQGANNNAST QRPSRNVNNF   180
PLGYNKEFLL YLAGFVDGDG SIFACIQPRQ QSKFKHSLQL WFYVTQKTQR RWFLDKLVDE   240
IGAGYVNDWG GASQYRLSEI KPLHNFLTQL QPFLKLKQKQ ANLVLKIIEQ LPSAKESPDK   300
FLEVCTWVDQ IAALNDSKTR KTTSETVRAV LDSLSEKKKS SP                      342

SEQ ID NO: 156          moltype = AA   length = 342
FEATURE                 Location/Qualifiers
source                  1..342
                        mol_type = protein
                        organism = synthetic construct
SEQUENCE: 156
MNTKYNKEFL LYLAGFVDGD GSIHACISPD QACKFKHYLR LRFNVAQKTQ RRWFLDKLVD    60
EIGVGYVHDQ GSVSYYQLSQ IKPLHNFLTQ LQPFLALKAD QANLVLKIIE QLPSAKESPD   120
KFLEVCTWVD QIAALNDSKT RKTTSETVRA VLDSLPGIRL SQGANNNAST QRPSRNVNNF   180
PLGYNKEFLL YLAGFVDGDG SIFACIQPRQ QSKFKHSLQL WFYVTQKTQR RWFLDYLVDT   240
IGAGYVNDWG GASQYRLSEI KPLHNFLTQL QPFLKLKQKQ ANLVLKIIEQ LPSAKESPDK   300
FLEVCTWVDQ IAALNDSKTR KTTSETVRAV LDSLSEKKKS SP                      342

SEQ ID NO: 157          moltype = AA   length = 342
FEATURE                 Location/Qualifiers
source                  1..342
                        mol_type = protein
                        organism = synthetic construct
SEQUENCE: 157
MNTKYNKEFL LYLAGFVDGD GSIHACISPD QACKFKYYLR LRFNVAQKTQ RRWFLDKLVD    60
EIGVGYVHDQ GSVSYYQLSQ IKPLHNFLTQ LQPFLALKAD QANLVLKIIE QLPSAKESPD   120
KFLEVCTWVD QIAALNDSKT RKTTSETVRA VLDSLPGIRL SQGANNNAST QRPSRNVNNF   180
PLGYNKEFLL YLAGFVDGDG SIFACIQPRQ QSKFKHSLQL WFYVTQKTQR RFFLDYLVDT   240
IGAGYVNDWG GASQYRLSEI KPLHNFLTQL QPFLKLKQKQ ANLVLKIIEQ LPSAKESPDK   300
FLEVCTWVDQ IAALNDSKTR KTTSETVRAV LDSLSEKKKS SP                      342

SEQ ID NO: 158          moltype = AA   length = 343
FEATURE                 Location/Qualifiers
source                  1..343
                        mol_type = protein
                        organism = synthetic construct
SEQUENCE: 158
MNTKYNKEFL LYLAGFVDGD GSIHACISPD QACKFKHYLR LRFNVAQKTQ RRWFLDKLVD    60
EIGVGYVHDQ GSVSYYQLSQ IKPLHNFLTQ LQPFLKLKQK QANLVLKIIE QLPSAKESPD   120
KFLEVCTWVD QIAALNDSKT RKTTSETVRA VLDSLPGARP GGVSNNNAST QRPSRNVNNF   180
PYSGYNKEFL LYLAGFVDGD GSIFACIQPR QQSKFKHSLQ LWFYVTQKTQ RRWFLDKLVD   240
EIGAGYVNDW GGASQYRLSE IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 159          moltype = AA   length = 343
FEATURE                 Location/Qualifiers
source                  1..343
                        mol_type = protein
                        organism = synthetic construct
SEQUENCE: 159
MNTKYNKEFL LYLAGFVDGD GSIHACISPD QACKFKHYLR LRFNVAQKTQ RRWFLDKLVD    60
EIGVGYVHDQ GSVSYYQLSQ IKPLHNFLTQ LQPFLALKAD QANLVLKIIE QLPSAKESPD   120
KFLEVCTWVD QIAALNDSKT RKTTSETVRA VLDSLPGARP GGVSNNNAST QRPSRNVNNF   180
PYSGYNKEFL LYLAGFVDGD GSIFACIQPR QQSKFKHSLQ LWFYVTQKTQ RRWFLDYLVD   240
TIGAGYVNDW GGASQYRLSE IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 160          moltype = AA   length = 343
FEATURE                 Location/Qualifiers
source                  1..343
                        mol_type = protein
                        organism = synthetic construct
SEQUENCE: 160
MNTKYNKEFL LYLAGFVDGD GSIHACISPD QACKFKYYLR LRFNVAQKTQ RRWFLDKLVD    60
EIGVGYVHDQ GSVSYYQLSQ IKPLHNFLTQ LQPFLALKAD QANLVLKIIE QLPSAKESPD   120
KFLEVCTWVD QIAALNDSKT RKTTSETVRA VLDSLPGARP GGVSNNNAST QRPSRNVNNF   180
PYSGYNKEFL LYLAGFVDGD GSIFACIQPR QQSKFKHSLQ LWFYVTQKTQ RRFFLDYLVD   240
TIGAGYVNDW GGASQYRLSE IKPLHNFLTQ LQPFLKLKQK QANLVLKIIE QLPSAKESPD   300
KFLEVCTWVD QIAALNDSKT RKTTSETVRA VLDSLSEKKK SSP                     343

SEQ ID NO: 161          moltype = AA   length = 354
```

-continued

```
FEATURE           Location/Qualifiers
source            1..354
                  mol_type = protein
                  organism = synthetic construct
SEQUENCE: 161
MNTKYNKEFL LYLAGFVDGD GSIFARIFKG QHWKFKHHIR LTFNVSQKTQ RRWFLDKLVD  60
EIGVGYVNDY GSTSNYYLSE IKPLHNFLTQ LQPFLKLKQK QANLVLKIIE QLPSAKESPD  120
KFLEVCTWVD QIAALNDSKT RKTTSETVRA VLDSLPGSVG GLSPSQASSA ASSASSSPGS  180
GISEALRAGA GSGTGYNKEF LLYLAGFVDG DGSIWASIIP EQGYKFKHRL RLSFTVAQKT  240
QRRWFLDKLV DEIGVGYVVD QGSVSEYRLS EIKPLHNFLT QLQPFLKLKQ KQANLVLKII  300
EQLPSAKESP DKFLEVCTWV DQIAALNDSK TRKTTSETVR AVLDSLSEKK KSSP        354

SEQ ID NO: 162      moltype = AA   length = 343
FEATURE             Location/Qualifiers
source              1..343
                    mol_type = protein
                    organism = synthetic construct
SEQUENCE: 162
MNTKYNKEFL LYLAGFVDGD GSIFARIFKG QHWKFKHHIR LTFNVSQKTQ RRWFLDKLVD  60
EIGVGYVNDY GSTSNYYLSE IKPLHNFLTQ LQPFLALKAD QANLVLKIIE QLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIWASIIPE QGYKFKHLR LSFTVAQKTQ RRWFLDYLVD  240
TIGVGYVVDQ GSVSEYRLSE IKPLHNFLTQ LQPFLKLKQK QANLVLKIIE QLPSAKESPD  300
KFLEVCTWVD QIAALNDSKT RKTTSETVRA VLDSLSEKKK SSP                   343

SEQ ID NO: 163      moltype = AA   length = 343
FEATURE             Location/Qualifiers
source              1..343
                    mol_type = protein
                    organism = synthetic construct
SEQUENCE: 163
MNTKYNKEFL LYLAGFVDGD GSIIAQIKPN QSYKFKHQLS LAFQVTQKTQ RRWFLDKLVD  60
EIGVGYVRDR GSVSDYILSE IKPLHNFLTQ LQPFLKLKQK QANLVLKIIW RLPSAKESPD  120
KFLEVCTWVD QIAALNDSKT RKTTSETVRA VLDSLPGIQL NKESNNNAST QRPSRNVNNF  180
PYSGYNKEFL LYLAGFVDGD GSIIAQIKPN QSYKFKHQLS LAFQVTQKTQ RRWFLDKLVD  240
EIGVGYVRDR GSVSDYILSE IKPLHNFLTQ LQPFLKLKQK QANLVLKIIW RLPSAKESPD  300
KFLEVCTWVD QIAALNDSKT RKTTSETVRA VLDSLSEKKK SSP                   343
```